US010370455B2

(12) United States Patent
Molloy et al.

(10) Patent No.: US 10,370,455 B2

(45) Date of Patent: Aug. 6, 2019

(54) IDENTIFICATION OF VSIG8 AS THE PUTATIVE VISTA RECEPTOR (V-R) AND USE THEREOF TO PRODUCE VISTA/VSIG8 AGONISTS AND ANTAGONISTS

(71) Applicant: IMMUNEXT, INC., Lebanon, NH (US)

(72) Inventors: Michael Molloy, Enfield, NH (US); Yalin Guo, Hanover, NH (US); Jay Rothstein, Norwich, VT (US); Michael Rosenzweig, Boston, MA (US)

(73) Assignee: IMMUNEXT, INC., Lebanon, NH (US)

( * ) Notice: Subject to any disclaimer, the term of this patent is extended or adjusted under 35 U.S.C. 154(b) by 355 days.

(21) Appl. No.: 14/960,973

(22) Filed: Dec. 7, 2015

(65) Prior Publication Data

US 2016/0159927 A1 Jun. 9, 2016

Related U.S. Application Data

(63) Continuation-in-part of application No. PCT/US2015/064146, filed on Dec. 5, 2015.

(60) Provisional application No. 62/088,058, filed on Dec. 5, 2014.

(51) Int. Cl.

| | |
|---|---|
| ***C07K 16/28*** | (2006.01) |
| ***A61K 39/395*** | (2006.01) |
| ***C07K 16/42*** | (2006.01) |
| ***C07K 14/705*** | (2006.01) |
| ***C12N 15/113*** | (2010.01) |
| *A61K 39/00* | (2006.01) |

(52) U.S. Cl.

CPC ........ *C07K 16/42* (2013.01); *C07K 14/70503* (2013.01); *C07K 16/2803* (2013.01); *C07K 16/2827* (2013.01); *C12N 15/1138* (2013.01); *A61K 2039/505* (2013.01); *C07K 2317/73* (2013.01); *C07K 2317/76* (2013.01); *C07K 2319/30* (2013.01); *C12N 2310/14* (2013.01); *C12N 2310/531* (2013.01)

(58) Field of Classification Search

None

See application file for complete search history.

(56) References Cited

U.S. PATENT DOCUMENTS

| | | | |
|---|---|---|---|
| 4,366,241 | A | 12/1982 | Tom et al. |
| 4,376,110 | A | 3/1983 | David et al. |
| 4,439,196 | A | 3/1984 | Higuchi |
| 4,447,224 | A | 5/1984 | DeCant, Jr. et al. |
| 4,447,233 | A | 5/1984 | Mayfield |
| 4,475,196 | A | 10/1984 | La Zor |
| 4,486,194 | A | 12/1984 | Ferrara |
| 4,487,603 | A | 12/1984 | Harris |
| 4,517,288 | A | 5/1985 | Giegel et al. |
| 4,522,811 | A | 6/1985 | Eppstein et al. |
| 4,596,556 | A | 6/1986 | Morrow et al. |
| 4,676,980 | A | 6/1987 | Segal et al. |
| 4,683,195 | A | 7/1987 | Mullis et al. |
| 4,683,202 | A | 7/1987 | Mullis |
| 4,699,880 | A | 10/1987 | Goldstein |
| 4,736,866 | A | 4/1988 | Leder et al. |
| 4,790,824 | A | 12/1988 | Morrow et al. |
| 4,816,567 | A | 3/1989 | Cabilly et al. |
| 4,837,168 | A | 6/1989 | de Jaeger et al. |
| 4,870,009 | A | 9/1989 | Evans et al. |
| 4,873,191 | A | 10/1989 | Wagner et al. |
| 4,873,316 | A | 10/1989 | Meade et al. |
| 4,881,175 | A | 11/1989 | Ladner |
| 4,941,880 | A | 7/1990 | Burns |
| 4,946,778 | A | 8/1990 | Ladner et al. |
| 4,954,617 | A | 9/1990 | Fanger et al. |
| 4,987,071 | A | 1/1991 | Cech et al. |
| 5,013,653 | A | 5/1991 | Huston et al. |
| 5,064,413 | A | 11/1991 | McKinnon et al. |
| 5,091,513 | A | 2/1992 | Huston et al. |

(Continued)

FOREIGN PATENT DOCUMENTS

| | | |
|---|---|---|
| CA | 2383456 | 3/2001 |
| CN | 1753912 | 3/2006 |

(Continued)

OTHER PUBLICATIONS

Le Mercier et al. (2014) VISTA Regulates the Development of Protective Antitumor Immunity. Cancer Research 74: 1933-1944.*

Le Mercier et al. (2015) Beyond CTLA-4 and PD-1, the generation Z of negative checkpoint regulators. Front. Immunol. 6:418. doi: 10.3389/fimmu.2015.00418; 1-15.*

Lines et al. (2014) VISTA Is an Immune Checkpoint Molecule for Human T Cells. Cancer Research 74: 1924-1932.*

Liu et al. (2015) Immune-checkpoint proteins VISTA and PD-1 nonredundantly regulate murine T-cell responses. Proc. Natl. Acad. Sci. USA 112: 6682-6687.*

(Continued)

*Primary Examiner* — Ilia I Ouspenski

(74) *Attorney, Agent, or Firm* — Robin L. Teskin; LeClairRyan PLLC

(57) ABSTRACT

The receptor for VISTA is identified (VSIG8) as well as the use of this receptor in the identification or synthesis of agonist or antagonist compounds, preferably antibodies, polypeptides and fusion proteins which agonize or antagonize the effects of VSIG8 and/or VISTA and/or the VSIG8/VISTA binding interaction. These antagonists may be used to suppress VISTA's suppressive effects on T cell immunity, and more particularly used in the treatment of cancer, or infectious disease. These agonist compounds may be used to potentiate or enhance VISTA's suppressive effects on T cell immunity and thereby suppress T cell immunity, such as in the treatment of autoimmunity, allergy or inflammatory conditions. Screening assays for identifying these agonists and antagonist compounds are also provided.

14 Claims, 24 Drawing Sheets

Specification includes a Sequence Listing.

(56) References Cited

U.S. PATENT DOCUMENTS

| | | | |
|---|---|---|---|
| 5,116,742 | A | 5/1992 | Cech et al. |
| 5,116,964 | A | 5/1992 | Capon et al. |
| 5,132,405 | A | 7/1992 | Huston et al. |
| 5,139,941 | A | 8/1992 | Muzyczka et al. |
| 5,190,878 | A | 3/1993 | Wilhelm |
| 5,223,409 | A | 6/1993 | Ladner et al. |
| 5,225,539 | A | 7/1993 | Winter |
| 5,258,498 | A | 11/1993 | Huston et al. |
| 5,260,203 | A | 11/1993 | Ladner et al. |
| 5,272,071 | A | 12/1993 | Chappel |
| 5,283,173 | A | 2/1994 | Fields et al. |
| 5,283,317 | A | 2/1994 | Saifer et al. |
| 5,288,641 | A | 2/1994 | Roizman |
| 5,312,335 | A | 5/1994 | McKinnon et al. |
| 5,328,470 | A | 7/1994 | Nabel et al. |
| 5,374,548 | A | 12/1994 | Caras |
| 5,383,851 | A | 1/1995 | McKinnon, Jr. et al. |
| 5,399,163 | A | 3/1995 | Peterson et al. |
| 5,399,331 | A | 3/1995 | Loughrey et al. |
| 5,403,484 | A | 4/1995 | Ladner et al. |
| 5,416,016 | A | 5/1995 | Low et al. |
| 5,427,908 | A | 6/1995 | Dower et al. |
| 5,455,030 | A | 10/1995 | Ladner et al. |
| 5,476,786 | A | 12/1995 | Huston |
| 5,476,996 | A | 12/1995 | Wilson et al. |
| 5,478,925 | A | 12/1995 | Wallach et al. |
| 5,482,858 | A | 1/1996 | Huston et al. |
| 5,530,101 | A | 6/1996 | Queen et al. |
| 5,545,806 | A | 8/1996 | Lonberg et al. |
| 5,545,807 | A | 8/1996 | Surani et al. |
| 5,547,853 | A | 8/1996 | Wallner et al. |
| 5,569,825 | A | 10/1996 | Lonberg et al. |
| 5,571,698 | A | 11/1996 | Ladner et al. |
| 5,580,717 | A | 12/1996 | Dower et al. |
| 5,580,756 | A | 12/1996 | Linsley et al. |
| 5,585,089 | A | 12/1996 | Queen et al. |
| 5,624,659 | A | 4/1997 | Bigner et al. |
| 5,624,821 | A | 4/1997 | Winter et al. |
| 5,625,126 | A | 4/1997 | Lonberg et al. |
| 5,633,425 | A | 5/1997 | Lonberg et al. |
| 5,648,260 | A | 7/1997 | Winter et al. |
| 5,661,016 | A | 8/1997 | Lonberg et al. |
| 5,677,425 | A | 10/1997 | Bodmer et al. |
| 5,693,762 | A | 12/1997 | Queen et al. |
| 5,698,767 | A | 12/1997 | Wilson et al. |
| 5,714,350 | A | 2/1998 | Co et al. |
| 5,723,125 | A | 3/1998 | Chang et al. |
| 5,731,168 | A | 3/1998 | Carter et al. |
| 5,770,429 | A | 6/1998 | Lonberg et al. |
| 5,776,427 | A | 7/1998 | Thorpe et al. |
| 5,789,650 | A | 8/1998 | Lonberg et al. |
| 5,811,097 | A | 9/1998 | Allison et al. |
| 5,814,318 | A | 9/1998 | Lonberg et al. |
| 5,821,333 | A | 10/1998 | Carter et al. |
| 5,837,243 | A | 11/1998 | Deo et al. |
| 5,844,095 | A | 12/1998 | Linsley et al. |
| 5,851,795 | A | 12/1998 | Linsley et al. |
| 5,869,046 | A | 2/1999 | Presta et al. |
| 5,874,299 | A | 2/1999 | Lonberg et al. |
| 5,877,397 | A | 3/1999 | Lonberg et al. |
| 5,885,793 | A | 3/1999 | Griffiths et al. |
| 5,888,807 | A | 3/1999 | Palsson et al. |
| 5,922,845 | A | 7/1999 | Deo et al. |
| 5,932,448 | A | 8/1999 | Tso et al. |
| 5,939,598 | A | 8/1999 | Kucherlapati et al. |
| 5,969,108 | A | 10/1999 | McCafferty et al. |
| 5,985,653 | A | 11/1999 | Armstrong et al. |
| 6,054,297 | A | 4/2000 | Carter et al. |
| 6,069,134 | A | 5/2000 | Roth et al. |
| 6,075,181 | A | 6/2000 | Kucherlapati et al. |
| 6,096,532 | A | 8/2000 | Armstrong et al. |
| 6,114,598 | A | 9/2000 | Kucherlapati et al. |
| 6,121,022 | A | 9/2000 | Presta et al. |
| 6,150,584 | A | 11/2000 | Kucherlapati et al. |
| 6,153,737 | A | 11/2000 | Manoharan et al. |
| 6,162,963 | A | 12/2000 | Kucherlapati et al. |
| 6,165,745 | A | 12/2000 | Ward et al. |
| 6,172,197 | B1 | 1/2001 | McCafferty et al. |
| 6,172,208 | B1 | 1/2001 | Cook |
| 6,180,370 | B1 | 1/2001 | Queen et al. |
| 6,187,287 | B1 | 2/2001 | Leung et al. |
| 6,194,551 | B1 | 2/2001 | Idusogie et al. |
| 6,277,375 | B1 | 8/2001 | Ward |
| 6,300,319 | B1 | 10/2001 | Manoharan |
| 6,335,434 | B1 | 1/2002 | Guzaev et al. |
| 6,335,437 | B1 | 1/2002 | Manoharan |
| 6,350,861 | B1 | 2/2002 | Co et al. |
| 6,395,437 | B1 | 5/2002 | Wollesen |
| 6,407,213 | B1 | 6/2002 | Carter et al. |
| 6,444,806 | B1 | 9/2002 | Veerapanani et al. |
| 6,486,308 | B2 | 11/2002 | Kutyavin et al. |
| 6,492,123 | B1 | 12/2002 | Holliger et al. |
| 6,521,404 | B1 | 2/2003 | Griffiths et al. |
| 6,525,031 | B2 | 2/2003 | Manoharan |
| 6,528,631 | B1 | 3/2003 | Cook et al. |
| 6,544,731 | B1 | 4/2003 | Griffiths et al. |
| 6,545,170 | B2 | 4/2003 | Pitzele et al. |
| 6,548,640 | B1 | 4/2003 | Winter |
| 6,555,313 | B1 | 4/2003 | Griffiths et al. |
| 6,559,279 | B1 | 5/2003 | Manoharan et al. |
| 6,562,576 | B2 | 5/2003 | Manfredi |
| 6,582,915 | B1 | 6/2003 | Griffiths et al. |
| 6,586,474 | B2 | 7/2003 | Webber et al. |
| 6,591,889 | B2 | 7/2003 | Bettio et al. |
| 6,593,081 | B1 | 7/2003 | Griffiths et al. |
| 6,593,372 | B2 | 7/2003 | Enikolopov et al. |
| 6,632,927 | B2 | 10/2003 | Adair et al. |
| 6,639,055 | B1 | 10/2003 | Carter et al. |
| 6,653,104 | B2 | 11/2003 | Goldenberg |
| 6,696,686 | B1 | 2/2004 | Wainer et al. |
| 6,790,624 | B2 | 9/2004 | Mayer |
| 6,809,117 | B2 | 10/2004 | Enikolopov et al. |
| 6,818,418 | B1 | 11/2004 | Lipovsek et al. |
| 6,924,355 | B2 | 8/2005 | Baker et al. |
| 6,936,436 | B2 | 8/2005 | Baker et al. |
| 6,936,697 | B2 | 8/2005 | Desnoyers et al. |
| 6,982,323 | B1 | 1/2006 | Wang et al. |
| 7,026,448 | B2 | 4/2006 | Baker et al. |
| 7,049,058 | B2 | 5/2006 | Singh |
| 7,196,118 | B2 | 3/2007 | Webber et al. |
| 7,226,759 | B2 | 6/2007 | Sun |
| 7,250,297 | B1 | 7/2007 | Beste et al. |
| 7,488,802 | B2 | 2/2009 | Collins et al. |
| 7,595,048 | B2 | 9/2009 | Honjo |
| 7,655,778 | B2 | 2/2010 | Yang |
| 7,919,585 | B2 | 4/2011 | Chen |
| 8,231,872 | B2 * | 7/2012 | Noelle ............... C07K 16/2827 424/130.1 |
| 8,236,304 | B2 | 8/2012 | Noelle et al. |
| 8,465,740 | B2 * | 6/2013 | Noelle ............... A61K 38/1709 424/130.1 |
| 8,501,915 | B2 | 8/2013 | Noelle et al. |
| 8,652,465 | B2 | 2/2014 | Freeman |
| 9,217,035 | B2 | 12/2015 | Noelle et al. |
| 9,381,244 | B2 | 7/2016 | Noelle et al. |
| 9,631,018 | B2 * | 4/2017 | Noelle ............. C07K 14/70503 |
| 9,890,215 | B2 | 2/2018 | Noelle et al. |
| 2003/0031671 | A1 | 2/2003 | Welt et al. |
| 2003/0054406 | A1 | 3/2003 | Baker et al. |
| 2004/0110704 | A1 | 6/2004 | Yamane et al. |
| 2004/0132028 | A1 | 7/2004 | Stumpp et al. |
| 2004/0259209 | A1 | 12/2004 | Sun et al. |
| 2005/0043519 | A1 | 2/2005 | Dooley et al. |
| 2005/0063948 | A1 | 3/2005 | Dickerson et al. |
| 2006/0025576 | A1 | 2/2006 | Miller et al. |
| 2006/0034852 | A1 | 2/2006 | Rixon et al. |
| 2006/0084082 | A1 | 4/2006 | Ruben et al. |
| 2007/0092512 | A1 | 4/2007 | Daaka et al. |
| 2007/0122378 | A1 | 5/2007 | Freeman et al. |
| 2007/0148167 | A1 | 6/2007 | Stohl |
| 2007/0224633 | A1 | 9/2007 | Skerra et al. |
| 2008/0069820 | A1 | 3/2008 | Fuh et al. |
| 2008/0139791 | A1 | 6/2008 | Lipovsek et al. |
| 2008/0166353 | A1 | 7/2008 | Cherwinski |

(56) References Cited

U.S. PATENT DOCUMENTS

| | | | | |
|---|---|---|---|---|
| 2008/0248007 | A1 | 10/2008 | Chen | |
| 2008/0287358 | A1 | 11/2008 | Noelle et al. | |
| 2009/0215991 | A1 | 8/2009 | Lazar et al. | |
| 2010/0316639 | A1 | 12/2010 | Lackner | |
| 2010/0317834 | A1 | 12/2010 | Lazar et al. | |
| 2011/0027278 | A1 | 2/2011 | Noelle et al. | |
| 2011/0158995 | A1 | 6/2011 | Tan et al. | |
| 2011/0206699 | A1 | 8/2011 | Hossain et al. | |
| 2011/0223188 | A1 | 9/2011 | Langermann | |
| 2011/0243942 | A1 | 10/2011 | Wang | |
| 2012/0195894 | A1 | 8/2012 | Noelle et al. | |
| 2013/0177557 | A1 | 7/2013 | Noelle et al. | |
| 2014/0037634 | A1 | 2/2014 | Noelle et al. | |
| 2014/0056890 | A1* | 2/2014 | Gurney .............. | A61K 39/3955 424/134.1 |
| 2014/0056892 | A1 | 2/2014 | Noelle et al. | |
| 2014/0105912 | A1 | 4/2014 | Noelle et al. | |
| 2014/0220012 | A1 | 8/2014 | Noelle et al. | |
| 2014/0341920 | A1 | 11/2014 | Noelle et al. | |
| 2015/0231215 | A1 | 8/2015 | Noelle et al. | |
| 2016/0008316 | A1 | 1/2016 | Bacha et al. | |
| 2016/0083472 | A1 | 3/2016 | Noelle et al. | |
| 2016/0159927 | A1 | 6/2016 | Molloy et al. | |
| 2016/0168248 | A1 | 6/2016 | Noelle et al. | |
| 2016/0318999 | A9 | 11/2016 | Noelle et al. | |
| 2016/0331803 | A1 | 11/2016 | Noelle et al. | |
| 2017/0119877 | A1 | 5/2017 | Green et al. | |
| 2017/0334990 | A1 | 11/2017 | Noelle et al. | |
| 2018/0051070 | A1 | 2/2018 | Noelle et al. | |

FOREIGN PATENT DOCUMENTS

| | | |
|---|---|---|
| EP | 0 045 665 | 2/1982 |
| EP | 0 125 023 | 11/1984 |
| EP | 0 154 316 | 9/1985 |
| EP | 0 171 496 | 2/1986 |
| EP | 0 173 494 | 3/1986 |
| EP | 0 184 187 | 6/1986 |
| EP | 0 264 166 | 4/1988 |
| EP | 0 401 384 | 12/1990 |
| EP | 1 176 195 | 1/2002 |
| EP | 1 641 818 | 4/2006 |
| JP | 08-506635 | 3/2008 |
| WO | 00/045665 | 2/1982 |
| WO | 86/001533 | 3/1986 |
| WO | 87/002671 | 5/1987 |
| WO | 87/005330 | 9/1987 |
| WO | 88/000052 | 1/1988 |
| WO | 88/009810 | 12/1988 |
| WO | 89/010134 | 11/1989 |
| WO | 91/006667 | 5/1991 |
| WO | 92/003918 | 3/1992 |
| WO | 93/008829 | 5/1993 |
| WO | 93/012227 | 6/1993 |
| WO | 94/010300 | 5/1994 |
| WO | 94/010332 | 5/1994 |
| WO | 94/025585 | 11/1994 |
| WO | 94/029351 | 12/1994 |
| WO | 94/029436 | 12/1994 |
| WO | 97/007668 | 3/1997 |
| WO | 97/007669 | 3/1997 |
| WO | 97/013852 | 4/1997 |
| WO | 97/028267 | 8/1997 |
| WO | 98/024884 | 6/1998 |
| WO | 99/045962 | 9/1999 |
| WO | 99/054342 | 10/1999 |
| WO | 00/006593 | 2/2000 |
| WO | 00/029004 | 5/2000 |
| WO | 00/031113 | 6/2000 |
| WO | 00/042072 | 7/2000 |
| WO | 01/000814 | 1/2001 |
| WO | 01/003737 | 1/2001 |
| WO | 01/014424 | 3/2001 |
| WO | 02/029072 | 4/2002 |
| WO | 02/043478 | 6/2002 |
| WO | 02/079449 | 10/2002 |
| WO | 02/092780 | 11/2002 |
| WO | 03/035835 | 5/2003 |
| WO | 03/074679 | 9/2003 |
| WO | 04/018520 | 3/2004 |
| WO | 04/037999 | 5/2004 |
| WO | 05/056764 | 6/2005 |
| WO | 05/112834 | 12/2005 |
| WO | 05/113606 | 12/2005 |
| WO | 06/012232 | 2/2006 |
| WO | 06/050247 | 5/2006 |
| WO | 06/050262 | 5/2006 |
| WO | 06/116181 | 11/2006 |
| WO | 07/030198 | 3/2007 |
| WO | 08/098796 | 8/2008 |
| WO | 09/089004 | 7/2009 |
| WO | 10/027827 | 3/2010 |
| WO | 11/120013 | 9/2011 |
| WO | 13/184912 | 12/2013 |
| WO | 13/192504 | 12/2013 |
| WO | 14/039983 | 3/2014 |
| WO | 14/190356 | 11/2014 |
| WO | 15/097536 | 7/2015 |
| WO | 15/109340 | 7/2015 |
| WO | 15/191881 | 12/2015 |
| WO | 16/090347 | 6/2016 |
| WO | 17/181109 | 10/2017 |
| WO | 17/181139 | 10/2017 |
| WO | 18/027042 | 2/2018 |

OTHER PUBLICATIONS

Colman P.M., Research in Immunology 1994, 145: 33-36.*
Lederman et al., Molecular Immunology 1991, 28: 1171-1181.*
Li et al., PNAS 1990, 77: 3211-3214.*
Rice et al. (2011) Localization of Hair Shaft Protein VSIG8 in the Hair Follicle, Nail Unit, and Oral Cavity. Journal of Investigative Dermatology 131: 1936-1938.*
Deng et al. (2016) A New VISTA on combination therapy for negative checkpoint regulator blockade. Journal for Immunotherapy of Cancer 4:86 DOI 10.1186/s40425-016-0190-5; 7 pages.*
Gao et al. (2017) VISTA is an inhibitory immune checkpoint that is increased after ipilimumab therapy in patients with prostate cancer. Nature Medicine 23: 551-557.*
Nowak et al. (2017) Immunoregulatory Functions of VISTA. Immunol Rev. 276: 66-79.*
Janssen Research & Development, LLC (2017) A Study of Safety, Pharmacokinetics, Pharmacodynamics of JNJ-61610588 in Participants With Advanced Cancer. ClinicalTrials.gov Identifier: NCT02671955; 9 pages.*
Curis, Inc. (2018) A Study of CA-170 (Oral PD-L1, PD-L2 and VISTA Checkpoint Antagonist) in Patients With Advanced Tumors and Lymphomas. ClinicalTrials.gov Identifier: NCT02812875; 8 pages.*
Sasikumar et al. Functional antagonism of VSIG8-mediated immune suppression by oral VISTA agents. In: Proceedings of the AACR-NCI-EORTC International Conference: Molecular Targets and Cancer Therapeutics; Oct. 26-30, 2017; Philadelphia, PA. Philadelphia (PA): AACR; Mol Cancer Ther 2018; 17(1 Suppl): Abstract B006.*
Wang L, et al. "VISTA, a novel mouse Ig superfamily ligand that negatively regulates T cell responses," J Exp Med. Mar. 14, 2011;208(3):577-92.
Aalberse Rc, et al. "IgG4 breaking the rules," Immunology. Jan. 2002;105(1):9-19.
Adriouch S, et al. "Improved Immunological Tolerance Following Combination Therapy with CTLA-4/Ig and AAV-Mediated PD-L1/2 Muscle Gene Transfer," Front Microbiol. Sep. 29, 2011;2:199.
Allen, et al., (2009), "Interchain disulfide bonding in human IgG2 antibodies probed by site-directed mutagenesis", Biochemistry, 48(17), 3755-3766.
Allen, T. M. "Ligand-targeted therapeutics in anticancer therapy," Nat Rev Cancer. Oct. 2002;2(10):750-63.

(56) References Cited

OTHER PUBLICATIONS

Almquist RG, et al. "Synthesis and biological activity of a ketomethylene analogue of a tripeptide inhibitor of angiotensin converting enzyme," J Med Chem. Dec. 1980;23(12):1392-8.
al-Obeidi F, et al. "Peptide and peptidomimetic libraries. Molecular diversity and drug design," Mol Biotechnol. Jun. 1998;9(3):205-23.
Altman JD, et al. "Phenotypic analysis of antigen-specific T lymphocytes," Science. Oct. 4, 1996;274(5284):94-6.
Altschul SF, et al. "Basic local alignment search tool," J Mol Biol. Oct. 5, 1990;215(3):403-10.
Altschul SF, et al. "Gapped BLAST and PSI-BLAST: a new generation of protein database search programs," Nucleic Acids Res. Sep. 1, 1997;25(17):3389-402.
Amancha PK, et al. "In vivo blockade of the programmed cell death-1 pathway using soluble recombinant PD-1-Fc enhanced CD+ and CD8+ T cell responses but has limited clinical benefit," J Immunol. Dec. 15, 2013;191(12):6060-70.
Ansari MJ, et al. "The programmed death-1 (PD-1) pathway regulates autoimmune diabetes in nonobese diabetic (NOD) mice," J Exp Med. Jul. 7, 2003;198(1):63-9.
Arkin Ap, et al. "An algorithm for protein engineering: simulations of recursive ensemble mutagenesis," Proc Natl Acad Sci U S A. Aug. 15, 1992;89(16):7811-5.
Attia, P., et al., Autoimmunity correlates with tumor regression in patients with metastatic melanoma treated with anti-cytotoxic T-lymphocyte antigen-4. J Clin Oncol, 2005. 23(25): p. 6043-53.
Auffray, C et al. "Blood monocytes: development, heterogeneity, and relationship with dendritic cells," Annu Rev Immunol, 2009. 27: p. 669-92.
Bagley Rg, et al. "sFLT01: a novel fusion protein with antiangiogenic activity," Mol Cancer Ther. Mar. 2011;10(3):404-15..
Bak, S. P., et al., Murine ovarian cancer vascular leukocytes require arginase-1 activity for T cell suppression. Mol Immunol, 2008. 46(2): p. 258-68.
Baldari C, et al. "A novel leader peptide which allows efficient secretion of a fragment of human interleukin 1 beta in Saccharomyces cerevisiae," EMBO J. Jan. 1987;6(1):229-34.
Banerji J, et al. "A lymphocyte-specific cellular enhancer is located downstream of the joining region in immunoglobulin heavy chain genes," Cell. Jul. 1983;33(3):729-40.
Barringer Kj, et al. "Blunt-end and single-strand ligations by *Escherichia coli* ligase: influence on an in vitro amplification scheme,"Gene. Apr. 30, 1990;89(1):117-22.
Bartel Dp, et al. "Isolation of new ribozymes from a large pool of random sequences," Science. Sep. 10, 1993;261(5127):1411-8.
Baskar S, et al. "Constitutive expression of B7 restores immunogenicity of tumor cells expressing truncated major histocompatibility complex class II molecules," Proc Natl Acad sci U S A. Jun. 15, 1993;90(12):5687-90.
Batzer Ma, et al. "Enhanced evolutionary PCR using oligonucleotides with inosine at the 3'-terminus," Nucleic Acids Res. Sep. 25, 1991;19(18):5081.
Bauer S, et al. "Immunotherapy of human tumors with T-cell-activating bispecific antibodies: stimulation of cytotoxic pathways in vivo," Cancer Res. Apr. 15, 1999;59(8):1961-5.
Beidler Cb, et al. "Cloning and high level expression of a chimeric antibody with specificity for human carcinoembryonic antigen," J Immunol. Dec. 1, 1988;141(11):4053-60.
Beilharz Mw, et al. "Timed ablation of regulatory CD4+ T cells can prevent murine AIDS progression," J Immunol. Apr. 15, 2004;172(8):4917-25.
Belousov Es, et al. "Sequence-specific targeting and covalent modification of human genomic DNAa," Nucleic Acids Res. Sep. 1, 1997;25(17):3440-4.
Béranger F, et al. "Getting more from the two-hybrid system: N-terminal fusions to LexA are efficient and sensitive baits for two-hybrid studies," Nucleic Acids Res. May 15, 1997;25(10):2035-6.
Berge Sm, et al. "Pharmaceutical salts," J Pharm Sci. Jan. 1977;66(1):1-19.
Berney C, et al. "A member of the dendritic cell family that enters B cell follicles and stimulates primary antibody responses identified by a mannose receptor fusion protein," J Exp Med. Sep. 20, 1999;190(6):851-60.
Better M, et al. "*Escherichia coli*secretion of an active chimeric antibody fragment," Science. May 20, 1988;240(4855):1041-3.
Bird Re, et al. "Single-chain antigen-binding proteins," Science. Oct. 21, 1988;242(4877):423-6.
Blank C, et al. "Interaction of PD-L1 on tumor cells with PD-1 on tumor-specific T cells as a mechanism of immune evasion: implications for tumor immunotherapy," Cancer Immunol Immunother. Apr. 2005;54(4):307-14.
Blank, C., et al., "PD-L1/B7H-1 inhibits the effector phase of tumor rejection by T cell receptor (TCR) transgenic CD8+ T cells," Cancer Res, 2004. 64(3): p. 1140-5.
Blazer et al., "Infusion of anti-B7. 1 (CD80) and anti-B7. 2 (CD86) monoclonal antibodies inhibits murine graft-verus-host disease lethality in part via direct effects on CD4+ and CD8+ T cells." The Journal of Immunology 157.8 (1996: 3250-3259.
Bloemen Pg, et al. "Adhesion molecules: a new target for immunoliposome-mediated drug delivery, " FEBS Lett. Jan. 3, 1995;357(2):140-4.
Blommers Mj, et al. "Effects of the introduction of L-nucleotides into DNA. Solution structure of the heterochiral duplex d(G-C-G-(L)T-G-C-G).d(C-G-C-A-C-G-C) studied by NMR spectroscopy," Biochemistry. Jun. 28, 1994;33(25):7886-96.
Bluestone Ja, et al. "Natural versus adaptive regulatory T cells," Nat Rev Immunol. Mar. 2003;3(3):253-7.
Bogdan C. "Nitric oxide and the immune response," Nat Immunol. Oct. 2001;2(10):907-16.
Bolhassani, A. et al., "Improvement of different vacine delivery systems for cancer therapy", Molecular Cancer, 2011, vol. 10, No. 1, Article No. 3.
Boon T, et al."Human T cell responses against melanoma," Annu. Rev. Immunol.. Apr. 23, 2006;24:175-208.
Borriello F, et al. "B7-1 and B7-2 have overlapping, critical roles in immunoglobulin class switching and germinal center formation," Immunity. Mar. 1997;6(3):303-13.
Borrok Mj, "pH- dependent Binding Engineering Reveals an FcRn Affinity Threshold That Governs IgG Recycling," The Journal of Biological Chemistry. 2015;290(7):4282-90.
Boulianne Gl, et al. "Production of functional chimaeric mouse/human antibody," Nature. Dec. 13-19, 1984;312(5995):643-6.
Bowen Jl, et al. "Innate immune CD11b+Gr-1+ cells, suppressor cells, affect the immune response during Theiler's virus-induced demyelinating disease," J Immunol. Dec. 1, 2009;183(11):6971-80.
Brahmer, J. R., et al., Phase I study of single-agent anti-programmed death-1 (MDX-1106) in refractory solid tumors: safety, clincal activity, pharmacodynamics, and immunologic correlates. J Clin Oncol, 2010 28(19): p. 3167-75.
Brandt C, et al. "The B7 family member B7-H6 is a tumor cell ligand for the activating natural killer cell receptor NKp30 in humans," J. Exp Med. Jul. 6, 2009;206(7):1495-503.
Brennan M, et al. "Preparation of bispecific antibodies by chemical recombination of monoclonal immunoglobulin G1 Fragments," Science. Jul. 5, 1985;229(4708):81-3.
Briscoe P, et al. "Delivery of superoxide dismutase to pulmonary epithelium via pH-sensitive liposomes," Am J Physiol. Mar. 1995;268(3 Pt 1):L374-80.
Brisson, et al. "Expression of a bacterial gene in plants by using a viral vector," Nature vol. 310 Aug. 1984, 511-14.
Broglie R, et al. "Light-regulated expression of a pea ribulose-1,5-bisphosphate carboxylase small subunit gene in transformed plant cells," Science. May 25, 1984;224(4651):838-43.
Brown Jp, et al. "Protein antigens of normal and malignant human cells identified by immunoprecipitation with monoclonal antibodies," J Biol Chem. Jun. 10, 1980;255(11):4980-3.
Brown Jp, et al. "Structural characterization of human melanoma-associated antigen p97 with monoclonal antibodies," J Immunol. Aug. 1981;127(2):539-46.

(56) References Cited

OTHER PUBLICATIONS

Brys L, et al. "Reactive oxygen species and 12/15-lipoxygenase contribute to the antiproliferative capacity of alternatively activated myeloid cells elicited during helminth infection," J Immunol. May 15, 2005;174(10):6095-104.
Burg Jl, et al. "Single molecule detection of RNA reporter probes by amplification with Q beta replicase," Mol Cell Probes. Aug. 1996;10(4):257-71.
Butte Mj, et al. "Programmed death-1 ligand 1 interacts specifically with the B7-1 costimulatory molecule to inhibit T cell responses," Immunity. Jul. 2007:27(1):111-22.
Byrne Gw, et al. "Multiplex gene regulation: a two-tiered approach to transgene regulation in transgenic mice," Proc Natl Acad Sci U S A. Jul. 1989;86(14):5473-7.
Cabilly S, et al. "Generation of antibody activity from immunoglobulin polypeptide chains produced in *Escherichia coli*," Proc Natl Acad Sci U S A. Jun. 1984;81(11):3273-7.
Cabilly S, et al. "Immunoglobulin transcripts and molecular history of a hybridoma that produces antibody to carcinoembryonic antigen," Gene. 1985;40(1):157-61.
Calabro, L., et al., "Clinical studies with anti-CTLA-4 antibodies in non-melanoma indications," Semin Oncol, 2010. 37(5): p. 460-7.
Calame K, et al. "Transcriptional controlling elements in the immunoglobulin and T cell receptor loci," Adv Immunol. 1988;43:235-75.
Camper Sa, et al. "Postnatal repression of the alpha-fetoprotein gene is enhancer independent," Genes Dev. Apr. 1989;3(4):537-46.
Cancer Prevention Overview (PDQ®), PDQ Cancer Information Summaries [Internet].2017, 14 pages.
Carell, et al. "A Solution-Phase Screening Procedure for the Isolation of Active Compounds from a Library of Molecules," Angew. Chem. Int. Ed. Engl. 1994, 33. No. 20, 2061-64.
Carter L, et al. "PD-1:PD-L inhibitory pathway affects both CD4(+) and CD8(+) T cells and is overcome by IL-2," Eur J Immunol. Mar. 2002;32(3):634-43.
Ceeraz S, et al. "VISTA Deficiency Accelerates the Development of Fatal Murine Lupus Nephritis," Arthritis Rheumatol. Apr. 2017;69(4):814-825.
Chambers Ca, et al. "Lymphoproliferation in CTLA-4-deficient mice is mediated by costimulation-dependent activation of CD4+ T cells," Immunity. Dec. 1997;7(6):885-95.
Chan Ac, et al. "Therapeutic antibodies for autoimmunity and inflammation," Nat Rev Immunol. May 2010;10(5):301-16.
Chen J, et al. "B cell development in mice that lack one or both immunoglobulin kappa light chain genes," EMBO J. Mar. 1993;12(3):821-30.
Chen J, et al. "Immunoglobulin gene rearrangement in B cell deficient mice generated by targeted deletion of the JH locus," Int Immunol. Jun. 1993;5(6):647-56.
Chen L, et al. "Costimulation of antitumor immunity by the B7 counterreceptor for the T lymphocyte molecules CD28 and CTLA-4," Cell. Dec. 24, 1992;71(7):1093-102.
Chen S, et al. "Immunosuppressive functions of hepatic myeloid-derived suppressor cells of normal mice and in a murine model of chronic hepatitis B virus," Clin Exp Immunol. Oct. 2011;166(1):134-42.
Chen Sh, et al. "Gene therapy for brain tumors: regression of experimental gliomas by adenovirus-mediated gene transfer in vivo," Proc Natl Acad Sci U S A. Apr. 12, 1994;91(8):3054-7.
Chen, Y., "Development of a sandwich ELISA for evaluating soluble PD-LI (CD274) in human sera of different ages as well as supernatants of PD-L1(+) cell lines," Cytokine 2011.
Cho Cy, et al. "An unnatural biopolymer," Science. Sep. 3, 1993;261(5126):1303-5.
Choi Tk, et al. "Transgenic mice containing a human heavy chain immunoglobulin gene fragment cloned in a yeast artificial chromosome," Nat Genet. Jun. 1993;4(2):117-23.
Chothia C, et al. "Canonical structures for the hypervariable regions of immunoglobulins," J Mol Biol. Aug. 20, 1987;196(4):901-17.
Church Gm, et al. "Genomic sequencing," Proc Natl Acad Sci U S A. Apr. 1984;81(7):1991-5.
Clark Kl, et al. "Association of the Arabidopsis CTR1 Raf-like kinase with the ETR1 and ERS ethylene receptors," Proc Natl Acad Sci U S A. Apr. 28, 1998;95(9):5401-6.
Cohen Aa, et al. "Structure design: an artificial intelligence-based method for the design of molecules under geometrical constraints," J Mol Graph. Sep. 1993;11(3):166-73.
Cole Sp, et al. "Human monoclonal antibodies," Mol Cell Biochem. Jun. 1984;62(2):109-20.
Colman PM. "Effects of amino acid sequence changes on antibody-antigen interactions," Res Immunol. Jan. 1994;145(1):33-6.
Conejo-Garcia, J. R., et al., "Tumor-infiltrating dendritic cell precursors recruited by a beta-defensin contribute to vasculogenesis under the influence of Vegf-A," Nat Med, 2004. 10(9): p. 950-8.
Copin, R., et al., "MyD88-dependent activation of B220-CD11b+ LY-6C+ dendritic cells during *Brucella melitensis* infection," J Immunol, 2007. 178(8): p. 5182-91.
Coruzzi G, et al. "Tissue-specific and light-regulated expression of a pea nuclear gene encoding the small subunit of ribulose-1,5-bisphosphate carboxylase," EMBO J. Aug. 1984;3(8):1671-9.
Corzo, C. A., et al., "HIF-1alpha regulates function and differentiation of myeloid-derived suppressor cells in the tumor microenvironment," J Exp Med, 2010. 207(11): p. 2439-53.
Cote Rj, et al. "Generation of human monoclonal antibodies reactive with cellular antigens," Proc Natl Acad Sci U S A. Apr. 1983;80(7):2026-30.
Cox Jp, et al. "A directory of human germ-line V kappa segments reveals a strong bias in their usage," Eur J Immunol. Apr. 1994;24(4):827-36.
Cubillos-Ruiz, J. R., et al., "Polyethylenimine-based siRNA nanocomplexes reprogram tumor-associated dendritic cells via TLRS to elicit therapeutic antitumor immunity," J Clin Invest, 2009. 119(8): p. 2231-44.
Cull Mg, et al. "Screening for receptor ligands using large libraries of peptides linked to the C terminus of the lac repressor," Proc Natl Acad Sci U S A. Mar. 1, 1992;89(5):1865-9.
Cunningham Bc, et al. "High-resolution epitope mapping of hGH-receptor interactions by alanine-scanning mutagenesis," Science. Jun. 2, 1989;244(4908):1081-5.
Curiel, T. J., et al., "Blockade of B7-H1 improves myeloid dendritic cell-mediated antitumor immunity," Nat Med, 2003. 9(5): p. 562-7.
Curiel, T. J., et al., "Specific recruitment of regulatory T cells in ovarian carcinoma fosters immune privilege and predicts reduced survival," Nat Med, 2004. 10(9): p. 942-9.
Curis, Inc. "A Study of CA-170 (Oral PD-L1, PD-L2 and VISTA Checkpoint Antagonist) in Patients With Advanced Tumors and Lymphomas," U.S. National Library of Medicine, ClinicalTrials.gov; (https://clinicaltrials.gov) 2018. 8 pages.
Cwirla Se, et al. "Peptides on phage: a vast library of peptides for identifying ligands," Proc Natl Acad Sci U S A. Aug. 1990;87(16):6378-82.
Dal Porto J, et al. "A soluble divalent class I major histocompatibility complex molecule inhibits alloreactive T cells at nanomolar concentrations," Proc Natl Acad Sci U S A. Jul. 15, 1993;90(14):6671-5.
David Gs, et al. "Protein iodination with solid state lactoperoxidase," Biochemistry. Feb. 26, 1974;13(5):1014-21.
de Vos Am, et al. "Human growth hormone and extracellular domain of its receptor: crystal structure of the complex," Science. Jan. 17, 1992;255(5042):306-12.
Dean PM. "Recent advances in drug design methods: where will they lead?" Bioessays. Sep. 1994;16(9):683-7.
Delagrave S, et al. "Recursive ensemble mutagenesis," Protein Eng. Apr. 1993;6(3):327-31.
Dellinger et al "International Guidelines for Management of Severe Sepsis and Septic Shock" (2013 Intensive Care Med 39: 165-228).
Deng J, et al. "A New VISTA on combination therapy for negative checkpoint regulator blockade," J Immunother Cancer. Dec. 20, 2016;4:86.
Deshayes S, et al. "Insight into the mechanism of internalization of the cell-penetrating carrier peptide Pep-1 through conformational analysis," Biochemistry. Feb. 17, 2004;43(6):1449-57.

(56) References Cited

OTHER PUBLICATIONS

D'Eustachio P, et al. "Somatic cell genetics and gene families," Science. May 27, 1983;220(4600):919-24.
Devlin Jj, et al. "Random peptide libraries: a source of specific protein binding molecules," Science. Jul. 27, 1990;249(4967):404-6.
DeWitt Sh, et al. "'Diversomers': an approach to nonpeptide, nonoligomeric chemical diversity," Proc Natl Acad Sci U S A. Aug. 1, 1993;90(15):6909-13.
Di Maro, Antimo, et al. "Isolation and characterization of four type-1 ribosome-inactivating proteins, with polynucleotide: adenosine glycosidase activity, from leaves of Phytolacca dioica L." Planta 208.1 (1999): 125-131.
DiLillo Dj, et al. "Fc-Receptor Interactions Regulate Both Cytotoxic and Immunomodulatory Therapeutic Antibody Effector Functions," Cancer Immunology Research. 2015;3(7):704-13.
Dillon et al., "Optimization of a reversed-phase high-performance liquid chromatography/mass spectrometry method for characterizing recombinant antibody heterogeneity and stability," J Chromatogr A. Jul. 7, 2006;1120(1-2):112-20.
Dong C, et al. "ICOS co-stimulatory receptor is essential for T-cell activation and function," Nature. Jan. 4, 2001;409(6816):97-101.
Dong H, et al. "B7-H1 pathway and its role in the evasion of tumor immunity," J Mol Med (Berl). May 2003;81(5):281-7.
Dong H, et al. "Tumor-associated B7-H1 promotes T-cell apoptosis: a potential mechanism of immune evasion," Nat Med. Aug. 2002;8(8):793-800.
Dubey Ak, et al. "Belimumab: First targeted biological treatment for systemic lupus erythematosus," J Pharmacol Pharmacother. 2011;2(4):317-9.
Duttagupta et al., "Costimulation signals for memory CD8+ T cells during viral infections." Critical Reviews™ in Immunology 29.6 (2009).
Edlund T, et al. "Cell-specific expression of the rat insulin gene: evidence for role of two distinct 5' flanking elements," Science. 1985 Nov 22;230(4728):912-6.
Ehst Bd, et al. "Development of a novel transgenic mouse for the study of interactions between CD4 and CD8 T cells during graft rejection," American Journal of Transplantation: 2003;3(11):1355-62.
Elbashir Sm, et al. "Duplexes of 21-nucleotide RNAs mediate RNA interference in cultured mammalian cells," Nature. May 24, 2001;411(6836):494-8.
Ellenberger Te, et al. "The GCN4 basic region leucine zipper binds DNA as a dimer of uninterrupted alpha helices: crystal structure of the protein-DNA complex," Cell. Dec. 24, 1992;71(7):1223-37.
Erb E, et al. "Recursive deconvolution of combinatorial chemical libraries," Proc Natl Acad Sci U S A. Nov. 22, 1994;91(24):11422-6.
Evans Be, et al. "Design of nonpeptidal ligands for a peptide receptor: cholecystokinin antagonists," J Med Chem. Jul. 1987;30(7):1229-39.
Fallarino F, et al. "B7-1 engagement of cytotoxic T lymphocyte antigen 4 inhibits T cell activation in the absence of CD28," J Exp Med. Jul. 6, 1998;188(1):205-10.
Fan Ys, et al. "Mapping small DNA sequences by fluorescence in situ hybridization directly on banded metaphase chromosomes," Proc Natl Acad Sci U S A. Aug. 1990;87(16):6223-7.
Felici F, et al. "Selection of antibody ligands from a large library of oligopeptides expressed on a multivalent exposition vector," J Mol Biol. Nov. 20, 1991;222(2):301-10.
Finn Pj, et al. "Synthesis and properties of DNA-PNA chimeric oligomers," Nucleic Acids Res. Sep. 1, 1996;24(17):3357-63.
Fishwild Dm, et al. "High-avidity human IgG kappa monoclonal antibodies from a novel strain of minilocus transgenic mice," Nat Biotechnol. Jul. 1996;14(7):845-51.
Flicek P, et al. "Ensembl 2008," Nucleic Acids Res. Jan. 2008;36(Database issue):D707-14.
Flies Db, et al. "Coinhibitory receptor PD-1H preferentially suppresses CD4+ T cell-mediated immunity," J Clin Invest. May 2014;124(5):1966-75.
Flies Db, et al. "Cutting edge: a monoclonal antibody specific for the programmed death-1 homolog prevents graft-versus-host disease in mouse models," J Immunol. Aug. 15, 2011;187(4):1537-41.
Flies Db, et al. "Mechanistic Assessment of PD-1H Coinhibitory Receptor-Induced T Cell Tolerance to Allogeneic Antigens," J Immunol. Jun. 1, 2015;194(11):5294-304.
Fodor Sp, et al. "Multiplexed biochemical assays with biological chips," Nature. Aug. 5, 1993;364(6437):555-6.
Fontenot Jd, et al. "Regulatory T cell lineage specification by the forkhead transcription factor foxp3," Immunity. Mar. 2005;22(3):329-41.
Formstecher E, et al. "Protein interaction mapping: a Drosophila case study," Genome Res. Mar. 2005;15(3):376-84.
Franklin, et al. "Immunologic differences between the 19 S and 7 S components of normal human gamma-globulin," J Immunol. Jan. 1957;78(1):11-8.
Freeman Gj, et al. "Engagement of the PD-1 immunoinhibitory receptor by a novel B7 family member leads to negative regulation of lymphocyte activation," J Exp Med. Oct. 2, 2000;192(7):1027-34.
Freeman Gj, et al. "Uncovering of functional alternative CTLA-4 counter-receptor in B7-deficient mice," Science. Nov. 5, 1993;262(5135):907-9.
Freeman Gj. "Structures of PD-1 with its ligands: sideways and dancing cheek to cheek," Proc Natl Acad Sci U S A. Jul. 29, 2008;105(30):10275-6.
Freier Sm, et al. "Improved free-energy parameters for predictions of RNA duplex stability," Proc Natl Acad Sci U S A. Dec. 1986;83(24):9373-7.
Frenkel K, et al. "7,12-dimethylbenz[a]anthracene induces oxidative DNA modification in vivo," Free Radic Biol Med. Sep. 1995;19(3):373-80.
Fromont-Racine M, et al. "Toward a functional analysis of the yeast genome through exhaustive two-hybrid screens," Nat Genet. Jul. 1997;16(3):277-82.
Futaki S. "Arginine-rich peptides: potential for intracellular delivery of macromolecules and the mystery of the translocation mechanisms," Int J Pharm. Oct. 1, 2002;245(1-2):1-7.
Gabrilovich D. "Mechanisms and functional significance of tumour-induced dendritic-cell defects," Nat Rev Immunol. Dec. 2004;4(12):941-52.
Gabrilovich Dl,et al. "Myeloid-derived suppressor cells as regulators of the immune system," Nat Rev Immunol. Mar. 2009;9(3):162-74.
Galfre, G. et al. "Antibodies to major histocompatibility anitigens produced by hybrid cell lines," Nature, vol. 266, Apr. 1977, 550-52.
Gallop Ma, et al. "Applications of combinatorial technologies to drug discovery. 1. Background and peptide combinatorial libraries," J Med Chem. Apr. 29, 1994;37(9):1233-51.
Gao J, et al. "Vista is an inhibitory immune checkpoint that is increased after ipilimumab therapy in patients with prostate cancer," Nat Med. May 2017;23(5):551-555.
Gao, Q., et al., "Overexpression of PD-L1 significantly associates with tumor aggressiveness and postoperative recurrence in human hepatocellular carcinoma," Clin Cancer Res, 2009. 15(3): p. 971-9.
Garg A, et al. "HIV type 1 gp120-induced expansion of myeloid derived suppressor cells is dependent on interleukin 6 and suppresses immunity," J Infect Dis. Feb. 1, 2014;209(3):441-51.
Gautier C, et al. "Alpha-DNA. IV: Alpha-anomeric and beta-anomeric tetrathymidylates covalently linked to intercalating oxazolopyridocarbazole. Synthesis, physicochemical properties and poly (rA) binding," Nucleic Acids Res. Aug. 25, 1987;15(16):6625-41.
Gavin Ma, et al. " Homeostasis and anergy of CD4(+)CD25(+) suppressor T cells in vivo," Nat Immunol. Jan. 2002;3(1):33-41.
Gefter Ml, et al. "A simple method for polyethylene glycol-promoted hybridization of mouse myeloma cells," Somatic Cell Genet. Mar. 1977;3(2):231-6.
Geissmann, F., et al. "Blood monocytes consist of two principal subsets with distinct migratory properties," Immunity, 2003. 19(1): p. 71-82.

(56) References Cited

OTHER PUBLICATIONS

Geissmann, F., et al., "Blood monocytes: distinct subsets, how they relate to dendritic cells, and their possible roles in the regulation of T-cell responses," Immunol Cell Biol, 2008. 86(5): p. 398-408.
Geissmann, F., et al., "Development of monocytes, macrophages, and dendritic cells," Science, 2010. 327(5966): p. 656-61.
GenBank Accession No. NP.sub.--071436 (Sep. 3, 2009), platelet receptor Gi24 precursor [*Homo spaiens*].
GenBank Accession No. NP.sub.--083008 (Mar. 3, 3010) platelet receptor Gi24 isoform 1 precursor [*Mus musculus*].
Genbank entry EGW09616.1 (Mar. 14, 2015) [retrieved on Jun. 22, 2015 from http://www.ncbi.nlm.nih.gov/protein/EGW09616.1] 1 page.
Geng H, et al. "HSP70 vaccine in combination with gene therapy with plasmid DNA encoding sPD-1 overcomes immune resistance and suppresses the progression of pulmonary metastatic melanoma," Int J Cancer. Jun. 1, 2006;118(11):2657-64.
Ghiringhelli, F., et al., "Tumor cells convert immature myeloid dendritic cells into TGF-beta-secreting cells inducing CD4+CD25+ regulatory T cell proliferation," J Exp Med, 2005. 202(7): p. 919-29.
Gilliland Dg, et al. "Antibody-directed cytotoxic agents: use of monoclonal antibody to direct the action of toxin A chains to colorectal carcinoma cells," Proc Natl Acad Sci U S A. Aug. 1980;77(8):4539-43.
Glennie Mj, et al. "Preparation and performance of bispecific F(ab' gamma)2 antibody containing thioether-linked Fab' gamma fragments," J Immunol. Oct. 1, 1987;139(7):2367-75.
Gluzman Y, et al. "SV40 early mutants that are defective for viral DNA synthesis but competent for transformation of cultured rat and simian cells," Virology. Nov. 1982;123(1):78-92.
Goeddel Dv. "Systems for heterologous gene expression," Methods Enzymol. 1990;185:3-7.
Gorczynski Rm, et al. "Checkpoint blockade in solid tumors and B-cell malignancies, with special consideration of the role of CD200," Cancer Manag Res. Nov. 13, 2017;9:601-609.
Grabie N, et al. "Endothelial programmed death-1 ligand 1 (PD-L1) regulates CD8+ T-cell mediated injury in the heart," Circulation. Oct. 30, 2007;116(18):2062-71.
Graziano Rf, et al. "Construction and characterization of a humanized anti-gamma-Ig receptor type I (Fc gamma RI) monoclonal antibody," J Immunol. Nov. 15, 1995;155(10):4996-5002.
Green Ka, et al. "Antibody to the ligand for CD40 (gp39) inhibits murine AIDS-associated splenomegaly, hypergammaglobulinemia, and immunodeficiency in disease-susceptible C57BL/6 mice," J Virol. Apr. 1996;70(4):2569-75.
Green Ka, et al. "Myeloid-derived suppressor cells in murine retrovirus-induced AIDS inhibit T- and B-cell responses in vitro that are used to define the immunodeficiency," J Virol. Feb. 2013;87(4):2058-71.
Greenwald Rj, et al. " The B7 family revisited," Annu Rev Immunol. 2005;23:515-48.
Groux H, et al. "A CD4+ T-cell subset inhibits antigen-specific T-cell responses and prevents colitis," Nature. Oct. 16, 1997;389(6652):737-42.
Gruber M, et al. "Efficient tumor cell lysis mediated by a bispecific single chain antibody expressed in *Escherichia coli*," J Immunol. Jun. 1, 1994;152(11):5368-74.
Guatelli Jc, et al. "Isothermal, in vitro amplification of nucleic acids by a multienzyme reaction modeled after retroviral replication," Proc Natl Acad Sci U S A. Mar. 1990;87(5):1874-8.
Guindon S, et al. "A simple, fast, and accurate algorithm to estimate large phylogenies by maximum likelihood," Syst Biol. Oct. 2003;52(5):696-704.
Guleria I, et al. "A critical role for the programmed death ligand 1 in fetomaternal tolerance," J Exp Med. Jul. 18, 2005;202(2):231-7.
Gurley Wb, et al. "Upstream sequences required for efficient expression of a soybean heat shock gene," Mol Cell Biol. Feb. 1986;6(2):559-65.
Hamilton Aj, et al. "A species of small antisense RNA in post-transcriptional gene silencing in plants," Science. Oct. 29, 1999;286(5441):950-2.
Hann M "On the Double Bond Isostere of the Peptide Bond: Preparation of an Enkephalin Analogue," Journal of the Chemical Society, Perkin Transactions 1982 (1), 307-14.
Hara M, et al. "IL-10 is required for regulatory T cells to mediate tolerance to alloantigens in vivo," J Immunol. Mar. 15, 2001;166(6):3789-96.
Harding Fa, et al. "Class switching in human immunoglobulin transgenic mice," nn N Y Acad Sci. Sep. 29, 1995;764:536-46.
Haseloff J, et al. "Simple RNA enzymes with new and highly specific endoribonuclease activities," Nature. Aug. 18, 1988;334(6183):585-91.
Hashida H, et al. "Fusion of HIV-1 Tat protein transduction domain to poly-lysine as a new DNA delivery tool," Br J Cancer. Mar. 22, 2004;90(6):1252-8.
Haskins K, et al. "The major histocompatibility complex-restricted antigen receptor on T cells. I. Isolation with a monoclonal antibody," The Journal of Experimental Medicine 1983;157(4):1149-69.
Hauser N, et al. "Interaction of cartilage matrix protein with aggrecan. Increased covalent cross-linking with tissue maturation," J Biol Chem. Dec. 13, 1996;271(50):32247-52.
Hauser N, et al. "Native cartilage matrix protein (CMP). A compact trimer of subunits assembled via a coiled-coil alpha-helix," J Biol Chem. Oct. 14, 1994;269(41):25747-53.
Haynes Jr, et al. "Particle-mediated nucleic acid immunization," J Biotechnol. Jan. 26, 1996;44(1-3):37-42.
Hedbom E, et al. "Cartilage matrix proteins. An acidic oligomeric protein (COMP) detected only in cartilage," J Biol Chem. Mar. 25, 1992;267(9):6132-6.
Helene C, et al. "Control of gene expression by triple helix-forming oligonucleotides. The antigene strategy," Ann N Y Acad Sci. Oct. 28, 1992;660:27-36.
Hellstrom I, et al. "CD3-mediated activation of tumor-reactive lymphocytes from patients with advanced cancer," Proc Natl Acad Sci U S A. Jun. 5, 2001;98(12):6783-8.
Hinton Pr, et al. "Engineered human IgG antibodies with longer serum half-lives in primates," J Biol Chem. Feb. 20, 2004;279(8):6213-6.
Hirano, F., et al., Blockade of B7-H1 and PD-1 by monoclonal antibodies potentiates cancer therapeutic immunity Cancer Res, 2005. 65(3): p. 1089-96.
Ho Sn, et al. "Site-directed mutagenesis by overlap extension using the polymerase chain reaction," Gene. Apr. 15, 1989;77(1):51-9.
Ho Vt, et al. "The history and future of T-cell depletion as graft-versus-host disease prophylaxis for allogeneic hematopoietic stem cell transplantation," Blood. Dec. 1, 2001;98(12):3192-204.
Hodi, F. S., Overcoming immunological tolerance to melanoma: Targeting CTLA-4. Asia Pac J Clin Oncol, 2010. 6 Suppl 1: p. S16-23.
Hogg N. "The structure and function of Fc receptors," Immunol Today. Jul.-Aug. 1998;9(7-8):185-7.
Holladay, M. W., et al. (1983). "Synthesis of hydroxyethylene and ketomethylene dipeptide isosteres," Tetrahedron Letters 1983 24(41), 4401-4404.
Hollenbaugh D, et al. "Cleavable CD40lg fusion proteins and the binding to sgp39," J Immunol Methods. Dec. 15, 1995;188(1):1-7.
Holliger P, et al. ""Diabodies": small bivalent and bispecific antibody fragments," Proc Natl Acad Sci U S A. Jul. 15, 1993;90(14):6444-8.
Holm L, et al. "DaliLite workbench for protein structure comparison," Bioinformatics. Jun. 2000;16(6):566-7.
Hoos, a., et al., "Development of ipilimumab: contribution to a new paradigm for cancer immunotherapy," Semin Oncol, 2010. 37(5): p. 533-46.
Hopp Tp, et al. "Prediction of protein antigenic determinants from amino acid sequences," Proc Natl Acad Sci U S A. Jun. 1981;78(6):3824-8.

(56) References Cited

OTHER PUBLICATIONS

Horn Jr, et al. "The role of protein dynamics in increasing binding affinity for an engineered protein-protein interaction established by H/D exchange mass spectrometry," Biochemistry Jul. 18, 2006;45(28):8488-98.
Hotchkiss Rs, et al. "Immunosuppression in sepsis: a novel understanding of the disorder and a new therapeutic approach," Lancet Infect Dis. Mar. 2013;13(3):260-8.
Houghten Ra, et al. "The use of synthetic peptide combinatorial libraries for the identification of bioactive peptides," Bioorganic & Medicianl Chemistry Letters, vol. 3, No. 3, 1993. pp. 405-412.
Hruby Vj, et al. "Conformational and topographical considerations in the design of biologically active peptides," Biopolymers. Jul. 1993;33(7):1073-82.
Hruby Vj, et al. "Synthesis of oligopeptide and peptidomimetic libraries," Curr Opin Chem Biol. Jun. 1997;1(1):114-9.
Hruby Vj. "Conformational restrictions of biologically active peptides via amino acid side chain groups," Life Sci. Jul. 19, 1982;31(3):189-99.
Huarte, E., et al., "Depletion of dendritic cells delays ovarian cancer progression by boosting antitumor immunity," Cancer Res, 2008. 68(18): p. 7684-91.
Hudson D, et al. "Methionine enkephalin and isosteric analogues. I. Synthesis on a phenolic resin support," Int J Pept Protein Res. 1979;14(3):177-85.
Huston Js, et al. "Protein engineering of antibody binding sites: recovery of specific activity in an anti-digoxin single-chain Fv analogue produced in *Escherichia coli*," Proc Natl Acad Sci U S A. Aug. 1988;85(16):5879-83.
Hutloff a, et al. "ICOS is an inducible T-cell co-stimulator structurally and functionally related to CD28," Nature. Jan. 21, 1999;397(6716):263-6.
Hyrup B, e al. "Peptide nucleic acids (PNA): synthesis, properties and potential applications," Bioorg Med Chem. Jan. 1996;4(1):5-23.
Ike Y, et al. "Solid phase synthesis of polynucleotides. VIII. Synthesis of mixed oligodeoxyribonucleotides by the phosphotriester solid phase method," Nucleic Acids Res Jan. 25, 1983;11(2):477-88.
Iliopoulos D, et al. "The negative costimulatory molecule PD-1 modulates the balance between immunity and tolerance via miR-21," Eur J Immunol. Jun. 2011;41(6):1754-63.
Inoue H, et al. "Sequence-dependent hydrolysis of RNA using modified oligonucleotide splints and RNase H," Febs Lett. May 11, 1987;215(2):327-30.
Inoue H, et al. "Synthesis and hybridization studies on two complementary nona(2'-O-methyl)ribonucleotides," Nucleic Acids Res. Aug. 11, 1987;15(15):6131-48.
Invitrogen (2002) "Guide to Baculovirus Expression Vector Systems (BEVs) and Insect Culture Techniques" Instruction Manual. 30 pages.
Itakura K, et al. "Expression in *Escherichia coli* of a chemically synthesized gene for the hormone somatostatin," Science. Dec. 9, 1977;198(4321):1056-63.
Itakura K, et al. "Synthesis and use of synthetic oligonucleotides," Annu Rev Biochem. 1984;53:323-56.
Iwai, Y., et al., "Involvement of PD-L1 on tumor cells in the escape from host immune system and tumor immunotherapy by PD-L1 blockade," Proc Natl Acad Sci USA, 2002. 99(19): p. 12293-7.
Janssen Clinical Trials "A Study of Safety, Pharmacokinetics, Pharmacodynamics of JNJ-61610588 in Participants With Advanced Cancer," U.S. National Library of Medicine, ClinicalTrials.gov; (https://clinicaltrials.gov) 2017. 9 pages.
Jarvinen Lz, et al. "CD154 on the surface of CD4+CD25+ regulatory T cells contributes to skin transplant tolerance," Transplantation. Nov. 15, 2003;76(9):1375-9.
Jeisy-Scott V, et al. "Increased MDSC accumulation and Th2 biased response to influenza a virus infection in the absence of TLR7 in mice," PLoS One. 2011;6(9):e25242.
Jennings-White, C. et al. (1982). "Synthesis of ketomethylene analogs of dipeptides," Tetrahedron Letters 1982 23(25), 2533-2534.
Jones E, et al. "Depletion of CD25+ regulatory cells results in suppression of melanoma growth and induction of autoreactivity in mice," Cancer Immun. Feb. 22, 2002;2:1.
Jones Pt, et al. "Replacing the complementarity-determining regions in a human antibody with those from a mouse," Nature. May 29-Jun. 4, 1986;321(6069):522-5.
Jones Td, et al. "The development of a modified human IFN-alpha2b linked to the Fc portion of human IgG1 as a novel potential therapeutic for the treatment of hepatitis C virus infection," J Interferon Cytokine Res. Sep. 2004;24(9):560-72.
Kaehler, K. C., et al., "Update on immunologic therapy with anti-CTLA-4 antibodies in melanoma: identification of clinical and biological response patterns, immune-related adverse events, and their management," Semin Oncol, 2010. 37(5): p. 485-98.
Kang Sm, et al. "Transactivation by AP-1 is a molecular target of T cell clonal anergy," Science. Aug. 21, 1992;257(5073):1134-8.
Karpovsky B, et al. "Production of target-specific effector cells using hetero-cross-linked aggregates containing anti-target cell and anti-Fc gamma receptor antibodies," J Exp Med. Dec. 1, 1984;160(6):1686-701.
Kashmiri Sv, et al. "SDR grafting—a new approach to antibody humanization," Methods. May 2005;36(1):25-34.
Kaufman Rj, et al. "Translational efficiency of polycistronic mRNAs and their utilization to express heterologous genes in mammalian cells," EMBO J. Jan. 1987;6(1):187-93.
Kay Ma, et al. "Transient immunomodulation with anti-CD40 ligand antibody and CTLA4lg enhances persistence and secondary adenovirus-mediated gene transfer into mouse liver," Proc Natl Acad Sci U S A. Apr. 29, 1997;94(9):4686-91.
Keinänen K, et al. "Biosynthetic lipid-tagging of antibodies," FEBS Lett. Jun. 6, 1994;346(1):123-6.
Keir Me, et al. "PD-1 and its ligands in tolerance and immunity," Annu Rev Immunol. 2008;26:677-704.
Keir Me, et al. "PD-1 regulates self-reactive CD8+ T cell responses to antigen in lymph nodes and tissues," mmunol. Oct. 15, 2007;179(8):5064-70.
Kessel M, et al. "Murine developmental control genes," Science. Jul. 27, 1990;249(4967):374-9.
Killion Jj, et al. "Systemic targeting of liposome-encapsulated immunomodulators to macrophages for treatment of cancer metastasis," Immunomethods. Jun. 1994;4(3):273-9.
Kimmel Ar, et al. "Preparation of cDNA and the generation of cDNA libraries: overview," Methods Enzymol. 1987;152:307-16.
Kipriyanov Sm, et al. "Recombinant single-chain Fv fragments carrying C-terminal cysteine residues: production of bivalent and biotinylated miniantibodies," Mol Immunol. Oct. 1994;31(14):1047-58.
Kipriyanov Sm, et al. "Single-chain antibody streptavidin fusions: tetrameric bifunctional scFv-complexes with biotin binding activity and enhanced affinity to antigen," Hum Antibodies Hybridomas. 1995;6(3):93-101.
Kiss I, et al. "Structure of the gene for cartilage matrix protein, a modular protein of the extracellular matrix. Exon/intron organization, unusual splice sites, and relation to alpha chains of beta 2 integrins, von Willebrand factor, complement factors B and C2, and epidermal growth factor," J Biol Chem. May 15, 1989;264(14):8126-34.
Klinken Sp, et al. "Evolution of B cell lineage lymphomas in mice with a retrovirus-induced immunodeficiency syndrome, MAIDS," J Immunol. Feb. 15, 1988;140(4):1123-31.
Kohl S, et al. "Human antibody-dependent cellular cytotoxicity and natural killer cytotoxicity to herpes simplex virus-infected autologous and allogeneic cells," Immunology. Jan. 1983;48(1):187-93.
Köhler G, et al. "Continuous cultures of fused cells secreting antibody of predefined specificity," Nature. Aug. 7, 1975;256(5517):495-7.
Kolaskar As, et al. "A semi-empirical method for prediction of antigenic determinants on protein antigens," FEBS Lett. Dec. 10, 1990;276(1-2):172-4.
Kostelny Sa, et al. "Formation of a bispecific antibody by the use of leucine zippers," J Immunol. Mar. 1, 1992;148(5):1547-53.

(56) References Cited

OTHER PUBLICATIONS

Kozbor D, et al. "Specific immunoglobulin production and enhanced tumorigenicity following ascites growth of human hybridomas," J Immunol Methods. Jul. 16, 1985;81(1):31-42.
Kozbor D, et al. "The production of monoclonal antibodies from human lymphocytes," Immunol Today. Mar. 1983;4(3):72-9.
Krishnamurthy S, et al. "Molecular and biologic markers of premalignant lesions of human breast," Adv Anat Pathol. May 2002;9(3):185-97.
Krolick Ka, et al. "Selective killing of normal or neoplastic B cells by antibodies coupled to the a chain of ricin," Proc Natl Acad Sci U S A. Sep. 1980;77(9):5419-23.
Kroll Dj, et al. "A multifunctional prokaryotic protein expression system: overproduction, affinity purification, and selective detection," DNA Cell Biol. Jun. 1993;12(5):441-53.
Krutzik, S. R., et al., "TLR activation triggers the rapid differentiation of monocytes into macrophages and dendritic cells," Nat Med, 2005. 11(6): p. 653-60.
Kryczek, I., et al., "B7-H4 expression identifies a novel suppressive macrophage population in human ovarian carcinoma," J Exp Med, 2006. 203(4): p. 871-81.
Kryczek, I., et al., "Cutting edge: induction of B7-H4 on APCs through IL-10: novel suppressive mode for regulatory T cells," J Immunol, 2006. 177(1): p. 40-4.
Kurjan J, et al. "Structure of a yeast pheromone gene (MF alpha): a putative alpha-factor precursor contains four tandem copies of mature alpha-factor," Cell. Oct. 1982;30(3):933-43.
Kuroiwa Y, et al. "Cloned transchromosomic calves producing human immunoglobulin," Nat Biotechnol. Sep. 2002;20(9):889-94.
Kwoh Dy, et al. "Transcription-based amplification system and detection of amplified human immunodeficiency virus type 1 with a bead-based sandwich hybridization format," Proc Natl Acad Sci U S A. Feb. 1989;86(4):1173-7.
Labrijn Af, et al. "Efficient generation of stable bispecific IgG1 by controlled Fab-arm exchange," Proc Natl Acad Sci U S A. Mar. 26, 2013;110(13):5145-50.
LaFace D, et al. "Meeting report: regulatory myeloid cells," Int Immunopharmacol. Jul. 2011;11(7):780-2.
Lakso M, et al. "Targeted oncogene activation by site-specific recombination in transgenic mice," Proc Natl Acad Sci U S A. Jul. 15, 1992;89(14):6232-6.
Lam Ks, et al. "A new type of synthetic peptide library for identifying ligand-binding activity," Nature. Nov. 7, 1991;354(6348):82-4.
Lam Ks. "Application of combinatorial library methods in cancer research and drug discovery," Anticancer Drug Des. Apr. 1997;12(3):145-67. [Abstract Only].
Landegren U, et al. "A ligase-mediated gene detection technique," Science. Aug. 26, 1988;241(4869):1077-80.
Landt O, et al. "A general method for rapid site-directed mutagenesis using the polymerase chain reaction," Gene. Nov. 30, 1990;96(1):125-8.
Latchman Y, et al. "PD-L2 is a second ligand for PD-1 and inhibits T cell activation," Nat Immunol. Mar. 2001;2(3):261-8.
Latchman Ye, et al. "PD-L1-deficient mice show that PD-L1 on T cells, antigen-presenting cells, and host tissues negatively regulates T cells," Proc Natl Acad Sci U S A. Jul. 20, 2004;101(29):10691-6.
Lathe R. "Synthetic oligonucleotide probes deduced from amino acid sequence data. Theoretical and practical considerations," J Mol Biol. May 5, 1985;183(1):1-12.
Laubach Ve, et al. "Mice lacking inducible nitric oxide synthase are not resistant to lipopolysaccharide-induced death," Proc Natl Acad Sci U S A. Nov. 7, 1995;92(23):10688-92.
Lázár-Molnár E, et al. "Crystal structure of the complex between programmed death-1 (PD-1) and its ligand PD-L2," Proc Natl Acad Sci U S A. Jul. 29, 2008;105(30):10483-8.
Le Borgne, M., et al., "Dendritic cells rapidly recruited into epithelial tissues via CCR6/CCL20 are responsible for CD8+ T cell crosspriming in vivo," Immunity, 2006. 24(2): p. 191-201.
Le Mercier I, et al. "Beyond CTLA-4 and PD-1, the Generation Z of Negative Checkpoint Regulators," Front Immunol. Aug. 21, 2015;6:418.
Le Mercier I, et al. "VISTA Regulates the Development of Protective Antitumor Immunity," Cancer Res. Apr. 1, 2014;74(7):1933-44.
Lederman, Seth, et al. "A single amino acid substitution in a common African allele of the CD4 molecule ablates binding of the monoclonal antibody, OKT4." Molecular immunology 28.11 (1991): 1171-1181.
Lee et al., "Increased vaccine-specific T cell frequency after peptide-based vaccination correlates with increased susceptibility to in vitro stimulation but does not lead to tumor regression." The Journal of Immunology 163.11 (1999): 6292-6300.
Lemaitre M, et al. " Specific antiviral activity of a poly(L-lysine)-conjugated oligodeoxyribonucleotide sequence complementary to vesicular stomatitis virus N protein mRNA initiation site," Proc Natl Acad Sci U S A. Feb. 1987;84(3):648-52.
Leng et al., "Potential roles of IL-9 in the pathogenesis of systemic lupus erythematosus", American Journal of Clinical and Experimental Immunology 2012;1(1):28-32.
Leon B, et al. "Monocyte-derived dendritic cells formed at the infection site control the induction of protective T helper 1 responses against Leishmania," Immunity. Apr. 2007;26(4):519-31.
León B, et al. "Monocyte-derived dendritic cells in innate and adaptive immunity," Immunol Cell Biol. May-Jun. 2008;86(4):320-4.
Lerner Ea. "How to make a hybridoma," Yale J Biol Med. Sep.-Oct. 1981;54(5):387-402.
Letsinger Rl, et al. "Cholesteryl-conjugated oligonucleotides: synthesis, properties, and activity as inhibitors of replication of human immunodeficiency virus in cell culture," Proc Natl Acad Sci U S A. Sep. 1989;86(17):6553-6.
Li Ch, et al. "beta-Endorphin omission analogs: dissociation of immunoreactivity from other biological activities," Proc Natl Acad Sci U S A. Jun. 1980;77(6):3211-4.
Li F, et al. "Inhibitory Fcγ receptor is required for the maintenance of tolerance through distinct mechanisms," J Immunol. Apr. 1, 2014;192(7):3021-8.
Li W, et al. "Immunotherapy of murine retrovirus-induced acquired immunodeficiency by CD4 T regulatory cell depletion and PD-1 blockade," J Virol. Dec. 2011;85(24):13342-53.
Li W, et al. "The role of CD4 T cells in the pathogenesis of murine AIDS," J Virol. Jun. 2006;80(12):5777-89.
Lin Dy, et al. "The PD-1/PD-L1 complex resembles the antigen-binding Fv domains of antibodies and T cell receptors," Proc Natl Acad Sci U S A. Feb. 26, 2008;105(8):3011-6.
Lines Jl, et al. "VISTA is a novel broad-spectrum negative checkpoint regulator for cancer immunotherapy," Cancer Immunol Res. Jun. 2014;2(6):510-7.
Lines Jl, et al. "VISTA is an immune checkpoint molecule for human T cells," Cancer Res. Apr. 1, 2014;74(7):1924-32.
Liu Ay, et al. "Chimeric mouse-human IgG1 antibody that can mediate lysis of cancer cells," Proc Natl Acad Sci U S A. May 1987;84(10):3439-43.
Liu J, et al. "Immune-checkpoint proteins VISTA and PD-1 nonredundantly regulate murine T-cell responses," Proc Natl Acad Sci U S A. May 26, 2015;112(21):6682-7.
Liu Ma, et al. "Heteroantibody duplexes target cells for lysis by cytotoxic T lymphocytes," Proc Natl Acad Sci U S A. Dec. 1985;82(24):8648-52.
Lobley a, et al. "pGenTHREADER and pDomTHREADER: new methods for improved protein fold recognition and superfamily discrimination," Bioinformatics. Jul. 15, 2009;25(14):1761-7.
Lonberg N, et al. "Antigen-specific human antibodies from mice comprising four distinct genetic modifications," Nature. Apr. 28, 1994;368(6474):856-9.
Lonberg N, et al. "Human antibodies from transgenic mice," Int Rev Immunol. 1995;13(1):65-93.
Lopez-Pedrera et al., "Accelerated atherosclerosis in systemic lupus erythematosus: role of proinflammatory cytokines and therapeutic approaches", Journal of Biomedicine & Biotechnology, 2010 Article ID 607084.

(56) References Cited

OTHER PUBLICATIONS

Lorain S, et al. "Transient immunomodulation allows repeated injections of AAV1 and correction of muscular dystrophy in multiple muscles," Mol Ther. Mar. 2008;16(3):541-7.
Luckow Va, et al. "High level expression of nonfused foreign genes with Autographa californica nuclear polyhedrosis virus expression vectors," Virology. May 1989;170(1):31-9.
Lutz Mb, et al. "An advanced culture method for generating large quantities of highly pure dendritic cells from mouse bone marrow," J Immunol Methods. Feb. 1, 1999;223(1):77-92.
Macatangay Bj, et al. "MDSC: a new player in HIV immunopathogenesis," AIDS. Jul. 31, 2012;26(12):1567-9.
Maher U. "DNA triple-helix formation: an approach to artificial gene repressors?" Bioessays. Dec. 1992;14(12):807-15.
Mahnke K, et al. "The dendritic cell receptor for endocytosis, DEC-205, can recycle and enhance antigen presentation via major histocompatibility complex class II-positive lysosomal compartments," J Cell Biol. Oct. 30, 2000;151(3):673-84.
Malashkevich Vn, et al. "The crystal structure of a five-stranded coiled coil in COMP: a prototype ion channel?" Science. Nov. 1, 1996;274(5288):761-5.
Marigo, I., et al. "Tumor-induced tolerance and immune suppression by myeloid derived suppressor cells," Immunol Rev, 2008. 222: p. 162-79.
Martinez T, et al. "Disulfide connectivity of human immunoglobulin G2 structural isoforms," Biochemistry. Jul. 15, 2008;47(28):7496-508.
McCafferty J, et al. "Phage antibodies: filamentous phage displaying antibody variable domains," Nature. Dec. 6, 1990;348(6301):552-4.
McConnell Hm, et al. "The cytosensor microphysiometer: biological applications of silicon technology," Science. Sep. 25, 1992;257(5078):1906-12.
McHugh Rs, et al. "CD4(+)CD25(+) immunoregulatory T cells: gene expression analysis reveals a functional role for the glucocorticoid-induced TNF receptor," Immunity. Feb. 2002;16(2):311-23.
Mclvor Rs, et al. "Isolation and characterization of a variant dihydrofolate reductase cDNA from methotrexate-resistant murine L5178Y cells," Nucleic Acids Res. Dec. 11, 1990;18(23):7025-32.
Medina D. "The preneoplastic phenotype in murine mammary tumorigenesis," J Mammary Gland Biol Neoplasia. Oct. 2000;5(4):393-407.
Melief Cj. "Cancer immunotherapy by dendritic cells," Immunity. Sep. 19, 2008;29(3):372-83.
Mencacci A, et al. "CD80+Gr-1+ myeloid cells inhibit development of antifungal Th1 immunity in mice with candidiasis," J Immunol. Sep. 15, 2002;169(6):3180-90.
Merrifield B. "Concept and early development of solid-phase peptide synthesis," Methods Enzymol. 1997;289:3-13.
Mezo Ar, et al. "Atrial natriuretic peptide-Fc, ANP-Fc, fusion proteins: semisynthesis, in vitro activity and pharmacokinetics in rats," Bioconjug Chem. Mar. 21, 2012;23(3):518-26.
Milstein C, et al. "Hybrid hybridomas and their use in immunohistochemistry," Nature. Oct. 6-12, 1983;305(5934):537-40.
Mingozzi F, et al. "Immune responses to AAV vectors: overcoming barriers to successful gene therapy," Blood. Jul. 4, 2013;122(1):23-36.
Monteiro Rc, et al. "Molecular heterogeneity of Fc alpha receptors detected by receptor-specific monoclonal antibodies," J Immunol. Mar. 15, 1992;148(6):1764-70.
Moore Gj. "Designing peptide mimetics," Trends Pharmacol Sci. Apr. 1994;15(4):124-9.
Morrison Sl, et al. "Chimeric human antibody molecules: mouse antigen-binding domains with human constant region domains," Proc Natl Acad Sci U S A. Nov. 1984;81(21):6851-5.
Morrison Sl. "Transfectomas provide novel chimeric antibodies," Science. Sep. 20, 1985;229(4719):1202-7.
Muller Py, et al. "Safety assessment and dose selection for first-in-human clinical trials with immunomodulatory monoclonal antibodies," Clin Pharmacol Ther. Mar. 2009;85(3):247-58.
Nakano H, et al. "Blood-derived inflammatory dendritic cells in lymph nodes stimulate acute T helper type 1 immune responses," Nat Immunol. Apr. 2009;10(4):394-402.
Nalbandian A, et al. "Interleukin-17 and systemic lupus erythematosus: current concepts," Clin Exp Immunol. Aug. 2009;157(2):209-15.
Nathwani Ac, et al. "Adenovirus-associated virus vector-mediated gene transfer in hemophilia B," N Engl J Med. Dec. 22, 2011;365(25):2357-65.
NCBI Accession No. AAH89443 [gi:59807841] with Revision History--Feb. 16, 2005-Jun. 6, 2006.
NCBI Accession No. AK004116 [gi:12835174] with Revision History--Feb. 8, 2001-Sep. 2, 2005.
NCBI Accession No. BC089443 [gi:59807840] with Revision History--Feb. 15, 2005-Jun. 6, 2006.
NCBI Accession No. NM.sub.--022153 [gi:62339431] with Revision History--Apr. 7, 2005-Jun. 26, 2007.
NCBI Accession No. NM.sub.--026125 [gi:13385631] with Revision History--Mar. 20, 2001-May 7, 2006. 142365660 which replaced 13385631 is provided.
NCBI Accession No. NM.sub.--028732 [gi:31980769] with Revision History--Mar. 20, 2001-May 7, 2006. 143249860 which replaced 31980769 is provided.
NCBI Accession No. NM.sub.--138530 [gi:51491892] with Revision History--Apr. 4, 2002-Nov. 18, 2006.
NCBI Accession No. NP.sub.--071436 [gi:62339432] with Revision History--Apr. 7, 2005-Aug. 13, 2006.
NCBI Accession No. NP.sub.--080401 [gi:13385632] with Revision History--Mar. 20, 2001-May 7, 2006.
NCBI Accession No. XM.sub.--233720 [gi:109475938] with Revision History--Jan. 13, 2003- Jun. 22, 2006.
Nesbeth Yc, et al. "CD4+ T cells elicit host immune responses to MHC class II-negative ovarian cancer through CCL5 secretion and CD40-mediated licensing of dendritic cells," J. Immunol. May 15, 2010;184(10):5654-62.
Neuberger Ms, et al. "A hapten-specific chimaeric IgE antibody with human physiological effector function," Nature. Mar. 21-27, 1985;314(6008):268-70.
Neuberger Ms, et al. "Recombinant antibodies possessing novel effector functions," Nature. Dec. 13-19, 1984;312(5995):604-8.
Nielsen Mb, et al. "Melanoma vaccines: the paradox of T cell activation without clinical response," Cancer Chemother Pharmacol. 2000;46 Suppl:S62-6.
Niklinski J, et al. "Molecular genetic abnormalities in premalignant lung lesions: biological and clinical implications," Eur J Cancer Prey. Jun. 2001;10(3):213-26.
Nishikawa H, et al. "Regulatory T cells in tumor immunity," Int J Cancer. Aug. 15, 2010;127(4):759-67.
Nishimura H, et al. "Autoimmune dilated cardiomyopathy in PD-1 receptor-deficient mice," Science. Jan. 12, 2001;291(5502):319-22.
Nishimura H, et al. "Development of lupus-like autoimmune diseases by disruption of the PD-1 gene encoding an ITIM motif-carrying immunoreceptor," Immunity. Aug. 1999;11(2):141-51.
Nomi, T. et al., Clinical significance and therapeutic potential of the programmed death-1 ligand/programmed death-1 pathway in human pancreatic cancer. Clin. Cancer Res. 2007, vol. 13, pp. 2152-2157.
Norde, W.J. et al., "Coinhibitory molecules in hematologic malignancies: targets for therapeutic intervention", Blood, Jul. 2012, vol. 120, No. 4, pp. 728-736.
Nowak Ec, et al. "Immunoregulatory functions of VISTA," Immunol Rev. Mar. 2017;276(1):66-79.
Nygren H. "Conjugation of horseradish peroxidase to Fab fragments with different homobifunctional and heterobifunctional cross-linking reagents. A comparative study," J Histochem Cytochem. May 1982;30(5):407-12.
O'Gorman S, et al. "Recombinase-mediated gene activation and site-specific integration in mammalian cells," Science. Mar. 15, 1991;251(4999):1351-5.

(56) References Cited

OTHER PUBLICATIONS

Ohtsuka E, et al. "An alternative approach to deoxyoligonucleotides as hybridization probes by insertion of deoxyinosine at ambiguous codon positions," J Biol Chem. Mar. 10, 1985;260(5):2605-8.
Okazaki T, et al. "The PD-1-PD-L pathway in immunological tolerance," Trends Immunol. Apr. 2006;27(4):195-201.
Orlandi R, et al. "Cloning immunoglobulin variable domains for expression by the polymerase chain reaction," Proc Natl Acad Sci U S A. May 1989;86(10):3833-7.
Ortler S, et al. "B7-H1 restricts neuroantigen-specific T cell responses and confines inflammatory CNS damage: implications for the lesion pathogenesis of multiple sclerosis," Eur J Immunol. Jun. 2008;38(6):1734-44.
Ostergaard S, et al. "Peptomers: a versatile approach for the preparation of diverse combinatorial peptidomimetic bead libraries," Mol Divers. 1997;3(1):17-27.
Ostrand-Rosenberg S, et al. "Myeloid-derived suppressor cells: linking inflammation and cancer," J Immunol. Apr. 15, 2009;182(8):4499-506.
Ostrand-Rosenberg S. "Myeloid-derived suppressor cells: more mechanisms for inhibiting antitumor immunity," Cancer Immunol Immunother. Oct. 2010;59(10):1593-600.
Ostresh Jm, et al. "Generation and use of nonsupport-bound peptide and peptidomimetic combinatorial libraries," Methods Enzymol. 1996;267:220-34.
Ottavi a, et al. "An improved method to obtain a single recombinant vasoactive intestinal peptide (VIP) analog," Biochimie. Apr. 1998;80(4):289-93.
Owais M, et al. "Chloroquine encapsulated in malaria-infected erythrocyte-specific antibody-bearing liposomes effectively controls chloroquine-resistant Plasmodium berghei infections in mice," Antimicrob Agents Chemother. Jan. 1995;39(1):180-4.
Oyarzun P, et al. "A bioinformatics tool for epitope-based vaccine design that accounts for human ethnic diversity: Application to emerging infectious diseases," Vaccine. 2015;33(10):1267-73.
Ozkaynak, E., et al. "Programmed death-1 targeting can promote al lograft survival," J Immunol 2002. 169: 6546-6553.
Pain D, et al. "Preparation of protein A-peroxidase monoconjugate using a heterobifunctional reagent, and its use in enzyme immunoassays," J Immunol Methods. 1981;40(2):219-30.
Parisi, S., et al. "A regulatory loop involving Diesl and miR-125a controls BMP4 signaling in mouse embryonic stem cells," FASEB J 2012. 26: 3957-3968.
Paulsson M, et al. "Purification and structural characterization of a cartilage matrix protein," Biochem J. Aug. 1, 1981;197(2):367-75.
Payne G. "Progress in immunoconjugate cancer therapeutics," Cancer Cell. Mar. 2003;3(3):207-12.2003.
Peranzoni E, et al. "Myeloid-derived suppressor cell heterogeneity and subset definition," Curr Opin Immunol. Apr. 2010;22(2):238-44.
Perry-O'Keefe H, et al. "Peptide nucleic acid pre-gel hybridization: an alternative to southern hybridization," Proc Natl Acad Sci U S A. Dec. 10, 1996;93(25):14670-5.
Piccirillo Ca, et al. "Naturally-occurring CD4+CD25+ immunoregulatory T cells: central players in the arena of peripheral tolerance," Semin Immunol. Apr. 2004;16(2):81-8.
Piccotti Jr, et al. "T-cell-dependent antibody response: assay development in cynomolgus monkeys," J Immunotoxicol. Oct. 1, 2005;2(4):191-6.
Picha, Kristen M. et al., "Protein Engineering Strategies for Sustained Glucagon-Like Peptide-1 Receptor-Dependent Control of Glucose Homeostasis", Diabetes, 2008. vol. 57, pp. 1926-1934.
Pilat N, et al. "Costimulatory pathways in transplantation," Semin Immunol. Aug. 2011;23(4):293-303.
Pinkert Ca, et al. "An albumin enhancer located 10 kb upstream functions along with its promoter to direct efficient, liver-specific expression in transgenic mice," Genes Dev. May 1987;1(3):268-76.
Platt et al., "Gene hunting in the genomic era: approaches to diagnostic dilemmas in patients with primary immunodeficiencies," J Allergy Clin Immunol 2014, 134: 262-268.
Podojil Jr, et al. "B7-H4Ig inhibits mouse and human T-cell function and treats Eae via IL-10/Treg-dependent mechanisms," J Autoimmun. Aug. 2013;44:71-81.
Polyak Sw, et al. "Introduction of spacer peptides N-terminal to a cleavage recognition motif in recombinant fusion proteins can improve site-specific cleavage," Protein Eng. Jun. 1997;10(6):615-9.
Pontén J. "Cell biology of precancer," Eur J Cancer. Oct. 2001;37 Suppl 8:S97-113.
Powell et al. "Peptide stability in drug development. II. Effect of single amino acid substitution and glycosylation on peptide reactivity in human serum," Pharm Res. Sep. 1993;10(9):1268-73.
Prasad, D. V., et al. "B7S1, a novel B7 family member that negatively regulates T cell activation," Immunity, 2003. 18(6): p. 863-73.
Prokunina, L., A regulatory polymorphism in PDCD1 is associated with susceptibility to systemic lupus erythematosus in humans. Nat Genet 2002. 32: 666-669.
Qin A, et al. "Expansion of monocytic myeloid-derived suppressor cells dampens T cell function in HIV-1-seropositive individuals," J Virol. Feb. 2013;87(3):1477-90.
Qin W, et al. "Fusion protein of CDR mimetic peptide with Fc inhibit TNF-alpha induced cytotoxicity," Mol Immunol. Feb. 2006;43(6):660-6.
Qu, C., et al., Role of CCR8 and other chemokine pathways in the migration of monocyte-derived dendritic cells to lymph nodes. J Exp Med, 2004. 200(10): p. 1231-41.
Queen C, et al. "Immunoglobulin gene transcription is activated by downstream sequence elements," Cell. Jul. 1983;33(3):741-8.
Queen, et al. "A humanized antibody that binds to the interleukin 2 receptor," Proc Natl Acad Sci U S A. Dec. 1989;86(24):10029-33.
Rabinovich, G. A., D. Gabrilovich, and E. M. Sotomayor, Immunosuppressive strategies that are mediated by tumor cells. Annu Rev Immunol, 2007. 25: p. 267-96.
Rai Bk, et al. "MMM: a sequence-to-structure alignment protocol," Bioinformatics. Nov. 1, 2006;22(21):2691-2.
Rain J.C. et al. (2001) The protein-protein interaction map of Helicobacter pylori. Nature 409: 211-15.
Ranade Vv. "Drug delivery systems. 1. site-specific drug delivery using liposomes as carriers," J Clin Pharmacol. Aug. 1989;29(8):685-94.
Randolph, G. J., et al. "Differentiation of phagocytic monocytes into lymph node dendritic cells in vivo," Immunity, 1999. 11(6): p. 753-61.
Rathore R, et al. "Current State of Tolerance: The Holy Grail," Arch Clin Nephrol 3(2): 057-063.
Rattan Si, et al. "Protein synthesis, posttranslational modifications, and aging," Ann N Y Acad Sci. Nov. 21, 1992;663:48-62.
Ravetch Jv, et al. "IgG Fc receptors," Annu Rev Immunol. 2001;19:275-90.
Rice Rh, et al. "Localization of hair shaft protein VSIG8 in the hair follicle, nail unit, and oral cavity," J Invest Dermatol. Sep. 2011;131(9):1936-8.
Rizo J, et al. "Constrained peptides: models of bioactive peptides and protein substructures," Annu Rev Biochem. 1992;61:387-418.
Robben, P. M., et al., Recruitment of Gr-1+ monocytes is essential for control of acute toxoplasmosis. J Exp Med, 2005. 201(11): p. 1761-9.
Roberge Jy, et al. "A strategy for a convergent synthesis of N-linked glycopeptides on a solid support," Science. Jul. 14, 1995;269(5221):202-4.
Robertson Jm, Jensen Pe, Evavold BD. DO11.10 and OT-II T Cells Recognize a C-Terminal Ovalbumin 323-339 Epitope. The Journal of Immunology. 2000;164(9):4706-12. doi: 10.4049/jimmunol.164.9.4706.
Roda G, Jharap B, Neeraj N, Colombel J-F. Loss of Response to Anti-TNFs: Definition, Epidemiology, and Ma nagement. Clin Trans Gastroenterol. 2016;7:e135. doi: 10.1038/ctg.2015.63.
Rose Tm, et al. "Consensus-degenerate hybrid oligonucleotide primers for amplification of distantly related sequences," Nucleic Acids Res. Apr. 1, 1998;26(7):1628-35.

(56) References Cited

OTHER PUBLICATIONS

Rossolini Gm, et al. "Use of deoxyinosine-containing primers vs degenerate primers for polymerase chain reaction based on ambiguous sequence information," Mol Cell Probes. Apr. 1994;8(2):91-8.
Rowe Wp, et al. "Plaque assay techniques for murine leukemia viruses," Virology. Dec. 1970;42(4):1136-9.
Saito G, et al. "Drug delivery strategy utilizing conjugation via reversible disulfide linkages: role and site of cellular reducing activities," Adv Drug Deliv Rev. Feb. 10, 2003;55(2):199-215.
Sakaguchi S, et al. "Immunologic self-tolerance maintained by activated T cells expressing IL-2 receptor alpha-chains (CD25). Breakdown of a single mechanism of self-tolerance causes various autoimmune diseases," J Immunol. Aug. 1, 1995;155(3):1151-64.
Sakaguchi S, et al. "Immunologic tolerance maintained by CD25+ CD4+ regulatory T cells: their common role in controlling autoimmunity, tumor immunity, and transplantation tolerance," Immunol Rev. Aug. 2001;182:18-32.
Sakaguchi S, et al. "Organ-specific autoimmune diseases induced in mice by elimination of T cell subset. I. Evidence for the active participation of T cells in natural self-tolerance; deficit of a T cell subset as a possible cause of autoimmune disease," J Exp Med. Jan. 1, 1985;161(1):72-87.
Sakaguchi S, et al. "Regulatory T cells: key controllers of immunologic self-tolerance," Cell. May 26, 2000;101(5):455-8.
Salama Ad, et al. "Critical role of the programmed death-1 (PD-1) pathway in regulation of experimental autoimmune encephalomyelitis," J Exp Med. Jul. 7, 2003;198(1):71-8.
Sasikumar P, et al. "Abstact B006: Functional antagonism of VISG8-mediated immune suppression by oral VISTA agents," Abstacts AACR-NCI-EORTC International Conference: Molecular Targets and Cancer Therapeutics; Oct. 2017. 5 pages.
Scaria A, et al. "Antibody to CD40 ligand inhibits both humoral and cellular immune responses to adenoviral vectors and facilitates repeated administration to mouse airway," Gene Ther. Jun. 1997;4(6):611-7.
Scarlett, U. K., et al., In situ stimulation of CD40 and Toll-like receptor 3 transforms ovarian cancerinfiltrating dendritic cells from immunosuppressive to immunostimulatory cells. Cancer Res, 2009. 69(18): p. 7329-37.
Schreier et al. "Targeting of liposomes to cells expressing CD4 using glycosylphosphatidylinositol-anchored gp120. Influence of liposome composition on intracellular trafficking," J Biol Chem. Mar. 25, 1994;269(12):9090-8.
Schubbert R, et al. "Foreign (M13) DNA ingested by mice reaches peripheral leukocytes, spleen, and liver via the intestinal wall mucosa and can be covalently linked to mouse DNA," Proc Natl Acad Sci U S A. Feb. 4, 1997;94(3):961-6.
Schultz Ld, et al. "Expression and secretion in yeast of a 400-kDa envelope glycoprotein derived from Epstein-Barr virus," Gene. 1987;54(1):113-23.
Scott Jk, et al. "Searching for peptide ligands with an epitope library," Science. Jul. 27, 1990;249(4967):386-90.
Sedy, J. R., "B and T lymphocyte attenuator regulates T cell activation through interaction with herpesvirus entry mediator," Nat Immunol 2005. 6: 90-98.
Seed B. "An LFA-3 cDNA encodes a phospholipid-linked membrane protein homologous to its receptor CD2," Nature. Oct. 29-Nov. 4, 1987;329(6142):840-2.
Seifter S, et al. "Analysis for protein modifications and nonprotein cofactors," Methods Enzymol. 1990;182:626-46.
Senter Pd, et al. "Selective activation of anticancer prodrugs by monoclonal antibody-enzyme conjugates," Adv Drug Deliv Rev. Dec. 31, 2001;53(3):247-64.
Sequence Alignment, 2010, 1 page. U.S. Pat. No. 8,236,304 (U.S. Appl. No. 11/912,397) dated May 14, 2010.
Sequence alignment, 2014, 2 pages. U.S. Pat. No. 9,631,018 (U.S. Appl. No. 13/637,381) dated Oct. 29, 2014.
Sequence alignment, 2015, 3 pages. U.S. Appl. No. 13/925,034 dated Oct. 16, 2015.
Serbina, N. V., et al., TNF/iNOS-producing dendritic cells mediate innate immune defense against bacterial infection. Immunity, 2003. 19(1): p. 59-70.
Seregin Ss, et al. "Improving adenovirus based gene transfer: strategies to accomplish immune evasion," Viruses. Sep. 2010;2(9):2013-36.
Sharma, M. D., et al., "Plasmacytoid dendritic cells from mouse tumor-draining lymph nodes directly activate mature Tregs via indoleamine 2,3-dioxygenase," J Clin Invest, 2007. 117(9): p. 2570-82.
Sharma, P. et al., "Novel cancer immunotherapy agents with survival benefit: recent successes and next steps", Nature Reviews Cancer, 2011, vol. 11, pp. 805-812.
Sharpe Ah, et al. "The B7-CD28 superfamily," Nat Rev Immunol. Feb. 2002;2(2):116-26.
Shaw Dr, et al. "Mouse/human chimeric antibodies to a tumor-associated antigen: biologic activity of the four human IgG subclasses," J Natl Cancer Inst. Dec. 7, 1988;80(19):1553-9.
Sheehan, K, et al. "The relationship between cyclooxygenase-2 expression and colorectal cancer," JAMA, 1999. 282: p. 1254-7.
Shevach Em. "Regulatory T cells in autoimmmunity," Annu Rev Immunol. 2000;18:423-49.
Shevach, E. M., CD4+ CD25+ suppressor T cells: more questions than answers. Nat Rev Immunol, 2002. 2(6): p. 389-400.
Shields Rl, et al. "High resolution mapping of the binding site on human IgG1 for Fc gamma RI, Fc gamma RII, Fc gamma RIII, and FcRn and design of IgG1 variants with improved binding to the Fc gamma R," J Biol Chem. Mar. 2, 2001;276(9):6591-604.
Shields Rl, et al. "Lack of fucose on human IgG1 N-linked oligosaccharide improves binding to human Fcgamma RIII and antibody-dependent cellular toxicity," J Biol Chem. Jul. 26, 2002;277(30):26733-40.
Shimizu J, et al. "Stimulation of CD25(+)CD4(+) regulatory T cells through GITR breaks immunological self-tolerance," Nat Immunol. Feb. 2002;3(2):135-42.
Shortman, K. et al. "Steady-state and inflammatory dendritic-cell development," Nat Rev Immunol, 2007. 7(1): p. 19-30.
Shulman M, et al. "A better cell line for making hybridomas secreting specific antibodies," Nature. Nov. 16, 1978;276(5685):269-70.
Sica Gl, et al. "B7-H4, a molecule of the B7 family, negatively regulates T cell immunity," Immunity. Jun. 2003;18(6):849-61.
Simard C, et al. " Studies of the susceptibility of nude, CD4 knockout, and SCID mutant mice to the disease induced by the murine AIDS defective virus," J Virol. Apr. 1997;71(4):3013-22.
Sizemore Dr, et al. "Attenuated Shigella as a DNA delivery vehicle for DNA-mediated immunization," Science. Oct. 13, 1995;270(5234):299-302.
Skehelll, et al. "Coiled coils in both intracellular vesicle and viral membrane fusion," Cell. Dec. 23, 1998;95(7):871-4.
Smith Db, et al. "Single-step purification of polypeptides expressed in *Escherichia coli* as fusions with glutathione S-transferase," Gene. Jul. 15, 1988;67(1):31-40.
Smith Ge, et al. "Production of human beta interferon in insect cells infected with a baculovirus expression vector," Mol Cell Biol. Dec. 1983;3(12):2156-65.
Smith Jh, et al. "Detection of *Mycobacterium tuberculosis* directly from sputum by using a prototype automated Q-beta replicase assay," J Clin Microbiol. Jun. 1997;35(6):1477-83.
Smith Jh, et al. "Performance of an automated Q-beta replicase amplification assay for *Mycobacterium tuberculosis* in a clinical trial," J Clin Microbiol. Jun. 1997;35(6):1484-91.
Smith Lj, et al. "Human interleukin 4. The solution structure of a four-helix bundle protein," J Mol Biol. Apr. 20, 1992;224(4):899-904.
Son Yi, et al. "A novel bulk-culture method for generating mature dendritic cells from mouse bone marrow cells," J Immunol Methods. Apr. 1, 2002;262(1-2):145-57.
Spatola Af, et al. "Structure-activity relationships of enkephalins containing serially replaced thiomethylene amide bond surrogates," Life Sci. Apr. 7, 1986;38(14):1243-9.
Steinman, R. M. et al. "Tolerogenic dendritic cells," Annu Rev Immunol, 2003. 21: p. 685-711.

(56) References Cited

OTHER PUBLICATIONS

Stewart Mj, et al. "Gene transfer in vivo with DNA-liposome complexes: safety and acute toxicity in mice," Hum Gene Ther. Jun. 1992;3(3):267-75.
Studier Fw, et al. "Use of T7 RNA polymerase to direct expression of cloned genes," Methods Enzymol. 1990;185:60-89.
Su Ai, et al. "Large-scale analysis of the human and mouse transcriptomes," Proc Natl Acad Sci U S A. Apr. 2, 2002;99(7):4465-70.
Suh, W. K., et al. "The B7 family member B7-H3 preferentially down-regulates T helper type 1-mediated immune responses," Nat Immunol 2003. 4: 899-906.
Sun Lk, et al. "Chimeric antibody with human constant regions and mouse variable regions directed against carcinoma-associated antigen 17-1A," Proc Natl Acad Sci U S A. Jan. 1987;84(1):214-8.
Sunderkotter, C., et al., "Subpopulations of mouse blood monocytes differ in maturation stage and inflammatory response," J Immunol, 2004. 172(7): p. 4410-7.
Tacke, F. et al. "Migratory fate and differentiation of blood monocyte subsets," Immunobiology, 2006. 211(6-8): p. 609-18.
Tafuri A, et al. "ICOS is essential for effective T-helper-cell responses," Nature. Jan. 4, 2001;409(6816):105-9.
Takamatsu N, et al. "Expression of bacterial chloramphenicol acetyltransferase gene in tobacco plants mediated by TMV-RNA," EMBO J. Feb. 1987;6(2):307-11.
Takamura S, et al. "Premature terminal exhaustion of Friend virus-specific effector CD8+ T cells by rapid induction of multiple inhibitory receptors," J Immunol. May 1, 2010;184(9):4696-707.
Takeda S, et al. "Construction of chimaeric processed immunoglobulin genes containing mouse variable and human constant region sequences," Nature. Apr. 4-10, 1985;314(6010):452-4.
Tarhini, A., E. Lo, and D. R. Minor, Releasing the brake on the immune system: ipilimumab in melanoma and other tumors. Cancer Biother Radiopharm, 2010. 25(6): p. 601-13.
Taylor Ld, et al. "A transgenic mouse that expresses a diversity of human sequence heavy and light chain immunoglobulins," Nucleic Acids Res. Dec. 11, 1992;20(23):6287-95.
Taylor Ld, et al. "Human immunoglobulin transgenes undergo rearrangement, somatic mutation and class switching in mice that lack endogenous IgM," Int Immunol. Apr. 1994;6(4):579-91.
Taylor Wr. "The classification of amino acid conservation," J Theor Biol. Mar. 21, 1986;119(2):205-18.
Teft Wa, et al. "A molecular perspective of CTLA-4 function," Annu Rev Immunol. 2006;24:65-97.
Terawaki, S., "Specific and high-affinity binding of tetramerized PD-LI extracellular domain to PD-I-expressing cells: possible application to enhance T cell function," Int Immunol 2007. 19: 881-890.
Thompson Ja, et al. "A phase I trial of CD3/CD28-activated T cells (Xcellerated T cells) and interleukin-2 in patients with metastatic renal cell carcinoma," Clin Cancer Res. Sep. 1, 2003;9(10 Pt 1):3562-70.
Thompson Jd, et al. "CLUSTAL W: improving the sensitivity of progressive multiple sequence alignment through sequence weighting, position-specific gap penalties and weight matrix choice," Nucleic Acids Res. Nov. 11, 1994;22(22):4673-80.
Thorpe et al., "The Preparation and Cytotoxic Properties of Antibody-Toxin Conjugates", Immunol. Rev., 62: 119-58 (1982).
Tivol Ea, et al. "Loss of CTLA-4 leads to massive lymphoproliferation and fatal multiorgan tissue destruction, revealing a critical negative regulatory role of CTLA-4," Immunity. Nov. 1995;3(5):541-7.
Tomizuka K, et al. "Double trans-chromosomic mice: maintenance of two individual human chromosome fragments containing Ig heavy and kappa loci and expression of fully human antibodies," Proc Natl Acad Sci U S A. Jan. 18, 2000;97(2):722-7.
Tomlinson, et al. (1992) "The Repertoire of Human Germline VH Sequences Reveals about Fifty Groups of VH Segments with Different Hypervariable Loops" J. Mol. Biol. 227: 776-798.
Townsend Se, et al. "Tumor rejection after direct costimulation of CD8+T cells by B7-transfected melanoma cells," Science. Jan. 15, 1993;259(5093):368-70.
Trail Pa, et al. "Monoclonal antibody drug immunoconjugates for targeted treatment of cancer," Cancer Immunol Immunother. May 2003;52(5):328-37.
Transmembrane Region Prediction, "SACS MEMSAT2" 2018, 16 pages.
Traunecker A, et al. "Bispecific single chain molecules (Janusins) target cytotoxic lymphocytes on HIV infected cells," EMBO J. Dec. 1991;10(12):3655-9.
Tuaillon N, et al. " Human immunoglobulin heavy-chain minilocus recombination in transgenic mice: gene-segment use in mu and gamma transcripts," Proc Natl Acad Sci U S A. Apr. 15, 1993;90(8):3720-4.
Tuaillon N, et al. "Biased utilization of DHQ52 and JH4 gene segments in a human Ig transgenic minilocus is independent of antigenic selection," J Immunol. Mar. 15, 1994;152(6):2912-20.
Tuladhar et al., "Role of Co-stimulation in Leishmaniasis." Int J Biol Sci. 2011;7(9):1382-90.
Tutt A, et al. "Trispecific F(ab')3 derivatives that use cooperative signaling via the TCR/CD3 complex and CD2 to activate and redirect resting cytotoxic T cells," J Immunol. Jul. 1, 1991;147(1):60-9.
Umaña P, et al. "Engineered glycoforms of an antineuroblastoma IgG1 with optimized antibody-dependent cellular cytotoxic activity," Nat Biotechnol. Feb. 1999;17(2):176-80.
Umezawa F, et al. "Liposome targeting to mouse brain: mannose as a recognition marker," Biochem Biophys Res Commun. Jun. 30, 1988;153(3):1038-44.
Uy R, et al. "Posttranslational covalent modification of proteins," Science. Dec. 2, 1977;198(4320):890-6.
Vaccaro C, et al. "Engineering the Fc region of immunoglobulin G to modulate in vivo antibody levels," Nature Biotechnology. 2005;23(10):1283-8.
van Elsas A, et al. "Combination immunotherapy of B16 melanoma using anti-cytotoxic T lymphocyte-associated antigen 4 (CTLA-4) and granulocyte/macrophage colony-stimulating factor (GM-CSF)-producing vaccines induces rejection of subcutaneous and metastatic tumors accompanied by autoimmune depigmentation," J Exp Med. Aug. 2, 1999;190(3):355-66.
Van Wauwe Jp, et al. "OKT3: a monoclonal anti-human T lymphocyte antibody with potent mitogenic properties," The Journal of Immunology. 1980;124(6):2708-13.
Velu V, et al. "Enhancing SIV-specific immunity in vivo by PD-1 blockade," Nature. Mar. 12, 2009;458(7235):206-10.
Verhoeyen M, et al. "Reshaping human antibodies: grafting an antilysozyme activity," Science. Mar. 25, 1988;239(4847):1534-6.
Via Cs. "Advances in lupus stemming from the parent-into-Fl model". Trends Immunol., Jun. 31, 2010(6):236-45).
Wada K, et al. "Codon usage tabulated from the GenBank genetic sequence data," Nucleic Acids Res. May 11, 1992;20 Suppl:2111-8.
Wadia Js, et al. "Protein transduction technology," Curr Opin Biotechnol. Feb. 2002;13(1):52-6.
Walch A, et al. "Microdissection of tissue sections: application to the molecular genetic characterisation of premalignant lesions," Pathobiology. Jan.-Feb. 2000;68(1):9-17.
Walker Jd, et al. "Oncolytic herpes simplex virus 1 encoding 15-prostaglandin dehydrogenase mitigates immune suppression and reduces ectopic primary and metastatic breast cancer in mice," J Virol. Jul. 2011;85(14):7363-71.
Wallace Dj, et al. "Long-Term Safety and Efficacy of Epratuzumab in the Treatment of Moderate-to- Severe Systemic Lupus Erythematosus: Results From an Open-Label Extension Study," Arthritis Care Res (Hoboken). Apr. 2016;68(4):534-43.
Wang et al. "Immune checkpoint protein VISTA regulate autoimmunity and anti-tumor immunity" J Immunol (May 2013) vol. 190 (Meeting Abstract Supplement) No. 53.35, abstract. 2 pages.
Wang G, et al. "The effects of PDL-Ig on collagen-induced arthritis," Rheumatol Int. Apr. 2011;31(4):513-9.
Wang Hc, et al. "Maximum immunobioactivity of murine small intestinal intraepithelial lymphocytes resides in a subpopulation of CD43+ T cells," J Immunol. Nov. 15, 2004;173(10):6294-302.

(56) References Cited

OTHER PUBLICATIONS

Wang H-X, "Immune mechanisms of Concanavalin a model of autoimmune hepatitis," World Journal of Gastroenterology: WJG. 2012;18(2):119-25.
Wang L, et al. "Disruption of the immune-checkpoint VISTA gene imparts a proinflammatory phenotype with predisposition to the development of autoimmunity," Proc Natl Acad Sci U S A. Oct. 14, 2014;111(41):14846-51.
Wang, L. et al., "Vista, a novel mouse Ig superfamily ligand that negatively regulates T cell response," J. Exp. Med. Mar. 7, 2011, vol. 208. No. 3, pp. 577-592.
Wang, L., et al., "Programmed death 1 ligand signaling regulates the generation of adaptive Foxp3+CD4+ regulatory T cells," Proc Natl Acad Sci USA, 2008. 105(27): p. 9331-6.
Wang, X., "B7-H4 induces donor-specific tolerance in mouse islet allografts," Cell Transplant 2012. 21: 99-111.
Wang, X., "B7-H4 Treatment of T Cells Inhibits ERK, JN K, p38, and AKT Activation," PLoS One 2012. 7: e28232.
Ward Es, et al. "Binding activities of a repertoire of single immunoglobulin variable domains secreted from *Escherichia coli*," Nature. Oct. 12, 1989;341(6242):544-6.
Warrington et al. Allergy, Asthma & Clinical Immunology 2011, 7(Suppl 1):S1, 8 pages.
Waterhouse P, et al. "Lymphoproliferative disorders with early lethality in mice deficient in CTLA-4," Science. Nov. 10, 1995;270(5238):985-8.
Weber, J., "Immune checkpoint proteins: a new therapeutic paradigm for cancer--preclinical background: CTLA-4 and PD-1 blockade," Semin Oncol, 2010. 37(5): p. 430-9.
Weiner Gj. "Building better monoclonal antibody-based therapeutics," Nat Rev Cancer. 2015;15(6):361-70.
Weintraub H., et al. "Anti-sense RNA as a molecular tool for] genetic analysis," Trends in Genetics, 1985, pp. 22-25.
Weissmuller S, "TGN1412 Induces Lymphopenia and Human Cytokine Release in a Humanized Mouse Model," PloS One. 2016;11(3):e0149093.
Welling Gw, et al. "Prediction of sequential antigenic regions in proteins," FEBS Lett. Sep. 2, 1985;188(2):215-8.
Wetmur Jg. "DNA probes: applications of the principles of nucleic acid hybridization," Crit Rev Biochem Mol Biol. 1991;26(3-4):227-59.
White et al., (2015), "Conformation of the human immunoglobulin G2 hinge imparts superagonistic properties to immunostimulatory anticancer antibodies", Cancer Cell, 27(1), 138-148.
Wilcox, R. A., "Cancer-associated myeloproliferation: old association, new therapeutic target," Mayo Clin Proc, 2010. 85(7): p. 656-63.
Wiley Ra, et al. "Peptidomimetics derived from natural products," Med Res Rev. May 1993;13(3):327-84.
Williams G, et al. "Dissection of the extracellular human interferon gamma receptor alpha-chain into two immunoglobulin-like domains. Production in an *Escherichia coli* thioredoxin gene fusion expression system and recognition by neutralizing antibodies," Biochemistry. Feb. 7, 1995;34(5):1787-97.
Willmon C, et al. "Vesicular stomatitis virus-induced immune suppressor cells generate antagonism between intratumoral oncolytic virus and cyclophosphamide," Mol Ther. Jan. 2011;19(1):140-9.
Wilmut I, et al. "Viable offspring derived from fetal and adult mammalian cells," Nature. Feb. 27, 1997;385(6619):810-3.
Wing, K., et al., "CTLA-4 control over Foxp3+ regulatory T cell function," Science, 2008. 322(5899): p. 271-5.
Winoto A, et al. "A novel, inducible and T cell-specific enhancer located at the 3' end of the T cell receptor alpha locus," EMBO J. Mar. 1989;8(3):729-33.
Winter G, et al. "Man-made antibodies," Nature. Jan. 24, 1991;349(6307):293-9.
Wojcik J, et al. "Prediction, assessment and validation of protein interaction maps in bacteria," J Mol Biol. Nov. 1, 2002;323(4):763-70.
Wolchok Jd, et al. "Nivolumab plus ipilimumab in advanced melanoma," N Engl J Med. Jul. 11, 2013;369(2):122-33.
Wood Cr, et al. "The synthesis and in vivo assembly of functional antibodies in yeast," Nature. Apr. 4-10, 1985;314(6010):446-9.
Wood Kj, et al. "Regulatory T cells in transplantation tolerance," Nat Rev Immunol. Mar. 2003;3(3):199-210.
Wu Dy, et al. "The ligation amplification reaction (LAR)--amplification of specific DNA sequences using sequential rounds of template-dependent ligation," Genomics. May 1989;4(4):560-9.
Wu S, et al. "Development and application of 'phosphoflow' as a tool for immunomonitoring," Expert Rev Vaccines. 2010;9(6):631-43.
Xu X, et al. "The genomic sequence of the Chinese hamster ovary (CHO)-K1 cell line," Nat Biotechnol. Jul. 31, 2011;29(8):735-41.
Yamaguchi, T. et al. "Regulatory T cells in immune surveillance and treatment of cancer," Semin Cancer Biol, 2006. 16(2): p. 115-23.
Yamane-Ohnuki N, et al. "Establishment of FUT8 knockout Chinese hamster ovary cells: an ideal host cell line for producing completely defucosylated antibodies with enhanced antibody-dependent cellular cytotoxicity," Biotechnol Bioeng. Sep. 5, 2004;87(5):614-22.
Yamaura, K., "In vivo function of immune inhibitory molecule B7-H4 in alloimmune responses," Am J Transplant 2010. 10: 2355-2362.
Yeh My, et al. "A cell-surface antigen which is present in the ganglioside fraction and shared by human melanomas," Int J Cancer. Mar. 15, 1982;29(3):269-75.
Yeh My, et al. "Cell surface antigens of human melanoma identified by monoclonal antibody," Proc Natl Acad Sci U S A. Jun. 1979;76(6):2927-31.
Yetter Ra, et al. "CD4+ T cells are required for development of a murine retrovirus-induced immunodeficiency syndrome (MAIDS)," J Exp Med. Aug. 1, 1988;168(2):623-35.
Yi, K. H., et al. "Fine tuning the immune response through B7-H3 and B7-H4," Immunol Rev, 2009. 229(1): p. 145-51.
Yoon Kw, et al. "Control of signaling-mediated clearance of apoptotic cells by the tumor suppressor p53," Science. 2015;349(6247):1261669.
Yoshinaga Sk, et al. "T-cell co-stimulation through B7RP-1 and ICOS," Nature. Dec. 16, 1999;402(6763):827-32.
Youle Rj, et al. "Anti-Thy 1.2 monoclonal antibody linked to ricin is a potent cell-type-specific toxin," Proc Natl Acad Sci U S A. Sep. 1980;77(9):5483-6.
Youn Ji, et al. "The biology of myeloid-derived suppressor cells: the blessing and the curse of morphological and functional heterogeneity," Eur J Immunol. Nov. 2010;40(11):2969-75.
Youngnak, P., "Differential binding properties of B7-H1 and B7-DC to programmed death-1," Biochem Biophys Res Commun 2003. 307: 672-677.
Zelinskyy G, et al. "The regulatory T-cell response during acute retroviral infection is locally defined and controls the magnitude and duration of the virus-specific cytotoxic T-cell response," Blood. Oct. 8, 2009;114(15):3199-207.
Zenewicz, et al. "CD4 T-cell differentiation and inflammatory bowel disease," Trends Mol Med. May 2009;15(5):199-207.
Zervos As, et al. "Mxi1, a protein that specifically interacts with Max to bind Myc-Max recognition sites," Cell. Jan. 29, 1993;72(2):223-32.
Zhang X, et al. "Bcr-Abl efficiently induces a myeloproliferative disease and production of excess interleukin-3 and granulocyte-macrophage colony-stimulating factor in mice: a novel model for chronic myelogenous leukemia," Blood. Nov. 15, 1998;92(10):3829-40.
Zhang, A., (2015), "Conformational difference in human IgG2 disulfide isoforms revealed by hydrogen/deuterium exchange mass spectrometry", Biochemistry, 54(10), 1956-1962.
Zheng, S. G., et al., "TGF-beta requires CTLA-4 early after T cell activation to induce FoxP3 and generate adaptive CD4+CD25+ regulatory cells," J Immunol, 2006. 176(6): p. 3321-9.
Zhu N, et al. "Systemic gene expression after intravenous DNA delivery into adult mice," Science. Jul. 9, 1993;261(5118):209-11.
Zhu Y, et al. "B7-H5 costimulates human T cells via CD28H," Nat Commun. 2013;4:2043.

(56) References Cited

OTHER PUBLICATIONS

Zhu Z, et al. "High level secretion of a humanized bispecific diabody from *Escherichia coli*," Biotechnology (N Y). Feb. 1996;14(2):192-6.
Zhu, G., "B7-H4-deficient mice display augmented neutrophil-mediated innate immunity," Blood 2009. 113: 1759-1767.
Zon G. "Oligonucleotide analogues as potential chemotherapeutic agents," Pharm Res. Sep. 1988;5(9):539-49.
Zou, W, et al. "Inhibitory B7-family molecules in the tumour microenvironment," Nat Rev Immunol, 2008. 8(6): p. 467-77.
Zou, W., "Regulatory T cells, tumour immunity and immunotherapy," Nat Rev Immunol, 2006. 6(4): p. 295-307.
Zuckermann Rn, et al. "Discovery of nanomolar ligands for 7-transmembrane G-protein-coupled receptors from a diverse N-(substituted)glycine peptoid library," J Med Chem. Aug. 19, 1994;37(17):2678-85.

* cited by examiner

Fig 1. VISTA inhibits early TCR-induced T cell activation.

Fig. 2. Hierarchy of NCR

Figure 3. VISTA mab treatment reduce tumor growth.

Figure 4. Therapeutic treatment with mVISTA-IgG2a reverses kidney damage and prolongs survival in SLE model.

Figure 5. Panning can be used to detect PD-1 →PD-L1 interactions.

Figure 6: VISTA-Ig mediated suppression of anti-CD3(OKT3) induced CD69 upregulation.

FIG 7: VSIG8 Expression Analysis by qPCR

VSIG8 expression analysis by qPCR in human tissues. cDNA samples were prepared from RNA isolated from the indicated cells.

Figure 8. VISTA fusion proteins specifically bind to VSIG8 over-expressing 293 cells.

Figure 9. Antibodies against VSIG8 and VISTA block the interaction between VISTA Ig and VSIG8.

Figure 10. VISTA-Ig shows low-level ability to bind to mouse VSIG8 over-expressing cells.

Figure 11. VISTA over-expressing cells conjugate to VSIG8 overexpressing cells.

Figure 12. Antibodies against VSIG8 are capable of binding to CD8 T cells and NK cells.

Figure 13. VSIG8 mRNA is expressed in human CD4 and CD8 T cells.

Figure 14. VISTA signals T cells via VSIG8 to suppress T cell activation.

FIG. 15: Surface Proteins upon V-Ig Treatment
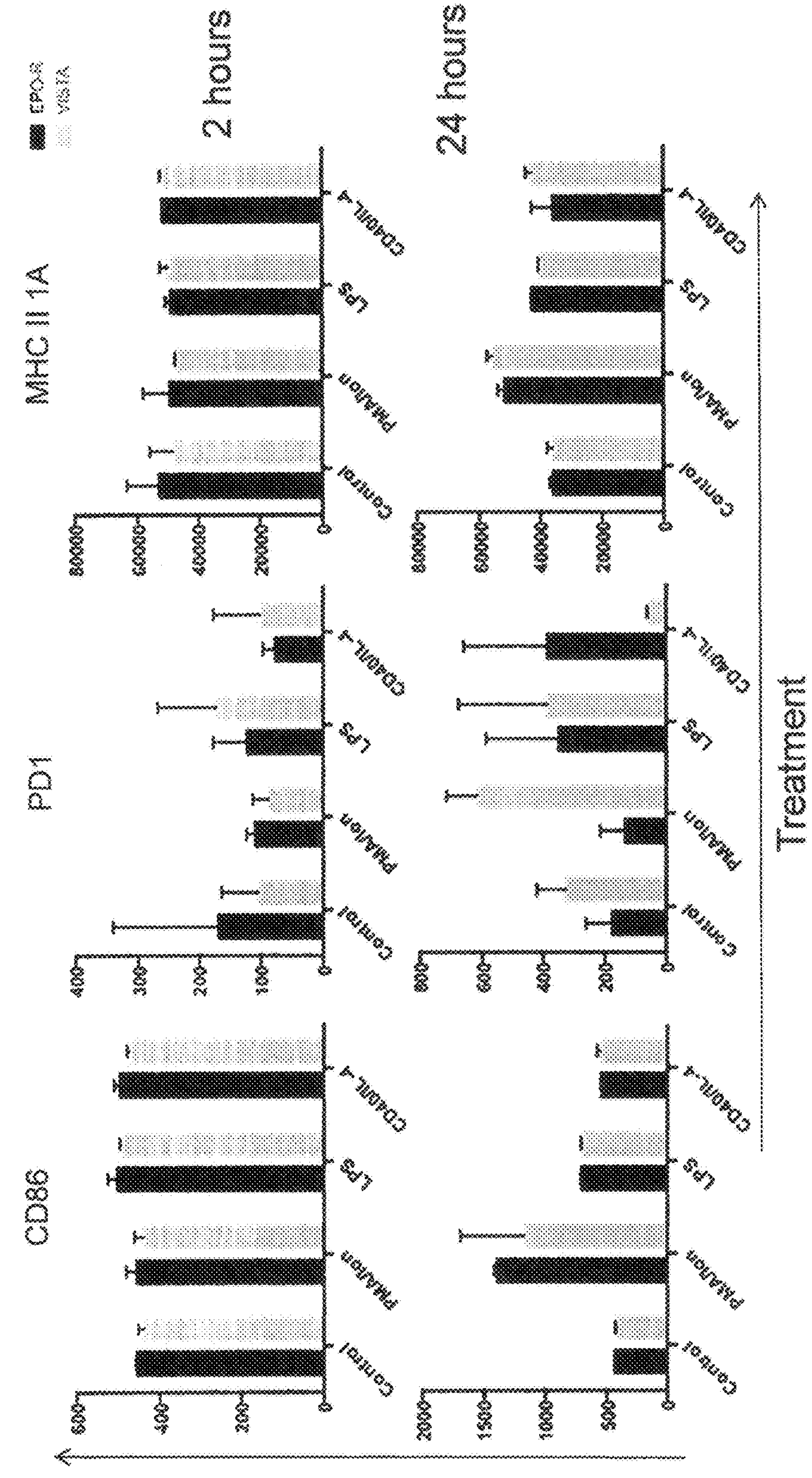

FIGURE 16 VSIG8 GENE SPECIES ORTHOLOGS

| Name/Gene ID | Description | Location | Aliases | MIM |
|---|---|---|---|---|
| 391123 VSIG8 ID: 391123 | V-set and immunoglobulin domain containing 8 [Homo sapiens (human)] | Chromosome 1, NC_000001.11 (159854316..159862657, complement) | | |
| 289236 Vsig8 ID: 289236 | V-set and immunoglobulin domain containing 8 [*Rattus norvegicus* (Norway rat)] | Chromosome 13, NC_005112.4 (90943255..90951443) | RGD1562464 | |
| Select item 100683194 VSIG8 ID: 100683194 | V-set and immunoglobulin domain containing 8 [Canis lupus familiaris (dog)] | Chromosome 38, NC_006620.3 (22278668..22285444) | | |
| Select item 745370 VSIG8 ID: 745370 | V-set and immunoglobulin domain containing 8 [Pan troglodytes (chimpanzee)] | Chromosome 1, NC_006468.3 (138192369..138199518, complement) | | |
| Select item 106835742 VSIG8 ID: 106835742 | V-set and immunoglobulin domain containing 8 [Equus asinus (ass)] | | | |
| Select item 106500502 VSIG8 ID: 106500502 | V-set and immunoglobulin domain containing 8 [Apteryx australis mantelli] | | | |
| Select item 105996481 Vsig8 ID: 105996481 | V-set and immunoglobulin domain containing 8 [Dipodomys ordii (Ord's kangaroo rat)] | | | |
| Select item 105862695 | V-set and immunoglobulin domain containing 8 | | | |

FIG. 16 (continued)

| Name/Gene ID | Description | Location | Aliases | MIM |
|---|---|---|---|---|
| VSIG8 ID: 105862695 | [Microcebus murinus (gray mouse lemur)] | | | |
| Select item 105824470 VSIG8 ID: 105824470 | V-set and immunoglobulin domain containing 8 [Propithecus coquereli (Coquerel's sifaka)] | | | |
| Select item 105532289 VSIG8 ID: 105532289 | V-set and immunoglobulin domain containing 8 [Mandrillus leucophaeus (drill)] | | | |
| Select item 105522631 VSIG8 ID: 105522631 | V-set and immunoglobulin domain containing 8 [Colobus angolensis palliatus] | | | |
| Select item 105498150 VSIG8 ID: 105498150 | V-set and immunoglobulin domain containing 8 [Macaca nemestrina (pig-tailed macaque)] | | | |
| Select item 105414216 VSIG8 ID: 105414216 | V-set and immunoglobulin domain containing 8 [Aquila chrysaetos canadensis] | | | |
| Select item 105086534 VSIG8 ID: 105086534 | V-set and immunoglobulin domain containing 8 [Camelus dromedarius (Arabian camel)] | | | |
| Select item 105069585 VSIG8 ID: | V-set and immunoglobulin domain containing 8 [Camelus bactrianus (Bactrian camel)] | | | |

FIG. 16 (continued)

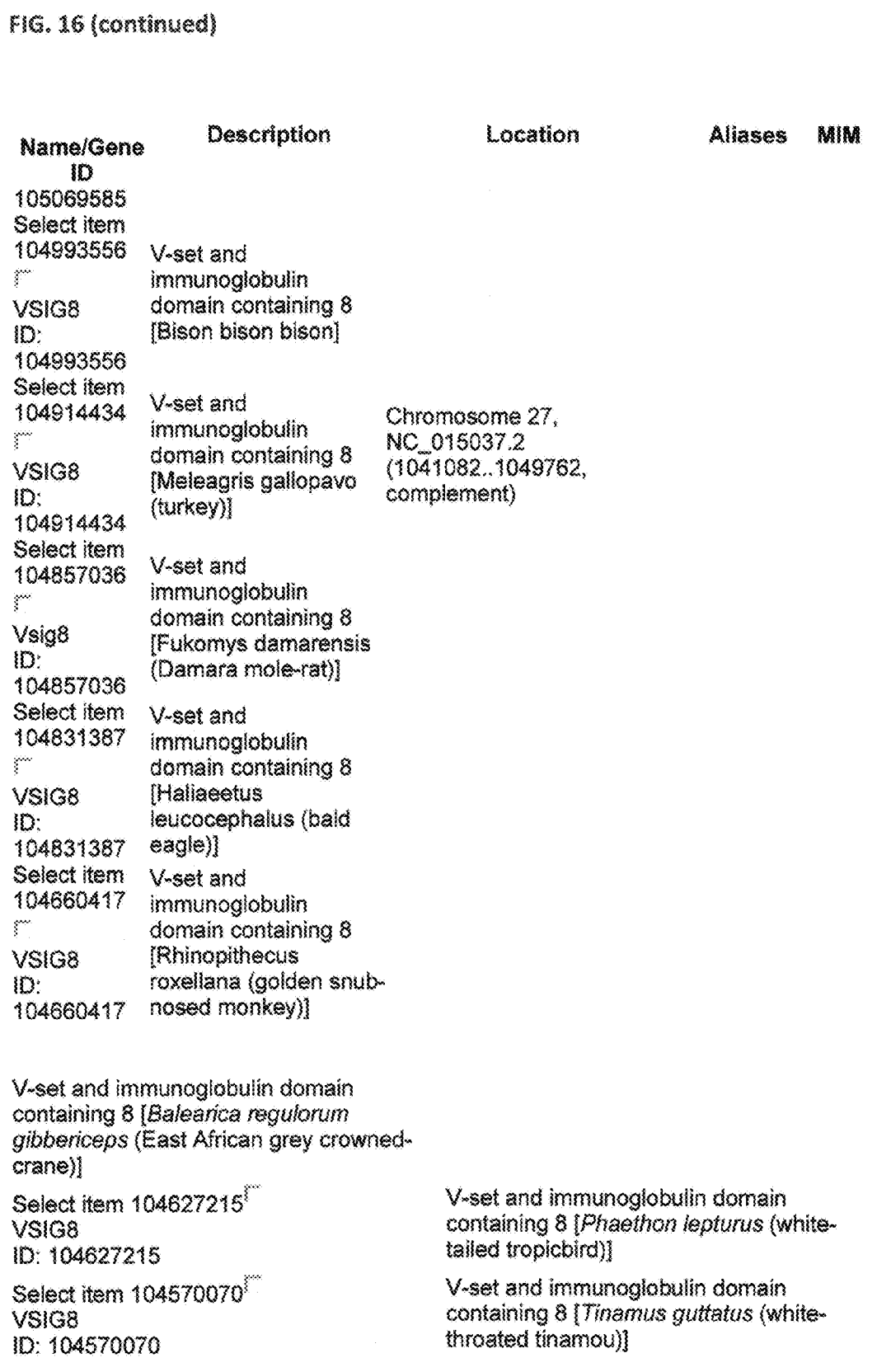

| Name/Gene ID | Description | Location | Aliases | MIM |
| --- | --- | --- | --- | --- |
| 105069585 | | | | |
| Select item 104993556 VSIG8 ID: 104993556 | V-set and immunoglobulin domain containing 8 [Bison bison bison] | | | |
| Select item 104914434 VSIG8 ID: 104914434 | V-set and immunoglobulin domain containing 8 [Meleagris gallopavo (turkey)] | Chromosome 27, NC_015037.2 (1041082..1049762, complement) | | |
| Select item 104857036 Vsig8 ID: 104857036 | V-set and immunoglobulin domain containing 8 [Fukomys damarensis (Damara mole-rat)] | | | |
| Select item 104831387 VSIG8 ID: 104831387 | V-set and immunoglobulin domain containing 8 [Haliaeetus leucocephalus (bald eagle)] | | | |
| Select item 104660417 VSIG8 ID: 104660417 | V-set and immunoglobulin domain containing 8 [Rhinopithecus roxellana (golden snub-nosed monkey)] | | | |

V-set and immunoglobulin domain containing 8 [*Balearica regulorum gibbericeps* (East African grey crowned-crane)]

| | |
| --- | --- |
| Select item 104627215 VSIG8 ID: 104627215 | V-set and immunoglobulin domain containing 8 [*Phaethon lepturus* (white-tailed tropicbird)] |
| Select item 104570070 VSIG8 ID: 104570070 | V-set and immunoglobulin domain containing 8 [*Tinamus guttatus* (white-throated tinamou)] |

FIG. 16 (continued)

| | |
|---|---|
| Select item 104559501<br>VSIG8<br>ID: 104559501 | V-set and immunoglobulin domain containing 8 [*Colius striatus* (speckled mousebird)] |
| Select item 104522716<br>VSIG8<br>ID: 104522716 | V-set and immunoglobulin domain containing 8 [*Caprimulgus carolinensis* (chuck-will's-widow)] |
| Select item 104388494<br>VSIG8<br>ID: 104388494 | V-set and immunoglobulin domain containing 8 [*Chaetura pelagica* (chimney swift)] |
| Select item 104336212<br>VSIG8<br>ID: 104336212 | V-set and immunoglobulin domain containing 8 [*Opisthocomus hoazin*] |
| Select item 104282688<br>VSIG8<br>ID: 104282688 | V-set and immunoglobulin domain containing 8 [*Charadrius vociferus* (killdeer)] |
| Select item 104254214<br>VSIG8<br>ID: 104254214 | V-set and immunoglobulin domain containing 8 [*Gavia stellata* (red-throated loon)] |
| Select item 104160964<br>VSIG8<br>ID: 104160964 | V-set and immunoglobulin domain containing 8 [*Cariama cristata* (red-legged seriema)] |
| Select item 104139612<br>VSIG8<br>ID: 104139612 | V-set and immunoglobulin domain containing 8 [*Struthio camelus australis*] |
| Select item 104066229<br>VSIG8<br>ID: 104066229 | V-set and immunoglobulin domain containing 8 [*Cuculus canorus* (common cuckoo)] |
| Select item 104012584<br>VSIG8<br>ID: 104012584 | V-set and immunoglobulin domain containing 8 [*Nipponia nippon* (crested ibis)] |
| Select item 103900558<br>VSIG8<br>ID: 103900558 | V-set and immunoglobulin domain containing 8 [*Aptenodytes forsteri* (emperor penguin)] |
| Select item 103740244<br>Vsig8<br>ID: 103740244 | V-set and immunoglobulin domain containing 8 [*Nannospalax galili* (Upper Galilee mountains blind mole rat)] |

| | | |
|---|---|---|
| ID: 103672119 | V-set and immunoglobulin domain containing 8 [*Ursus maritimus* (polar bear)] | NW_007907182.1 (1184725..1200182) |
| Select item 103587965<br>VSIG8<br>ID: 103587965 | V-set and immunoglobulin domain containing 8 [*Galeopterus variegatus* (Sunda flying lemur)] | NW_007726617.1 (326539..336095) |

FIG. 16 (continued)

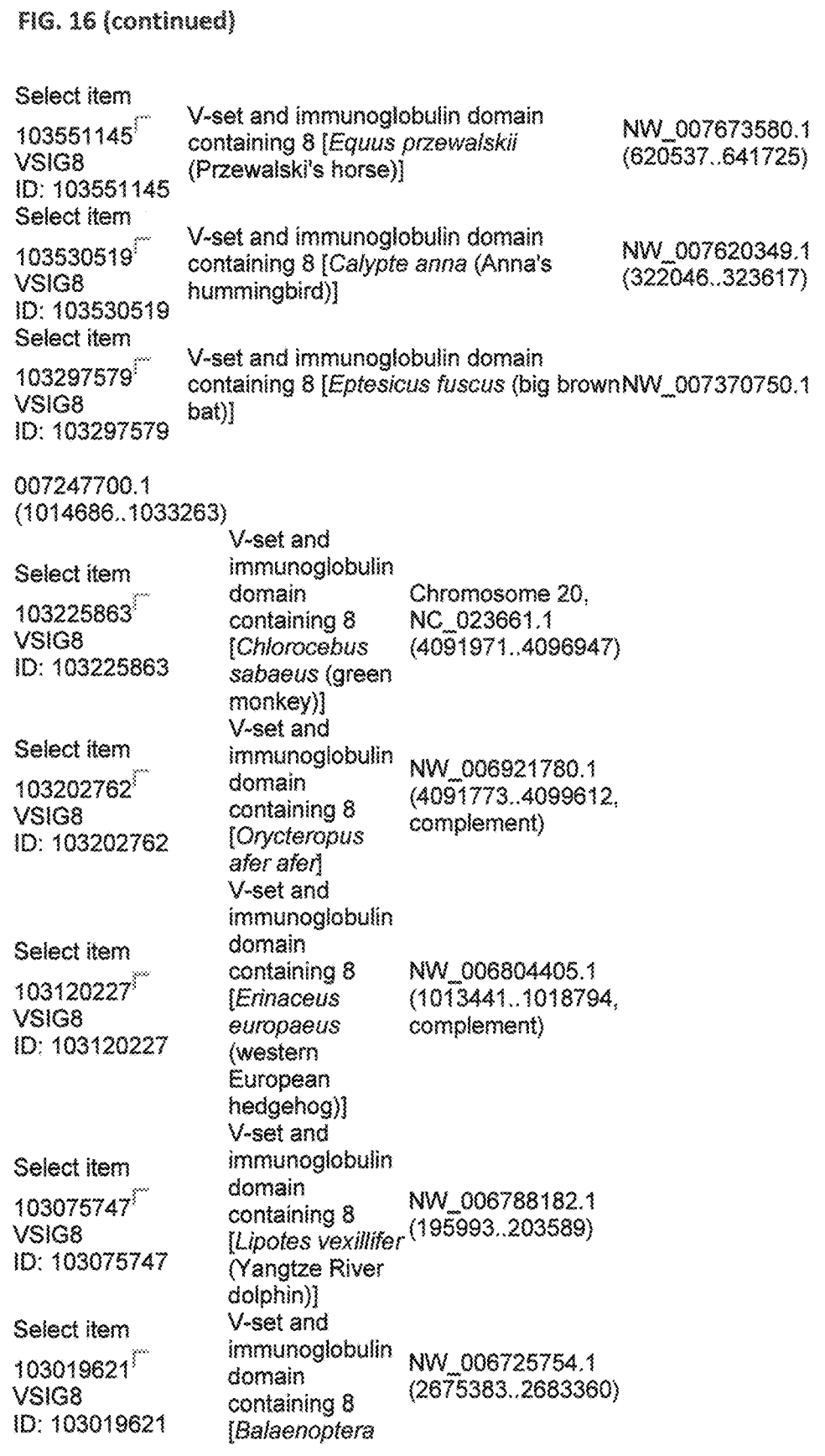

| | | |
|---|---|---|
| Select item 103551145 VSIG8 ID: 103551145 | V-set and immunoglobulin domain containing 8 [*Equus przewalskii* (Przewalski's horse)] | NW_007673580.1 (620537..641725) |
| Select item 103530519 VSIG8 ID: 103530519 | V-set and immunoglobulin domain containing 8 [*Calypte anna* (Anna's hummingbird)] | NW_007620349.1 (322046..323617) |
| Select item 103297579 VSIG8 ID: 103297579 | V-set and immunoglobulin domain containing 8 [*Eptesicus fuscus* (big brown bat)] | NW_007370750.1 |

007247700.1
(1014686..1033263)

| | | |
|---|---|---|
| Select item 103225863 VSIG8 ID: 103225863 | V-set and immunoglobulin domain containing 8 [*Chlorocebus sabaeus* (green monkey)] | Chromosome 20, NC_023661.1 (4091971..4096947) |
| Select item 103202762 VSIG8 ID: 103202762 | V-set and immunoglobulin domain containing 8 [*Orycteropus afer afer*] | NW_006921780.1 (4091773..4099612, complement) |
| Select item 103120227 VSIG8 ID: 103120227 | V-set and immunoglobulin domain containing 8 [*Erinaceus europaeus* (western European hedgehog)] | NW_006804405.1 (1013441..1018794, complement) |
| Select item 103075747 VSIG8 ID: 103075747 | V-set and immunoglobulin domain containing 8 [*Lipotes vexillifer* (Yangtze River dolphin)] | NW_006788182.1 (195993..203589) |
| Select item 103019621 VSIG8 ID: 103019621 | V-set and immunoglobulin domain containing 8 [*Balaenoptera* | NW_006725754.1 (2675383..2683360) |

FIG. 16 (continued)

| | | |
|---|---|---|
| | *acutorostrata scammoni*] | |
| Select item 102979316 VSIG8 ID: 102979316 | V-set and immunoglobulin domain containing 8 [*Physeter catodon* (sperm whale)] | NW_006724380.1 (118120..126348, complement) |
| Select item 102964438 VSIG8 ID: 102964438 | V-set and immunoglobulin domain containing 8 [*Panthera tigris altaica* (Amur tiger)] | NW_006711884.1 (1767019..1785253, complement) |
| Select item 102929783 VSIG8 ID: 102929783 | V-set and immunoglobulin domain containing 8 [*Chelonia mydas* (green sea turtle)] | NW_006654175.1 (571930..579597) |
| Select item 102927561 Vsig8 ID: 102927561 | V-set and immunoglobulin domain containing 8 [*Peromyscus maniculatus bairdii* (prairie deer mouse)] | NW_006501506.1 (1068834..1076639, complement) |
| Select item 102886859 VSIG8 ID: 102886859 | V-set and immunoglobulin domain containing 8 [*Pteropus alecto* (black flying fox)] | NW_006443119.1 (3929174..3936521) |
| Select item 102869101 VSIG8 ID: 102869101 | V-set and immunoglobulin domain containing 8 [*Elephantulus edwardii* (Cape elephant shrew)] | NW_006399918.1 (4633616..4640782, complement) |
| Select item 102827385 VSIG8 ID: 102827385 | V-set and immunoglobulin domain containing 8 [*Chrysochloris asiatica* (Cape | NW_006408560.1 (19577995..19585089, complement) |

FIG. 16 (continued)

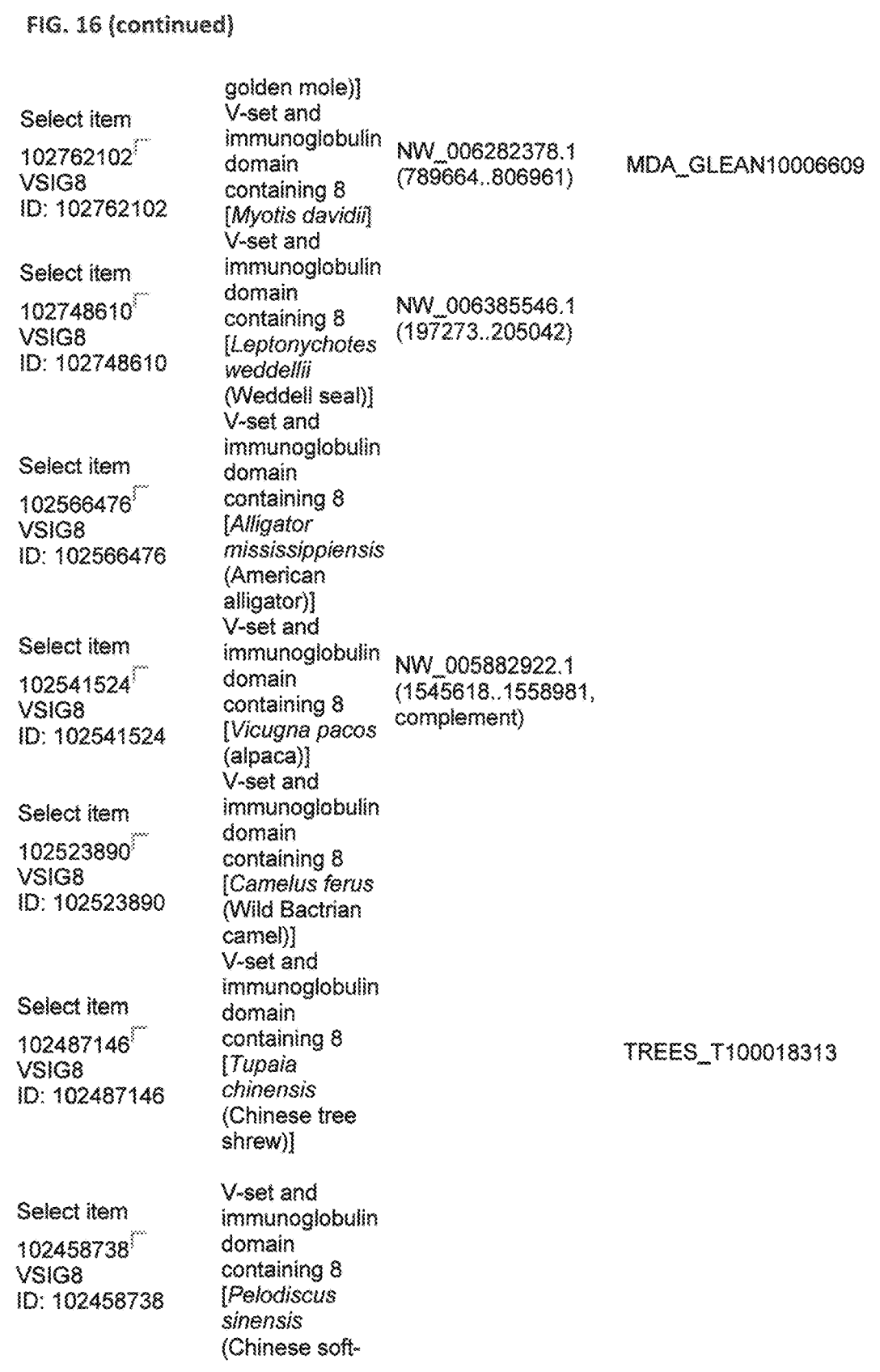

| | | | |
|---|---|---|---|
| | golden mole)] | | |
| Select item 102762102 VSIG8 ID: 102762102 | V-set and immunoglobulin domain containing 8 [*Myotis davidii*] | NW_006282378.1 (789664..806961) | MDA_GLEAN10006609 |
| Select item 102748610 VSIG8 ID: 102748610 | V-set and immunoglobulin domain containing 8 [*Leptonychotes weddellii* (Weddell seal)] | NW_006385546.1 (197273..205042) | |
| Select item 102566476 VSIG8 ID: 102566476 | V-set and immunoglobulin domain containing 8 [*Alligator mississippiensis* (American alligator)] | | |
| Select item 102541524 VSIG8 ID: 102541524 | V-set and immunoglobulin domain containing 8 [*Vicugna pacos* (alpaca)] | NW_005882922.1 (1545618..1558981, complement) | |
| Select item 102523890 VSIG8 ID: 102523890 | V-set and immunoglobulin domain containing 8 [*Camelus ferus* (Wild Bactrian camel)] | | |
| Select item 102487146 VSIG8 ID: 102487146 | V-set and immunoglobulin domain containing 8 [*Tupaia chinensis* (Chinese tree shrew)] | | TREES_T100018313 |
| Select item 102458738 VSIG8 ID: 102458738 | V-set and immunoglobulin domain containing 8 [*Pelodiscus sinensis* (Chinese soft- | | |

FIG. 16 (continued)

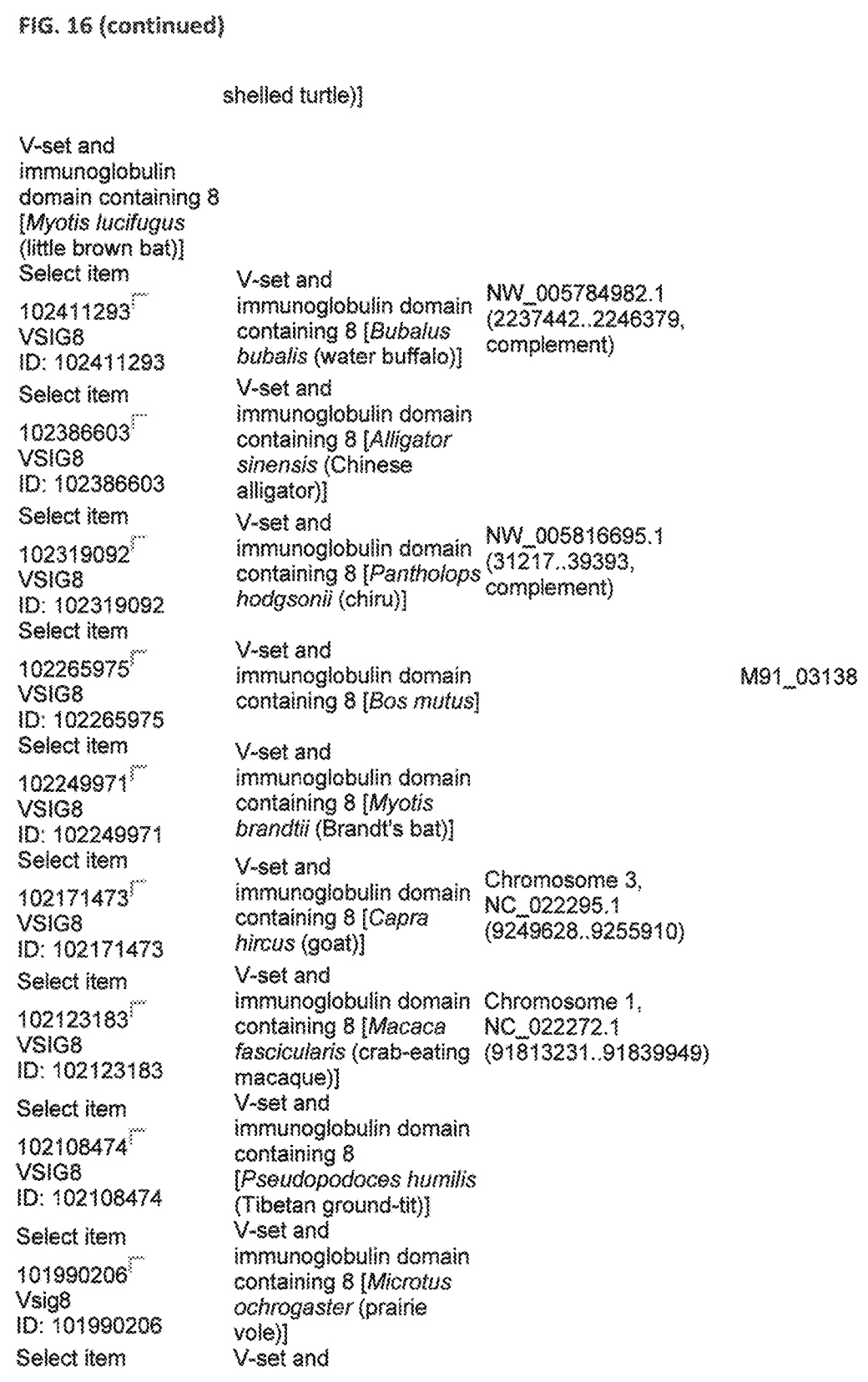

| | | | |
|---|---|---|---|
| | shelled turtle)] | | |
| V-set and immunoglobulin domain containing 8 [*Myotis lucifugus* (little brown bat)] | | | |
| Select item 102411293 VSIG8 ID: 102411293 | V-set and immunoglobulin domain containing 8 [*Bubalus bubalis* (water buffalo)] | NW_005784982.1 (2237442..2246379, complement) | |
| Select item 102386603 VSIG8 ID: 102386603 | V-set and immunoglobulin domain containing 8 [*Alligator sinensis* (Chinese alligator)] | | |
| Select item 102319092 VSIG8 ID: 102319092 | V-set and immunoglobulin domain containing 8 [*Pantholops hodgsonii* (chiru)] | NW_005816695.1 (31217..39393, complement) | |
| Select item 102265975 VSIG8 ID: 102265975 | V-set and immunoglobulin domain containing 8 [*Bos mutus*] | | M91_03138 |
| Select item 102249971 VSIG8 ID: 102249971 | V-set and immunoglobulin domain containing 8 [*Myotis brandtii* (Brandt's bat)] | | |
| Select item 102171473 VSIG8 ID: 102171473 | V-set and immunoglobulin domain containing 8 [*Capra hircus* (goat)] | Chromosome 3, NC_022295.1 (9249628..9255910) | |
| Select item 102123183 VSIG8 ID: 102123183 | V-set and immunoglobulin domain containing 8 [*Macaca fascicularis* (crab-eating macaque)] | Chromosome 1, NC_022272.1 (91813231..91839949) | |
| Select item 102108474 VSIG8 ID: 102108474 | V-set and immunoglobulin domain containing 8 [*Pseudopodoces humilis* (Tibetan ground-tit)] | | |
| Select item 101990206 Vsig8 ID: 101990206 | V-set and immunoglobulin domain containing 8 [*Microtus ochrogaster* (prairie vole)] | | |
| Select item | V-set and | | |

FIG. 16 (continued)

| | |
|---|---|
| 101969069 Vsig8 ID: 101969069 | immunoglobulin domain containing 8 [*Ictidomys tridecemlineatus* (thirteen-lined ground squirrel)] |
| Select item 101951393 VSIG8 ID: 101951393 | V-set and immunoglobulin domain containing 8 [*Chrysemys picta* (painted turtle)] NW_007281607.1 (892706..900683) |
| Select item 101911659 VSIG8 ID: 101911659 | V-set and immunoglobulin domain containing 8 [*Falco peregrinus* (peregrine falcon)] |
| Select item 101827428 Vsig8 ID: 101827428 | V-set and immunoglobulin domain containing 8 [*Mesocricetus auratus* (golden hamster)] |
| Select item 101697042 Vsig8 ID: 101697042 | V-set and immunoglobulin domain containing 8 [*Heterocephalus glaber* (naked mole-rat)] |
| VSIG8 101674224 | V-set and immunoglobulin domain containing 8 [*Mustela putorius furo* (domestic ferret)] |
| Select item 101663482 VSIG8 ID: 101663482 | V-set and immunoglobulin domain containing 8 [*Echinops telfairi* (small Madagascar hedgehog)] |
| Select item 101627866 VSIG8 ID: 101627866 | V-set and immunoglobulin domain containing 8 [*Condylura cristata* (star-nosed mole)] |
| Select item 101605862 Vsig8 ID: 101605862 | V-set and immunoglobulin domain containing 8 [*Jaculus jaculus* (lesser Egyptian jerboa)] |
| Select item 101565541 Vsig8 ID: 101565541 | V-set and immunoglobulin domain containing 8 [*Octodon degus* (degu |
| ID: 101527572 | V-set and immunoglobulin domain containing 8 [*Ochotona* |

FIG. 16 (continued)

| | | | |
|---|---|---|---|
| | *princeps* (American pika)] | | |
| Select item 101387103 LOC101387103 ID: 101387103 | V-set and immunoglobulin domain containing 8 [*Ceratotherium simum simum* (southern white rhinoceros)] | | VSIG8 |
| Select item 101377134 VSIG8 ID: 101377134 | V-set and immunoglobulin domain containing 8 [*Odobenus rosmarus divergens* (Pacific walrus)] | | |
| Select item 101332961 VSIG8 ID: 101332961 | V-set and immunoglobulin domain containing 8 [*Tursiops truncatus* (bottlenosed dolphin)] | NW_004198036.1 (171624..179822) | |
| Select item 101270104 VSIG8 ID: 101270104 | V-set and immunoglobulin domain containing 8 [*Orcinus orca* (killer whale)] | | |
| Select item 101123344 VSIG8 ID: 101123344 | V-set and immunoglobulin domain containing 8 [*Ovis aries* (sheep)] | Chromosome 1, NC_019458.1 (109195314..109203023, complement) | |
| Select item 101098428 VSIG8 ID: 101098428 | V-set and immunoglobulin domain containing 8 [*Felis catus* (domestic cat)] | Chromosome F1, NC_018739.2 (65520231..65526427) | |
| Select item 101009472 VSIG8 ID: 101009472 | V-set and immunoglobulin domain containing 8 [*Papio anubis* (olive baboon)] | Chromosome 1, NC_018152.1 (133753171..133757411, complement) | |
| Select item 100971651 VSIG8 ID: 100971651 | V-set and immunoglobulin domain containing 8 [*Pan paniscus* (pygmy chimpanzee)] | Chromosome 1, NC_027868.1 (139126959..139134922, complement) | |
| Select item 100955994 VSIG8 ID: 100955994 | V-set and immunoglobulin domain containing 8 [*Otolemur garnettii* (small-eared galago)] | | |
| Select item 100916557 VSIG8 ID: 100916557 | V-set and immunoglobulin domain containing 8 [*Sarcophilus harrisii* (Tasmanian devil)] | | |

FIG. 16 (continued)

| | | | |
|---|---|---|---|
| Select item 100771377 Vsig8 ID: 100771377 | V-set and immunoglobulin domain containing 8 [*Cricetulus griseus* (Chinese hamster)] | NW_003613783.1 (1044024..1050052) | I79_006491 |
| Select item 100727929 Vsig8 ID: 100727929 | V-set and immunoglobulin domain containing 8 [*Cavia porcellus* (domestic guinea pig)] | | |
| Select item 100672638 VSIG8 ID: 100672638 | V-set and immunoglobulin domain containing 8 [*Loxodonta africana* (African savanna elephant)] | | |
| Select item 100584000 VSIG8 ID: 100584000 | V-set and immunoglobulin domain containing 8 [*Nomascus leucogenys* (northern white-cheeked gibbon)] | Chromosome 12, NC_019827.1 (42590722..42597668) | |
| Select item 100562394 vsig8 ID: 100562394 | V-set and immunoglobulin domain containing 8 [*Anolis carolinensis* (green anole)] | | |
| Select item 100514765 VSIG8 ID: 100514765 | V-set and immunoglobulin domain containing 8 [*Sus scrofa* (pig)] | Chromosome 4, NC_010446.4 (98638510..98646086) | |
| Select item 100466626 VSIG8 ID: 100466626 | V-set and immunoglobulin domain containing 8 [*Ailuropoda melanoleuca* (giant panda)] | | |
| Select item 100444780 VSIG8 ID: 100444780 | V-set and immunoglobulin domain containing 8 [*Pongo abelii* (Sumatran orangutan)] | Chromosome 1, NC_012591.1 (91524072..91532197) | |
| Select item VSIG8 100423832 LOC100423832 ID: 100423832 | v-set and immunoglobulin domain-containing protein 8-like [*Macaca mulatta* (Rhesus monkey)] | Chromosome 1, NC_007858.1 (138468417..138477576, complement) | |
| 100403027 | V-set and immunoglobulin domain containing 8 [*Callithrix jacchus* (white-tufted-ear marmoset)] | Chromosome 18, NC_013913.1 (13411498..13416017, complement) | |

FIG. 16 (continued)

| | | |
|---|---|---|
| Select item 100346033 VSIG8 ID: 100346033 | V-set and immunoglobulin domain containing 8 [*Oryctolagus cuniculus* (rabbit)] | Chromosome 13, NC_013681.1 (33263970..33274518) |
| Select item 100090563 VSIG8 ID: 100090563 | V-set and immunoglobulin domain containing 8 [*Ornithorhynchus anatinus* (platypus)] | NW_001699398.1 (10996..16291, complement) |
| Select item 100053565 VSIG8 ID: 100053565 | V-set and immunoglobulin domain containing 8 [*Equus caballus* (horse)] | Chromosome 5, NC_009148.2 (37662328..37669027) |
| Select item 100023434 VSIG8 ID: 100023434 | V-set and immunoglobulin domain containing 8 [*Monodelphis domestica* (gray short-tailed opossum)] | Chromosome 2, NC_008802.1 (166113517..166123267) |
| Select item 101357103 LOC101357103 ID: 101357103 | V-set and immunoglobulin domain containing 8 [*Trichechus manatus latirostris* (Florida manatee)] | |

IDENTIFICATION OF VSIG8 AS THE PUTATIVE VISTA RECEPTOR (V-R) AND USE THEREOF TO PRODUCE VISTA/VSIG8 AGONISTS AND ANTAGONISTS

RELATED APPLICATIONS

This application claims priority to PCT Application No. PCT/US15/64146 filed Dec. 5, 2015, and U.S. Provisional Ser. No. 62/088,058 filed on Dec. 5, 2014, the contents of each of which is hereby incorporated by reference in its entirety.

SEQUENCE LISTING

The sequence listing in the file named "43260o1209" having a size of 33,060 bytes that was created Dec. 7, 2015 is hereby incorporated by reference in its entirety.

FIELD

The present application generally relates to the identification of the receptor for VISTA (V-region Immunoglobulin-containing Suppressor of T cell Activation[1]), a previously identified immunomodulatory polypeptide in the B7 family that regulates T cell activation and proliferation. The invention also relates to the use of the resultant receptor to produce compounds that agonize or antagonize the effects of VSIG8 which may be used as therapeutics, especially in the treatment of cancer, infectious conditions, autoimmunity, inflammation and allergic disorders. The invention specifically relates to the use of the resultant receptor to produce compounds that agonize or antagonize the VISTA/VISTA-R binding interaction. Also, the invention relates to the use of such agonists or antagonists to enhance or inhibit immune functions affected by VISTA such as $CD4^+$ or $CD8^+$ T cell proliferation, $CD4^+$ or $CD8^+$ T cell activation and the production of immune cytokines.

BACKGROUND

Immune negative checkpoint regulator (NCR) pathways have proven to be extraordinary clinical targets in the treatment of human immune-related diseases. Blockade of two NCRs, CTLA-4 and PD-1, using monoclonal antibodies (mAbs) to enhance tumor immunity is revolutionizing the treatment of cancer and has established these pathways as clinically validated targets in human disease. More recently, soluble versions of NCR ligands that trigger NCR pathways have entered the clinic as immunosuppressive drugs to treat autoimmunity (i.e., AMP-110/B7-H4-Ig for Rheumatoid arthritis), and early clinical results are eagerly awaited.

VISTA (V-region Immunoglobulin-containing Suppressor of T cell Activation (1), is a recently-identified, NCR ligand, whose closest phylogenetic relative is PD-L1. Like PD-L1, VISTA is a ligand that profoundly suppresses immunity (1), and like PD-L1, blocking VISTA allows for the development of therapeutic immunity to cancer in pre-clinical oncology models (2). Whereas blocking VISTA enhances immunity, especially $CD8^+$ and $CD4^+$ mediated T cell immunity, treatment with a soluble Ig fusion protein of the extracellular domain of VISTA (VISTA-Ig) suppresses immunity and has been shown to arrest the progression of multiple murine models of autoimmune disease.

Clear scientific evidence has shown that VISTA is a ligand that induces profound T cell suppression; however, the identity of the receptor that transduces this suppressive effect is currently unknown. Identification of receptors in the field of NCR pathways has been particularly challenging given their extremely low uM affinity and low density.

Herein we present experimental methods which have identified that "V-Set and Immunoglobulin domain containing 8" as the receptor for VISTA (hereinafter "V-R" or "VSIG8"). We further disclose assays that validate that VSIG8 specifically interacts with VISTA in vitro and in vivo and that the interaction of VISTA with VSIG8 has a suppressive effect on T cell activation, proliferation and/or immune cytokine production.

The identification of VSIG8 as the receptor for VISTA has much clinical and scientific promise. It is known that VISTA antagonists, e.g., αVISTA mAbs are useful as therapeutics in the treatment of oncology and infection. Also, fragments of VISTA may be used as VISTA antagonists and are potentially useful as therapeutics in the treatment of oncology and infection. Further, VISTA polypeptides, e.g., VISTA-Ig fusion proteins have been demonstrated to be useful in preventing and treating autoimmunity, inflammation and allergic disorders.

Therefore, VSIG8 will similarly be useful as it will provide a second, independent target for the development of VISTA-R agonists and antagonists. Indeed, with regard to receptors in the B7 family, the most effective therapeutics to emerge thus far are (αCTLA4 {Yervoy} and αPD-1 {Novolumab}) which both are antibodies that block receptor signaling rather than antibodies to the respective ligands.

Therefore, antibodies to VSIG8 which block or inhibit the VISTA/VISTA-R interaction should be effective in treating oncology and infectious disease. Particularly, VISTA-R antagonists will be potentially useful in the treatment of cancer or infectious disease indications such as melanoma and lung cancer or HIV infection. By contrast, VISTA-R agonists which promote or enhance the VISTA/VISTA-R binding interaction will potentially be useful in the treatment of autoimmune, allergic, and inflammatory indications, GVHD, transplant or other indications wherein the suppression of T cell activation, T cell proliferation or cytokine production is desired.

Moreover, the identification of the V-R will greatly expedite the clinical development of VISTA-Ig as an immunosuppressive drug, and further facilitate the ascertainment of pharmacodynamics, target engagement, and pharmacokinetic studies, which may be used to ascertain the level of receptor occupancy required to produce optimal clinical results.

The present invention satisfies these objectives by identifying VSIG8 as the receptor for VISTA.

SUMMARY

It is an object of the invention to identify and confirm using binding and functional assays that VSIG8 is the receptor for VISTA.

It is also an object of the invention to use the identified receptor to produce compounds, such as agonistic and antagonistic anti-VISTA-R antibodies, and VISTA-R polypeptides, VISTA-R fragments and derivatives and VISTA-R fusion proteins that agonize or antagonize the VISTA/VISTA-R binding interaction.

It is also an object of the invention to use VSIG8 agonists or antagonists, e.g., agonistic and antagonistic anti-VSIG8 antibodies, and VSIG8 polypeptides, VSIG8 fragments and derivatives and VISTA-R fusion proteins that agonize or antagonize VISTA-R and/or the VISTA/VISTA-R binding interaction to modulate immunity, especially T cell and dendritic cell immunity.

It is also a specific object of the invention to use VISTA-R agonists or antagonists, e.g., agonistic and antagonistic anti-VISTA-R antibodies, and VISTA-R polypeptides, VISTA-R fragments and derivatives and VISTA-R fusion proteins that agonize or antagonize VISTA-R and/or the VISTA/VISTA-R binding interaction to modulate $CD4^+$ or $CD8^+$ T cell activation, proliferation, and the production of cytokines.

It is also a specific object of the invention to use VISTA-R agonists or antagonists, e.g., agonistic and antagonistic anti-VISTA-R antibodies, and VISTA-R polypeptides, VISTA-R fragments and derivatives and VISTA-R fusion proteins that agonize or antagonize VISTA-R and/or the VISTA/VISTA-R binding interaction to treat cancer, infectious disease such as viral infection.

It is also a specific object of the invention to use VISTA-R agonists or antagonists, e.g., agonistic and antagonistic anti-VISTA-R antibodies, and VISTA-R polypeptides, VISTA-R fragments and derivatives and VISTA-R fusion proteins that agonize or antagonize VISTA-R and/or the VISTA/VISTA-R binding interaction to treat autoimmune, allergic and inflammatory disease indications.

It is a further object of the invention to use the identified V-R to expedite the clinical development of VISTA-Ig as an immunosuppressive drug, and facilitate the ascertainment of pharmacodynamics, target engagement, and pharmacokinetic studies and to define the level of receptor occupancy, and dosage required to produce optimal clinical results for VISTA-Ig therapeutic compounds.

It is a specific object of the invention to provide a compound which agonizes or antagonizes the interaction of VISTA and VSIG8, e.g., an antibody or antibody fragment that specifically binds VSIG8, such as an agonistic anti-VSIG8 antibody or antibody fragment or an antagonistic anti-VSIG8 antibody or antibody fragment.

It is a specific object of the invention to provide a compound which agonizes or antagonizes the interaction of VISTA and VSIG8, e.g. a humanized, human, primatized, or chimeric anti-VSIG8 antibody or antibody fragment, e.g., a Fab, Fab', scFv or $Fab_2$.

It is a specific object of the invention to provide a compound which agonizes or antagonizes the interaction of VISTA and VSIG8, e.g. a compound comprising all or a portion of the extracellular region of VSIG8 or a derivative of said extracellular region that possesses at least 80, 90, 95, or greater % sequence identity to the extracellular region of VSIG8, preferably human, primate or murine VSIG8.

It is a specific object of the invention to provide a compound which agonizes or antagonizes the interaction of VISTA and VSIG8, e.g., a compound which comprises the entire or at least 90% of the entire extracellular region of VSIG8.

It is a specific object of the invention to provide a compound which antagonizes the interaction of VISTA and VSIG8, preferably human, primate or murine VSIG8 and/or VISTA.

It is a specific object of the invention to provide a compound which agonizes or antagonizes the interaction of VISTA and VSIG8, e.g., a VSIG8 fusion protein such as a VSIG8-Ig fusion protein, preferably one comprising a human IgG1, IgG2, IgG3 or IgG4 constant region or fragment thereof, which optionally is mutagenized to eliminate FcR or complement binding or another Fc effector function.

It is a specific object of the invention to provide a compound which agonizes or antagonizes the interaction of VISTA and VSIG8, e.g. one which comprises an IgG1 or IgG3 constant region or portion thereof, which optionally is mutagenized to enhance FcR or complement binding or another Fc effector function.

It is a specific object of the invention to provide a compound which agonizes or antagonizes the interaction of VISTA and VSIG8, e.g. which is attached to a water soluble polymer to increase serum half-life such as a Pegylated protein.

It is a specific object of the invention to provide an isolated complex comprising VISTA and VSIG8, e.g., wherein either or both of said VISTA and/or VSIG8 are multimeric.

It is a specific object of the invention to provide a recombinant cell or an isolated cell membrane that is engineered to express VISTA and/or VSIG8 and which comprises on its surface a complex comprising VISTA and VSIG8.

It is a specific object of the invention to provide an antibody or antibody fragment that specifically binds to an isolated complex comprising VISTA and VSIG8, e.g., wherein said VISTA and/or VSIG8 is multimeric, and further wherein the antibody is preferably human, humanized, primatized or chimeric or is a is a Fab, Fab', scFv or $Fab_2$.

It is another specific object of the invention to provide an antibody or antibody fragment that specifically binds to an isolated complex comprising VISTA and VSIG8, e.g., wherein said VISTA and/or VSIG8 is multimeric, wherein the antibody does not appreciably bind monovalent or non-complexed VISTA or VSIG8 and further wherein the antibody is preferably human, humanized, primatized or chimeric or is a FAb, FAb', scFv or $Fab_2$.

It is another specific object of the invention to provide methods of using an antagonist compound according to the invention to inhibit the interaction of VISTA and VSIG8, e.g. to inhibit or block VISTA-associated suppression of T cell activation, proliferation or cytokine production, e.g., to treat a cancer or infectious disease such as a viral, bacterial, protozoan, yeast or fungal, or parasitic disease.

It is another specific object of the invention to provide methods of using an agonist compound according to the invention to enhance the Interaction of VISTA and VSIG8 and thereby potentiate VISTA-associated suppression of T cell activation, proliferation or cytokine production e.g., to treat an autoimmune, allergic or inflammatory condition.

It is another specific object of the invention to provide an agonist or antagonist compound according to the invention which is attached to a detectable label, linker or a therapeutic moiety.

It is another specific object of the invention to provide a diagnostic or therapeutic composition comprising a diagnostically or therapeutically effective amount of an agonist or antagonist compound according to the invention, e.g., which is suitable for use in human therapy, such as an Intravenous, subcutaneous or intramuscularly administrable composition.

It is another specific object of the invention to provide a diagnostic or therapeutic methods which use an agonist or antagonist compound according to the invention in association with a PD-1 or PD-L1 agonist or antagonist, e.g., wherein the PD-1 or PD-L1 agonist or antagonist is selected from an anti-PD-1 antibody or antibody fragment, an anti-PD-L1 antibody or antibody fragment, a PD-L1 polypeptide or fragment thereof which may be monovalent or multimeric, a PD-1 polypeptide or fragment thereof which may be monovalent or multimeric, or a complex or fusion protein comprising any of the foregoing.

It is another specific object of the invention to provide methods of contacting immune cells in vitro or in vivo with an agonist or antagonist compound according to the invention, e.g., human immune cells, e.g., wherein the contacted cells are infused into a human subject such as a subject who has cancer or an infectious disease or one who has an inflammatory, allergic or autoimmune condition.

It is another specific object of the invention to provide a screening assay which comprises the use of VSIG8 alone or in association with VISTA-R to identify VSIG8/VISTA agonists or antagonists, preferably a binding assay that identifies compounds that bind VSIG8 and inhibit the VSIG8/VISTA interaction such as compounds that bind VSIG8 and enhance the VSIG8/VISTA interaction or compounds that inhibit the effects the VISTA/VSIG8 interaction on T cell immunity or cytokine production.

It is another specific object of the invention to provide a screening assay which comprises the use of VSIG8 alone or in association with VISTA-R to identify VSIG8/VISTA agonists or antagonists, preferably a functional assay that screens for compounds that enhance the effects the VISTA/VSIG8 interaction on T cell immunity or cytokine production. These assays may be in vitro or use a transgenic animal that expresses human or rodent VISTA and/or human or rodent VSIG8, and may be high throughput screening assays.

BRIEF DESCRIPTION OF THE DRAWINGS

FIG. 15 contains experiments showing the upregulation of different immune proteins on VSIG8 expressing A20 cells treated with VISTA-Ig including PD-1.

FIG. 16 contains a Table identifying different sequences of species orthologs of VSIG8.

DETAILED DESCRIPTION

Figure 1:
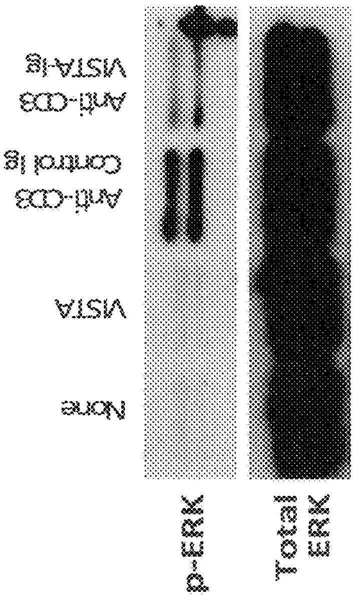
FIG. 1 contains the results of an experiment showing that VISTA inhibits early TCR-induced T cell activation. In the experiment T cells were isolated and cultured for 10 minutes with the □CD3+/− control Ig or VISTA-Ig. Total ERK and phosphor-Erk was detected.

Unless defined otherwise, all technical and scientific terms used herein have the same meaning as those commonly understood by one of ordinary skill in the art to which this invention belongs. Although methods and materials similar or equivalent to those described herein may be used in the invention or testing of the present invention, suitable methods and materials are described herein. The materials, methods and examples are illustrative only, and are not intended to be limiting. The nomenclatures utilized in connection with, and the laboratory procedures and techniques of, analytical chemistry, synthetic organic chemistry, and medicinal and pharmaceutical chemistry described herein are those well-known and commonly used in the art. Standard techniques may be used for chemical syntheses, chemical analyses, pharmaceutical preparation, formulation, and delivery, and treatment of patients.

As used in the description herein and throughout the claims that follow, the meaning of "a," "an," and "the" includes plural reference unless the context clearly dictates otherwise.

"Activating receptor," as used herein, refers broadly to immune cell receptors that bind antigen, complexed antigen (e.g., in the context of MHC molecules), Ig-fusion proteins, ligands, or antibodies. Activating receptors but are not limited to T cell receptors (TCRs), B cell receptors (BCRs), cytokine receptors, LPS receptors, complement receptors, and Fc receptors. For example, T cell receptors are present on T cells and are associated with CD3 molecules. T cell receptors are stimulated by antigen in the context of MHC molecules (as well as by polyclonal T cell activating reagents). T cell activation via the TCR results in numerous changes, e.g., protein phosphorylation, membrane lipid changes, ion fluxes, cyclic nucleotide alterations, RNA transcription changes, protein synthesis changes, and cell volume changes. For example, T cell receptors are present on T cells and are associated with CD3 molecules. T cell receptors are stimulated by antigen in the context of MHC molecules (as well as by polyclonal T cell activating reagents). T cell activation via the TCR results in numerous changes, e.g., protein phosphorylation, membrane lipid changes, ion fluxes, cyclic nucleotide alterations, RNA transcription changes, protein synthesis changes, and cell volume changes.

"Adjuvant" as used herein, refers to an agent used to stimulate the immune system and increase the response to a vaccine, without having any specific antigenic effect in itself.

"Aids in the diagnosis" or "aids in the detection" of a disease herein means that the expression level of a particular marker polypeptide or expressed RNA is detected alone or in association with one or more other markers in order to assess whether a subject has cells characteristic of a particular disease condition or the onset of a particular disease condition or comprises immune dysfunction such as immunosuppression characterized by VSIG8 and/or VISTA expression or abnormal immune upregulation characterized by cells having reduced VSIG8 levels, such as during autoimmunity, inflammation or allergic responses, e.g., in individuals with chronic and non-chronic diseases.

"Allergic disease," as used herein, refers broadly to a disease involving allergic reactions. More specifically, an "allergic disease" is defined as a disease for which an allergen is identified, where there is a strong correlation between exposure to that allergen and the onset of pathological change, and where that pathological change has been proven to have an immunological mechanism. Herein, an immunological mechanism means that leukocytes show an immune response to allergen stimulation.

"Amino acid," as used herein refers broadly to naturally occurring and synthetic amino acids, as well as amino acid analogs and amino acid mime tics that function in a manner similar to the naturally occurring amino acids. Naturally occurring amino acids are those encoded by the genetic code, as well as those amino acids that are later modified (e.g., hydroxyproline, γ-carboxyglutamate, and O-phosphoserine.) Amino acid analogs refers to compounds that have the same basic chemical structure as a naturally occurring amino acid (i.e., a carbon that is bound to a hydrogen, a carboxyl group, an amino group), and an R group (e.g., homoserine, norleucine, methionine sulfoxide, methionine methyl sulfonium.) Analogs may have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

"Anergy" or "tolerance," or "prolonged antigen-specific T cell suppression" or "prolonged immunosuppression" as used herein refers broadly to refractivity to activating receptor-mediated stimulation. Refractivity is generally antigen-specific and persists after exposure to the tolerizing antigen has ceased. For example, anergy in T cells (as opposed to unresponsiveness) is characterized by lack of cytokine production, e.g., IL-2. T cell anergy occurs when T cells are exposed to antigen and receive a first signal (a T cell receptor or CD-3 mediated signal) in the absence of a second signal (a costimulatory signal). Under these conditions, reexposure of the cells to the same antigen (even if reexposure occurs in the presence of a costimulatory molecule) results in failure to produce cytokines and, thus, failure to proliferate. Anergic T cells can, however, mount responses to unrelated antigens and can proliferate if cultured with cytokines (e.g., IL-2). For example, T cell anergy can also be observed by the lack of IL-2 production by T lymphocytes as measured by ELISA or by a proliferation assay using an indicator cell line. Alternatively, a reporter gene construct can be used. For example, anergic T cells fail to initiate IL-2 gene transcription induced by a heterologous promoter under the control of the 5' IL-2 gene enhancer or by a multimer of the API sequence that can be found within the enhancer (Kang et al. (1992) Science 257: 1134). Modulation of a costimulatory signal results in modulation of effector function of an immune cell.

"Antibody", as used herein, refers broadly to an "antigen-binding portion" of an antibody (also used interchangeably with "antibody portion," "antigen-binding fragment," "antibody fragment"), as well as whole antibody molecules. The term "antigen-binding portion", as used herein, refers to one or more fragments of an antibody that retain the ability to specifically bind to an antigen (e.g., VSIG8 and/or VISTA or specific portions thereof)). The term "antibody" as referred to herein includes whole polyclonal and monoclonal antibodies and any antigen-binding fragment (i.e., "antigen-binding portion") or single chains thereof. An "antibody" refers to a glycoprotein comprising at least two heavy (H) chains and two light (L) chains interconnected by disulfide bonds, or an antigen-binding portion thereof. Each heavy chain is comprised of at least one heavy chain variable region (abbreviated herein as $V_H$) and a heavy chain constant region. The heavy chain constant region is comprised of three domains, CHI, Cm and Cm—Each light chain is comprised of at least one light chain variable region (abbreviated herein as VL) and a light chain constant region. The light chain constant region is comprised of one domain, CL—The VH and $V_L$ regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, and FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system. More generally, the term "antibody" is intended to include any polypeptide chain-containing molecular structure with a specific shape that fits to and recognizes an epitope, where one or more non-covalent binding interactions stabilize the complex between the molecular structure and the epitope. The archetypal antibody molecule is the immunoglobulin, and all types of immunoglobulins, IgG, IgM, IgA, IgE, IgD, etc., from all sources, e.g. human, rodent, rabbit, cow, sheep, pig, dog, other mammals, chicken, other avians, etc., are considered to be "antibodies."

The antigen-binding function of an antibody can be performed by fragments of a full-length antibody. Non-limiting examples of antigen-binding fragments encompassed within the term "antigen-binding portion" of an antibody include (a) a Fab fragment, a monovalent fragment consisting of the $V_L$, $V_H$, $C_L$ and $C_{HI}$ domains; (b) a $F_{(ab')}^2$ fragment, a bivalent fragment comprising two Fab fragments linked by a disulfide bridge at the hinge region; (c) a Fd fragment consisting of the $V_H$ and $C_{HI}$ domains; (d) a $F_v$ fragment consisting of the $V_L$ and $V_H$ domains of a single arm of an antibody; (e) a dAb fragment (Ward, et al. (1989) Nature 341: 544-546), which consists of a $V_H$ domain; and (f) an isolated complementarily determining region (CDR). Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv). See e.g., Bird, et al. (1988) Science 242: 423-426; Huston, et al. (1988) Proc Natl. Acad. Sci. USA 85: 5879-5883; and Osbourn, et al. (1998) Nat. Biotechnol. 16: 778. Single chain antibodies are also intended to be encompassed within the term "antigen-binding portion" of an antibody. Any $V_H$ and $V_L$ sequences of specific scFv can be linked to human immunoglobulin constant region cDNA or genomic sequences, in order to generate expression vectors encoding complete IgG molecules or other isotypes. $V_H$ and $V_L$ can also be used in the generation of Fab, Fv, or other fragments of immunoglobulins using either protein chemistry or recombinant DNA technology. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen-binding sites. See e.g. Holliger, et al. (1993) *Proc Natl. Aced. Sci. USA* 90: 6444-6448; Poljak, et al. (1994) *Structure* 2: 1121-1123. Still further, an antibody or antigen-binding portion thereof (antigen-binding fragment, antibody fragment, antibody portion) may be part of a larger immunoadhesion molecules, formed by covalent or noncovalent association of the antibody or antibody portion with one or more other proteins or peptides. Examples of immunoadhesion molecules include use of the streptavidin core region to make a tetrameric scFv molecule (Kipriyanov, et al. (1995) *Hum. Antibodies Hybridomas* 6: 93-101) and use of a cysteine residue, a marker peptide and a C-terminal polyhistidine tag to make bivalent and biotinylated scFv molecules. Kipriyanov, et al. (1994) *Mol. Immunol.* 31: 1047-1058. Antibody portions, such as Fab and $F(ab')_2$ fragments, can be prepared from whole antibodies using conventional techniques, such as papain or pepsin digestion, respectively, of whole antibodies. Moreover, antibodies, antibody portions and immunoadhesion molecules can be obtained using standard recombinant DNA techniques, as described herein. Antibodies may be polyclonal, monoclonal, xenogeneic, allogeneic, syngeneic, or modified forms thereof, e.g., humanized, or chimeric antibodies.

"Antibody recognizing an antigen" and "an antibody specific for an antigen" is used interchangeably herein with the term "an antibody which binds specifically to an antigen" and refers to an immunoglobulin or fragment thereof that specifically binds an antigen.

"Antigen," as used herein, refers broadly to a molecule or a portion of a molecule capable of being bound by an antibody which is additionally capable of inducing an animal to produce an antibody capable of binding to an epitope of that antigen. An antigen may have one epitope, or have more than one epitope. The specific reaction referred to herein indicates that the antigen will react, in a highly selective manner, with its corresponding antibody and not with the multitude of other antibodies which may be evoked by other antigens. In the case of a desired enhanced immune response to particular antigens of interest, antigens include, but are not limited to; infectious disease antigens for which a protective immune response may be elicited are exemplary.

"Antigen presenting cell," as used herein, refers broadly to professional antigen presenting cells (e.g., B lymphocytes, monocytes, dendritic cells, and Langerhans cells) as well as other antigen presenting cells (e.g., keratinocytes, endothelial cells, astrocytes, fibroblasts, and oligodendrocytes).

"Antisense nucleic acid molecule," as used herein, refers broadly to a nucleotide sequence which is complementary to a "sense" nucleic acid encoding a protein (e.g., complementary to the coding strand of a double-stranded cDNA molecule) complementary to an mRNA sequence or complementary to the coding strand of a gene. Accordingly, an antisense nucleic acid molecule can hydrogen bond to a sense nucleic acid molecule.

"Apoptosis," as used herein, refers broadly to programmed cell death which can be characterized using techniques which are known in the art. Apoptotic cell death can be characterized by cell shrinkage, membrane blebbing, and chromatin condensation culminating in cell fragmentation. Cells undergoing apoptosis also display a characteristic pattern of internucleosomal DNA cleavage.

"Autoimmunity" or "autoimmune disease or condition," as used herein, refers broadly to a disease or disorder arising from and directed against an individual's own tissues or a co-segregate or manifestation thereof or resulting condition therefrom, and includes. Herein autoimmune conditions include inflammatory or allergic conditions, e.g., chronic diseases characterized by a host immune reaction against self-antigens potentially associated with tissue destruction such as rheumatoid arthritis.

"B cell receptor" (BCR)," as used herein, refers broadly to the complex between membrane Ig (mIg) and other transmembrane polypeptides (e.g., IgA, and Ig) found on B cells. The signal transduction function of mIg is triggered by crosslinking of receptor molecules by oligomeric or multimeric antigens. B cells can also be activated by anti-immunoglobulin antibodies. Upon BCR activation, numerous changes occur in B cells, including tyrosine phosphorylation.

"Cancer," as used herein, refers broadly to any neoplastic disease (whether invasive or metastatic) characterized by abnormal and uncontrolled cell division causing malignant growth or tumor (e.g., unregulated cell growth.) The term "cancer" or "cancerous" as used herein should be understood to encompass any neoplastic disease (whether invasive, non-invasive or metastatic) which is characterized by abnormal and uncontrolled cell division causing malignant growth or tumor, non-limiting examples of which are described herein. This includes any physiological condition in mammals that is typically characterized by unregulated cell growth. Examples of cancer are exemplified in the working examples. Further cancers include but are not limited to, carcinoma, lymphoma, blastoma, sarcoma, and leukemia. More particular examples of such cancers include squamous cell cancer, lung cancer (including small-cell lung cancer, non-small cell lung cancer, adenocarcinoma of the lung, and squamous carcinoma of the lung), cancer of the peritoneum, hepatocellular cancer, gastric or stomach cancer (including gastrointestinal cancer), pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney or renal cancer, liver cancer, prostate cancer, vulval cancer, thyroid cancer, hepatic carcinoma and various types of head and neck cancer, as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenström's Macroglobulinemia); chronic lymphocytic leukemia (CLL); acute lymphoblastic leukemia (ALL); Hairy cell leukemia; chronic myeloblasts leukemia; multiple myeloma and post-transplant lymphoproliferative disorder (PTLD). Other cancers amenable for treatment by the present invention include, but are not limited to, carcinoma, lymphoma, blastoma, sarcoma, and leukemia or lymphoid malignancies. More particular examples of such cancers include colorectal, bladder, ovarian, melanoma, squamous cell cancer, lung cancer (including small-cell lung cancer, non-small cell lung cancer, adenocarcinoma of the lung, and squamous carcinoma of the lung), cancer of the peritoneum, hepatocellular cancer, gastric or stomach cancer (including gastrointestinal cancer), pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney or renal cancer, liver cancer, prostate cancer, vulval cancer, thyroid cancer, hepatic carcinoma and various types of head and neck cancer, as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenström's Macroglobulinemia); chronic lymphocytic leukemia (CLL); acute lymphoblastic leukemia (ALL); Hairy cell leukemia; chronic myeloblastic leukemia; and post-transplant lymphoproliferative disorder (PTLD), as well as abnormal vascular proliferation associated with phakomatoses, edema (such as that associated with brain tumors), and Meigs' syndrome. Preferably, the cancer is selected from the group consisting of colorectal cancer, breast cancer, colorectal cancer, rectal cancer, non-small cell lung cancer, non-Hodgkin's lymphoma (NHL), renal cell cancer, prostate cancer, liver cancer, pancreatic cancer, soft-tissue sarcoma, Kaposi's sarcoma, carcinoid carcinoma, head and neck cancer, melanoma, ovarian cancer, mesothelioma, and multiple myeloma. In an exemplary embodiment the cancer is an early or advanced (including metastatic) bladder, ovarian or melanoma. In another embodiment the cancer is colorectal cancer. The cancerous conditions amenable for treatment of the invention include cancers that express or do not express VSIG8 and/or VISTA and further include non-metastatic or non-invasive as well as invasive or metastatic cancers wherein VSIG8 and/or VISTA expression by immune, stromal or diseased cells suppress antitumor responses and anti-invasive immune responses. The method of the present invention is particularly suitable for the treatment of vascularized tumors.

Cancers according to the invention include cancers that express or do not express VSIG8 and/or VISTA and further include non-metastatic or non-invasive as well as invasive or metastatic cancers wherein VSIG8 and/or VISTA expression by immune, stromal or diseased cells suppress antitumor responses and anti-invasive immune responses, and those characterized by vascularized tumors.

"Cancer therapy" herein refers to any method which prevents or treats cancer or ameliorates one or more of the symptoms of cancer. Typically such therapies will comprise the administration of an immunostimulatory VSIG8 and/or VISTA polypeptide or fusion protein, conjugate, multimer (homomultimer or heteromultimer) or composition containing according to the invention either alone or more typically in combination with chemotherapy or radiotherapy or other biologies and for enhancing the activity thereof, i.e., in individuals wherein VSIG8 and/or VISTA expression suppress antitumor responses and the efficacy of chemotherapy or radiotherapy or biologic efficacy. Any chemotherapeutic agent exhibiting anticancer activity can be used according to the present invention. Preferably, the chemotherapeutic agent is selected from the group consisting of alkylating agents, antimetabolites, folic acid analogs, pyrimidine analogs, purine analogs and related inhibitors, *vinca* alkaloids, epipodophyllotoxins, antibiotics, L-Asparaginase, topoisomerase inhibitor, interferons, platinum coordination complexes, anthracenedione substituted urea, methyl hydrazine derivatives, adrenocortical suppressant, adrenocorticosteroids, progestins, estrogens, antiestrogen, androgens, antiandrogen, and gonadotropin-releasing hormone analog. More preferably, the chemotherapeutic agent is selected from the group consisting of 5-fluorouracil (5-FU), leucovorin (LV), irinotecan, oxaliplatin, capecitabine, paclitaxel and docetaxel. Two or more chemotherapeutic agents can be used in a cocktail to be administered in combination with administration of the anti-VEGF antibody. One preferred combination chemotherapy is fluorouracil-based, comprising 5-FU and one or more other chemotherapeutic agent(s). Suitable dosing regimens of combination chemotherapies are known in the art and described in, for example, Saltz et al. Proc ASCO 18:233 (1999) and Douillard et al. Lancet 355: 1041-7 (2000). The biologic may be another immune potentiator such as antibodies to PD-L1, PD-L2, CTLA-4, or VISTA as well as PD-L1, PD-L2, CTLA-4 or VISTA fusion proteins as well as cytokines, growth factor antagonists and agonists, hormones and anti-cytokine antibodies.

"Chimeric antibody," as used herein, refers broadly to an antibody molecule in which the constant region, or a portion thereof, is altered, replaced or exchanged so that the antigen-binding site (variable region) is linked to a constant region of a different or altered class, effector function and/or species, or an entirely different molecule which confers new properties to the chimeric antibody, e.g., an enzyme, toxin, hormone, growth factor, drug, the variable region or a portion thereof, is altered, replaced or exchanged with a variable region having a different or altered antigen specificity.

"Coding region," as used herein, refers broadly to regions of a nucleotide sequence comprising codons which are translated into amino acid residues, whereas the term "non-coding region" refers to regions of a nucleotide sequence that are not translated into amino acids (e.g., 5' and 3' untranslated regions).

"Conservatively modified variants," as used herein, applies to both amino acid and nucleic acid sequences, and with respect to particular nucleic acid sequences, refers broadly to conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. "Silent variations" are one species of conservatively modified nucleic acid variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) may be modified to yield a functionally identical molecule.

"Complementarity determining region," "hypervariable region," or "CDR," as used herein, refers broadly to one or more of the hyper-variable or complementarily determining regions (CDRs) found in the variable regions of light or heavy chains of an antibody. See Kabat, et al. (1987) *Sequences of Proteins of Immunological Interest* National Institutes of Health, Bethesda, Md. These expressions include the hypervariable regions as defined by Kabat, et al. (1983) Sequences of Proteins of Immunological Interest, U. S. Dept. of Health and Human Services or the hypervariable loops in 3-dimensional structures of antibodies. Chothia and Lesk (1987) *J. Mol. Biol.* 196: 901-917. The CDRs in each chain are held in close proximity by framework regions and, with the CDRs from the other chain, contribute to the formation of the antigen-binding site. Within the CDRs there are select amino acids that have been described as the selectivity determining regions (SDRs) which represent the critical contact residues used by the CDR in the antibody-antigen interaction. (Kashmiri *Methods* 36: 25-34(2005)).

"Control amount," as used herein, refers broadly to a marker can be any amount or a range of amounts to be compared against a test amount of a marker. For example, a control amount of a marker may be the amount of a marker in a patient with a particular disease or condition or a person without such a disease or condition. A control amount can be either in absolute amount (e.g., microgram/ml) or a relative amount (e.g., relative intensity of signals).

"Costimulatory receptor," as used herein, refers broadly to receptors which transmit a costimulatory signal to an immune cell, e.g., CD28 or ICOS. As used herein, the term "inhibitory receptors" includes receptors which transmit a negative signal to an immune cell, e.g., a T cell or an NK cell.

"Costimulate," as used herein, refers broadly to the ability of a costimulatory molecule to provide a second, non-activating, receptor-mediated signal (a "costimulatory signal") that induces proliferation or effector function. For example, a costimulatory signal can result in cytokine secretion (e.g., in a T cell that has received a T cell-receptor-mediated signal) Immune cells that have received a cell receptor-mediated signal (e.g., via an activating receptor) may be referred to herein as "activated immune cells." With respect to T cells, transmission of a costimulatory signal to a T cell involves a signaling pathway that is not inhibited by cyclosporin A. In addition, a costimulatory signal can induce cytokine secretion (e.g., IL-2 and/or IL-10) in a T cell and/or can prevent the induction of unresponsiveness to antigen, the induction of anergy, or the induction of cell death in the T cell.

"Costimulatory polypeptide" or "costimulatory molecule" herein refers to a polypeptide that, upon interaction with a cell-surface molecule on T cells, modulates T cell responses.

"Costimulatory signaling" as used herein is the signaling activity resulting from the interaction between costimulatory polypeptides on antigen presenting cells and their receptors on T cells during antigen-specific T cell responses. Without wishing to be limited by a single hypothesis, the antigen-specific T cell response is believed to be mediated by two signals: 1) engagement of the T cell Receptor (TCR) with antigenic peptide presented in the context of MHC (signal 1), and 2) a second antigen-independent signal delivered by contact between different costimulatory receptor/ligand pairs (signal 2). Without wishing to be limited by a single hypothesis, this "second signal" is critical in determining the type of T cell response (activation vs inhibition) as well as the strength and duration of that response, and is regulated by both positive and negative signals from costimulatory molecules, such as the B7 family of proteins.

"B7" polypeptide herein means a member of the B7 family of proteins that costimulate T cells including, but not limited to B7-1, B7-2, B7-DC, B7-H5, B7-HI, B7-H2, B7-H3, B7-H4, B7-H6, B7-S3 and biologically active fragments and/or variants thereof. Representative biologically active fragments include the extracellular domain or fragments of the extracellular domain that costimulate T cells.

"Cytoplasmic domain," as used herein, refers broadly to the portion of a protein which extends into the cytoplasm of a cell.

"Diagnostic," as used herein, refers broadly to identifying the presence or nature of a pathologic condition. Diagnostic methods differ in their sensitivity and specificity. The "sensitivity" of a diagnostic assay is the percentage of diseased individuals who test positive (percent of "true positives"). Diseased individuals not detected by the assay are "false negatives." Subjects who are not diseased and who test negative in the assay are termed "true negatives." The "specificity" of a diagnostic assay is 1 minus the false positive rate, where the "false positive" rate is defined as the proportion of those without the disease who test positive. While a particular diagnostic method may not provide a definitive diagnosis of a condition, it suffices if the method provides a positive indication that aids in diagnosis.

"Diagnosing," or "aiding in the diagnosis" as used herein refers broadly to classifying a disease or a symptom, and/or determining the likelihood that an individual has a disease condition (e.g., based on absence or presence of VSIG8 and/or VISTA expression, and/or increased or decreased expression by immune, stromal and/or putative diseased cells); determining a severity of the disease, monitoring disease progression, forecasting an outcome of a disease and/or prospects of recovery. The term "detecting" may also optionally encompass any of the foregoing. Diagnosis of a disease according to the present invention may, in some embodiments, be affected by determining a level of a polynucleotide or a polypeptide of the present invention in a biological sample obtained from the subject, wherein the level determined can be correlated with predisposition to, or presence or absence of the disease. It should be noted that a "biological sample obtained from the subject" may also optionally comprise a sample that has not been physically removed from the subject.

"Effective amount," as used herein, refers broadly to the amount of a compound, antibody, antigen, or cells that, when administered to a patient for treating a disease, is sufficient to effect such treatment for the disease. The effective amount may be an amount effective for prophylaxis, and/or an amount effective for prevention. The effective amount may be an amount effective to reduce, an amount effective to prevent the incidence of signs/symptoms, to reduce the severity of the incidence of signs/symptoms, to eliminate the incidence of signs/symptoms, to slow the development of the Incidence of signs/symptoms, to prevent the development of the incidence of signs/symptoms, and/or effect prophylaxis of the incidence of signs/symptoms. The "effective amount" may vary depending on the disease and its severity and the age, weight, medical history, susceptibility, and pre-existing conditions, of the patient to be treated. The term "effective amount" is synonymous with "therapeutically effective amount" for purposes of this invention.

"Extracellular domain" or "ECD" as used herein refers broadly to the portion of a protein that extends from the surface of a cell.

"Expression vector," as used herein, refers broadly to any recombinant expression system for the purpose of expressing a nucleic acid sequence of the invention in vitro or in vivo, constitutively or inducibly, in any cell, including prokaryotic, yeast, fungal, plant, insect or mammalian cell. The term includes linear or circular expression systems. The term includes expression systems that remain episomal or integrate into the host cell genome. The expression systems can have the ability to self-replicate or not, i.e., drive only transient expression in a cell. The term includes recombinant expression cassettes which contain only the minimum elements needed for transcription of the recombinant nucleic acid.

"Family," as used herein, refers broadly to the polypeptide and nucleic acid molecules of the Invention is intended to mean two or more polypeptide or nucleic acid molecules having a common structural domain or motif and having sufficient amino acid or nucleotide sequence homology as defined herein. Family members can be naturally or non-naturally occurring and can be from either the same or different species. For example, a family can contain a first polypeptide of human origin, as well as other, distinct polypeptides of human origin or alternatively, can contain homologues of non-human origin (e.g., monkey polypeptides.) Members of a family may also have common functional characteristics.

"Fc receptor" (FcRs) as used herein, refers broadly to cell surface receptors for the Fc portion of immunoglobulin molecules (Igs). Fc receptors are found on many cells which participate in immune responses. Among the human FcRs that have been identified so far are those which recognize IgG (designated FcyR), IgE (FceRI), IgA (FcaR), and polymerized IgM/A (FcεμR). FcRs are found in the following cell types: FceRI (mast cells), FceRII (many leukocytes), FcaR (neutrophils), and FcμR (glandular epithelium, hepatocytes). (Hogg *Immunol. Today* 9: 185-86 (1988)). The widely studied FcyRs are central in cellular immune defenses, and are responsible for stimulating the release of mediators of inflammation and hydrolytic enzymes involved in the pathogenesis of autoimmune disease. (Unkeless, *Annu. Rev. Immunol.* 6: 251-87 (1988)). The FcyRs provide a crucial link between effector cells and the lymphocytes that secrete Ig, since the macrophage/monocyte, polymorphonuclear leukocyte, and natural killer (NK) cell FcyRs confer an element of specific recognition mediated by IgG. Human leukocytes have at least three different receptors for IgG: hFcμRI (found on monocytes/macrophages), hFcyRII (on monocytes, neutrophils, eosinophils, platelets, possibly B cells, and the K562 cell line), and FcyIII (on NK cells, neutrophils, eosinophils, and macrophages).

"Framework region" or "FR," as used herein refers broadly to one or more of the framework regions within the variable regions of the light and heavy chains of an antibody. See Kabat, et al. "*Sequences of Proteins of Immunological Interest*" National Institutes of Health, Bethesda, Md. (1987). These expressions include those amino acid sequence regions interposed between the CDRs within the variable regions of the light and heavy chains of an antibody.

"Heterologous," as used herein, refers broadly to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid (e.g., a promoter from one source and a coding region from another source.) Similarly, a heterologous protein indicates that the protein comprises two or more subsequences that are not found in the same relationship to each other in nature (e.g., a fusion protein).

"High affinity," as used herein, refers broadly to an antibody or fusion protein having a $K_D$ of at least $10^{-6}$ M, more preferably $10^{-7}$ M, even more preferably at least $10^{-8}$ M and even more preferably at least $10^{-9}$ M, $10^{-10}$ M, $10^{-11}$ M, or $10^{-12}$ M for a target antigen or receptor.

"High affinity" for an IgG antibody or fusion protein herein refers to an antibody having a KD of $10^{-6}$ M or less, more preferably $10^{-7}$ M or less, preferably $10^{-8}$ M or less, more preferably $10^{-9}$ M or less and even more preferably $10^{-10}$ M, $10"^{-11}$ M, or $10^{-12}$ M or less for a target antigen or receptor. With particular respect to antibodies, "high affinity" binding can vary for different antibody isotypes. For example, "high affinity" binding for an IgM isotype refers to an antibody having a $K_D$ of $10^{-7}$ M or less, more preferably $10^{-8}$ M or less.

"Homology," as used herein, refers broadly to a degree of similarity between a nucleic acid sequence and a reference nucleic acid sequence or between a polypeptide sequence and a reference polypeptide sequence. Homology may be partial or complete. Complete homology indicates that the nucleic acid or amino acid sequences are identical. A partially homologous nucleic acid or amino acid sequence is one that is not identical to the reference nucleic acid or amino acid sequence. The degree of homology can be determined by sequence comparison, for example using BlastP software of the National Center of Biotechnology Information (NCBI) using default parameters. The term "sequence identity" may be used interchangeably with "homology."

"Host cell," as used herein, refers broadly to refer to a cell into which a nucleic acid molecule of the invention, such as a recombinant expression vector of the invention, has been introduced. Host cells may be prokaryotic cells (e.g., *E. coli*), or eukaryotic cells such as yeast, insect (e.g., SF9), amphibian, or mammalian cells such as CHO, HeLa, HEK-293, e.g., cultured cells, explants, and cells in vivo. The terms "host cell" and "recombinant host cell" are used interchangeably herein. It should be understood that such terms refer not only to the particular subject cell but to the progeny or potential progeny of such a cell. Because certain modifications may occur in succeeding generations due to either mutation or environmental influences, progeny may not, in fact, be identical to the parent cell, but are still included within the scope of the term as used herein.

"Human monoclonal antibody" refers to antibodies displaying a single binding specificity which have variable regions in which both the framework and CDR regions are derived from human germline immunoglobulin sequences. In one embodiment, the human monoclonal antibodies are produced by a hybridoma which includes a B cell obtained from a transgenic nonhuman animal, e.g., a transgenic mouse, having a genome comprising a human heavy chain transgene and a light chain transgene fused to an immortalized cell. This includes fully human monoclonal antibodies and conjugates and variants thereof, e.g., which are bound to effector agents such as therapeutics or diagnostic agents.

"Humanized antibody," as used herein, refers broadly to include antibodies made by a non-human cell having variable and constant regions which have been altered to more closely resemble antibodies that would be made by a human cell. For example, by altering the non-human antibody amino acid sequence to incorporate amino acids found in human germline immunoglobulin sequences. The humanized antibodies of the invention may include amino acid residues not encoded by human germline immunoglobulin sequences (e.g., mutations introduced by random or site-specific mutagenesis in vitro or by somatic mutation in vivo), for example in the CDRs. The term "humanized antibody", as used herein, also includes antibodies in which CDR sequences derived from the germline of another mammalian species, such as a mouse, have been grafted onto human framework sequences.

"Hybridization," as used herein, refers broadly to the physical interaction of complementary (including partially complementary) polynucleotide strands by the formation of hydrogen bonds between complementary nucleotides when the strands are arranged antiparallel to each other.

"IgV domain" and "IgC domain" as used herein, refer broadly to Ig superfamily member domains. These domains correspond to structural units that have distinct folding patterns called Ig folds. Ig folds are comprised of a sandwich of two β sheets, each consisting of antiparallel β strands of 5-10 amino acids with a conserved disulfide bond between the two sheets in most, but not all, domains. IgC domains of Ig, TCR, and MHC molecules share the same types of sequence patterns and are called the CI set within the Ig superfamily. Other IgC domains fall within other sets. IgV domains also share sequence patterns and are called V set domains. IgV domains are longer than C-domains and form an additional pair of β strands.

"Immune cell," as used herein, refers broadly to cells that are of hematopoietic origin and that play a role in the immune response. Immune cells include but are not limited to lymphocytes, such as B cells and T cells; natural killer cells; dendritic cells, and myeloid cells, such as monocytes, macrophages, eosinophils, mast cells, basophils, and granulocytes.

"Immunoassay," as used herein, refers broadly to an assay that uses an antibody to specifically bind an antigen. The immunoassay may be characterized by the use of specific binding properties of a particular antibody to isolate, target, and/or quantify the antigen.

"Immune related disease (or disorder or condition)" as used herein should be understood to encompass any disease disorder or condition selected from the group including but not limited to autoimmune diseases, inflammatory disorders and immune disorders associated with graft transplantation rejection, such as acute and chronic rejection of organ transplantation, allogenic stem cell transplantation, autologous stem cell transplantation, bone marrow transplantation, and graft versus host disease.

"Immune response," as used herein, refers broadly to T cell-mediated and/or B cell-mediated immune responses that are influenced by modulation of T cell costimulation. Exemplary immune responses include B cell responses (e.g., antibody production) T cell responses (e.g., cytokine production, and cellular cytotoxicity) and activation of cytokine responsive cells, e.g., macrophages. As used herein, the term "downmodulation" with reference to the immune response includes a diminution in any one or more immune responses, while the term "upmodulation" with reference to the immune response includes an increase in any one or more immune responses. It will be understood that upmodulation of one type of immune response may lead to a corresponding downmodulation in another type of immune response. For example, upmodulation of the production of certain cytokines (e.g., IL-10) can lead to downmodulation of cellular immune responses.

"Immunologic", "immunological" or "immune" response herein refer to the development of a humoral (antibody mediated) and/or a cellular (mediated by antigen-specific T cells or their secretion products) response directed against a peptide in a recipient patient. Such a response can be an active response Induced by administration of immunogen or a passive response induced by administration of antibody or primed T-cells. Without wishing to be limited by a single hypothesis, a cellular immune response is elicited by the presentation of polypeptide epitopes in association with Class II or Class I MHC molecules to activate antigen-specific $CD4^+$ T helper cells and/or $CD8^+$ cytotoxic T cells, respectively. The response may also involve activation of monocytes, macrophages, NK cells, basophils, dendritic cells, astrocytes, microglia cells, eosinophils, activation or recruitment of neutrophils or other components of innate immunity. The presence of a cell-mediated immunological response can be determined by proliferation assays ($CD4^+$ T cells) or CTL (cytotoxic T lymphocyte) assays. The relative contributions of humoral and cellular responses to the protective or therapeutic effect of an immunogen can be distinguished by separately isolating antibodies and T cells from an immunized syngeneic animal and measuring protective or therapeutic effect in a second subject.

"Immunogenic agent" or "immunogen" is a moiety capable of inducing an immunological response against itself on administration to a mammal, optionally in conjunction with an adjuvant.

"Infectious agent" herein refers to any pathogen or agent that infects mammalian cells, preferably human cells and causes a disease condition. Examples thereof include bacteria, yeast, fungi, protozoans, *mycoplasma*, viruses, prions, and parasites. Examples of such infectious agents include by way of example those involved in (a) viral diseases such as, for example, diseases resulting from infection by an adenovirus, a herpesvirus (e.g., HSV-I, HSV-II, CMV, or VZV), a poxvirus (e-g-, an orthopoxvirus such as variola or vaccinia, or molluscum contagiosum), a picornavirus (e.g., rhinovirus or enterovirus), an orthomyxovirus (e.g., influenzavirus), a paramyxovirus (e.g., parainfluenza virus, mumps virus, measles virus, and respiratory syncytial virus (RSV)), a coronavirus (e.g., SARS), a papovavirus (e.g., papillomaviruses, such as those that cause genital warts, common warts, or plantar warts), a hepadnavirus (e.g., hepatitis B virus), a flavivirus (e.g., hepatitis C virus or Dengue virus), or a retrovirus (e.g., a lentivirus such as HIV); (b) bacterial diseases such as, for example, diseases resulting from infection by bacteria of, for example, the genus *Escherichia, Enterobacter, Salmonella, Staphylococcus, Shigella, Listeria, Aerobacter, Helicobacter, Klebsiella, Proteus, Pseudomonas, Streptococcus, Chlamydia, Mycoplasma, Pneumococcus, Neisseria, Clostridium, Bacillus, Corynebacterium, Mycobacterium, Campylobacter, Vibrio, Serratia, Providencia, Chromobacterium, Brucella, Yersinia, Haemophilus*, or *Bordetella*; (c) other infectious diseases, such *chlamydia*, fungal diseases including but not limited to candidiasis, aspergillosis, histoplasmosis, cryptococcal meningitis, parasitic diseases including but not limited to malaria, *Pneumocystis carnii* pneumonia, leishmaniasis, cryptosporidiosis, toxoplasmosis, and trypanosome infection and prions that cause human disease such as Creutzfeldt-Jakob Disease (CJD), variant Creutzfeldt-Jakob Disease (vCJD), Gerstmann-Straüssler-Scheinker syndrome, Fatal Familial Insomnia and kuru.

"Infectious agent antigen" herein means a compound, e.g., peptide, polypeptide, glycopeptide, glycoprotein, and the like, or a conjugate, fragment or variant thereof, which compound is expressed by a specific infectious agent and which antigen may be used to elicit a specific immune response, e.g., antibody or cell-mediated immune response against the infectious agent such as a virus. Typically the antigen will comprise a moiety, e.g., polypeptide or glycoprotein expressed on the surface of the virus or other infectious agent, such as a capsid protein or other membrane protein.

"Inflammatory bowel disease" herein comprises any inflammatory bowel condition and especially includes Inflammatory bowel disease, Crohn's disease, ulcerative colitis (UC), collagenous colitis, lymphocytic colitis, ischemic colitis, diversion colitis, Behçet's disease, and indeterminate colitis.

"Inflammatory disorders", "inflammatory conditions" and/or "inflammation", used interchangeably herein, refers broadly to chronic or acute inflammatory diseases, and expressly includes inflammatory autoimmune diseases and inflammatory allergic conditions. These conditions include by way of example inflammatory abnormalities characterized by dysregulated immune response to harmful stimuli, such as pathogens, damaged cells, or irritants. Inflammatory disorders underlie a vast variety of human diseases. Non-immune diseases with etiological origins in inflammatory processes include cancer, atherosclerosis, and ischemic heart disease. Examples of disorders associated with inflammation include: Chronic prostatitis, Glomerulonephritis, Hypersensitivities, Pelvic inflammatory disease, Reperfusion injury, Sarcoidosis, Vasculitis, Interstitial cystitis, normocomplementemic urticarial vasculitis, pericarditis, myositis, anti-synthetase syndrome, scleritis, macrophage activation syndrome, Behçet's Syndrome, PAPA Syndrome, Blau's Syndrome, gout, adult and juvenile Still's disease, cryropyrinopathy, Muckle-Wells syndrome, familial cold-induced auto-inflammatory syndrome, neonatal onset multisystemic inflammatory disease, familial Mediterranean fever, chronic infantile neurologic, cutaneous and articular syndrome, systemic juvenile idiopathic arthritis, Hyper IgD syndrome, Schnitzler's syndrome, TNF receptor-associated periodic syndrome (TRAPSP), gingivitis, periodontitis, hepatitis, cirrhosis, pancreatitis, myocarditis, vasculitis, gastritis, gout, gouty arthritis, and inflammatory skin disorders, selected from the group consisting of psoriasis, atopic dermatitis, eczema, rosacea, urticaria, and acne.

"Inhibitory signal," as used herein, refers broadly to a signal transmitted via an inhibitory receptor molecule on an immune cell. A signal antagonizes a signal via an activating receptor (e.g., via a TCR, CD3, BCR, or Fc molecule) and can result, e.g., in inhibition of: second messenger generation; proliferation; or effector function in the immune cell, e.g., reduced phagocytosis, antibody production, or cellular cytotoxicity, or the failure of the immune cell to produce mediators (e.g., cytokines (e.g., IL-2) and/or mediators of allergic responses); or the development of anergy.

"Isolated," as used herein, refers broadly to material removed from its original environment in which it naturally occurs, and thus is altered by the hand of man from its natural environment and includes "recombinant" polypeptides. Isolated material may be, for example, exogenous nucleic acid included in a vector system, exogenous nucleic acid contained within a host cell, or any material which has been removed from its original environment and thus altered by the hand of man (e.g., "isolated antibody"). For example, "isolated" or "purified," as used herein, refers broadly to a protein, DNA, antibody, RNA, or biologically active portion thereof, that is substantially free of cellular material or other contaminating proteins from the cell or tissue source from which the biological substance is derived, or substantially free from chemical precursors or other chemicals when chemically synthesized. As used herein the term "isolated" refers to a compound of interest (for example a polynucleotide or a polypeptide) that is in an environment different from that in which the compound naturally occurs e.g., separated from its natural milieu such as by concentrating a peptide to a concentration at which it is not found in nature. "Isolated" includes compounds that are within samples that are substantially enriched for the compound of interest and/or in which the compound of interest is partially or substantially purified.

"Isolated antibody", as used herein, is intended to refer to an antibody that is substantially free of other antibodies having different antigenic specificities (e.g., an isolated antibody that specifically binds VSIG8 and/or VISTA) is substantially free of antibodies that specifically bind antigens other than VSIG8). Moreover, an isolated antibody may be substantially free of other cellular material and/or chemicals.

"Isotype" herein refers to the antibody class (e.g., IgM or IgG1) that is encoded by the heavy chain constant region genes.

"K-assoc" or "$K_a$", as used herein, refers broadly to the association rate of a particular antibody-antigen interaction, whereas the term "Kdiss" or "Kd," as used herein, refers to the dissociation rate of a particular antibody-antigen interaction.

The term "$K_D$", as used herein, is intended to refer to the dissociation constant, which is obtained from the ratio of Kd to Ka (i.e., $Kd/K_a$) and is expressed as a molar concentration (M). $K_D$ values for antibodies can be determined using methods well established in the art such as plasmon resonance (BIAcore®), ELISA and KINEXA. A preferred method for determining the $K_D$ of an antibody is by using surface Plasmon resonance, preferably using a biosensor system such as a BIAcore® system or by ELISA.

"Label" or a "detectable moiety" as used herein, refers broadly to a composition detectable by spectroscopic, photochemical, biochemical, immunochemical, chemical, or other physical means.

"Low stringency," "medium stringency," "high stringency," or "very high stringency conditions," as used herein, refers broadly to conditions for nucleic acid hybridization and washing. Guidance for performing hybridization reactions can be found in Ausubel, et al., Short Protocols in Molecular Biology ($5^{th}$ Ed.) John Wiley & Sons, NY (2002). Exemplary specific hybridization conditions include but are not limited to: (1) low stringency hybridization conditions in 6× sodium chloride/sodium citrate (SSC) at about 45° C., followed by two washes in 0.2×SSC, 0.1% SDS at least at 50° C. (the temperature of the washes can be increased to 55° C. for low stringency conditions); (2) medium stringency hybridization conditions in 6×SSC at about 45° C., followed by one or more washes in 0.2×SSC, 0.1% SDS at 60° C.; (3) high stringency hybridization conditions in 6×SSC at about 45° C. followed by one or more washes in 0.2×. SSC, 0.1% SDS at 65° C.; and (4) very high stringency hybridization conditions are 0.5M sodium phosphate, 7% SDS at 65° C., followed by one or more washes at 0.2×SSC, and 1% SDS at 65° C.

"Mammal," as used herein, refers broadly to any and all warm-blooded vertebrate animals of the class Mammalia, including humans, characterized by a covering of hair on the skin and, in the female, milk-producing mammary glands for nourishing the young. Examples of mammals include but are not limited to alpacas, armadillos, capybaras, cats, camels, chimpanzees, chinchillas, cattle, dogs, goats, gorillas, hamsters, horses, humans, lemurs, llamas, mice, non-human primates, pigs, rats, sheep, shrews, squirrels, tapirs, and voles. Mammals include but are not limited to bovine, canine, equine, feline, murine, ovine, porcine, primate, and rodent species. Mammal also includes any and all those listed on the Mammal Species of the World maintained by the National Museum of Natural History, Smithsonian Institution in Washington D.C.

"Naturally-occurring nucleic acid molecule," as used herein, refers broadly refers to an RNA or DNA molecule having a nucleotide sequence that occurs in nature (e.g., encodes a natural protein).

"Nucleic acid" or "nucleic acid sequence," as used herein, refers broadly to a deoxy-ribonucleotide or ribonucleotide oligonucleotide in either single- or double-stranded form. The term encompasses nucleic acids, i.e., oligonucleotides, containing known analogs of natural nucleotides. The term also encompasses nucleic-acid-like structures with synthetic backbones. Unless otherwise indicated, a particular nucleic acid sequence also implicitly encompasses conservatively modified variants thereof (e.g., degenerate codon substitutions) and complementary sequences, as well as the sequence explicitly indicated. The term nucleic acid is used interchangeably with gene, cDNA, mRNA, oligonucleotide, and polynucleotide.

"Oligomerization domain", or "multimerization domain" or "dimerization domain" are used interchangeably herein, and refer broadly to a domain that when attached to a VSIG8 and/or VISTA extracellular domain or fragment thereof, facilitates oligomerization. Said oligomerization domains comprise self-associating, α-helices, for example, leucine zippers, that can be further stabilized by additional disulfide bonds. The domains are designed to be compatible with vectorial folding across a membrane, a process thought to facilitate in vivo folding of the polypeptide into a functional binding protein. Examples thereof are known in the art and include by way of example coiled GCN4, and COMP. The a-helical coiled coil is probably the most widespread subunit oligomerization motif found in proteins. Accordingly, coiled coils fulfill a variety of different functions. In several families of transcriptional activators, for example, short leucine zippers play an important role in positioning the DNA-binding regions on the DNA. Ellenberger, et al. (1992) *Cell* 71: 1223-1237. Coiled coils are also used to form oligomers of intermediate filament proteins. Coiled-coil proteins furthermore appear to play an important role in both vesicle and viral membrane fusion. (Skehel and Wiley *Cell* 95: 871-874 (1998)). In both cases hydrophobic sequences, embedded in the membranes to be fused, are located at the same end of the rod-shaped complex composed of a bundle of long α-helices. This molecular arrangement is believed to cause close membrane apposition as the complexes are assembled for membrane fusion. The coiled coil is often used to control oligomerization. It is found in many types of proteins, including transcription factors include, but not limited to GCN4, viral fusion peptides, SNARE complexes and certain tRNA synthetases, among others. Very long coiled coils are found in proteins such as tropomyosin, intermediate filaments and spindle-pole-body components. Coiled coils involve a number of α-helices that are supercoiled around each other in a highly organized manner that associate in a parallel or an antiparallel orientation. Although dimers and trimers are the most common. The helices may be from the same or from different proteins. The coiled-coil is formed by component helices coming together to bury their hydrophobic seams. As the hydrophobic seams twist around each helix, so the helices also twist to coil around each other, burying the hydrophobic seams and forming a supercoil. It is the characteristic interdigitation of side chains between neighboring helices, known as knobs-into-holes packing, that defines the structure as a coiled coil. The helices do not have to run in the same direction for this type of interaction to occur, although parallel conformation is more common. Antiparallel conformation is very rare in trimers and unknown in pentamers, but more common in intramolecular dimers, where the two helices are often connected by a short loop. In the extracellular space, the heterotrimeric coiled-coil protein laminin plays an important role in the formation of basement membranes. Other examples are the thrombospondins and cartilage oligomeric matrix protein (COMP) in which three (thrombospondins 1 and 2) or five (thrombospondins 3, 4 and COMP) chains are connected. The molecules have a flower bouquet-like appearance, and the reason for their oligomeric structure is probably the multivalent interaction of the C-terminal domains with cellular receptors. The yeast transcriptional activator GCN4 is 1 of over 30 identified eukaryotic proteins containing the basic region leucine zipper (bZIP) DNA-binding motif. Ellenberger, et al. *Cell* 71: 1223-1237 (1992). The bZIP dimer is a pair of continuous a helices that form a parallel coiled-coil over their carboxy-terminal 34 residues and gradually diverge toward their amino termini to pass through the major groove of the DNA binding site. The coiled-coil dimerization interface is oriented almost perpendicular to the DNA axis, giving the complex the appearance of the letter T. bZIP contains a 4-3 heptad repeat of hydrophobic and nonpolar residues that pack together in a parallel a-helical coiled-coil. (Ellenberger, et al. *Cell* 71: 1223-1237 (1992)). The stability of the dimer results from the side-by-side packing of leucines and nonpolar residues in positions a and d of the heptad repeat, as well as a limited number of intra- and interhelical salt bridges, shown in a crystal structure of the GCN4 leucine zipper peptide. (Ellenberger, et al. *Cell* 71: 1223-1237 (1992)). Another example is CMP (matrilin-1) isolated from bovine tracheal cartilage as a homotrimer of subunits of Mr 52,000 (Paulsson & Heinegard (1981), *Biochem. J.* 197: 367-375), where each subunit consists of a vWFAI module, a single EGF domain, a vWFA2 module and a coiled coil domain spanning five heptads. (Kiss, et al. *J. Biol. Chem.* 264:8126-8134 (1989); Hauser and Paulsson *J. Biol. Chem.* 269:25747-25753 (1994)). Electron microscopy of purified CMP showed a bouquet-like trimer structure in which each subunit forms an ellipsoid emerging from a common point corresponding to the coiled coil. (Hauser and Paulsson *J. Biol. Chem.* 269: 25747-25753 (1994)). The coiled coil domain in matrilin-1 has been extensively studied. The trimeric structure is retained after complete reduction of interchain disulfide bonds under non-denaturing conditions. (Hauser and Paulsson *J. Biol. Chem.* 269: 25747-25753 (1994)). Yet another example is Cartilage Oligomeric Matrix Protein (COMP). A non-collagenous glycoprotein, COMP, was first identified in cartilage. (Hedbom, et al. *J. Biol. Chem.* 267:6132-6136(1992)). The protein is a 524 kDa homopentamer of five subunits which consists of an N-terminal heptad repeat region (cc) followed by four epidermal growth factor (EGF)-like domains (EF), seven calcium-binding domains (T3) and a C-terminal globular domain (TC). According to this domain organization, COMP belongs to the family of thrombospondins. Heptad repeats $(abcdefg)_n$ with preferentially hydrophobic residues at positions a and d form-helical coiled-coil domains. (Cohen and Parry *Science* 263: 488-489 (1994)). Recently, the recombinant five-stranded coiled-coil domain of COMP (COMPcc) was crystallized and its structure was solved at 0.2 nm resolution. (Malashkevich, et al. *Science* 274: 761-765 (1996)).

"Operatively linked", as used herein, refers broadly to when two DNA fragments are joined such that the amino acid sequences encoded by the two DNA fragments remain in-frame.

"Paratope," as used herein, refers broadly to the part of an antibody which recognizes an antigen (e.g., the antigen-binding site of an antibody.) Paratopes may be a small region (e.g., 15-22 amino acids) of the antibody's Fv region and may contain parts of the antibody's heavy and light chains. See Goldsby, et al. Antigens (Chapter 3) *Immunology* ($5^{th}$ Ed.) New York: W. H. Freeman and Company, pages 57-75.

"Patient," or "subject" or "recipient", "individual", or "treated individual" are used interchangeably herein, and refers broadly to any animal that is in need of treatment either to alleviate a disease state or to prevent the occurrence or reoccurrence of a disease state. Also, "Patient" as used herein, refers broadly to any animal that has risk factors, a history of disease, susceptibility, symptoms, and signs, was previously diagnosed, is at risk for, or is a member of a patient population for a disease. The patient may be a clinical patient such as a human or a veterinary patient such as a companion, domesticated, livestock, exotic, or zoo animal.

"Polypeptide," "peptide" and "protein," are used interchangeably and refer broadly to a polymer of amino acid residues s of any length, regardless of modification (e.g., phosphorylation or glycosylation). The terms apply to amino acid polymers in which one or more amino acid residue is an analog or mimetic of a corresponding naturally occurring amino acid, as well as to naturally occurring amino acid polymers. The terms apply to amino acid polymers in which one or more amino acid residue is an artificial chemical mimetic of a corresponding naturally occurring amino acid, as well as to naturally occurring amino acid polymers and non-naturally occurring amino acid polymer. Polypeptides can be modified, e.g., by the addition of carbohydrate residues to form glycoproteins. The terms "polypeptide," "peptide" and "protein" expressly include glycoproteins, as well as non-glycoproteins.

"Promoter," as used herein, refers broadly to an array of nucleic acid sequences that direct transcription of a nucleic acid. As used herein, a promoter includes necessary nucleic acid sequences near the start site of transcription, such as, in the case of a polymerase II type promoter, a TATA element. A promoter also optionally includes distal enhancer or repressor elements, which can be located as much as several thousand base pairs from the start site of transcription. A constitutive" promoter is a promoter that is active under most environmental and developmental conditions. An "inducible" promoter is a promoter that is active under environmental or developmental regulation.

"Prophylactically effective amount," as used herein, refers broadly to the amount of a compound that, when administered to a patient for prophylaxis of a disease or prevention of the reoccurrence of a disease, is sufficient to effect such prophylaxis for the disease or reoccurrence. The prophylactically effective amount may be an amount effective to prevent the incidence of signs and/or symptoms. The "prophylactically effective amount" may vary depending on the disease and its severity and the age, weight, medical history, predisposition to conditions, preexisting conditions, of the patient to be treated.

"Prophylactic vaccine" and/or "Prophylactic vaccination" refers to a vaccine used to prevent a disease or symptoms associated with a disease such as cancer or an infectious condition.

"Prophylaxis," as used herein, refers broadly to a course of therapy where signs and/or symptoms are not present in the patient, are in remission, or were previously present in a patient. Prophylaxis includes preventing disease occurring subsequent to treatment of a disease in a patient. Further, prevention includes treating patients who may potentially develop the disease, especially patients who are susceptible to the disease (e.g., members of a patent population, those with risk factors, or at risk for developing the disease).

"Recombinant" as used herein, refers broadly with reference to a product, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

The term "recombinant human antibody", as used herein, includes all human antibodies that are prepared, expressed, created or isolated by recombinant means, such as (a) antibodies isolated from an animal (e.g., a mouse) that is transgenic or transchromosomal for human immunoglobulin genes or a hybridoma prepared therefrom (described further below), (b) antibodies isolated from a host cell transformed to express the human antibody, e.g., from a transfectoma, (c) antibodies isolated from a recombinant, combinatorial human antibody library, and (d) antibodies prepared, expressed, created or isolated by any other means that involve splicing of human immunoglobulin gene sequences to other DNA sequences. Such recombinant human antibodies have variable regions in which the framework and CDR regions are derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo.

"Signal sequence" or "signal peptide," as used herein, refers broadly to a peptide containing about 15 or more amino acids which occurs at the N-terminus of secretory and membrane bound polypeptides and which contains a large number of hydrophobic amino acid residues. For example, a signal sequence contains at least about 10-30 amino acid residues, preferably about 15-25 amino acid residues, more preferably about 18-20 amino acid residues, and even more preferably about 19 amino acid residues, and has at least about 35-65%, preferably about 38-50%, and more preferably about 40-45% hydrophobic amino acid residues (e.g., Valine, Leucine, Isoleucine or Phenylalanine). A "signal sequence," also referred to in the art as a "signal peptide," serves to direct a polypeptide containing such a sequence to a lipid bilayer, and is cleaved in secreted.

"Specifically (or selectively) binds" to an antibody or "specifically (or selectively) immunoreactive with," or "specifically interacts or binds," as used herein, refers broadly to a protein or peptide (or other epitope), refers, in some embodiments, to a binding reaction that is determinative of the presence of the protein in a heterogeneous population of proteins and other biologies. For example, under designated immunoassay conditions, the specified antibodies bind to a particular protein at least two times greater than the background (non-specific signal) and do not substantially bind in a significant amount to other proteins present in the sample. Typically a specific or selective reaction will be at least twice background signal or noise and more typically more than about 10 to 100 times background.

"Specifically hybridizable" and "complementary" as used herein, refer broadly to a nucleic acid can form hydrogen bond(s) with another nucleic acid sequence by either traditional Watson-Crick or other non-traditional types. The binding free energy for a nucleic acid molecule with its complementary sequence is sufficient to allow the relevant function of the nucleic acid to proceed, e.g., RNAi activity. Determination of binding free energies for nucleic acid molecules is well known in the art. (See, e.g., Turner, et al. *CSH Symp. Quant. Biol. LII:* 123-33 (1987); Frier, et al. *PNAS* 83: 9373-77 1986); Turner, et al. *J. Am. Chem. Soc.* 109:3783-85 (1987)). A percent complementarity indicates the percentage of contiguous residues in a nucleic acid molecule that can form hydrogen bonds (e.g., Watson-Crick base pairing) with a second nucleic acid sequence (e.g., about at least 5, 6, 7, 8, 9, 10 out of 10 being about at least 50%, 60%, 70%, 80%, 90%, and 100% complementary, inclusive). "Perfectly complementary" or 100% complementarity refers broadly all of the contiguous residues of a nucleic acid sequence hydrogen bonding with the same number of contiguous residues in a second nucleic acid sequence.

"Substantial complementarity" refers to polynucleotide strands exhibiting about at least 90% complementarity, excluding regions of the polynucleotide strands, such as overhangs, that are selected so as to be noncomplementary. Specific binding requires a sufficient degree of complementarity to avoid non-specific binding of the oligomeric compound to non-target sequences under conditions in which specific binding is desired, i.e., under physiological conditions in the case of in vivo assays or therapeutic treatment, or in the case of in vitro assays, under conditions in which the assays are performed. The non-target sequences typically may differ by at least 5 nucleotides.

"Signs" of disease, as used herein, refers broadly to any abnormality indicative of disease, discoverable on examination of the patient; an objective indication of disease, in contrast to a symptom, which is a subjective indication of disease.

"Solid support," "support," and "substrate," as used herein, refers broadly to any material that provides a solid or semi-solid structure with which another material can be attached including but not limited to smooth supports (e.g., metal, glass, plastic, silicon, and ceramic surfaces) as well as textured and porous materials.

"Soluble ectodomain (ECD)" or "ectodomain" or "soluble VSIG8 or VISTA protein(s)/molecule(s)" of VSIG8 and/or VISTA as used herein means non-cell-surface-bound VSIG8 and/or VISTA molecules or any portion thereof, including, but not limited to: VSIG8 and/or VISTA fusion proteins or VSIG8 and/or VISTA ECD-Ig fusion proteins, wherein the extracellular domain of VSIG8 and/or VISTA or fragment thereof is fused to an immunoglobulin (Ig) moiety rendering the fusion molecule soluble, or fragments and derivatives thereof, proteins with the extracellular domain of VSIG8 and/or VISTA fused or joined with a portion of a biologically active or chemically active protein such as the papillomavirus E7 gene product, melanoma-associated antigen p97 or HIV env protein, or fragments and derivatives thereof; hybrid (chimeric) fusion proteins such as VSIG8 and/or VISTA-Ig, or fragments and derivatives thereof. Such fusion proteins are described in greater detail below.

"Soluble VSIG8 or VISTA protein(s)/molecule(s)" herein also include VSIG8 or VISTA molecules with the transmembrane domain removed to render the protein soluble, or fragments and derivatives thereof; fragments, portions or derivatives thereof, and soluble VSIG8 or VISTA mutant molecules. The soluble VSIG8 or VISTA molecules used in the methods according to at least some embodiments of the invention may or may not include a signal (leader) peptide sequence.

"Subject" or "patient" or "individual" in the context of therapy or diagnosis herein includes any human or nonhuman animal. The term "nonhuman animal" includes all vertebrates, e.g., mammals and non-mammals, such as nonhuman primates, sheep, dogs, cats, horses, cows, chickens, amphibians, reptiles, etc., i.e., anyone suitable to be treated according to the present invention include, but are not limited to, avian and mammalian subjects, and are preferably mammalian. Any mammalian subject in need of being treated according to the present invention is suitable. Human subjects of both genders and at any stage of development (i.e., neonate, infant, juvenile, adolescent, and adult) can be treated according to the present invention. The present invention may also be carried out on animal subjects, particularly mammalian subjects such as mice, rats, dogs, cats, cattle, goats, sheep, and horses for veterinary purposes, and for drug screening and drug development purposes. "Subjects" is used interchangeably with "individuals" and "patients."

"Substantially free of chemical precursors or other chemicals," as used herein, refers broadly to preparations of VSIG8 or VISTA protein in which the protein is separated from chemical precursors or other chemicals which are involved in the synthesis of the protein. In one embodiment, the language "substantially free of chemical precursors or other chemicals" Includes preparations of VSIG8 or VISTA protein having less than about 30% (by dry weight) of chemical precursors or non-VSIG8 chemicals, more preferably less than about 20% chemical precursors or non-VSIG8 or VISTA chemicals, still more preferably less than about 10% chemical precursors or non-VSIG8 or VISTA chemicals, and most preferably less than about 5% chemical precursors or non-VSIG8 or VISTA chemicals.

"Symptoms" of disease as used herein, refers broadly to any morbid phenomenon or departure from the normal in structure, function, or sensation, experienced by the patient and indicative of disease.

"T cell," as used herein, refers broadly to $CD4^+$ T cells and $CD8^+$ T cells. The term T cell also includes both T helper 1 type T cells and T helper 2 type T cells.

"Therapy," "therapeutic," "treating," or "treatment", as used herein, refers broadly to treating a disease, arresting, or reducing the development of the disease or its clinical symptoms, and/or relieving the disease, causing regression of the disease or its clinical symptoms. Therapy encompasses prophylaxis, treatment, remedy, reduction, alleviation, and/or providing relief from a disease, signs, and/or symptoms of a disease. Therapy encompasses an alleviation of signs and/or symptoms in patients with ongoing disease signs and/or symptoms (e.g., inflammation, pain). Therapy also encompasses “prophylaxis”. The term “reduced”, for purpose of therapy, refers broadly to the clinical significant reduction in signs and/or symptoms. Therapy includes treating relapses or recurrent signs and/or symptoms (e.g., inflammation, pain). Therapy encompasses but is not limited to precluding the appearance of signs and/or symptoms anytime as well as reducing existing signs and/or symptoms and eliminating existing signs and/or symptoms. Therapy includes treating chronic disease (“maintenance”) and acute disease. For example, treatment includes treating or preventing relapses or the recurrence of signs and/or symptoms (e.g., inflammation, pain).

“Therapeutic vaccine” and/or “therapeutic vaccination” refers to a vaccine used to treat a disease such as cancer or an infectious condition.

“Treg cell” (sometimes also referred to as suppressor T cells or inducible Treg cells or iTregs) as used herein refers to a subpopulation of T cells which modulate the immune system and maintain tolerance to self-antigens and can abrogate autoimmune diseases. $Foxp3^+$ $CD4^+CD25^+$ regulatory T cells (Tregs) are critical in maintaining peripheral tolerance under normal “Transmembrane domain,” as used herein, refers broadly to an amino acid sequence of about 15 amino acid residues in length which spans the plasma membrane. More preferably, a transmembrane domain includes about at least 20, 25, 30, 35, 40, or 45 amino acid residues and spans the plasma membrane. Transmembrane domains are rich in hydrophobic residues, and typically have an a-helical structure. In an embodiment, at least 50%, 60%, 70%, 80%, 90%, 95% or more of the amino acids of a transmembrane domain are hydrophobic, e.g., leucines, isoleucines, tyrosines, or tryptophans. Transmembrane domains are described in, for example, Zagotta, et al. *Annu. Rev. Neurosci.* 19:235-263 (1996).

“Transgenic animal,” as used herein, refers broadly to a non-human animal, preferably a mammal, more preferably a mouse, in which one or more of the cells of the animal includes a “transgene”. The term “transgene” refers to exogenous DNA which is integrated into the genome of a cell from which a transgenic animal develops and which remains in the genome of the mature animal, for example directing the expression of an encoded gene product in one or more cell types or tissues of the transgenic animal.

“Tumor,” as used herein, refers broadly to at least one cell or cell mass in the form of a tissue neoformation, in particular in the form of a spontaneous, autonomous and irreversible excess growth, which is more or less disinhibited, of endogenous tissue, which growth is as a rule associated with the more or less pronounced loss of specific cell and tissue functions. This cell or cell mass is not effectively inhibited, in regard to its growth, by itself or by the regulatory mechanisms of the host organism, e.g., colorectal cancer, melanoma or carcinoma. Tumor antigens not only include antigens present in or on the malignant cells themselves, but also include antigens present on the stromal supporting tissue of tumors including endothelial cells and other blood vessel components.

“Unresponsiveness,” as used herein, refers broadly to refractivity of immune cells to stimulation, e.g., and stimulation via an activating receptor or a cytokine. Unresponsiveness can occur, e.g., because of exposure to immunosuppressants or high doses of antigen.

“Vaccine” as used herein, refers to a biological preparation that as improves immunity to a particular disease, e.g., cancer or an infectious disease, wherein the vaccine includes a disease specific antigen, e.g., a cancer antigen or infectious agent antigen, against which immune responses are elicited. A vaccine typically includes an adjuvant as immune potentiator to stimulate the immune system. This includes prophylactic (which prevent disease) and therapeutic vaccines (which treat the disease or its symptoms).

“Variable region” or “$V_R$,” as used herein, refers broadly to the domains within each pair of light and heavy chains in an antibody that are involved directly in binding the antibody to the antigen. Each heavy chain has at one end a variable domain ($V_H$) followed by a number of constant domains. Each light chain has a variable domain ($V_L$) at one end and a constant domain at its other end; the constant domain of the light chain is aligned with the first constant domain of the heavy chain, and the light chain variable domain is aligned with the variable domain of the heavy chain.

“Vector,” as used herein, refers broadly to a nucleic acid molecule capable of transporting another nucleic acid molecule to which it has been linked. One type of vector is a “plasmid”, which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Vectors are referred to herein as “recombinant expression vectors” or simply “expression vectors”. In general, expression vectors of utility in recombinant DNA techniques are often in the form of plasmids. In the present specification, “plasmid” and “vector” may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions. The techniques and procedures are generally performed according to conventional methods well known in the art and as described in various general and more specific references that are cited and discussed throughout the present specification. See, e.g., Sambrook, et al. Molec. Cloning: Lab. Manual [3rd Ed] Cold Spring Harbor Laboratory Press (2001). Standard techniques may be used for recombinant DNA, oligonucleotide synthesis, and tissue culture, and transformation (e.g., electroporation, lipofection). Enzymatic reactions and purification techniques may be performed according to manufacturer’s specifications or as commonly accomplished in the art or as described herein.

Having defined certain terms and phrases used in the present application, specific types of VSIG8 polypeptides, fusion proteins, anti-VSIG8 antibodies and antigen binding antibody fragments and methods for the production and use thereof which are embraced by the invention are further described below As shown in Table 1, the Ig superfamily comprises many critical immune regulators, including the B7 family ligands and receptors. Of these, the best characterized co-stimulatory ligands are CD80 and CD86 who are expressed on professional antigen-presenting cells (APCs) and whose receptors are CD28, PD-L1 and CTLA-4 (12). These targets have proven to be valuable clinical targets in the treatment of autoimmunity and cancer.

TABLE 1

Positive and Negative T-cell Regulation by the B7 Family Ligands and Receptors

| Ligand | Receptor | Pathway | Knock-out Mouse Phenotype |
|---|---|---|---|
| B7-H2 (ICOSL) | ICOS | T-cell | Impaired T-helper differentiation & function |
| B7-H3 | Unknown | co-stimulation | Enhanced Th1 differentiation & EAE disease |
| B7-1 (CD80); | CD28 | | Impaired adaptive immunity |
| B7-2 (CD86) | CTLA-4 | T-cell | Severe autoimmunity |
| B7-DC (PD-L2) | PD-1 | co-inhibition | Mild autoimmunity |
| B7-H1 (PD-L1) | PD-1 | | Enhanced disease in NOD & EAE models |
| B7-H4 (B7S1, B7X) | Unknown | | Enhanced innate immunity & host defense |
| VISTA | Unknown | | Mild autoimmunity |

The B7 family ligands have expanded to include co-stimulatory B7-H2 (ICOS Ligand) and B7-H3 (receptor unknown), as well as co-inhibitory B7-H1 (PD-L1), B7-DC (PD-L2), B7-H4 (B7S1 or B7x; receptor unknown), B7-H5 (only human) 13 and B7-H6 (12, 14). Studies into the mechanisms of PD-L1→PD-1 interactions, CTLA-4 and it engagement by its ligands, B7-1 and B7-2, have all empowered the pharmaceutical and biotechnology industries to predict outcomes, strategically design PK and PD studies, and understand toxicities associated with therapeutic intervention. The success of these therapeutics has been greatly enhanced by a comprehensive understanding of the MOA, which includes an understanding of receptor-ligand interactions. Notably, some of the less developed NCR ligands have no identified receptors because of the peculiar difficulties in identifying the receptors, likely due to low density and low affinity of ligand binding.

V-region Immunoglobulin-containing Suppressor of T cell Activation (15) (VISTA) is a negative checkpoint regulator (NCR) ligand, whose nearest phylogenetic relative is PD-L1. VISTA has been shown to profoundly suppress the activation of resting T cells. Both in the human and mouse, VISTA expression appears to be hematopoietically restricted and abundantly expressed in the myeloid compartment, and to a lower intensity on T cells (16). Blocking VISTA, like blocking PD-L1 and PD-1, enhances immunity in murine models of cancer (17).

Antibodies that block or inhibit the effects of VISTA may be used to enhance human immune responses, in particular immune responses to malignancies and infection. By contrast molecules that agonize VISTA such as soluble VISTA, e.g., VISTA-Ig, may be used to suppress undesired human immune responses such as autoimmune, allergic or inflammatory immune responses. Prior to the present invention, the receptor for VISTA has not been reported. It is anticipated that the identification of this receptor as herein disclosed will facilitate the design of other therapeutics for treating oncology, infectious disease, autoimmune, allergic and inflammatory indications. As well the identification of the receptor will facilitate a greater understanding of the manner that VISTA in association with its receptor modulates immunity.

Based thereon, the objective of the present invention was to identify the receptor for VISTA. Analogous to VISTA, compounds which antagonize this receptor or which modulate (inhibit or block) the binding of this receptor to VISTA should be useful in treating conditions wherein upregulation of T or NK cell immunity is desirable such as cancer or infectious disease conditions. Further analogous to VISTA, compounds which agonize this receptor or which modulate (promote or enhance) the binding of this receptor to VISTA should be useful in treating conditions wherein downregulation of T or NK cell immunity is desirable such as autoimmunity, allergy, inflammation, GVHD, transplant or cell or gene therapy.

The VISTA receptor was predicted by the inventors to be a member of the B7 family as all identified members of the B7 receptor family are members of the Ig superfamily. This Ig superfamily includes proteins that are both soluble and membrane proteins that are involved in cell-cell signaling/interaction, adhesion and communication. All of these molecules contain domains that are similar to those domains of Ig V regions (IgV) or constant regions (IgC). The domains are typically 70-110 amino acids in length, have characteristic Ig folds, which has a sandwich-like structure formed by two α parallel sheets which are formed between cysteine residues in the B and F strands and stabilize the Ig-fold.

B7 receptors (CTLA-4, ICOS, PD-1) have one IgV domain, in contrast to the ligands for these receptors (CD80, CD86, ICOSL, PD-L1 and PD-L2) that have one IgV domain and one Ig-C domain. Curiously, VISTA has one Ig-V domain like the receptors in the family. Accordingly, VISTA may also have a cell signaling function in addition to its ligand-like activity (of suppressing T cell activation). Notwithstanding, because all currently identified receptors and ligands in this family are members of the Ig superfamily, the inventors predicted that the binding partner for VISTA would comprise a member of the B7 family.

Published studies and references in press (15, 16 and 17), have shown that VISTA is a novel and structurally-distinct, Ig-superfamily inhibitory ligand whose key features are:

(i) Expression of VISTA is exclusively within the hematopoietic compartment and is high on mature myeloid cells (DCs and Macs, CD11bbright), with lower levels of expression on $CD4^+$ T cells, Treg and $CD8^+$ T cells.

(ii) Immobilized, and not soluble murine VISTA-Ig fusion protein, or VISTA expression on APCs, suppresses in vitro murine $PD-1^+$ and $PD-1-CD4^+$ and $CD8^+$ T cell proliferation 15 and cytokine production. This establishes that VISTA is immunosuppressive and PD-1 is not the receptor for VISTA (iii) VISTA-Ig suppresses expression of early T cell activation antigens (CD69, CD44) as well as p-ERK activation suggesting that the receptor for VISTA (V-R) is expressed on resting T cells.

(iv) A blocking αVISTA mAb (13F3) exacerbated autoimmunity (EAE) (15).

(v) αVISTA mAb induces tumor remission in multiple murine tumor models (17).

(vi) VISTA induces the expression of Foxp3 in both human (16) and mouse (17) $CD4^+$ T cells.

(vii) VISTA-Ig administration induces suppression of murine SLE and murine EAE.

(viii) All findings with murine VISTA have been recapitulated with human VISTA on human T cells in vitro (16).

In addition, while all of the effects of VISTA on immune regulation have yet to be elucidated, this NCR ligand appears to be as active as PD-L1 at shutting down T cell proliferation (16) and inducing Foxp3 expression (17). VISTA is constitutively expressed at high levels on myeloid cells (15, 16), and can suppress the activation of resting T cells, overtly activated T cells, as well as memory T cells (15, 16).

Further based on the foregoing, the inventors further theorized that the VISTA receptor would likely be expressed on resting T cells. This theory was in part based on the fact that TCR-induced phospho-ERK activation (at 10 minutes post activation) can be completely arrested by VISTA-Ig (FIG. 1). In addition, the earliest changes in T cell activation (CD69, CD62L, CD44) are also completely arrested by VISTA-Ig1 (15, 16).

Also, BiaCore analysis has shown that VISTA-Ig does not bind to any of the known B7 or PD family members (data not shown) or to cells that overexpress CD28, CTLA-4, PD-1, TLT-2, TLT4, CD300A, and CD300D (unpublished data). Expression of VISTA-R is predicted on resting T cells based on the ability of VISTA-Ig to suppress αCD3 phospho-ERK signals at 10 minutes post-stimulation (FIG. 1).

In addition, given the fact that the VISTA has no functional effect on B cells the inventors further predicted that the VISTA receptor will likely have no effect on B cell activation or proliferation and will likely not be appreciably expressed on resting or activated B cells.

VISTA as a Negative Regulator.

Figure 2:
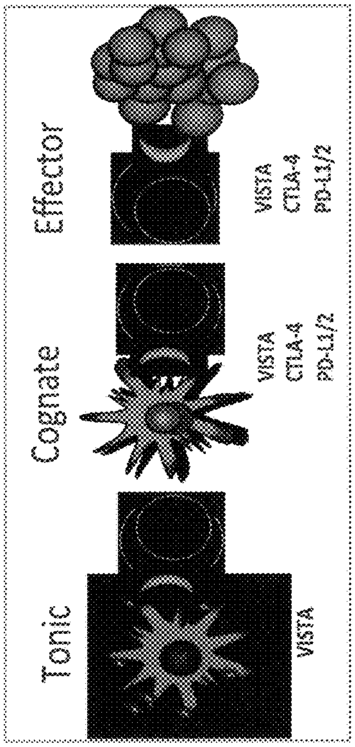
FIG. 2 contains a schematic showing the hierarchy of NCR.

VISTA appears to negatively regulate (at least) tonic signaling of TCR (prior to cognate activation; FIG. 2), serving a homeostatic function as a rheostat to prevent promiscuous T cell activation. This would agree with the high frequencies of activated T cells seen in the VISTA−/− mice (data not shown). However, the observation that VISTA can also suppress T cell function post-activation, suggests that it may be an effective negative regulator after cognate activation of T cells as well.

PD-L1/PD-1 and CTLA-4/CD80/86 are inherently different pathways where receptors are only upregulated after T cell activation. By contrast, VISTA is exclusively hematopoietically-restricted, and therefore its major role would seem to be played in secondary lymphoid organs (SLO), or in sites where there is heavy leukocyte infiltration (like TME), unlike PD-L1 that is expressed in tissue on non-hematopoietic cells. Therefore, com[pounds which modulate VSIG8 or VISTA and/or the VISTA/VISTA-R interaction should have a fundamentally different role in controlling early T cell activities.

Figure 3:
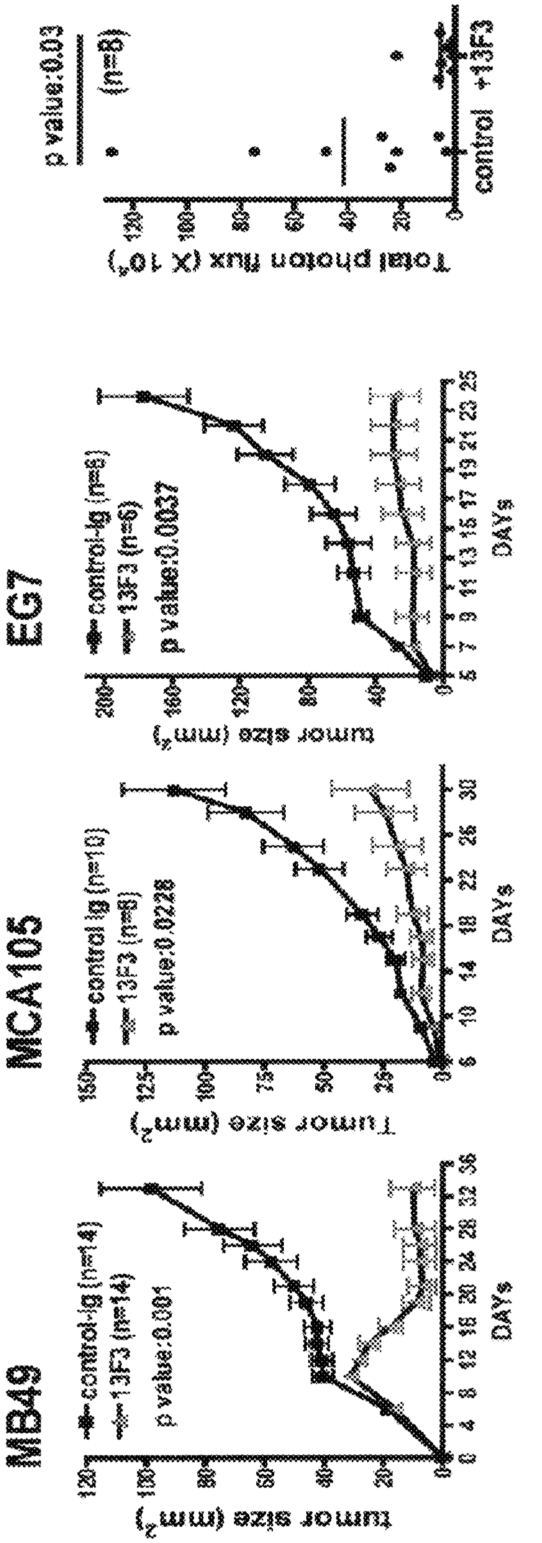
FIG. 3 contains the results of an experiment showing that VISTA mAb treatment reduces tumor growth. In the experiment, mice were inoculated either sq with A. MB49, B. MCA105, or C. EG7 tumor cells, or D. i.p with ID8-luciferase tumor cells, and treated with VISTA mAb 13F3 every other day (300 μg) beginning on day +1. Subcutaneous tumor growth was monitored. For ID8-luciferase tumor, mice were imaged on day 30 using Xenogen IVIS.

VISTA as a Negative Checkpoint Regulator in Cancer,

Studies in murine models of cancer have shed significant, additional insights into the suppressive function of VISTA. While VISTA is expressed at high levels on myeloid cells in naïve mice, VISTA expression on myeloid derived suppressor cells (MDSC) within the tumor microenvironment (TME) is extraordinarily high. Furthermore, αVISTA treatment of mice in four different tumor models dramatically impairs tumor growth (FIG. 3). These findings suggest that VISTA expressed on MDSC is a major suppressive molecule that interferes with the development of protective anti-tumor immunity, and αVISTA relieves this suppressive activity allowing immune intervention and slowing growth of tumor. These findings further support the hypothesis that VISTA on myeloid cells in autoimmune disease plays a pivotal function in regulating the extent of inflammation. VISTA is not expressed on these tumors.

Checkpoint Regulator Ig Ligands.

There is little doubt that NCRs play a critical role in controlling the development of autoimmunity. On a WT C57Bl/6 bkg, CTLA-4−/− mice develop aggressive systemic autoimmune disease (4-6), and PD-1−/− mice on a Balb/c bkg develop cardiomyopathy and mild lupus (7,19) In humans, a major immune related toxicity in blocking PD-1 or CTLA-4 is the emergence of autoimmune disorders. Beyond "simple" negative regulation, many NCRs impact on Treg function through an effect on natural (n)Treg or via enhancing the conversion of naïve T cells to adaptive (a)Treg. Emerging data show that positively engaging NCR pathways with agonists will provide therapeutic efficacy by inducing immune suppression. Ig fusion proteins of NCR ligands (B7-Igs) (B7-H4-Ig, VISTA-Ig, PD-L1-Ig) that actively induce immunosuppressive signals through their respective receptors appear as effective therapeutics in the treatment of autoimmunity.

Studies have shown compelling data that PD-L1-Ig and PD-L2-Ig could markedly prolonged cardiac allograft survival (23) and corneal allograft survival 24 in combination with immunosuppressive drugs. B7-H4 has shown suppressive activity in CIA, EAE, and diabetes (25-29). Depending on the model, this seems to be due to enhancement of Treg function and/or inhibition of Th1 or Th17 populations (25-29). We have shown that VISTA, like PD-L1 and B7-H4, can enhance the conversion to a Treg, and this may be important in their control of self-reactivities (16). Of interest to the development of human therapeutics, in January 2013, Daiichi Sankyo began a Phase 1 trial in rheumatoid arthritis with a B7-H4-Ig (27, 29, 30)

Figure 4:
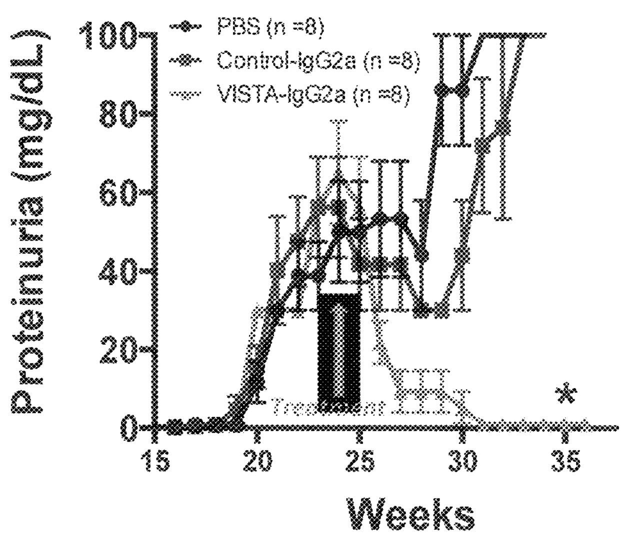
FIG. 4 contains the results of an experiment showing that therapeutic treatment with mVISTA-IgG2a reverses kidney damage and prolongs survival in the NZBWF1 SLE model. In this experiment NZBWF1 female mice were treated therapeutically Q3D from 24 weeks of age with PBS (black circles), 150 □g control-IgG2a (blue squares), or 150 □g mVISTA-IgG2a (red triangles). (A) Disease severity was monitored weekly by proteinuria. Data is shown as the mean of 6 animals per group ±SEM and is representative of 3 experiments. Statistical significance was determined between control-IgG2a vs. mVISTA-IgG2a; $p=0.0156$ by the unpaired Mann Whitney test. 5 of 6 VISTA treated mice survived vs zero PBS or IgG2a control treated mice.

Like other B7-Igs, VISTA-Ig can completely arrest αCD3-induced proliferation of T cells in vitro and a shutdown of virtually all early T cell activities (15-17). Given that VISTA-Ig can impair T cell activation, we assessed its therapeutic efficacy in a murine model of systemic lupus erythematosus. One of the prevailing mechanisms underlying the progression of SLE nephritis implicates chronic activation of T cells with the subsequent recruitment of inflammatory myeloid cells into the kidney that facilitate pathology. The well-characterized mouse strain, BWF1, develop an autoimmune renal disease similar to that seen in human lupus, including the presence of circulating self-reactive antibodies, increased pro-inflammatory cytokines, immune complex deposition glomerulonephritis (GN), progressive proteinuria, and ultimately death due to renal failure. To determine if VISTA-Ig could suppress established renal disease, BW F1 mice were treated at 24 weeks with VISTA-IgG2a. This intervention resulted in rapid and dramatic reversal of proteinuria and significantly prolonged survival in these mice (FIG. 4). We have also shown a reduction in the frequency of activated T cells, an increase in Foxp3 signal and cytokine production in vivo with VISTA-Ig treatment (data not shown). We propose that active signaling via V-R induces T cell unresponsiveness and/or the emergence of aTreg (15, 16) depending on the strength of signal through the V-R. Similar therapeutic efficacy of VISTA-Ig has also been shown in a murine model of multiple sclerosis, a conventional T cell mediated disease (not shown).

Based on the foregoing, effective therapeutic development of VISTA-Ig would greatly benefit from the identification of the V-R to clearly define the target cell populations for VISTA and to further aid in PK and PD studies.

A. Methods Used to Identify Vista Receptor

1. Identification of V-R by Detection of Multimeric VISTA Binding.

Critical to the identification of the VISTA receptor is the production of high quality, multimeric ligands. The reason for this is that the predicted interaction of VISTA with its receptor is likely very low (uM). This prediction is based on the fact that the interaction between PD-1 and PD-L1 is low (Kd 526 nM; as is PD-L2 (Kd 89 nM). One can observe the PD-1→PD-L1 interaction if either the ligand or receptor is overexpressed (34). However, to otherwise observe PD-1→PD-L1 binding, one must use a multimeric ligand, like a tetramer. Alternatively, cells that are overexpressing ligand or receptor can be readily panned on plastic dishes coated with the complementary binding protein (35).

Based on this prediction, we have produced VISTA ligands suitable for dimerization, oligomerization or multimerization and for panning. For example, VISTA-Ig has been engineered with N-terminal BirA sites for production of multimers with high molecular weight backbones. We have worked with ImmuDex (http://www.immudex.com) to produce Dextramers© of VISTA-Ig (VISTA-dextramer). These are very high MW multimers that are created by attachment of ligands to a dextran backbone at pre-specified stoichiometries. These multimers are far more sensitive at detection of receptors than using conventional avidin-based tetramers. Preliminary data shows that VISTA-dextramer has activity of suppressing T cells in vitro (data not shown).

In particular VISTA dimers may be used for V-R identification. The original structural description of VISTA was modeled using structural motifs in the PD-L1 molecule (15). However, an alternative model based on a Fab fragment suggests that VISTA may form a dimer involving a disulphide bridge using a cysteine residue. In support of this putative dimer structure three glycosylation sites were located in the VISTA polypeptide which appear to be located a sufficient distance from the putative dimer interface site to allow dimer formation. These findings are supportive of the fact that native functional VISTA could exist as a dimer. This theory is moreover not refuted by the use of VISTA-Fc protein in functional studies. It is not as this fusion protein contains interchain disulphide bridges in the Fc part which may permit dimerization. In addition, it has been found that a relatively long and flexible linker results in a VISTA Ig fusion protein much more potent in activity than a fusin lacking such a long, flexible linker.

This observation is also supportive of VISTA forming a functional dimer as this linker may facilitate the two chains to interact (dimerize) in a specific way. Accordingly a fusion protein composed of the VISTA extracellular IgV domain and a CH3 protein (VISTA-CH3) was created which should allow for VISTA dimer formation (i.e. would not force the C-terminal ends of two chains too close together). Under non-reducing conditions only, SDS-PAGE shows this protein to be dimeric, suggesting the presence of a VISTA interchain disulphide bridge. The only location this could occur is in the VISTA IgV, therefore this further indicates that VISTA under appropriate conditions forms covalent homodimers.

Therefore, it was theorized that VISTA-CH3 may be a preferred ligand compared to VISTA-Ig for V-R detection. Therefore, VISTA-CH3 with a C-terminal BirA site was envisioned to be suitable for use in enzymatic biotinylation for receptor discovery efforts. These VISTA ligands have not thus far been demonstrated to detectably bind to T cells. However, this is not surprising, due to the low affinity of the interactions of ligand and receptors in this family. As with other PD ligands, it was anticipated that these VISTA ligands when overexpressed would detectably bind V-R. This was a reasonable belief as it has been shown that tetrameric PD-L1 bound 100× higher (Kd $6\times10^{-8}$ M) than monomeric PD-L131 to PD-1. Higher avidity ligands have been used for receptor detection and expression cloning based on ligand binding have been successful (BTLA-4) (31,32).

Based on the foregoing the inventors focused their efforts on V-R identification when using soluble ligands, wherein the soluble ligand used in the assay comprises a VISTA-dextramer (VISTA19-dex: 19 molecules of VISTA on a 250K dextran backbone) or comprises a VISTA dimer.

2. Candidate Library Screening by Dannin and by Soluble Ligand Binding

Figure 5:
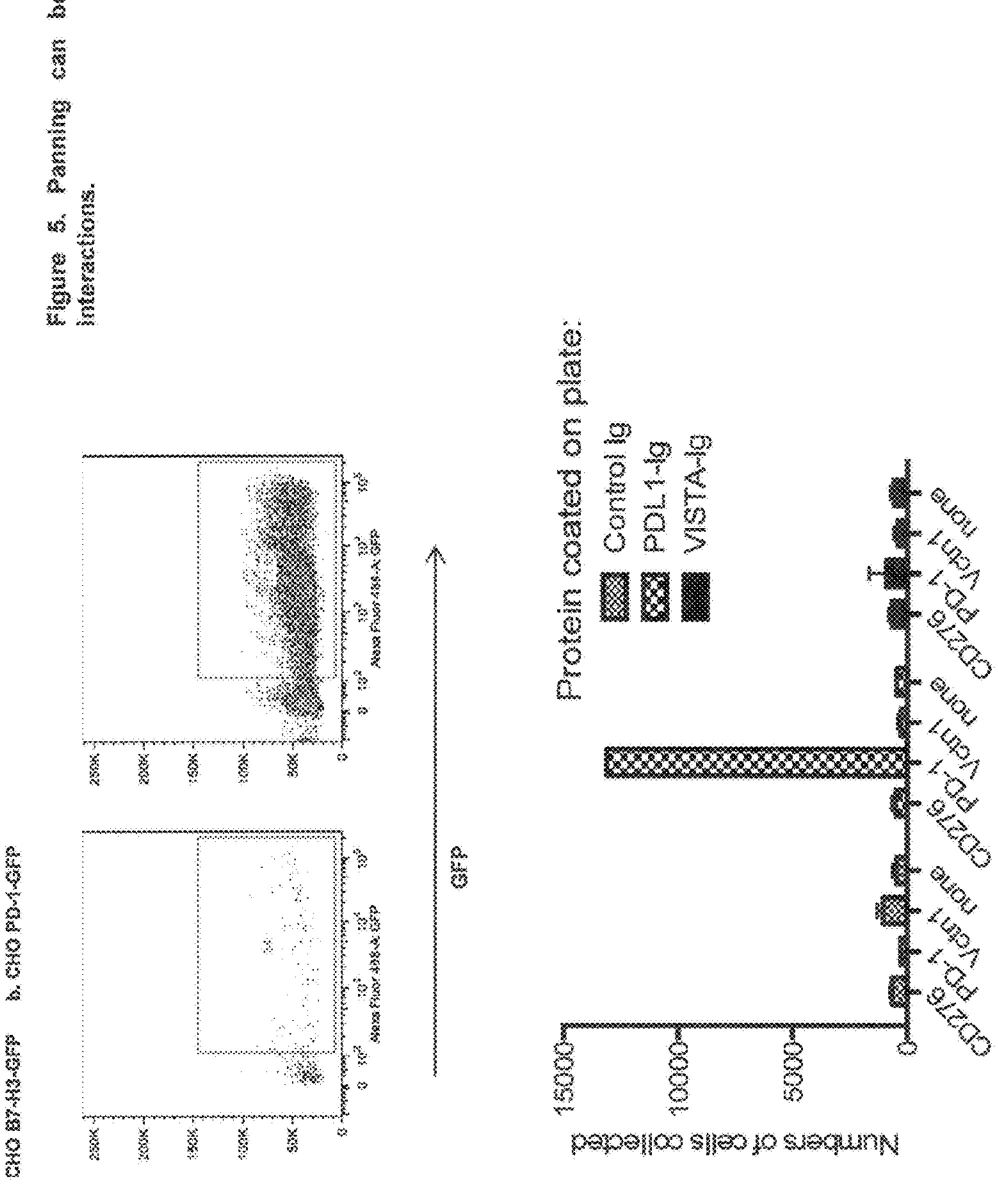
FIG. 5 shows the use of panning to detect PD-1→PD-L1 interactions. CHO-S cells were transfected with the indicated GFP-tagged proteins. 48 hours later, cells were cultured on 10 ug/ml of plate-bound Fc protein for 1 hour. Non-adherent cells were removed, and bound cells were released with trypsin-EDTA. A) Representative positive and negative plots after binding on PDL1-Fc. B) number of cells recovered after panning.

We have chosen and purchased plasmids encoding approximately 200 candidate transmembrane Ig/TNF-family members from the UniProt/SwissProt database. The selection of these genes was based on their expression in hematopoletic cells and the known activities of some of the genes from the literature. These plasmids contain both an open reading frame for the candidate gene in question, as well as GFP to confirm transfection and expression of the plasmid. As POC, PD-1/GFP was transfected into s-CHO cells. After overnight culture, the specific adherence of GFP cells can be easily observed and quantified to PD-L1 and not other plate-bound ligands (FIG. 5).

For high throughput efforts, CHO-S cells (Life Technologies) are transfected in a 96-well format with CMV-expression vectors for GFP-tagged proteins (Origene) from a candidate list of >200 selected genes. 24-hours later, cells are divided onto plates coated with either VISTA-Fc fusion protein or irrelevant Fc fusion protein and cultured for 1 hour. Non-adherent cells will be harvested by gentle pipetting to a new 96-well plate. Adherent cells are released by trypsin-EDTA treatment and both populations are examined by flow cytometry. This technique shows very little background, and positives are clearly visible even with light microscopy. Based thereon, CHO-S cells which overexpress V-R should detectably bind to VISTA-Ig coated plates.

3. Array Candidate Screening by Ligand Binding.

Recombinant, fluorescent VISTA19-dex may be used to screen a membrane protein library, e.g., the (~3800 unique genes) created by Retrogenix (UK) http://www.retrogenix.com to identify putative binding partners in a simple high throughput binding assay. Genes are expressed in an array of HEK293 cells and fluorochrome coupled ligand is used for detection of cells expressing a binding partner.

4. Yeast Two-Hybrid Screening.

Alternatively, or in addition the yeast two hybrid system, such as the system developed by Hybrigenics (France) may be used to identify the putative receptor of VISTA, (http://www.hybrigenics-services.com) using VISTA-ECD bait and prey library constructed from activated and non activated healthy human PBMCs.

In these methods the coding sequence for the extracellular domain of VISTA (aa 33-195; GenBank accession number gi: 62339431) is PCR-amplified and cloned into pB29 as an N-terminal fusion to LexA (N-VISTA-LexA-C). The construct is corroborated for correctness by sequencing the entire insert and is then used as a bait to screen a random-primed leucocytes and activated mononuclear cells cDNA library constructed into pP6, pB29 and pP6 derived from the original pBTM116 (37, 38) and pGADGH (39) plasmids, respectively.

63 million clones (6-fold the complexity of the library) may be screened using a mating approach with YHGX13 (Y187 ade2-101:loxP-kanMX-loxP, matα) and L40αGal4 (mata) yeast strains as previously described (40). 161 His+ colonies are selected on a medium lacking tryptophan, leucine and histidine. The prey fragments of the positive clones are amplified by PCR and sequenced at their 5' and 3' junctions. The resulting sequences are used to identify the corresponding interacting proteins in the GenBank database (NCBI) using a fully automated procedure. A confidence score (PBS, for Predicted Biological Score) is then attributed to each interaction as previously described (41).

5. Global Silencing.

Figure 6:
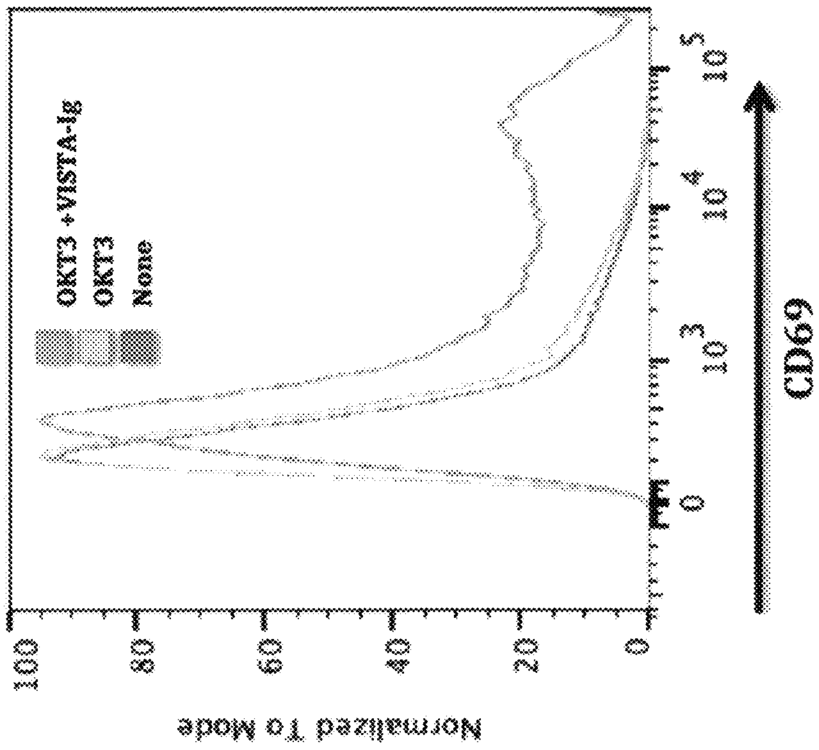
FIG. 6 contains an experiment which shows that VISTA-Ig can suppress αCD3 activation of primary human T cells. This data establishes that the upregulation of CD69 in Jurkat T cells, a transformed human T cell line, can be prevented using VISTA-Ig.

We have shown that VISTA-Ig can suppress αCD3 activation of primary human T cells. One of the limitations to only having an activity in primary cells is that genetic manipulation of primary cells is difficult. Preliminary data now establishes that the upregulation of CD69 in Jurkat T cells, a transformed human T cell line, can be prevented using VISTA-Ig (FIG. 6). This finding allows the use of Jurkat cells to attempt to genetically silence the suppression of CD69 expression induced by VISTA to identify the V-R. In these methods the Mission shRNA whole genome library from Sigma is used. The library is divided into 10 tubes, each tube containing ≈12,000 shRNA constructs targeting ≈2,000 genes. The Jurkat cells are transfected with the library at a MOI such that only one gene is knocked down per cell.

The transduced cells will be cultured in the presence of Puromycin and/or sorted to select shRNA expressing cells. The stably knocked down cells will be stimulated with anti-CD3+/− VISTA-Ig for 24 hrs and the $CD69^+$ cells in the presence of VISTA-Ig will be counted as positive hits. In addition to CD69, the restoration of IL-2 production will also be used to address receptor silencing. The CD69+ cells will be sorted and the identity of shRNA will be carried out by Sigma using deep sequencing and deconvolution techniques. The specificity of top candidates will be tested by single gene knockdown and over expression approaches in both the Jurkat cells and primary T cells using additional assay e.g. proliferation and multiple cytokines.

6. Expression Cloning.

A proven strategy for B7 receptor discovery that has been used repeatedly by Freeman and colleagues (35, 36). An uncut, full-length ORF cDNA library containing approximately $3\times10^6$ primary inserts will be directionally cloned from total mRNA isolated from a VISTA-responsive human T cell line using a CloneMiner™ II cDNA Library Construction Kit and the Gateway® recombination system (Life Technologies), followed by normalization using subtractive hybridization to enhance representation of less frequent mRNA species. The resulting cDNA library will be directly swapped into a Gateway® compatible DEST expression vector downstream of a human elongation factor 1-alpha promoter and upstream of an IRES (internal ribosome entry site)-ZsGreen1 fluorescent protein cassette to track co-expression of cloned cDNA inserts from the same mRNA species. Serial rounds of panning of library-transfected CHO-S cells on VISTA-Ig coated plates will be performed to enrich for VISTA receptor expression. When a high frequency of cells adhere to plates (>50%), plasmid will be isolated, transformed into bacteria for clonal expansion and sequenced.

B. Functional Assays to Confirm that a Putative V-R (VISTA-R) is the Authentic Vista Receptor A putative VISTA-R candidate identified by any of the afore-described methods may be evaluated in functional assays to confirm that the binding interaction of the putative V-R has a modulatory effect on VISTA's effects on immunity, most particularly its suppressive effects on T cell activation, proliferation and cytokine production. Exemplary assays are described below.

1. Blocking of VISTA Function by Anti-V-R Monoclonal Antibody: Reversal of VISTA-Ig Mediated T Cell Suppression in the Presence of Anti-V-R Monoclonal Antibody Recombinant VISTA-Ig fusion protein suppresses anti-CD3 (OKT3) mediated in vitro T cell proliferation and cytokine production in a dose dependent manner. Therefore, in the presence of anti-V-R antibody (which is a blocking/neutralizing antibody without agonistic or antagonistic activity) the suppressive effect of the VISTA-Fc will be inhibited.

For example, in an exemplary anti-V-R antibody blocking assay, 96 well plates are coated with either anti-CD3 antibody (OKT3) alone or anti-CD3 plus VISTA-Ig at 37° C. for 1 hr. The anti-CD3 and VISTA-Ig may be used at a final concentration of 2.5 and 10 ug/ml respectively. Two hundred thousand purified human T cells from healthy donor peripheral blood are added to each well. The duplicate experiment will be carried out in the presence of anti-V-R mAb. The plates are incubated at 37° C. for 5 days. On the day $5^{th}$ 30 ul of supernatant will be removed for cytokine (IFN-γ and IL-2) analysis and 25 μl of tritiated Thymidine is added to the cell culture. The cells are then cultured for another 8 hrs before cell proliferation is measured by tritium incorporation.

2. Blocking of VISTA Function by Creating VISTA Receptor Knockout Cell Line.

The effects of V-R on VISTA function may be further corroborated using T or Jurkat cell lines wherein the expression of the putative V-R is knocked out. Exemplary methods are described below.

Method A

The recombinant VISTA-Ig fusion protein suppresses anti-CD3 (OKT3) induced CD69 and IL-2 upregulation in Jurkat cells, a lymphoma cell line, in a dose dependent manner. The VISTA receptor candidate is knocked down in Jurkat cells using lentivirus shRNA silencing technique. Such knocked-out cells will be unresponsive to VISTA-Ig mediated suppression.

The gene specific shRNA lentiviral particles are constructed to knock down the VSIG8 (Mission shRNA particles, TCR library from Sigma). The Jurkat cells will be transduced with shRNA lentiviral particles at an optimized multiplicity of infection to achieve greater than 90% knock down of target gene without nonspecific gene deletion. The transduced cells are selected in the presence of puromycin drug. The specificity and the level of knockdown of the target gene is confirmed by quantitative PCR. The cells will be stimulated with anti-CD3 in the presence or absence of VISTA-Ig. The level of CD69 will be assessed by flow cytometry and IL-2 will be measured by ELISA in the culture supernatant after 72 hrs.

Method B

The recombinant VISTA-Ig fusion protein suppresses anti-CD3 (OKT3) mediated in vitro T cell proliferation and cytokine production in a dose dependent manner. The VISTA receptor candidate is knocked down in T cells using lentivirus shRNA silencing technique. Such knocked-out cells will should be unresponsive to VISTA-Ig mediated suppression.

The gene specific shRNA lentiviral particles are constructed to knock down the VSIG8 (Mission shRNA particles, TCR library from Sigma). The T cells from healthy donor will be transduced with shRNA lentiviral particles at an optimized multiplicity of infection to achieve greater than 90% knock down of target gene without nonspecific gene deletion. The transduced cells will be selected in the presence of puromycin drug. The specificity and the level of knockdown of the target gene will be confirmed by quantitative PCR. The anti-CD3 mediated T cell proliferation assay will be performed as described above in the presence or absence of VISTA-Ig. The cytokine and cell proliferation will be assessed.

3. V-R Expression Assays

In addition to silencing methods using primary human T cells and Jurkat cells to silence a putative V-R, or antibody blocking assays using plate-bound anti-V-R antibodies to induce suppression of T cell activation, the confirmation of a putative V-R as being the authentic receptor for VISTA may be further corroborated by detecting mRNA and protein expression on T cells.

These assays will detect V-R mRNA or protein levels in T cells or Jurkat cells as compared to appropriate controls. It is predicted that these expression assays will indicate that the authentic V-R is constitutively expressed by resting T cells as well as by Jurkat cells.

As described in detail in the working examples, the VISTA receptor was elucidated and found to be V-set and immunoglobulin domain-containing protein 8 or VSIG8.

C. Use of VSIG8 to Produce VISTA/V-R Agonists and Antagonists and Use in Therapy and Diagnosis The identified V-R is used to identify VISTA/V-R agonists or antagonists. These agonist and antagonist compounds will include in particular antibodies and antibody fragments that agonize or antagonize the effects of VSIG8 on T or NK immunity and preferably those which inhibit or promote the interaction of VISTA and VSIG8. These antibodies may be obtained by well-known in vivo or in vitro immunization using the VSIG8 polypeptide or a fragment or conjugate thereof as an immunogen. Preferably these antibodies and antibody fragments will include human, humanized, primatized and chimeric antibodies an antibody fragments such as Fab, Fab', scFv, $(Fab)_2$. IgNars, metMabs, and other known types of antibodies and antibody fragments.

These agonist and antagonist compounds will further include polypeptides, i.e., polypeptides which comprise all or a portion of the extracellular region of VSIG8 or a polypeptide which possesses at least 80, 90, 95 or 99% sequence identity to the extracellular region of VSIG8 or a portion thereof such as an IgV or IgC domain therein. These VSIG8 polypeptides may also be fused to another polypeptide such as an Ig constant region, e.g., an IgG1, IgG2, IgG3 or IgG4 constant region which optionally may be mutagenized to enhance or inhibit FcR and/or complement binding or other effector function. Also, the agonist or antagonist may comprise one or more copies of the VSIG8 polypeptide or fragment, i.e., the compound may be multimeric and the copies of the VSIG8 polypeptide may be intervened by a linker, e.g., a long, flexible peptide such as one which is at least 15-25 amino acids and containing one or more serine residues.

In addition agonist and antagonist compounds according to the invention will further include small molecules which agonize or antagonize the VISTA/VSIG8 binding interaction.

Preferably an antagonist according to the invention will substantially inhibit or prevent the suppressive effects of VISTA on T or NK cell immunity. This may be detected using in vitro cell based assays with cells that express VISTA and/or VSIG8. An antagonist will inhibit or block the suppressive effects mediated by VISTA on T cell activation or proliferation or NK T cell activation or proliferation, e.g., it will increase $CD8^+$ or $CD4^+$ T cell activation or $CD8^+$ or $CD4^+$ T cell proliferation and/or promote NK cell mediated activities compared to suitable controls.

Conversely, an agonist according to the invention preferably will potentiate or enhance the suppressive effects of VISTA on T or NK cell immunity. This may be detected using in vitro using cell based assays with cells that express VISTA and/or VSIG-8. An agonist will promote the suppressive effects mediated by VISTA on T cell activation or proliferation or on NK cell mediated activities, e.g., it will suppress $CD8^+$ or $CD4^+$ T cell activation or proliferation or NK mediated cellular functions such as lysis compared to suitable controls.

The screening methods used to identify such agonists and antagonists may be affected in high throughput format if desired.

The identified agonists and antagonists may be formulated for use in human therapy. This may comprise the addition of suitable stabilizers, excipients or carriers. In addition, the agonist or antagonist may be modified to enhance in vivo stability such as by the attachment to one or more water-soluble polymers such as polyethylene glycol polymers or by acylation. Methods for attaching such moieties to proteins are well known in the art.

As mentioned, compositions containing agonists according to the invention may be used to inhibit T cell immunity and to treat conditions where this is therapeutically desirable such as autoimmunity, allergy or inflammatory conditions. These compositions will comprise an amount of an agonist according to the invention effective to suppress T cell activation or proliferation in a subject in need thereof. Such autoimmune, inflammatory and allergic conditions include for example arthritic conditions such as RA, psoriatic arthritis, scleroderma, multiple sclerosis, lupus, IBD, ITP, diabetes, sarcoidosis, allergic asthma, and the like.

Compositions containing antagonists according to the invention may be used to promote T cell immunity and to treat conditions where this is therapeutically desirable such as cancer and infectious disease indications. These compositions will comprise an amount of an antagonist according to the invention effective to promote T cell activation or proliferation in a subject in need thereof, e.g. a subject with a cancerous condition.

Cancers treatable with the subject antagonists include any way of example melanoma, lymphoma, leukemia, lung cancer, ovarian cancer, cervical cancer, testicular cancer, digestive cancers, esophageal cancer, liver cancers, pancreatic cancer, kidney cancer, skin cancer.

Infectious diseases treatable with antagonists according to the invention include viral diseases such as HIV, HPV, EBV, encephalitis, herpes, other pox viruses, and other known human viruses, parasitic diseases, bacterial diseases, fungal or yeast associated diseases, as well as other infectious disease conditions that affect humans.

It should be understood that the disease conditions identified above are intended to be exemplary and not exhaustive. In addition, the subject agonists or antagonists may be combined with other therapeutics which may be administered in the same or different compositions, at the same or different time. For example, the subject agonists or antagonists may be administered in a therapeutic regimen that includes the administration ofd a PD-1 or PD-L1 agonist or antagonist, CTLA4-Ig, a cytokine, a cytokine agonist or antagonist, or another receptor agonist or antagonist.

Anti-VSIG8 Antibodies Having Particular Germline Sequences

In certain embodiments, an anti-VSIG8 antibody according to the invention comprises a heavy chain variable region from a particular germline heavy chain immunoglobulin gene and/or a light chain variable region from a particular germline light chain immunoglobulin gene. For example, such anti-VSIG8 antibody may comprise or consist of a human antibody comprising heavy or light chain variable regions that are "the product of" or "derived from" a particular germline sequence if the variable regions of the antibody are obtained from a system that uses human germline immunoglobulin genes. Such systems include immunizing a transgenic mouse carrying human immunoglobulin genes with the antigen of interest or screening a human immunoglobulin gene library displayed on phage with the antigen of interest. A human antibody that is "the product of" or "derived from" a human germline immunoglobulin sequence can be identified as such by comparing the amino acid sequence of the human antibody to the amino acid sequences of human germline immunoglobulins and selecting the human germline immunoglobulin sequence that is closest in sequence (i.e., greatest % identity) to the sequence of the human antibody.

A human antibody that is "the product of" or "derived from" a particular human germline immunoglobulin sequence may contain amino acid differences as compared to the germline sequence, due to, for example, naturally-occurring somatic mutations or intentional introduction of site-directed mutation. However, a selected human antibody typically is at least 90% identical in amino acids sequence to an amino acid sequence encoded by a human germline immunoglobulin gene and contains amino acid residues that identify the human antibody as being human when compared to the germline immunoglobulin amino acid sequences of other species (e.g., murine germline sequences). In certain cases, a human antibody may be at least 95, 96, 97, 98 or 99%, or even at least 96%, 97%, 98%, or 99% identical in amino acid sequence to the amino acid sequence encoded by the germline immunoglobulin gene. Typically, a human antibody derived from a particular human germline sequence will display no more than 10 amino acid differences from the amino acid sequence encoded by the human germline immunoglobulin gene. In certain cases, the human antibody may display no more than 5, or even no more than 4, 3, 2, or 1 amino acid difference from the amino acid sequence encoded by the germline immunoglobulin gene.

Homologous Antibodies

In certain embodiments, an anti-VSIG8 antibody according to the invention comprises heavy and light chain variable regions comprising amino acid sequences that are homologous to isolated anti-VSIG8 amino acid sequences of preferred anti-VSIG8 antibodies, respectively, wherein the antibodies retain the desired functional properties of the parent anti-VSIG8 antibodies. As used herein, the percent homology between two amino acid sequences is equivalent to the percent identity between the two sequences. The percent identity between the two sequences is a function of the number of identical positions shared by the sequences (i.e., % homology=# of identical positions/total # of positions×100), taking into account the number of gaps, and the length of each gap, which need to be introduced for optimal alignment of the two sequences. The comparison of sequences and determination of percent identity between two sequences can be accomplished using a mathematical algorithm, as described in the non-limiting examples below.

The percent identity between two amino acid sequences can be determined using the algorithm of E. Meyers and W. Miller (Comput. Appl. Biosci., 4: 11-17 (1988)) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (J. Mol. Biol. 48:444-453 (1970)) algorithm which has been incorporated into the GAP program in the GCG software package (available commercially), using either a Blossum 62 matrix or a PAM250 matrix, and a gap weight of 16, 14, 12, 10, 8, 6, or 4 and a length weight of 1, 2, 3, 4, 5, or 6.

Additionally or alternatively, the protein sequences of the present invention can further be used as a "query sequence" to perform a search against public databases to, for example, identify related sequences. Such searches can be performed using the XBLAST program (version 2.0) of Altschul, et al. (1990) J Mol. Biol. 215:403-10. BLAST protein searches can be performed with the XBLAST program, score=50, wordlength=3 to obtain amino acid sequences homologous to the antibody molecules according to at least some embodiments of the invention. To obtain gapped alignments for comparison purposes, Gapped BLAST can be utilized as described in Altschul et al., (1997) Nucleic Acids Res. 25(17):3389-3402. When utilizing BLAST and Gapped BLAST programs, the default parameters of the respective programs (e.g., XBLAST and NBLAST) can be used.

Antibodies with Conservative Modifications

In certain embodiments, an anti-VSIG8 antibody according to the invention comprises a heavy chain variable region comprising CDRI, CDR2 and CDR3 sequences and a light chain variable region comprising CDRI, CDR2 and CDR3 sequences, wherein one or more of these CDR sequences comprise specified amino acid sequences based on preferred anti-anti-VSIG8 antibodies isolated and produced using methods herein, or conservative modifications thereof, and wherein the antibodies retain the desired functional properties of anti-VSIG8 antibodies according to at least some embodiments of the invention, respectively.

In various embodiments, the anti-VSIG8 antibody can be, for example, human antibodies, humanized antibodies or chimeric antibodies. As used herein, the term "conservative sequence modifications" is intended to refer to amino acid modifications that do not significantly affect or alter the binding characteristics of the antibody containing the amino acid sequence. Such conservative modifications include amino acid substitutions, additions and deletions. Modifications can be introduced into an antibody according to at least some embodiments of the invention by standard techniques known in the art, such as site-directed mutagenesis and PCR-mediated mutagenesis. Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), β-branched side chains (e.g., threonine, valine, isoleucine) and aromatic side chains (e.g., tyrosine, phenylalanine, tryptophan, histidine). Thus, one or more amino acid residues within the CDR regions of an antibody according to at least some embodiments of the invention can be replaced with other amino acid residues from the same side chain family and the altered antibody can be tested for retained function (i.e., the functions set forth in (c) through j) above) using the functional assays described herein.

Anti-VSIG8 Antibodies that Bind to the Same Epitope

In certain embodiments, an anti-VSIG8 antibody according to the invention possesses desired functional properties such as modulation of immune stimulation and related functions. Other antibodies with the same epitope specificity may be selected and will have the ability to cross-compete for binding to VSIG8 antigen with the desired antibodies. Alternatively, the epitopic specificity of a desired antibody may be determined using a library of overlapping peptides comprising the entire VSIG8 polypeptide, e.g., 15-mers or an overlapping peptide library constituting a portion containing a desired epitope of VSIG8 and antibodies which bind to the same peptides or one or more residues thereof in the library are determined to bind the same linear or conformational epitope.

Engineered and Modified Antibodies

In certain embodiments, an anti-VSIG8 antibody according to the invention can be prepared using an antibody having one or more of the VH and/or VL sequences derived from an anti-VSIG8 antibody starting material to engineer a modified antibody, which modified antibody may have altered properties from the starting antibody. An antibody can be engineered by modifying one or more residues within one or both variable regions (i.e., VH and/or VL), for example within one or more CDR regions and/or within one or more framework regions. Additionally or alternatively, an antibody can be engineered by modifying residues within the constant regions, for example to alter the effector functions of the antibody.

One type of variable region engineering that can be performed is CDR grafting. Antibodies interact with target antigens predominantly through amino acid residues that are located in the six heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties (see, e.g., Riechmann, L. et al. (1998) Nature 332:323-327; Jones, P. et al. (1986) Nature 321:522-525; Queen, C. et al. (1989) Proc. Natl. Acad. See. U.S. 86: 10029-10033; U.S. Pat. No. 5,225,539 to Winter, and U.S. Pat. Nos. 5,530,101; 5,585,089; 5,693,762 and 6,180,370 to Queen et al.)

Suitable framework sequences can be obtained from public DNA databases or published references that include germline antibody gene sequences. For example, germline DNA sequences for human heavy and light chain variable region genes can be found in the "VBase" human germline sequence database (available on the Internet), as well as in Kabat, E. A., et al. (1991) Sequences of Proteins of Immunological Interest, Fifth Edition, U.S. Department of Health and Human Services, NIH Publication No. 91-3242; Tomlinson, I. M., et al. (1992) "The Repertoire of Human Germline VH Sequences Reveals about Fifty Groups of VH Segments with Different Hypervariable Loops" J. Mol. Biol. 227:776-798; and Cox, J. P. L. et al. (1994) "A Directory of Human Germ-line $V_H$ Segments Reveals a Strong Bias in their Usage" Eur. J Immunol. 24:827-836; the contents of each of which are expressly incorporated herein by reference.

Another type of variable region modification is to mutate amino acid residues within the VH and/or VL CDR 1, CDR2 and/or CDR3 regions to thereby improve one or more binding properties (e.g., affinity) of the antibody of interest. Site-directed mutagenesis or PCR-mediated mutagenesis can be performed to introduce the mutations and the effect on antibody binding, or other functional property of interest, can be evaluated in appropriate in vitro or in vivo assays. Preferably conservative modifications (as discussed above) are introduced. The mutations may be amino acid substitutions, additions or deletions, but are preferably substitutions. Moreover, typically no more than one, two, three, four or five residues within a CDR region are altered.

Engineered antibodies according to at least some embodiments of the invention include those in which modifications have been made to framework residues within VH and/or VL, e.g. to improve the properties of the antibody. Typically such framework modifications are made to decrease the immunogenicity of the antibody. For example, one approach is to "backmutate" one or more framework residues to the corresponding germline sequence. More specifically, an antibody that has undergone somatic mutation may contain framework residues that differ from the germline sequence from which the antibody is derived. Such residues can be identified by comparing the antibody framework sequences to the germline sequences from which the antibody is derived.

In addition or alternative to modifications made within the framework or CDR regions, antibodies according to at least some embodiments of the invention may be engineered to include modifications within the Fc region, typically to alter one or more functional properties of the antibody, such as serum half-life, complement fixation, Fc receptor binding, and/or antigen-dependent cellular cytotoxicity. Furthermore, an antibody according to at least some embodiments of the invention may be chemically modified (e.g., one or more chemical moieties can be attached to the antibody) or be modified to alter its glycosylation, again to alter one or more functional properties of the antibody. Such embodiments are described further below. The numbering of residues in the Fc region is that of the EU index of Kabat.

In one embodiment, the hinge region of CHI is modified such that the number of cysteine residues in the hinge region is altered, e.g., increased or decreased. This approach is described further in U.S. Pat. No. 5,677,425 by Bodmer et al. The number of cysteine residues in the hinge region of CHI is altered to, for example, facilitate assembly of the light and heavy chains or to increase or decrease the stability of the antibody.

In another embodiment, the Fc hinge region of an antibody is mutated to decrease the biological half-life of the antibody. More specifically, one or more amino acid mutations are introduced into the CH2-CH3 domain interface region of the Fc-hinge fragment such that the antibody has impaired Staphylococcal protein A (SpA) binding relative to native Fc-hinge domain SpA binding. This approach is described in further detail in U.S. Pat. No. 6,165,745 by Ward et al.

In another embodiment, the antibody is modified to increase its biological half-life. Various approaches are possible. For example, one or more of the following mutations can be introduced: T252L, T254S, T256F, as described in U.S. Pat. No. 6,277,375 to Ward. Alternatively, to increase the biological half-life, the antibody can be altered within the CHI or CL region to contain a salvage receptor binding epitope taken from two loops of a CH2 domain of an Fc region of an IgG, as described in U.S. Pat. Nos. 5,869,046 and 6,121,022 by Presta et al.

In yet other embodiments, the Fc region is altered by replacing at least one amino acid residue with a different amino acid residue to alter the effector functions of the antibody. For example, one or more amino acids selected from amino acid residues 234, 235, 236, 237, 297, 318, 320 and 322 can be replaced with a different amino acid residue such that the antibody has an altered affinity for an effector ligand but retains the antigen-binding ability of the parent antibody. The effector ligand to which affinity is altered can be, for example, an Fc receptor or the CI component of complement. This approach is described in further detail in U.S. Pat. Nos. 5,624,821 and 5,648,260, both by Winter et al.

In another example, one or more amino acids selected from amino acid residues 329, 331 and 322 can be replaced with a different amino acid residue such that the antibody has altered Clq binding and/or reduced or abolished complement dependent cytotoxicity (CDC). This approach is described in further detail in U.S. Pat. No. 6,194,551 by Idusogie et al.

In another example, one or more amino acid residues within amino acid positions 231 and 239 are altered to thereby alter the ability of the antibody to fix complement. This approach is described further in PCT Publication WO 94/29351 by Bodmer et al.

In yet another example, the Fc region is modified to increase the ability of the antibody to mediate antibody dependent cellular cytotoxicity (ADCC) and/or to increase the affinity of the antibody for an Fey receptor by modifying one or more amino acids at the following positions: 238, 239, 248, 249, 252, 254, 255, 256, 258, 265, 267, 268, 269, 270, 272, 276, 278, 280, 283, 285, 286, 289, 290, 292, 293, 294, 295, 296, 298, 301, 303, 305, 307, 309, 312, 315, 320, 322, 324, 326, 327, 329, 330, 331, 333, 334, 335, 337, 338, 340, 360, 373, 376, 378, 382, 388, 389, 398, 414, 416, 419, 430, 434, 435, 437, 438 or 439. This approach is described further in PCT Publication WO 00/42072 by Presta. Moreover, the binding sites on human IgGl for FcyRI, FcyRII, FcyRIII and FcRn have been mapped and variants with improved binding have been described (see Shields, R. L. et al. (2001) J. Biol. Chem. 276:6591-6604). Specific mutations at positions 256, 290, 298, 333, 334 and 339 are shown to improve binding to FcyRIII. Additionally, the following combination mutants are shown to improve FcyRIII binding: T256A/S298A, S298A/E333A, S298A/K224A and S298A/E333A/K334A. Furthermore, mutations such as M252Y/S254T/T256E or M428L/N434S improve binding to FcRn and increase antibody circulation half-life (see Chan C A and Carter P J (2010) Nature Rev Immunol 10:301-316).

In still another embodiment, the antibody can be modified to abrogate in vivo Fab arm exchange. Specifically, th s process involves the exchange of IgG4 half-molecules (one heavy chain plus one light chain) between other IgG4 antibodies that effectively results in b specific antibodies which are functionally monovalent. Mutations to the hinge region and constant domains of the heavy chain can abrogate this exchange (see Aalberse, R C, Schuurman J., 2002, Immunology 105:9-19).

In still another embodiment, the glycosylation of an antibody is modified. For example, an aglycosylated antibody can be made (i.e., the antibody lacks glycosylation). Glycosylation can be altered to, for example, increase the affinity of the antibody for antigen. Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglyclosylation may increase the affinity of the antibody for antigen. Such an approach is described in further detail in U.S. Pat. Nos. 5,714,350 and 6,350,861 by Co et al.

Additionally or alternatively, an antibody can be made that has an altered type of glycosylation, such as a hypofucosylated antibody having reduced amounts of fucosyl residues or an antibody having increased bisecting GlcNac structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies according to at least some embodiments of the invention to thereby produce an antibody with altered glycosylation. For example, the cell lines Ms704, Ms705, and Ms709 lack the fucosyltransferase gene, FUT8 (a (1,6) fucosyltransferase), such that antibodies expressed in the Ms704, Ms705, and Ms709 cell lines lack fucose on their carbohydrates. The Ms704, Ms705, and Ms709 FUT8 cell lines are created by the targeted disruption of the FUT8 gene in CHO/DG44 cells using two replacement vectors (see U.S. Patent Publication No. 20040110704 by Yamane et al. and Yamane-Ohnuki et al. (2004) Biotechnol Bioeng 87:614-22). As another example, EP 1,176,195 by Hanai et al. describes a cell line with a functionally disrupted FUT8 gene, which encodes a fucosyl transferase, such that antibodies expressed in such a cell line exhibit hypofucosylation by reducing or eliminating the a 1,6 bond-related enzyme. Hanai et al. also describe cell lines which have a low enzyme activity for adding fucose to the N-acetylglucosamine that binds to the Fc region of the antibody or does not have the enzyme activity, for example the rat myeloma cell line YB2/0 (ATCC CRL 1662). PCT Publication WO 03/035835 by Presta describes a variant CHO cell line, Lecl3 cells, with reduced ability to attach fucose to Asn(297)-linked carbohydrates, also resulting in hypofucosylation of antibodies expressed in that host cell (see also Shields, R. L. et al. (2002) J. Biol. Chem. 277:26733-26740). PCT Publication WO 99/54342 by Umana et al. describes cell lines engineered to express glycoprotein-modifying glycosyl transferases (e.g., P(l,4)-N-acetylglucosaminyltransferase III (GnTIII)) such that antibodies expressed in the engineered cell lines exhibit increased bisecting GlcNac structures which results in increased ADCC activity of the antibodies (see also Umana et al. (1999) Nat. Biotech. 17: 176-180). Alternatively, the fucose residues of the antibody may be cleaved off using a fucosidase enzyme. For example, the fucosidase a-L-fucosidase removes fucosyl residues from antibodies (Tarentino, A. L. et al. (1975) Biochem. 14:5516-23).

Another modification of the antibodies herein that is contemplated by the invention is pegylation or the addition of other water soluble moieties, typically polymers, e.g., in order to enhance half-life. An antibody can be pegylated to, for example, increase the biological (e.g., serum) half-life of the antibody. To pegylate an antibody, the antibody, or fragment thereof, typically is reacted with polyethylene glycol (PEG), such as a reactive ester or aldehyde derivative of PEG, under conditions in which one or more PEG groups become attached to the antibody or antibody fragment. Preferably, the pegylation is carried out via an acylation reaction or an alkylation reaction with a reactive PEG molecule (or an analogous reactive water-soluble polymer). As used herein, the term "polyethylene glycol" is Intended to encompass any of the forms of PEG that have been used to derivatize other proteins, such as mono (Ci-Cio) alkoxy- or aryloxy-polyethylene glycol or polyethylene glycol-maleimide. In certain embodiments, the antibody to be pegylated is an aglycosylated antibody. Methods for pegylating proteins are known in the art and can be applied to the antibodies according to at least some embodiments of the invention. See for example, EP 0 154 316 by Nishimura et al. and EP 0 401 384 by Ishikawa et al.

Methods of Engineering Antibodies

In certain embodiments, an anti-VSIG8 antibody according to the invention having $V_H$ and $V_L$ sequences can be used to create new anti-VSIG8 antibodies, respectively, by modifying the $V_H$ and/or $V_L$ sequences, or the constant regions attached thereto. Thus, in another aspect according to at least some embodiments of the invention, the structural features of an anti-VSIG8 antibody according to at least some embodiments of the invention, are used to create structurally related anti-VSIG8 antibodies that retain at least one functional property of the antibodies according to at least some embodiments of the invention, such as binding to human VSIG8. For example, one or more CDR regions of one VSIG8 antibody or mutations thereof can be combined recombinantly with known framework regions and/or other CDRs to create additional, recombinantly-engineered, anti-VSIG8 antibodies according to at least some embodiments of the invention, as discussed above. Other types of modifications include those described in the previous section. The starting material for the engineering method is one or more of the $V_H$ and/or $V_L$ sequences provided herein, or one or more CDR regions thereof. To create the engineered antibody, it is not necessary to actually prepare (i.e., express as a protein) an antibody having one or more of the $V_H$ and/or $V_L$ sequences provided herein, or one or more CDR regions thereof. Rather, the information contained in the sequences is used as the starting material to create a "second generation" sequences derived from the original sequences and then the "second generation" sequences is prepared and expressed as a protein.

Standard molecular biology techniques can be used to prepare and express altered antibody sequence. Preferably, the anti-VSIG8 antibody encoded by the altered antibody sequences is one that retains one, some or all of the functional properties of the anti-VSIG8 antibodies, respectively, produced by methods and with sequences provided herein, which functional properties include binding to VSIG8 antigen with a specific KD level or less and/or modulating immune responses and/or selectively binding to desired target cells such as for example, that express VSIG8 antigen.

The functional properties of the altered antibodies can be assessed using standard assays available in the art and/or described herein. In certain embodiments of the methods of engineering antibodies according to at least some embodiments of the invention, mutations can be introduced randomly or selectively along all or part of an anti-VSIG8 antibody coding sequence and the resulting modified anti-VSIG8 antibodies can be screened for binding activity and/or other desired functional properties.

Mutational methods have been described in the art. For example, PCT Publication WO 02/092780 by Short describes methods for creating and screening antibody mutations using saturation mutagenesis, synthetic ligation assembly, or a combination thereof. Alternatively, PCT Publication WO 03/074679 by Lazar et al. describes methods of using computational screening methods to optimize physiochemical properties of antibodies.

VSIG8 Fragment Polypeptides

The term the "soluble ectodomain (ECD)" or "ectodomain" or "soluble" form of VSIG8 refers also to the nucleic acid sequences encoding the corresponding proteins. Optionally, the VSIG8 ECD proteins and fragments thereof refer to any one of the polypeptide sequences listed in any of SEQ ID NOs: 1-3, and/or variants thereof possessing at least 80% sequence identity, more preferably at least 90% sequence identity therewith and even more preferably at least 95, 96, 97, 98 or 99% sequence identity therewith, and/or fusions and or conjugates thereof, and/or polynucleotides encoding same.

In particular, the fragments of the extracellular domain of VSIG8 can include any sequence corresponding to any portion of or comprising the IgV domain of the extracellular domain of VSIG8.

The VSIG8 proteins contain an immunoglobulin domain within the extracellular domain, the IgV domain (or V domain), which is related to the variable domain of antibodies. The IgV domain may be responsible for receptor binding, by analogy to the other B7 family members. The Ig domain of the extracellular domain includes one disulfide bond formed between intra domain cysteine residues, as is typical for this fold and may be important for structure-function.

In one embodiment, there is provided a soluble fragment of VSIG8; as described in greater detail below with regard to the section on fusion proteins, such a soluble fragment may optionally be described as a first fusion partner. Useful fragments are those that alone or when comprised in fusion proteins or multimerized retain the ability to bind to their natural receptor or receptors, e.g., expressed on T and NK cells, and/or which modulate (inhibit or promote) T cell and/or NK cell activation. A VSIG8 polypeptide that is a fragment of full-length VSIG8 typically has at least 20 percent, 30 percent, 40 percent, 50 percent, 60 percent, 70 percent, 80 percent, 90 percent, 95 percent, 98 percent, 99 percent, 100 percent, or even more than 100 percent of the ability to bind its natural receptor(s) and/or the modulation (agonism or antagonism) of one or more of the functional effects of VSIG8 on immunity and on specific immune cells as compared to full-length VSIG8. Soluble VSIG8 polypeptide fragments are fragments of VSIG8 polypeptides that may be shed, secreted or otherwise extracted from the producing cells. In other embodiments, the soluble fragments of VSIG8 polypeptides include fragments of the VSIG8 extracellular domain that retain VSIG8 biological activity, such as fragments that retain the ability to bind to their natural receptor or receptors and/or which modulate (inhibit or promote) T or NK cell activation. The extracellular domain can include 1, 2, 3, 4, or 5 contiguous amino acids from the transmembrane domain, and/or 1, 2, 3, 4, or 5 contiguous amino acids from the signal sequence.

Alternatively, the extracellular domain can have 1, 2, 3, 4, 5 or more amino acids removed from the C-terminus, N-terminus, or both.

In some embodiments the VSIG8 extracellular domain polypeptide comprises the amino acid sequence of the IgV domain as set forth in any one of SEQ ID NO: 1, 2 or 3, or fragments or variants thereof. In other embodiments the VSIG8 extracellular domain polypeptide consists essentially of the amino acid sequence of the IgV domain as set forth in any one of SEQ ID NOs: 1-3.

Generally, the VSIG8 polypeptide fragments are expressed from nucleic acids that include sequences that encode a signal sequence. The signal sequence is generally cleaved from the immature polypeptide to produce the mature polypeptide lacking the signal sequence. The signal sequence of VSIG8 can be replaced by the signal sequence of another polypeptide using standard molecule biology techniques to affect the expression levels, secretion, solubility, or other property of the polypeptide. The signal peptide sequence that is used to replace the VSIG8 signal peptide sequence can be any known in the art.

Preferably such "soluble ectodomain (ECD)" or "ectodomain" or "soluble" form of VSIG8 will modulate (agonize or antagonize) one or more of VSIG8's effects on immunity and specific types of immune cells such as cytotoxic or effector T cells, Tregs and NK cells.

Variants of VSIG8 Polypeptides

In at least some embodiments, the present invention encompasses useful variants of VSIG8 polypeptides including those that increase biological activity, as indicated by any of the assays described herein, or that increase half-life or stability of the protein. Soluble VSIG8 proteins or fragments, or fusions thereof having VSIG8 protein activity, respectively, can be engineered to increase biological activity. In a further embodiment, the VSIG8 protein or fusion protein is modified with at least one amino acid substitution, deletion, or insertion that increases the binding of the molecule to an immune cell, for example a T cell, and transmits an inhibitory signal into the T cell. An isolated or recombinant VSIG8 polypeptide or fusion protein according to any of the foregoing claims which comprises at least one half-life extending moiety.

Such half-life extending moieties may include by way of example polyethylene glycol (PEG), monomethoxy PEG (mPEG), an XTEN molecule, an rPEG molecule, an adnectin, a serum albumin, human serum albumin, immunoglobulin constant region or fragment thereof, or acyl group. In some embodiments the half-life modified isolated or recombinant VSIG8 polypeptide or fusion protein according to the invention which comprises a heterologous polypeptide, or half-life extending moiety, or other heterologous molecule may increase the in vivo half-life of the VSIG8 polypeptide or fusion protein by at least about 2-fold, at least about 3-fold, at least about 4-fold, at least about 5-fold, at least about 10-fold, or more compared to an otherwise identical molecule that lacks said heterologous polypeptide, half-life extending moiety, or other heterologous molecule.

Other optional variants are those VSIG8 proteins that are engineered to selectively bind to one type of T cell versus other Immune cells or to NK cells. For example, the VSIG8 polypeptide can be engineered to bind optionally to Tregs, Th0, Th1, Thl7, Th2 or Th22 cells or to NK cells. Preferential binding refers to binding that is at least 10%, 20%, 30%, 40%, 50%, 60%, 70%, 80%, 90%, 95%, or greater for one type of cell over another type of cell. Still other variants of VSIG8 protein can be engineered to have reduced binding to immune cells relative to wild-type VSIG8 protein, respectively. These variants can be used in combination with variants having stronger binding properties to modulate the immune response with a moderate impact.

Also optionally, variant VSIG8 protein can be engineered to have an increased half-life relative to wild-type. These variants typically are modified to resist enzymatic degradation. Exemplary modifications include modified amino acid residues and modified peptide bonds that resist enzymatic degradation. Various modifications to achieve this are known in the art.

Preferably such variant form of VSIG8 will modulate (agonize or antagonize) one or more of VSIG8's effects on immunity and on specific types of immune cells such as cytotoxic or effector T cells, Tregs, MDSCs, other suppressor cell types or on NK cells.

VSIG8 Fusion Proteins

According to at least some embodiments, VSIG8 fusion polypeptides have a first fusion partner comprising all or a part of a VSIG8 protein fused to a second polypeptide directly or via a linker peptide sequence or a chemical linker useful to connect the two proteins. The VSIG8 polypeptide may optionally be fused to a second polypeptide to form a fusion protein as described herein. The presence of the second polypeptide can alter the solubility, stability, affinity and/or valency of the VSIG8 fusion polypeptide. As used herein, "valency" refers to the number of binding sites available per molecule. In one embodiment the second polypeptide is a polypeptide from a different source or different protein.

According to at least some embodiments, the VSIG8 protein or fragment is selected for its activity for the treatment of immune related disorder, infectious disorder, sepsis, cancer, and/or for blocking the undesirable immune activation that follows gene transfer, as described herein.

In one embodiment, the second polypeptide contains one or more domains of an immunoglobulin heavy chain constant region, preferably having an amino acid sequence corresponding to the hinge, Cm and Cm regions of a human immunoglobulin Cyl, Cy2, Cy3 or Cy4 chain or to the hinge, Cm and Cm regions of a murine immunoglobulin Cy2a chain. According to at least some embodiments, the fusion protein is a dimeric fusion protein which optionally is capable of cross-linking two or more targets. In an optional dimeric fusion protein, the dimer results from the covalent bonding of Cys residue in the hinge region of two of the Ig heavy chains that are the same Cys residues that are disulfide linked in dimerized normal Ig heavy chains. Such proteins are referred to as VSIG8 polypeptides, fragments or fusion proteins thereof.

In one embodiment, the immunoglobulin constant domain may contain one or more amino acid insertions, deletions or substitutions that enhance or decrease binding to specific cell types, increase the bioavailability, or increase the stability of the VSIG8 polypeptides, fusion proteins, or fragments thereof. Suitable amino acid substitutions include conservative and non-conservative substitutions, as described above.

The fusion proteins optionally contain a domain that functions to dimerize or multimerize two or more fusion proteins. The peptide/polypeptide linker domain can either be a separate domain, or alternatively can be contained within one of the other domains (VSIG8 polypeptide or second polypeptide) of the fusion protein. Similarly, the domain that functions to dimerize or multimerize the fusion proteins can either be a separate domain, or alternatively can be contained within one of the other domains (VSIG8 polypeptide, second polypeptide or peptide/polypeptide linker domain) of the fusion protein. In one embodiment, the dimerization/multimerization domain and the peptide/polypeptide linker domain are the same. Further specific, illustrative and non-limiting examples of dimerization/multimerization domains and linkers are given below.

Fusion proteins disclosed herein according to at least some embodiments of the present invention are of formula I: N-R1-R2-R3-C wherein "N" represents the N-terminus of the fusion protein, "C" represents the C-terminus of the fusion protein. In the further embodiment, "RI" is a VSIG8 polypeptide, "R2" is an optional peptide/polypeptide or chemical linker domain, and "R3" is a second polypeptide. Alternatively, R3 may be a VSIG8 polypeptide and RI may be a second polypeptide. Various non-limiting examples of linkers are described in greater detail below.

Optionally, the fusion protein comprises the VSIG8 polypeptide fragments as described herein, fused, optionally by a linker peptide of one or more amino acids (e.g. GS) to one or more "half-life extending moieties". A "half-life extending moiety" is any moiety, for example, a polypeptide, small molecule or polymer, that, when appended to protein, extends the in vivo half-life of that protein in the body of a subject (e.g., in the plasma of the subject). For example, a half-life extending moiety is, in an embodiment of the invention, polyethylene glycol (PEG), monomethoxy PEG (mPEG), XTEN molecule, an rPEG molecule, an adnectin, a serum albumin, human serum albumin, immunoglobulin constant region or fragment thereof, or acyl group. In an embodiment of the invention, PEG is a 5, 10, 12, 20, 30, 40 or 50 kDa moiety or larger or comprises about 12000 ethylene glycol units (PEG12000). An isolated or recombinant VSIG8 polypeptide or fusion protein according to the invention may optionally comprise at least one half-life extending moiety. Half-life extending moieties include PEG's, an XTEN molecule, an rPEG molecule, an adnectin, a serum albumin, human serum albumin, immunoglobulin constant region or fragment thereof, or acyl group. In some embodiments the heterologous polypeptide, half-life extending moiety, or other heterologous molecule contained in a VSIG8 polypeptide or fusion protein according to the invention may increase the in vivo half-life of said isolated or recombinant VSIG8 polypeptide or fusion protein by at least about 2-fold, at least about 3-fold, at least about 4-fold, at least about 5-fold, at least about 10-fold, or more compared to an otherwise identical molecule that lacks said heterologous polypeptide, half-life extending moiety, or other heterologous molecule.

The fusion protein may also optionally be prepared by chemical synthetic methods and the "join" effected chemically, either during synthesis or post-synthesis.

Cross-linking and other such methods may optionally be used (optionally also with the above described genetic level fusion methods), as described for example in U.S. Pat. No. 5,547,853 to Wallner et al, which is hereby incorporated by reference as if fully set forth herein as a non-limiting example only.

According to the present invention, a fusion protein may be prepared from a protein of the invention by fusion with a portion of an immunoglobulin comprising a constant region of an immunoglobulin. More preferably, the portion of the immunoglobulin comprises a heavy chain constant region which is optionally and more preferably a human heavy chain constant region. The heavy chain constant region is most preferably an IgG heavy chain constant region, and optionally and most preferably is an Fc chain, most preferably an IgG Fc fragment that comprises the hinge, Cm and Cm domains. The Fc chain may optionally be a known or "wild type" Fc chain, or alternatively may be mutated or truncated. The $F_c$ portion of the fusion protein may optionally be varied by isotype or subclass, may be a chimeric or hybrid, and/or may be modified, for example to improve effector functions, control of half-life, tissue accessibility, augment biophysical characteristics such as stability, and improve efficiency of production (and less costly). Many modifications useful in construction of disclosed fusion proteins and methods for making them are known in the art, see for example Mueller, et al, *Mol. Immun.*, 34(6): 441-452 (1997), Swann, et al., *Curr. Opin. Immun.*, 20:493-499 (2008), and Presta, *Curr. Opin. Immun.* 20:460-470 (2008). In some embodiments the Fc region is the native IgGl, IgG2, IgG3 or IgG4 Fc region. In some embodiments the Fc region is a hybrid, for example a chimeric consisting of IgG2/IgG4 Fc constant regions.

Modifications to the Fc region include, but are not limited to, IgG4 modified to prevent binding to Fey receptors and complement, IgGl modified to improve binding to one or more Fc y receptors, IgGl modified to minimize effector function (amino acid changes), IgGl with altered/no glycan (typically by changing expression host or substituting the Asn at position 297), and IgGl with altered pH-dependent binding to FcRn. The Fc region may include the entire hinge region, or less than the entire hinge region. In another embodiment, the Fc domain may contain one or more amino acid insertions, deletions or substitutions that reduce binding to the low affinity inhibitory Fc receptor CD32B (FcyRIIB) and retain wild-type levels of binding to or enhance binding to the low affinity activating Fc receptor CD16A (FcyRIIIA).

Another embodiment includes IgG2-4 hybrids and IgG4 mutants that have reduced binding to FcR ($F_c$ receptor) which increase their half-life. Representative IgG2-4 hybrids and IgG4 mutants are described in Angal, S. et al., *Molecular Immunology,* 30(1):105-108 (1993); Mueller, J. et al, *Molecular Immunology,* 34(6): 441-452 (1997); and U.S. Pat. No. 6,982,323 to Wang et al. In some embodiments the IgGl and/or IgG2 domain is deleted; for example, Angal et al. *Molecular Immunology,* 30(1): 105-108 (1993) describe IgGl and IgG2 having serine 241 replaced with a proline.

In a further embodiment, the Fc domain contains amino acid insertions, deletions or substitutions that enhance binding to CD 16 A. A large number of substitutions in the Fc domain of human IgGl that increase binding to CD16A and reduce binding to CD32B are known in the art and are described in Stavenhagen, et al., *Cancer Res.,* 57(18):8882-90 (2007). Exemplary variants of human IgGl Fc domains with reduced binding to CD32B and/or increased binding to CD16A contain F243L, R929P, Y300L, V305I or P296L substitutions. These amino acid substitutions may be present in a human IgGl Fc domain in any combination.

In one embodiment, the human IgG1 Fc domain variant contains a F243L, R929P and Y300L substitution. In another embodiment, the human IgGl Fc domain variant contains a F243L, R929P, Y300L, V305I and P296L substitution. In another embodiment, the human IgGl Fc domain variant contains an N297A/Q substitution, as these mutations abolish FcyR binding. Non-limiting, illustrative, exemplary types of mutations are described in US Patent Application No. 20060034852, published on Feb. 16, 2006, hereby Incorporated by reference as if fully set forth herein. The term "Fc chain" also optionally comprises any type of Fc fragment.

Several of the specific amino acid residues that are important for antibody constant region-mediated activity in the IgG subclass have been identified. Inclusion, substitution or exclusion of these specific amino acids therefore allows for inclusion or exclusion of specific immunoglobulin constant region-mediated activity. Furthermore, specific changes may result in aglycosylation for example and/or other desired changes to the Fc chain. At least some changes may optionally be made to block a function of Fc which is considered to be undesirable, such as an undesirable immune system effect, as described in greater detail below.

Non-limiting, illustrative examples of mutations to Fc which may be made to modulate the activity of the fusion protein include the following changes (given with regard to the Fc sequence nomenclature as given by Kabat, from Kabat E A et al: Sequences of Proteins of Immunological Interest, US Department of Health and Human Services, NIH, (1991)): 220C→S; 233-238 ELLGGP→EAEGAP; 265D→A, preferably in combination with 434N→A; 297N→A (for example to block N-glycosylation); 318-322 EYKCK→AYACA; 330-331AP→SS; or a combination thereof (see for example M. Clark, Chemical Immunol and Antibody Engineering, pp 1-31 for a description of these mutations and their effect). The construct for the Fc chain which features the above changes optionally and preferably comprises a combination of the hinge region with the Cm and Cm domains.

The above mutations may optionally be implemented to enhance desired properties or alternatively to block non-desired properties. For example, aglycosylation of antibodies was shown to maintain the desired binding functionality while blocking depletion of T-cells or triggering cytokine release, which may optionally be undesired functions (see M. Clark, Chemical Immunol and Antibody Engineering, pp 1-31). Substitution of 331 proline for serine may block the ability to activate complement, which may optionally be considered an undesired function (see M. Clark, Chemical Immunol and Antibody Engineering, pp 1-31). Changing the alanine to serine at position 330 in combination with this change may also enhance the desired effect of blocking the ability to activate complement.

Residues 235 and 237 were shown to be involved in antibody-dependent cell-mediated cytotoxicity (ADCC), such that changing the block of residues from 233-238 as described may also block such activity if ADCC is considered to be an undesirable function. Residue 220 is normally a cysteine for $F_c$ from IgGl, which is the site at which the heavy chain forms a covalent linkage with the light chain. Optionally, this residue may be changed to another amino acid residue (e.g., serine), to avoid any type of covalent linkage (see M. Clark, Chemical Immunol and Antibody Engineering, pp 1-31) or by deletion or truncation.

The above changes to residues 265 and 434 may optionally be implemented to reduce or block binding to the Fc receptor, which may optionally block undesired functionality of Fc related to its immune system functions (see "Binding site on Human IgGl for Fc Receptors", Shields et al, Vol 276, pp 6591-6604, 2001).

The above changes are intended as illustrations only of optional changes and are not meant to be limiting in any way. Furthermore, the above explanation is provided for descriptive purposes only, without wishing to be bound by a single hypothesis. In a further embodiment, the fusion protein includes the extracellular domain of VSIG8 or a fragment thereof fused to an Ig $F_c$ region. Recombinant Ig VSIG8 polypeptides, fragments or fusion proteins thereof fusion proteins can be prepared by fusing the coding region of the extracellular domain of VSIG8 or a fragment thereof to the Fc region of human IgGl or mouse IgG2a, as described previously (Chapoval, et al., Methods Mol. Med, 45:247-255 (2000)).

Optionally, VSIG8 ECD refers also to fusion protein, comprising an amino acid sequence of human VSIG8 ECD fused to human immunoglobulin $F_c$. Optionally, said fusion protein comprises the amino acid sequence of the human or non-human VSIG8 ECD set forth in SEQ ID NOs: 1, 2, 3 or fragment thereof In another embodiment the second polypeptide may have a conjugation domain through which additional molecules can be bound to the VSIG8 fusion proteins. In one such embodiment, the conjugated molecule is capable of targeting the fusion protein to a particular organ or tissue; further specific, illustrative, non-limiting examples of such targeting domains and/or molecules are given below.

In another such embodiment the conjugated molecule is another immunomodulatory agent that can enhance or augment the effects of the VSIG8 fusion protein. In another embodiment the conjugated molecule is Polyethylene Glycol (PEG). In some embodiments VSIG8 polypeptides or fusion proteins according to the invention will comprise a binding domain, wherein the binding protein is capable of cross-linking two or more targets. In some embodiments VSIG8 polypeptides or fusion proteins according to the invention will comprise another binding moiety, wherein the binding moiety targets a tumor cell, infectious agent, e.g., a virus, bacterium, mycoplasm, fungus, yeast or parasite, or cell infected thereby, an immune cell, or a disease site.

In some embodiments VSIG8 polypeptides or fusion proteins according to the invention will comprise at least one heterologous polypeptide which may be a receptor, hormone, cytokine, antigen, B-cell target, NK cell target, T cell target, TNF receptor superfamily member, Hedgehog family member, a receptor tyrosine kinase, a proteoglycan-related molecule, a TGF-β superfamily member, a Wnt-related molecule, a receptor ligand, a Dendritic cell target, a myeloid cell target, a monocyte/macrophage cell target or an angiogenesis target.

In some embodiments VSIG8 polypeptides or fusion proteins according to the invention will comprise at least one antigen, e.g., a tumor antigen, autoantigen, allergen, or an infectious agent antigen.

In some embodiments VSIG8 polypeptides or fusion proteins according to the invention will comprise a T cell target selected from the group consisting of 2B4/SLAMF4, IL-2 Ra, 4-1BB/TNFRSF9, IL-2R, ALCAM, B7-1/CD80, IL-4R, B7-H3, BLAME/SLAMF8, BTLA, IL-6R, CCR3, IL-7 Ra, CCR4, CXCRI/IL-8 RA, CCR5, CCR6, IL-10 R a, CCR7, IL-10 R, CCR8, IL-12 R i, CCR9, IL-12 Rβ2, CD2, IL-13Ral, IL-13, CD3, CD4, ILT2/CD85j, ILT3/CD85k, ILT4/CD85d, ILT5/CD85a, Integrin a 4/CD49d, CD5, IntegrinaE/CD103, CD6, Integrin a M/CDI Ib, CD8, Integrin a X/CD 11c, Integrin 2/CD18, KIR/CD158, CD27/TNFRSF7, KIR2DL1, CD28, KIR2DL3, CD30/TNFRSF8, KIR2DL4/CD158d, CD31/PECAM-1, KIR2DS4, CD40 Ligand/TNFSF5, LAG-3, CD43, LAIR1, CD45, LAIR2, CD83, Leukotriene B4 RI, CD84/SLAMF5, NCAM-LI, CD94, NKG2A, CD97, NKG2C, CD229/SL AMF3, NKG2D, CD2F-10/SLAMF9, NT-4, CD69, NTB-A/SLAMF6, Common γ Chain/IL-2 Ry, Osteopontin, CRACC/SLAMF7, PD-1, CRT AM, PSGL-1, CTLA-4, RANK/TNFRSF11 A, CX3CR1, CX3CL1, L-Selectin, CXCR3, SIRP βi, CXCR4, SLAM, CXCR6, TCCRAVSX-1, DNAM-1, Thymopoietin, EMMPRIN/CD 147, TIM-1, EphB6, TIM-2, Fas/TNFRSF6, TIM-3, Fas Ligand/TNFSF6, TIM-4, Fey RIII/CD16, TIM-6, GITR/TNFRSF18, TNF R1/TNFRSFIA, Granulysin, TNF R11/TNFRSF1B, H VEM/TNFRSF 14, TRAIL R1/TNFRSF10A, ICAM-1/CD54, TRAIL R2/TNFRSF10B, ICAM-2/CD102, TRAIL R3/TNFRSF10C, IFN-yRI, TRAIL R4/TNFRSF10D, IFN-yR2, TSLP, IL-1 RI and TSLP R.

In some embodiments VSIG8 polypeptides or fusion proteins according to the invention will comprise at least one monocyte/macrophage cell target selected from the group consisting of B7-1/CD80, ILT4/CD85d, B7-H1, ILT5/CD85a, Common β Chain, Integrin a 4/CD49d, BLAME/SLAMF8, Integrin a X/CD1 Ic, CCL6/C10, Integrin β2/CD18, CD155/PVR, Integrin β3/CD61, CD31/PECAM-1, Latexin, CD36/SR-B3, Leukotriene B4 RI, CD40/TNFRSF5, LIMPII/SR-B2, CD43, LMIR1/CD300A, CD45, LMIR2/CD300c, CD68, LMIR3/CD300LF, CD84/SLAMF5, LMIR5/CD300LB, CD97, LMIR6/CD300LE, CD163, LRP-1, CD2F-10/SLAMF9, MARCO, CRACC/SLAMF7, MD-1, ECF-L, MD-2, EMMPRIN/CD 147, MGL2, Endoglin/CD105, Osteoactivin/GPNMB, Fc yRI/CD64, Osteopontin, Fc y RIIB/CD32b, PD-L2, Fc yRIIC/CD32c, Siglec-3/CD33, Fey RIIA/CD32a, SIGNR1/CD209, Fey RIII/CD16, SLAM, GM-CSF R a, TCCR WSX-1, ICAM-2/CD102, TLR3, IFN-y RI, TLR4, IFN-y R2, TREM-1, IL-1 RII, TREM-2, ILT2/CD85j, TREM-3, ILT3/CD85k, TREMLI/TLT-1, 2B4/SLAMF4, IL-10 R a, ALCAM, IL-10 R β, Aminopeptidase N/ANPEP, ILT2/CD85j, Common β Chain, ILT3/CD85k, Clq R1/CD93, ILT4/CD85d, CCR1, ILT5/CD85a, CCR2, Integrin a 4/CD49d, CCR5, Integrin a M/CD I ib, CCR8, Integrin a X/CD 11c, CD155/PVR, Integrin β2/CD18, CD14, Integrin β3/CD61, CD36/SR-B3, LAIR1, CD43, LAIR2, CD45, Leukotriene B4 RI, CD68, LIMPII/SR-B2, CD84/SLAMF5, LMIR1/CD300A, CD97, LMIR2/CD300c, CD163, LMIR3/CD300LF, Coagulation Factor III/Tissue Factor, LMIR5/CD300LB, CX3CR1, CX3CL1, LMIR6/CD300LE, CXCR4, LRP-1, CXCR6, M-CSF R, DEP-1/CD148, MD-1, DNAM-1, MD-2, EMMPRIN/CD 147, MMR, Endoglin/CD105, NCAM-L1, Fc γ R1/CD64, PSGL-1, Fc Y RIII/CD16, RP105, G-CSF R, L-Selectin, GM-CSF R a, Siglec-3/CD33, H VEM/TNFRSF 14, SLAM, ICAM-1/CD54, TCCRAVSX-1, ICAM-2/CD102, TREM-1, IL-6 R, TREM-2, CXCRI/IL-8 RA, TREM-3 and TREMLI/TLT-1.

In some embodiments VSIG8 polypeptides or fusion proteins according to the invention will comprise at least one Dendritic cell target is selected from the group consisting of CD36/SR-B3, LOX-1/SR-E1, CD68, MARCO, CD1863, SR-AI/MSR, CD5L, SREC-I, CL-P 1/COLEC 12, SREC-II, LIMPII/SR-B2, RP105, TLR4, TLRI, TLR5, TLR2, TLR6, TLR3, TLR9, 4-IBB Ligand/TNFSF9, IL-12/IL-23 p40, 4-Amino-l,8-naphthalimide, ILT2/CD85j, CCL21/6Ckine, ILT3/CD85k, 8-oxo-dG, ILT4/CD85d, 8D6A, ILT5/CD85a, A2B5, Integrin a 4/CD49d, Aag, Integrin β2/CD18, AMICA, Langerin, B7-2/CD86, Leukotriene B4 RI, B7-H3, LMIR1/CD300A, BLAME/SLAMF8, LMIR2/CD300c, Clq R1/CD93, LMIR3/CD300LF, CCR6, LMIR5/CD300LB, CCR7, LMIR6/CD300LE, CD40/TNFRSF5, MAG/Siglec-4a, CD43, MCAM, CD45, MD-1, CD68, MD-2, CD83, MDL-1/CLEC5A, CD84/SLAMF5, MMR, CD97, NCAM-L1, CD2F-10/SLAMF9, Osteoactivin/GPNMB, Chem 23, PD-L2, CLEC-1, RP105, CLEC-2, Siglec-2/CD22, CRACC/SLAMF7, Siglec-3/CD33, DC-SIGN, Siglec-5, DC-SIGNR/CD299, Siglec-6, DCAR, Siglec-7, DCIR/CLEC4A, Siglec-9, DEC-205, Siglec-10, Dectin-1/CLEC7A, Siglec-F, Dectin-2/CLEC6A, SIGNR1/CD209, DEP-1/CD148, SIGNR4, DLEC, SLAM, EMMPRIN/CD 147, TCCR/WSX-1, Fc γ R1/CD64, TLR3, Fc γ RIIB/CD32b, TREM-1, Fc γ RIIC/CD32c, TREM-2, Fcy RIIA/CD32a, TREM-3, Fc γ RIII/CD16, TREMLI/TLT-1, ICAM-2/CD102 and Vanilloid RI.

In some embodiments VSIG8 polypeptides or fusion proteins according to the invention will comprise at least one TNF receptor superfamily member is selected from the group consisting of 4-1BB/TNFRSF9, NGF R/TNFRSF16, BAFF R/TNFRSF13C, Osteoprotegerin/TNFRSFI IB, B CMA/TNFRSF 17, OX40/TNFRSF4, CD27/TNFRSF7, RANK/TNFRSF11 A, CD30/TNFRSF8, RELT/TNFRSF19L, CD40/TNFRSF5, T ACI/TNFRSF 13B, DcR3/TNFRSF6B, TNF RI/TNFRSF1A, DcTRAIL R1/TNFRSF23, TNF RII/TNFRSF1B, DcTRAIL R2/TNFRSF22, TRAIL R1/TNFRSF10A, DR3/TNFRSF25, TRAIL R2/TNFRSF10B, DR6/TNFRSF21, TRAIL R3/TNFRSF10C, EDAR, TRAIL R4/TNFRSF 10D, Fas/TNFRSF6, TRO Y/TNFRSF 19, GITR/TNFRSF18, TWEAK R/TNFRSF12, HVEM/TNFRSF14, XEDAR, Lymphotoxin β R/TNFRSF3, 4-1BB Ligand/TNFSF9, Lymphotoxin, APRIL/TNFSF 13, Lymphotoxin/TNFSF3, BAFF/TNFSF13C, OX40 Ligand/TNFSF4, CD27 Ligand/TNFSF7, TL1A/TNFSF15, CD30 Ligand/TNFSF8, TNF-a/TNFSFIA, CD40 Ligand/TNFSF5, TNF-/TNFSFIB, EDA-A2, TRAIL/TNFSFIO, Fas Ligand/TNFSF6, TR ANCE/TNFSF 11, GITR Ligand/TNFSF18, TWEAK/TNFSFI 2 and LIGHT/TNFSF14.

In some embodiments VSIG8 polypeptides or fusion proteins according to the invention will comprise at least one Hedgehog family member selected from the group consisting of Patched and Smoothened.

In some embodiments VSIG8 polypeptides or fusion proteins according to the invention will comprise at least one receptor tyrosine kinase selected from the group consisting of Axl, FGF R4, Clq R1/CD93, FGF R5, DDR1, Flt-3, DDR2, HGF R, Dtk, IGF-I R, EGF R, IGF-II R, Eph, INSRR, EphAI, Insulin R/CD220, EphA2, M-CSF R, EphA3, Mer, EphA4, MSP R/Ron, EphA5, MuSK, EphA6, PDGF R a, EphA7, PDGF R β, EphA8, Ret, EphBI, RORI, EphB2, ROR2, EphB3, SCF R/c-kit, EphB4, Tie-1, EphB6, Tie-2, ErbB2, TrkA, ErbB3, TrkB, ErbB4, TrkC, FGF RI, VEGF RI/Flt-1, FGF R2, VEGF R2/Flk-1, FGF R3 and VEGF R3/Flt-4.

In some embodiments VSIG8 polypeptides or fusion proteins according to the invention will comprise at least one Transforming Growth Factor (TGF)-superfamily member selected from the group consisting of Activin RIA/ALK-2, GFR a-1, Activin RIB/ALK-4, GFR a2, Activin RHA, GFR a-3, Activin RUB, GFR a-4, ALK-1, MIS RII, ALK-7, Ret, BMPR-IA/ALK-3, TGF-beta RI/ALK-5, BMPR-IB/ALK-6, TGF-β RII, BMPR-II, TGF-β RIIb, Endoglin/CD 105 and TGF-β RIII.

In some embodiments VSIG8 polypeptides or fusion proteins according to the invention will comprise at least one Wnt-related molecule selected from the group consisting of Frizzled-1, Frizzled-8, Frizzled-2, Frizzled-9, Frizzled-3, sFRP-1, Frizzled-4, sFRP-2, Frizzled-5, sFRP-3, Frizzled-6, sFRP-4, Frizzled-7, MFRP, LRP 5, LRP 6, Wnt-1, Wnt-8a, Wnt-3a, Wnt-IOb, Wnt-4, Wnt-11, Wnt-5a, Wnt-9a and Wnt-7a.

In some embodiments VSIG8 polypeptides or fusion proteins according to the invention will comprise at least one receptor ligand selected from the group consisting of 4-1BB Ligand/TNFSF9, Lymphotoxin, APRIL/TNFSF 13, Lymphotoxin/TNFSF3, BAFF/TNFSF13C, OX40 Ligand/TNFSF4, CD27 Ligand/TNFSF7, TL1A/TNFSF15, CD30 Ligand/TNFSF8, TNF-a/TNFSFIA, CD40 Ligand/TNFSF5, TNF-β/TNFSF 1 B, EDA-A2, TRAIL/TNFSF10, Fas Ligand/TNFSF6, RANCE/TNFSFI I, GITR Ligand/TNFSF18, TWEAK TNFSF12, LIGHT/TNFSF14, Amphiregulin, NRG1 isoform GGF2, Betacellulin, NRG1 Isoform SMDF, EGF, NRGI-a HRGI-a, Epigen, NRGI-β I/HRGI-β 1, Epiregulin, TGF-a, HB-EGF, TMEFFI/Tomoregulin-1, Neuregulin-3, TMEFF2, IGF-I, IGF-II, Insulin, Activin A, Activin B, Activin AB, Activin C, BMP-2, BMP-7, BMP-3, BMP-8, BMP-3b/GDF-10, BMP-9, BMP-4, BMP-15, BMP-5, Decapentaplegic, BMP-6, GDF-1, GDF-8, GDF-3, GDF-9, GDF-5, GDF-11, GDF-6, GDF-15, GDF-7, Artemin, Neurturin, GDNF, Persephin, TGF-β, TGF-β 2, TGF-β 1, TGF-β 3, LAP (TGF-β 1), TGF-β 5, Latent TGF-β 1, Latent TGF-β bpl, TGF-β 1.2, Lefty, Nodal, MIS/AMH, FGF acidic, FGF-12, FGF basic, FGF-13, FGF-3, FGF-16, FGF-4, FGF-17, FGF-5, FGF-19, FGF-6, FGF-20, FGF-8, FGF-21, FGF-9, FGF-23, FGF-10, KGF/FGF-7, FGF-11, Neuropilin-1, P1GF, Neuropilin-2, P1GF-2, PDGF, PDGF-A, VEGF, PDGF-B, VEGF-B, PDGF-C, VEGF-C, PDGF-D, VEGF-D and PDGF-AB.

In some embodiments VSIG8 polypeptides or fusion proteins according to the invention will comprise at least one tumor antigen selected from the group consisting of Squamous Cell Carcinoma Antigen 1 (SCCA-1), (PROTEIN T4-A), Squamous Cell Carcinoma Antigen 2 (SCCA-2), Ovarian carcinoma antigen CA125 (1A1-3B; KIAA0049), MUCIN 1 (TUMOR-ASSOCIATED MUCIN; Carcinoma-Associated Mucin; Polymorphic Epithelial Mucin; PEM; PEMT; EPISIALIN; Tumor-Associated Epithelial Membrane Antigen; EMA; H23AG; Peanut-Reactive Urinary Mucin; PUM; and Breast Carcinoma-Associated Antigen DF3), CTCL tumor antigen sel-1, CTCL tumor antigen sel4-3, CTCL tumor antigen se20-4, CTCL tumor antigen se20-9, CTCL tumor antigen se33-I, CTCL tumor antigen se37-2, CTCL tumor antigen se57-I, CTCL tumor antigen se89-I, Prostate-specific membrane antigen, 5T4 oncofetal trophoblast glycoprotein, Orf73 Kaposi's sarcoma-associated herpesvirus, MAGE-C1 (cancer/testis antigen CT7), MAGE-B 1 ANTIGEN (MAGE-XP Antigen; DAM10), MAGE-B2 Antigen (DAM6), MAGE-2 ANTIGEN, MAGE-4a antigen, MAGE-4b antigen, Colon cancer antigen NY-CO-45, Lung cancer antigen NY-LU-12 variant A, Cancer associated surface antigen, Adenocarcinoma antigen ART1, Paraneoplastic associated brain-testis-cancer antigen (onconeuronal antigen MA2; paraneoplastic neuronal antigen), Neuro-oncological ventral antigen 2 (NOVA2), Hepatocellular carcinoma antigen gene 520, Tumor-Associated Antigen CO-029, Tumor-associated antigen MAGE-X2, Synovial sarcoma, X breakpoint 2, Squamous cell carcinoma antigen recognized by T cell, Serologically defined colon cancer antigen 1, Serologically defined breast cancer antigen NY-BR-15, Serologically defined breast cancer antigen NY-BR-16, Chromogranin A, parathyroid secretory protein 1, DUPAN-2, CA 19-9, CA 72-4, CA 195 and L6.

In some embodiments VSIG8 polypeptides or fusion proteins according to the invention will comprise at least one B cell target selected from the group consisting of CD10, CD19, CD20, CD21, CD22, CD23, CD24, CD37, CD38, CD39, CD40, CD72, CD73, CD74, CDw75, CDw76, CD77, CD78, CD79a/b, CD80, CD81, CD82, CD83, CD84, CD85, CD86, CD89, CD98, CD126, CD127, CDwl30, CD138 and CDwl50.

In some embodiment VSIG8 polypeptides or fusion proteins according to the invention will comprise at least one angiogenesis target is selected from the group consisting of Angiopoietin-1, Angiopoietin-like 2, Angiopoietin-2, Angiopoietin-like 3, Angiopoietin-3, Angiopoietin-like 7/CDT6, Angiopoietin-4, Tie-1, Angiopoietin-like 1, Tie-2, Angiogenin, iNOS, Coagulation Factor III/Tissue Factor, nNOS, CTGF/CCN2, NOV/CCN3, DANCE, OSM, EDG-1, Plfr, EG-VEGF/PK1, Proliferin, Endostatin, ROB 04, Erythropoietin, Thrombospondin-1, Kininostatin, Thrombospondin-2, MFG-E8, Thrombospondin-4, Nitric Oxide, VG5Q, eNOS, EphAI, EphA5, EphA2, EphA6, EphA3, EphA7, EphA4, EphA8, EphBI, EphB4, EphB2, EphB6, EphB3, Ephrin-AI, Ephrin-A4, Ephrin-A2, Ephrin-A5, Ephrin-A3, Ephrin-BI, Ephrin-B3, Ephrin-B2, FGF acidic, FGF-12, FGF basic, FGF-13, FGF-3, FGF-16, FGF-4, FGF-17, FGF-5, FGF-19, FGF-6, FGF-20, FGF-8, FGF-21, FGF-9, FGF-23, FGF-10, KGF/FGF-7, FGF-11, FGF RI, FGF R4, FGF R2, FGF R5, FGF R3, Neuropilin-1, Neuropilin-2, Semaphorin 3A, Semaphorin 6B, Semaphorin 3C, Semaphorin 6C, Semaphorin 3E, Semaphorin 6D, Semaphorin 6A, Semaphorin 7 A, MMP, MMP-11, MMP-1, MMP-12, MMP-2, MMP-13, MMP-3, MMP-14, MMP-7, MMP-15, MMP-8, MMP-16/MT3-MMP, MMP-9, MMP-24/MT5-MMP, MMP-10, MMP-25/MT6-MMP, TIMP-1, TIMP-3, TIMP-2, TIMP-4, ACE, IL-13 R a 1, IL-13, Clq R1/CD93, Integrin a 4/CD49d, VE-Cadherin, Integrin β2/CD18, CD31/PE-CAM-1, KLF4, CD36/SR-B3, LYVE-1, CD151, MCAM, CL-P1/COLEC12, Nectin-2/CD112, Coagulation Factor III/Tissue Factor, E-Selectin, D6, P-Selectin, DC-SIGNR/CD299, SLAM, EMMPRIN/CD 147, Tie-2, Endoglin/CD105, TNF RI/TNFRSF1A, EPCR, TNF RII/TNFRSF1B, Erythropoietin R, TRAIL R1/TNFRSF10A, ESAM, TRAIL R2/TNFRSF10B, FABP5, VCAM-1, ICAM-1/CD54, VEGF R2/Flk-1, ICAM-2/CD102, VEGF R3/Flt-4, IL-1 RI and VG5Q.

In some embodiments VSIG8 polypeptides or fusion proteins according to the invention will comprise a VSIG8 polypeptide according to the invention and at least one heterologous polypeptide and/or or binding moiety or VSIG8 polypeptides are linked to one another by an amino acid spacer.

In some embodiments VSIG8 polypeptides or fusion proteins according to the invention will a VSIG8 polypeptide and at least one heterologous polypeptide and/or or binding moiety or VSIG8 polypeptides are linked to one another by an amino acid spacer of sufficient length of amino acid residues so that the different moieties can successfully bind to their individual targets.

In some embodiments VSIG8 polypeptides or fusion proteins according to the invention will comprise 2-10 of any of the VSIG8 ECD polypeptides or fragments thereof disclosed herein.

In some embodiments VSIG8 polypeptides or fusion proteins according to the invention will comprise one or more VSIG8 polypeptide(s) and at least one heterologous polypeptide optionally intervened by a heterologous linker which optionally comprises a polypeptide that is not a fragment of a VSIG8 polypeptide.

In some embodiments VSIG8 polypeptides or fusion proteins according to the invention will comprise a linker which is a peptide comprising 5-50 amino acid residues, more preferably 5-25 amino acid residues.

In some embodiments VSIG8 polypeptides or fusion proteins according to the invention will comprise a linker which comprises, consists essentially of, glycine, serine, and/or alanine residues.

In some embodiments VSIG8 polypeptides or fusion proteins according to the invention will comprise a linker which comprises 5-50, 5-25, 5-15, 4-14, 4-12, or more amino acid residues, e.g., which may include or consist of glycine, serine, and/or alanine residues.

Peptide or Polypeptide Linker Domain

VSIG8 fusion proteins optionally may contain a peptide or polypeptide linker domain that separates the VSIG8 polypeptide from the second polypeptide. Various non-limiting examples of such linker domains are described herein. In one embodiment, the linker domain contains the hinge region of an immunoglobulin. In a further embodiment, the hinge region is derived from a human immunoglobulin. Suitable human immunoglobulins that the hinge can be derived from include IgG, IgD and IgA. In a further embodiment, the hinge region is derived from human IgG. Amino acid sequences of immunoglobulin hinge regions and other domains are well known in the art. In another embodiment, the linker domain optionally contains a hinge region of an immunoglobulin as described above, and further includes one or more additional immunoglobulin domains.

Other suitable peptide/polypeptide linker domains optionally include naturally occurring or non-naturally occurring peptides or polypeptides. Peptide linker sequences are at least 2 amino acids in length. Optionally the peptide or polypeptide domains are flexible peptides or polypeptides. A "flexible linker" herein refers to a peptide or polypeptide containing two or more amino acid residues joined by peptide bond(s) that provides increased rotational freedom for two polypeptides linked thereby than the two linked polypeptides would have in the absence of the flexible linker. Such rotational freedom allows two or more antigen binding sites joined by the flexible linker to each access target antigen(s) more efficiently.

Exemplary flexible peptides/polypeptides include, but are not limited to, the amino acid sequences Gly-Ser, Gly-Ser-Gly-Ser, Ala-Ser, Gly-Gly-Gly-Ser, Gly4-Ser, (Gly4-Ser)2, (Gly4-Ser)3, (Gly4-Ser)4, [Gly4-Set]2 Gly-Ala-Gly-Ser-Gly4-Ser Gly-(Gly4-Ser)2, Gly4-Ser-Gly, Gly-Ser-Gly2 and Gly-Ser-Gly2-Ser. Additional flexible peptide/polypeptide sequences are well known in the art. Other suitable peptide linker domains optionally include the TEV linker ENLYFQG, a linear epitope recognized by the Tobacco Etch Virus protease. Exemplary peptides/polypeptides include, but are not limited to, GSENLYFQGSG and helix forming linkers such as Ala-(Glu-Ala-Ala-Ala-Lys)n-Ala (n=1-5). Additional helix forming peptide/polypeptide sequences are well known in the art. In some optionally embodiments VSIG8 fragments, e.g., ECD fragments, are linked to each other (multimers) and/or one or more VSIG8 fragments, e.g., ECD fragments, are linked to a heterologous polypeptide such as an immunoglobulin or fragment thereof, especially an immunoglobulin heavy chain or fragment thereof by a peptide linker, preferably a "flexible linker" sequence. The linker sequence should allow effective positioning of the VSIG8 fragments and the heterologous polypeptide such as an immunoglobulin polypeptide or domains thereof to allow functional activity of both moieties and the domains thereof. Successful presentation of the polypeptide fusion can modulate the activity of a cell either to induce or to inhibit T-cell proliferation, or to initiate or inhibit an immune response to a particular site. This can be determined in appropriate assays such as disclosed herein below, including the in vitro assays that includes sequential steps of culturing T cells to proliferate same, and contacting the T cells with a fusion polypeptide according to the invention or a cell expressing same and then evaluating whether the fusion polypeptide promotes or inhibits T cell proliferation.

As used herein, the phrase "effective positioning of the heterologous polypeptide and the VSIG8 polypeptide", or other similar phrase, is intended to mean that the domains of these moieties are positioned so that VSIG8 domains and heterologous polypeptide domains are capable of interacting with immune or other target cells, e.g., cancer or other VSIG8 expressing cells to initiate or inhibit an immune reaction, or to inhibit or stimulate cell development.

With respect to VSIG8-Ig fusion proteins the linker sequence also preferably permits effective positioning of the $F_c$ domain and VSIG8 domains to allow functional activity of each domain. In certain embodiments, the Fc domains are effectively positioned to allow proper fusion protein complex formation and/or interactions with $F_c$ receptors on immune cells or proteins of the complement system to stimulate $F_c$-mediated effects including opsonization, cell lysis, degranulation of mast cells, basophils, and eosinophils, and other Fc receptor-dependent processes; activation of the complement pathway; and enhanced in vivo half-life of the fusion protein complex.

Linker sequences are discussed supra in connection with fusion proteins according to the invention. Linker sequences can optionally be used to link two or more VSIG8 polypeptides of the biologically active polypeptide to generate a single-chain molecule with the desired functional activity. In some preferred embodiments the linker sequence comprises from about 5 to 20 amino acids, more preferably from about 7 or 8 to about 16 amino acids. The linker sequence is preferably flexible so as not hold the VSIG8 polypeptide and moiety linked thereto, e.g., an effector molecule in a single undesired conformation. The linker sequence can be used, e.g., to space the recognition site from the fused molecule. Specifically, the peptide linker sequence can be positioned between the biologically active VSIG8 polypeptide and the effector molecule, e.g., to chemically cross-link same and to provide molecular flexibility. The linker in some embodiments will predominantly comprise amino acids with small side chains, such as glycine, alanine and serine, to provide for flexibility. Preferably about 80 or 90 percent or greater of the linker sequence comprise glycine, alanine or serine residues, particularly glycine and serine residues. Other suitable linker sequences include flexible linker designs that have been used successfully to join antibody variable regions together, see Whitlow, M. et al., (1991) *Methods: A Companion to Methods in Enzymology* 2:97-105. In some examples, for covalently linking an effector molecule to a VSIG8 molecule, the amino sequence of the linker should be capable of spanning a suitable distance from the C-terminal residue of the VSIG8 polypeptide to the N-terminal residue of the effector molecule. Suitable linker sequences can be readily identified empirically. Additionally, suitable size and sequences of linker sequences also can be determined by known computer modeling techniques based on the predicted size and shape of the fusion polypeptide. Other linker sequences are discussed supra in connection with fusion proteins according to the invention.

Optionally a polypeptide as described herein comprises 2-20 VSIG8 ECD polypeptide fragments linked together. Optionally the fragments are intervened by a heterologous linker which optionally comprises a polypeptide that is not a fragment of a VSIG8 polypeptide.

Optionally the linker is a peptide comprising 5-50 amino acid residues, more preferably 5-25 amino acid residues. Optionally the linker comprises, consists essentially of, or consists of 4-12 glycine, serine, and/or alanine residues.

Dimerization, Multimerization and Targeting Domains

VSIG8 fusion proteins disclosed herein optionally contain a dimerization or multimerization or oligomerization domain that functions to dimerize, oligomerize or multimerize two or more fusion proteins, which may be the same or different (heteromultimers or homomultimers). For example a VSIG8 fusion protein may be attached to another VSIG8 fusion protein or another moiety, e.g. another costimulatory fusion protein. The domain that functions to dimerize or multimerize the fusion proteins can either be a separate domain, or alternatively can be contained within one of the other domains (VSIG8 polypeptide, second polypeptide, or peptide/polypeptide linker domain) of the fusion protein.

Dimerization or multimerization can occur between or among two or more fusion proteins through dimerization or multimerization domains. Alternatively, dimerization or multimerization of fusion proteins can occur by chemical crosslinking. The dimers or multimers that are formed can be homodimeric/homomultimeric or heterodimeric/heteromultimeric. The second polypeptide "partner" in the VSIG8 fusion polypeptides may be comprised of one or more other proteins, protein fragments or peptides as described herein, including but not limited to any immunoglobulin (Ig) protein or portion thereof, preferably the Fc region, or a portion of a biologically or chemically active protein such as the papillomavirus E7 gene product, melanoma-associated antigen p97), and HIV env protein (gpl20). The "partner" is optionally selected to provide a soluble dimer/multimer and/or for one or more other biological activities as described herein.

A "dimerization domain" is formed by the association of at least two amino acid residues or of at least two peptides or polypeptides (which may have the same, or different, amino acid sequences). The peptides or polypeptides may interact with each other through covalent and/or non-covalent associations). Optional dimerization domains contain at least one cysteine that is capable of forming an intermolecular disulfide bond with a cysteine on the partner fusion protein. The dimerization domain can contain one or more cysteine residues such that disulfide bond(s) can form between the partner fusion proteins. In one embodiment, dimerization domains contain one, two or three to about ten cysteine residues. In a further embodiment, the dimerization domain is the hinge region of an immunoglobulin.

Additional exemplary dimerization domains can be any known in the art and include, but not limited to, coiled coils, acid patches, zinc fingers, calcium hands, a CHI-CL pair, an "interface" with an engineered "knob" and/or "protuberance" as described in U.S. Pat. No. 5,821,333, leucine zippers (e.g., from jun and/or fos) (U.S. Pat. No. 5,932,448), and/or the yeast transcriptional activator GCN4, SH2 (src homology 2), SH3 (src Homology 3) (Vidal, et al, Biochemistry, 43, 7336-44 ((2004)), phosphotyrosine binding (PTB) (Zhou, et al, Nature, 378:584-592 (1995)), WW (Sudol, Prog. Biochys. Mol Biol., 65: 113-132 (1996)), PDZ (Kim, et al, Nature, 378: 85-88 (1995); Komau, et al, Science, 269, 1737-1740 (1995)) 14-3-3, WD40 (Hu5 et al., I Biol Chem., 273: 33489-33494 (1998)) E H, Lim, "An isoleucine zipper, a receptor dimer pair (e.g., interleukin-8 receptor (IL-8R); and integrin heterodimers such as LFA-I and GPIIIb/IIIa), or the dimerization region(s) thereof, dimeric ligand polypeptides (e.g., nerve growth factor (NGF), neurotrophin-3 (NT-3), interleukin-8 (IL-8), vascular endothelial growth factor (VEGF), VEGF-C, VEGF-D, PDGF members, and brain-derived neurotrophic factor (BDNF) (Arakawa, et al., J Biol. Chem., 269(45): 27833-27839 (1994) and Radziejewski, et al, Biochem., 32(48): 1350 (1993)) and can also be variants of these domains in which the affinity is altered. The polypeptide pairs can be identified by methods known in the art, including yeast two hybrid screens. Yeast two hybrid screens are described in U.S. Pat. Nos. 5,283,173 and 6,562,576. Affinities between a pair of interacting domains can be determined using methods known in the art, including as described in Katahira, et al., I. Biol Chem, 277, 9242-9246 (2002)). Alternatively, a library of peptide sequences can be screened for heterodimerization, for example, using the methods described in WO 01/00814. Useful methods for protein-protein interactions are also described in U.S. Pat. No. 6,790,624.

A "multimerization domain" or "oligomerization domain" referred to herein is a domain that causes three or more peptides or polypeptides to interact with each other through covalent and/or non-covalent association(s). Suitable multimerization or oligomerization domains include, but are not limited to, coiled-coil domains. A coiled-coil is a peptide sequence with a contiguous pattern of mainly hydrophobic residues spaced 3 and 4 residues apart, usually in a sequence of seven amino acids (heptad repeat) or eleven amino acids (undecad repeat), which assembles (folds) to form a multimeric bundle of helices. Coiled-coils with sequences including some irregular distribution of the 3 and 4 residues spacing are also contemplated. Hydrophobic residues are in particular the hydrophobic amino acids Val, He, Leu, Met, Tyr, Phe and Trp. "Mainly hydrophobic" means that at least 50% of the residues must be selected from the mentioned hydrophobic amino acids.

The coiled coil domain may be derived from laminin. In the extracellular space, the heterotrimeric coiled coil protein laminin plays an important role in the formation of basement membranes. Apparently, the multifunctional oligomeric structure is required for laminin function. Coiled coil domains may also be derived from the thrombospondins in which three (TSP-I and TSP-2) or five (TSP-3, TSP-4 and TSP-5) chains are connected, or from COMP (COMPcc) (Guo, et al., EMBO J, 1998, 17: 5265-5272) which folds into a parallel five-stranded coiled coil (Malashkevich, et al., Science, 274: 761-765 (1996)). Additional non-limiting examples of coiled-coil domains derived from other proteins, and other domains that mediate polypeptide multimerization are known in the art such as the vasodilator-stimulated phosphoprotein (VASP) domain, matrilin-1 (CMP), viral fusion peptides, soluble NSF (N-ethylmaleimide-sensitive factor) Attachment Protein receptor (SNARE) complexes, leucine-rich repeats, certain tRNA synthetases, are suitable for use in the disclosed fusion proteins.

In another embodiment, VSIG8 polypeptides, fusion proteins, or fragments thereof can be induced to form multimers by binding to a second multivalent polypeptide, such as an antibody. Antibodies suitable for use to multimerize VSIG8 polypeptides, fusion proteins, or fragments thereof include, but are not limited to, IgM antibodies and cross-linked, multivalent IgG, IgA, IgD, or IgE complexes.

Dimerization or multimerization can occur between or among two or more fusion proteins through dimerization or multimerization domains, including those described above. Alternatively, dimerization or multimerization of fusion proteins can occur by chemical crosslinking. Fusion protein dimers can be homodimers or heterodimers. Fusion protein multimers can be homomultimers or heteromultimers.

Fusion protein dimers as disclosed herein are of formula II:

N—R1-R2-R3-C

N—R4-R5-R6-C or, alternatively, are of formula III:

N—R1-R2-R3-C

C—R4-R5-R6-N wherein the fusion proteins of the dimer provided by formula II are defined as being in a parallel orientation and the fusion proteins of the dimer provided by formula III are defined as being in an antiparallel orientation. Parallel and antiparallel dimers are also referred to as cis and trans dimers, respectively. "N" and "C" represent the N- and C-termini of the fusion protein, respectively. The fusion protein constituents "RI", "R2" and "R3" are as defined above with respect to formula I. With respect to both formula II and formula III, "R4" is a VSIG8 polypeptide or a second polypeptide, "R5" is an optional peptide/polypeptide linker domain, and "R6" Is a VSIG8 polypeptide or a second polypeptide, wherein "R6" is a VSIG8 polypeptide when "R4" is a second polypeptide, and "R6'" is a second polypeptide when "R4" is a VSIG8 polypeptide. In one embodiment, "RI" is a VSIG8 polypeptide, "R4" is also a VSIG8 polypeptide, and "R3" and "R6" are both second polypeptides.

Fusion protein dimers of formula II are defined as homodimers when "RI"="R4", "R2"="R5" and "R3"="R6". Similarly, fusion protein dimers of formula III are defined as homodimers when "RI"="R6", "R2"="R5" and "R3"="R4". Fusion protein dimers are defined as heterodimers when these conditions are not met for any reason. For example, heterodimers may contain domain orientations that meet these conditions (i.e., for a dimer according to formula II, "RI" and "R4" are both VSIG8 polypeptides, "R2" and "R5" are both peptide/polypeptide linker domains and "R3" and "R6" are both second polypeptides), however the species of one or more of these domains is not identical. For example, although "R3" and "R6" may both be VSIG8 polypeptides, one polypeptide may contain a wild-type VSIG8 amino acid sequence while the other polypeptide may be a variant VSIG8 polypeptide. An exemplary variant VSIG8 polypeptide is VSIG8, polypeptide that has been modified to have increased or decreased binding to a target cell, increased activity on immune cells, increased or decreased half-life or stability. Dimers of fusion proteins that contain either a CHI or CL region of an immunoglobulin as part of the polypeptide linker domain preferably form heterodimers wherein one fusion protein of the dimer contains a CHI region and the other fusion protein of the dimer contains a CL region.

Fusion proteins can also be used to form multimers. As with dimers, multimers may be parallel multimers, in which all fusion proteins of the multimer are aligned in the same orientation with respect to their N- and C-termini. Multimers may be antiparallel multimers, in which the fusion proteins of the multimer are alternatively aligned in opposite orientations with respect to their N- and C-termini. Multimers (parallel or antiparallel) can be either homomultimers or heteromultimers. The fusion protein is optionally produced in dimeric form; more preferably, the fusion is performed at the genetic level as described below, by joining polynucleotide sequences corresponding to the two (or more) proteins, portions of proteins and/or peptides, such that a joined or fused protein is produced by a cell according to the joined polynucleotide sequence. A description of preparation for such fusion proteins is described with regard to U.S. Pat. No. 5,851,795 to Linsley et al, which is hereby incorporated by reference as if fully set forth herein as a non-limiting example only.

Targeting Domains

The VSIG8 polypeptides and fusion proteins can contain a targeting domain to target the molecule to specific sites in the body. Optional targeting domains target the molecule to areas of inflammation. Exemplary targeting domains are antibodies, or antigen binding fragments thereof that are specific for inflamed tissue or to a proinflammatory cytokine including but not limited to IL17, IL-4, IL-6, IL-12, IL-21, IL-22, IL-23, MIF, TNF-a, and TNF-β and combinations thereof. In the case of neurological disorders such as Multiple Sclerosis, the targeting domain may target the molecule to the CNS or may bind to VCAM-I on the vascular epithelium. Additional targeting domains can be peptide aptamers specific for a proinflammatory molecule. In other embodiments, the VSIG8 fusion protein can include a binding partner specific for a polypeptide displayed on the surface of an immune cell, for example a T cell. In still other embodiments, the targeting domain specifically targets activated immune cells. Optional immune cells that are targeted include Th0, Th1, Th17, Th2 and Th22 T cells, other cells that secrete, or cause other cells to secrete inflammatory molecules including, but not limited to, IL-Iβ, TNF-a, TGF-β, IFN-y, IL-17, IL-6, IL-23, IL-22, IL-21, and MMPs, and Tregs. For example, a targeting domain for Tregs may bind specifically to CD25.

Other targeting moieties or heterologous polypeptides that optionally may be attached or contained within VSIG8 polypeptides or fusion proteins according to the invention are discussed supra in connection with the synthesis of exemplary fusion proteins according to the invention.

The above changes are intended as illustrations only of optional changes and are not meant to be limiting in any way. Furthermore, the above explanation is provided for descriptive purposes only, without wishing to be bound by a single hypothesis.

Addition of Groups

If a protein according to the present invention is a linear molecule, it is possible to place various functional groups at various points on the linear molecule which are susceptible to or suitable for chemical modification. Functional groups can be added to the termini of linear forms of the protein according to at least some embodiments of the invention. In some embodiments, the functional groups improve the activity of the protein with regard to one or more characteristics, including but not limited to, improvement in stability, penetration (through cellular membranes and/or tissue barriers), tissue localization, efficacy, decreased clearance, decreased toxicity, improved selectivity, improved resistance to expulsion by cellular pumps, and the like. For convenience sake and without wishing to be limiting, the free N-terminus of one of the sequences contained in the compositions according to at least some embodiments of the invention will be termed as the N-terminus of the composition, and the free C-terminal of the sequence will be considered as the C-terminus of the composition. Either the C-terminus or the N-terminus of the sequences, or both, can be linked to a carboxylic acid functional groups or an amine functional group, respectively.

Non-limiting examples of suitable functional groups are described in Green and Wuts, "Protecting Groups in Organic Synthesis", John Wiley and Sons, Chapters 5 and 7, (1991), the teachings of which are incorporated herein by reference. Preferred protecting groups are those that facilitate transport of the active ingredient attached thereto into a cell, for example, by reducing the hydrophilicity and increasing the lipophilicity of the active ingredient, these being an example for "a moiety for transport across cellular membranes".

These moieties can optionally and preferably be cleaved in vivo, either by hydrolysis or enzymatically, inside the cell. (Ditter et al., I. Pharm Sci. 57:783 (1968); Ditter et al., J. Pharm. Sci. 57:828 (1968); Ditter et al., I. Pharm. Sci. 58:557 (1969); King et al., Biochemistry 26:2294 (1987); Lindberg et al., Drug Metabolism and Disposition 17:311 (1989); and Tunek et al, Biochem. Pharm. 37:3867 (1988), Anderson et al., Arch. Biochem. Biophys. 239:538 (1985)

and Singhal et al., FASEB J. 1:220 (1987)). Hydroxyl protecting groups include esters, carbonates and carbamate protecting groups. Amine protecting groups include alkoxy and aryloxy carbonyl groups, as described above for N-terminal protecting groups. Carboxylic acid protecting groups include aliphatic, benzylic and aryl esters, as described above for C-terminal protecting groups. In one embodiment, the carboxylic acid group in the side chain of one or more glutamic acid or aspartic acid residue in a composition of the present invention is protected, preferably with a methyl, ethyl, benzyl or substituted benzyl ester, more preferably as a benzyl ester.

Non-limiting, illustrative examples of N-terminal protecting groups include acyl groups (—CO—R1) and alkoxy carbonyl or aryloxy carbonyl groups (—CO—O—R1), wherein RI is an aliphatic, substituted aliphatic, benzyl, substituted benzyl, aromatic or a substituted aromatic group. Specific examples of acyl groups include but are not limited to acetyl, (ethyl)-CO—, n-propyl-CO—, iso-propyl-CO—, n-butyl-CO—, sec-butyl-CO—, t-butyl-CO—, hexyl, lauroyl, palmitoyl, myristoyl, stearyl, oleoyl phenyl-CO—, substituted phenyl-CO—, benzyl-CO— and (substituted benzyl)-CO—. Examples of alkoxy carbonyl and aryloxy carbonyl groups include CH3-0-CO—, (ethyl)-O—CO—, n-propyl-O—CO, iso-propyl-O—CO, n-butyl-O—CO, sec-butyl-O—CO, t-butyl-O—CO, phenyl-O—CO—, substituted phenyl-O—CO— and benzyl-O—CO—, (substituted benzyl)-0-CO—, Adamantan, naphtalen, myristoleyl, toluen, biphenyl, cinnamoyl, nitrobenzoy, toluoyl, furoyl, benzoyl, cyclohexane, norbornane, or Z-caproic. In order to facilitate the N-acylation, one to four glycine residues can be present in the N-terminus of the molecule.

The carboxyl group at the C-terminus of the compound can be protected, for example, by a group including but not limited to an amide (i.e., the hydroxyl group at the C-terminus is replaced with —NH 2, —NHR2 and —NR2R3) or ester (i.e., the hydroxyl group at the C-terminus is replaced with —OR2). R2 and R3 are optionally independently an aliphatic, substituted aliphatic, benzyl, substituted benzyl, aryl or a substituted aryl group. In addition, taken together with the nitrogen atom, R2 and R3 can optionally form a C4 to C8 heterocyclic ring with from about 0-2 additional heteroatoms such as nitrogen, oxygen or sulfur. Non-limiting suitable examples of suitable heterocyclic rings include piperidinyl, pyrrolidinyl, morpholino, thiomorpholino or piperazinyl. Examples of C-terminal protecting groups include but are not limited to $—NH_2$, —NHCH3, $—N(CH_3)_2$, —NH(ethyl), $—N(ethyl)_2$, —N(methyl) (ethyl), —NH(benzyl), —N(C1-C4 alkyl)(benzyl), —NH (phenyl), —N(C1-C4 alkyl) (phenyl), —OCH3-O-(ethyl), —O-(n-propyl), —O-(n-butyl), —O-(iso-propyl), —O-(sec-butyl), —O-(t-butyl), —O-benzyl and —O-phenyl.

Substitution by Peptidomimetic Moieties

A "peptidomimetic organic moiety" can optionally be substituted for amino acid residues in the composition of this invention both as conservative and as non-conservative substitutions. These moieties are also termed "non-natural amino acids" and may optionally replace amino acid residues, amino acids or act as spacer groups within the peptides in lieu of deleted amino acids. The peptidomimetic organic moieties optionally and preferably have steric, electronic or configurational properties similar to the replaced amino acid and such peptidomimetics are used to replace amino acids in the essential positions, and are considered conservative substitutions. However such similarities are not necessarily required. According to preferred embodiments of the present invention, one or more peptidomimetics are selected such that the composition at least substantially retains its physiological activity as compared to the native protein according to the present invention.

Peptidomimetics may optionally be used to inhibit degradation of the peptides by enzymatic or other degradative processes. The peptidomimetics can optionally and preferably be produced by organic synthetic techniques. Non-limiting examples of suitable peptidomimetics include D amino acids of the corresponding L amino acids, tetrazol (Zabrocki et al., I. Am. Chem. Soc. 110:5875-5880 (1988)); isosteres of amide bonds (Jones et al., Tetrahedron Lett. 29: 3853-3856 (1988)); LL-3-amino-2-propenidone-6-carboxylic acid (LL-Acp) (Kemp et al., J. Org. Chem. 50:5834-5838 (1985)). Similar analogs are shown in Kemp et al., Tetrahedron Lett. 29:5081-5082 (1988) as well as Kemp et al., Tetrahedron Lett. 29:5057-5060 (1988), Kemp et al., Tetrahedron Lett. 29:4935-4938 (1988) and Kemp et al., I. Org. Chem. 54: 109-115 (1987). Other suitable but exemplary peptidomimetics are shown in Nagai and Sato, Tetrahedron Lett. 26:647-650 (1985); Di Maio et al., I. Chem. Soc. Perkin Trans., 1687 (1985); Kahn et al., Tetrahedron Lett. 30:2317 (1989); Olson et al, I. Am. Chem. Soc. 112:323-333 (1990); and Garvey et al., J. Org. Chem. 56:436 (1990). Further suitable exemplary peptidomimetics include hydroxy-1,2,3,4-tetrahydroisoquinoline-3-carboxylate (Miyake et al., I. Takeda Res. Labs 43:53-76 (1989)); 1,2,3,4-tetrahydro-isoquinoline-3-carboxylate (Kazmierski et al., I. Am. Chem. Soc. 133:2275-2283 (1991)); histidine isoquinolone carboxylic acid (HIC) (Zechel et al., Int. J. Pep. Protein Res. 43 (1991)); (2S,S)-methyl-phenylalanine, (2S, 3R)-methyl-phenylalanine, (2R,3S)-methyl-phenylalanine and (2R,3R)-methyl-phenylalanine (Kazmierski and Hruby, Tetrahedron Lett. (1991)).

Exemplary, illustrative but non-limiting non-natural amino acids include β-amino acids (β3 and β2), homo-amino acids, cyclic amino acids, aromatic amino acids, Pro and Pyr derivatives, 3-substituted Alanine derivatives, Glycine derivatives, ring-substituted Phe and Tyr Derivatives, linear core amino acids or diamino acids. They are available from a variety of suppliers, such as Sigma-Aldrich (USA).

Protein Chemical Modifications

In the present invention, according to at least some embodiments, any part of a protein according to at least some embodiments of the invention may optionally be chemically modified, i.e. changed by addition of functional groups. For example the side amino acid residues appearing in the native sequence may optionally be modified, although as described below alternatively other parts of the protein may optionally be modified, in addition to or in place of the side amino acid residues. The modification may optionally be performed during synthesis of the molecule if a chemical synthetic process is followed, for example by adding a chemically modified amino acid. However, chemical modification of an amino acid when it is already present in the molecule ("in situ" modification) is also possible.

The amino acid of any of the sequence regions of the molecule can optionally be modified according to any one of the following exemplary types of modification (in the peptide conceptually viewed as "chemically modified"). Non-limiting exemplary types of modification include carboxymethylation, acylation, phosphorylation, glycosylation or fatty acylation. Ether bonds can optionally be used to join the serine or threonine hydroxyl to the hydroxyl of a sugar. Amide bonds can optionally be used to join the glutamate or aspartate carboxyl groups to an amino group on a sugar (Garg and Jeanloz, Advances in Carbohydrate Chemistry and Biochemistry, Vol. 43, Academic Press (1985); Kunz, Ang. Chem. Int. Ed. English 26:294-308 (1987)). Acetal and ketal bonds can also optionally be formed between amino acids and carbohydrates. Fatty acid acyl derivatives can optionally be made, for example, by acylation of a free amino group (e.g., lysine) (Toth et al., Peptides: Chemistry, Structure and Biology, Rivier and Marshal, eds., ESCOM Publ., Leiden, 1078-1079 (1990)).

As used herein the term "chemical modification", when referring to a protein or peptide according to the present invention, refers to a protein or peptide where at least one of its amino acid residues is modified either by natural processes, such as processing or other post-translational modifications, or by chemical modification techniques which are well known in the art. Examples of the numerous known modifications typically include, but are not limited to: acetylation, acylation, amidation, ADP-ribosylation, glycosylation, GPI anchor formation, covalent attachment of a lipid or lipid derivative, methylation, myristoylation, pegylation, prenylation, phosphorylation, ubiquitination, or any similar process.

Other types of modifications optionally include the addition of a cycloalkane moiety to a biological molecule, such as a protein, as described in PCT Application No. WO 2006/050262, hereby incorporated by reference as if fully set forth herein. These moieties are designed for use with biomolecules and may optionally be used to impart various properties to proteins.

Furthermore, optionally any point on a protein may be modified. For example, pegylation of a glycosylation moiety on a protein may optionally be performed, as described in PCT Application No. WO 2006/050247, hereby incorporated by reference as if fully set forth herein. One or more polyethylene glycol (PEG) groups may optionally be added to O-linked and/or N-linked glycosylation. The PEG group may optionally be branched or linear. Optionally any type of water-soluble polymer may be attached to a glycosylation site on a protein through a glycosyl linker.

Altered Glycosylation

Proteins according to at least some embodiments of the invention may be modified to have an altered glycosylation pattern (i.e., altered from the original or native glycosylation pattern). As used herein, "altered" means having one or more carbohydrate moieties deleted, and/or having at least one glycosylation site added to the original protein. Glycosylation of proteins is typically either N-linked or O-linked. N-linked refers to the attachment of the carbohydrate moiety to the side chain of an asparagine residue. The tripeptide sequences, asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-acetylgalactosamine, galactose, or xylose to a hydroxyamino acid, most commonly serine or threonine, although 5-hydroxyproline or 5-hydroxylysine may also be used.

Addition of glycosylation sites to proteins according to at least some embodiments of the invention is conveniently accomplished by altering the amino acid sequence of the protein such that it contains one or more of the above-described tripeptide sequences (for N-linked glycosylation sites). The alteration may also be made by the addition of, or substitution by, one or more serine or threonine residues in the sequence of the original protein (for O-linked glycosylation sites). The protein's amino acid sequence may also be altered by introducing changes at the DNA level.

Another means of increasing the number of carbohydrate moieties on proteins is by chemical or enzymatic coupling of glycosides to the amino acid residues of the protein. Depending on the coupling mode used, the sugars may be attached to (a) arginine and histidine, (b) free carboxyl groups, (c) free sulfhydryl groups such as those of cysteine, (d) free hydroxyl groups such as those of serine, threonine, or hydroxyproline, (e) aromatic residues such as those of phenylalanine, tyrosine, or tryptophan, or (f) the amide group of glutamine. These methods are described in WO 87/05330, and in Aplin and Wriston, CRC Crit. Rev. Biochem., 22: 259-306 (1981).

Removal of any carbohydrate moieties present on proteins according to at least some embodiments of the invention may be accomplished chemically or enzymatically. Chemical deglycosylation requires exposure of the protein to trifluoromethanesulfonic acid, or an equivalent compound. This treatment results in the cleavage of most or all sugars except the linking sugar (N-acetylglucosamine or N-acetylgalactosamine), leaving the amino acid sequence intact.

Chemical deglycosylation is described by Hakimuddin et al., Arch. Biochem. Biophys., 259: 52 (1987); and Edge et al., Anal. Biochem., 118: 131 (1981). Enzymatic cleavage of carbohydrate moieties on proteins can be achieved by the use of a variety of endo- and exo-glycosidases as described by Thotakura et al., Meth. EnzymoL, 138: 350 (1987).

Nucleic Acid Molecules Encoding Antibodies

The invention further provides nucleic acids which encode an anti-VSIG8 antibody according to the invention, or a fragment or conjugate thereof. The nucleic acids may be present in whole cells, in a cell lysate, or in a partially purified or substantially pure form. A nucleic acid is "isolated" or "rendered substantially pure" when purified away from other cellular components or other contaminants, e.g., other cellular nucleic acids or proteins, by standard techniques, including alkaline/SDS treatment, CsCl banding, column chromatography, agarose gel electrophoresis and others well known in the art. See, F. Ausubel, et al., ed. (1987) Current Protocols in Molecular Biology, Greene Publishing and Wiley Interscience, New York. A nucleic acid according to at least some embodiments of the invention can be, for example, DNA or RNA and may or may not contain intronic sequences. In a preferred embodiment, the nucleic acid is a cDNA molecule.

Nucleic acids according to at least some embodiments of the invention can be obtained using standard molecular biology techniques. For antibodies expressed by hybridomas (e.g., hybridomas prepared from transgenic mice carrying human immunoglobulin genes as described further below), cDNAs encoding the light and heavy chains of the antibody made by the hybridoma can be obtained by standard PCR amplification or cDNA cloning techniques. For antibodies obtained from an immunoglobulin gene library (e.g., using phage display techniques), nucleic acid encoding the antibody can be recovered from the library.

Once DNA fragments encoding VH and VL segments are obtained, these DNA fragments can be further manipulated by standard recombinant DNA techniques, for example to convert the variable region genes to full-length antibody chain genes, to Fab fragment genes or to a scFv gene. In these manipulations, a $V_L$- or $V_H$-encoding DNA fragment is operatively linked to another DNA fragment encoding another protein, such as an antibody constant region or a flexible linker. As previously defined, "operatively linked", means that that the two DNA fragments are joined such that the amino acid sequences encoded by the two DNA fragments remain in-frame.

The isolated DNA encoding the VH region can be converted to a full-length heavy chain gene by operatively linking the $V_H$-encoding DNA to another DNA molecule encoding heavy chain constant regions (CHI, CH2 and CH3). The sequences of human heavy chain constant region genes are known in the art (see e.g., Kabat, E. A., el al. (1991) Sequences of Proteins of Immunological Interest, Fifth Edition, U.S. Department of Health and Human Services, NIH Publication No. 91-3242) and DNA fragments encompassing these regions can be obtained by standard PCR amplification. The heavy chain constant region can be an IgGl, IgG2, IgG3, IgG4, IgA, IgE, IgM or IgD constant region, but most preferably is an IgGl, IgG2 or IgG4 constant region. For a Fab fragment heavy chain gene, the Vn-encoding DNA can be operatively linked to another DNA molecule encoding only the heavy chain CHI constant region.

The isolated DNA encoding the $V_L$ region can be converted to a full-length light chain gene (as well as a Fab light chain gene) by operatively linking the $V_L$-encoding DNA to another DNA molecule encoding the light chain constant region, CL—The sequences of human light chain constant region genes are known in the art (see e.g., Kabat, E. A., et al. (1991) Sequences of Proteins of Immunological Interest, Fifth Edition, U.S. Department of Health and Human Services, NIH Publication No. 91-3242) and DNA fragments encompassing these regions can be obtained by standard PCR amplification. The light chain constant region can be a kappa (κ) or lambda constant region, but most preferably is a κ constant region.

To create a scFv gene, the VR- and VL-encoding DNA fragments are operatively linked to another fragment encoding a flexible linker, e.g., encoding the amino acid sequence (Gly4-Ser)3, such that the $V_H$ and $V_L$ sequences can be expressed as a contiguous single-chain protein, with the VL and VH regions joined by the flexible linker (see e.g., Bird et al. (1988) Science 242:423-426; Huston et al. (1988) Proc. Natl. Acad. Sci. USA 85:5879-5883; McCafferty et al., (1990) Nature 348:552-554).

Production of Anti-VSIG8 Monoclonal Antibodies

Anti-VSIG8 monoclonal antibodies (mAbs) and antigen-binding fragments according to the present invention can be produced by a variety of techniques, including conventional monoclonal antibody methodology e.g., the standard somatic cell hybridization technique of Kohler and Milstein (1975) *Nature* 256:495. Although somatic cell hybridization procedures are preferred, in principle, other techniques for producing monoclonal antibody can be employed e.g., viral or oncogenic transformation of B lymphocytes.

A preferred animal system for preparing hybridomas is the murine system. Hybridoma production in the mouse is a very well-established procedure. Immunization protocols and techniques for isolation of immunized splenocytes for fusion are known in the art. Fusion partners (e.g., murine myeloma cells) and fusion procedures are also known. Chimeric or humanized antibodies of the present invention can be prepared based on the sequence of a murine monoclonal antibody prepared as described above. DNA encoding the heavy and light chain immunoglobulins can be obtained from the murine hybridoma of interest and engineered to contain non-murine (e.g., human) immunoglobulin sequences using standard molecular biology techniques. For example, to create a chimeric antibody, the murine variable regions can be linked to human constant regions using methods known in the art (see e.g., U.S. Pat. No. 4,816,567 to Cabilly et al.). To create a humanized antibody, the murine CDR regions can be inserted into a human framework using methods known in the art (see e.g., U.S. Pat. No. 5,225,539 to Winter and U.S. Pat. Nos. 5,530,101; 5,585,089; 5,693,762 and 6,180,370 to Queen et al.).

According to at least some embodiments of the invention, the antibodies are human monoclonal antibodies. Such human monoclonal antibodies directed against VSIG8 can be generated using transgenic or transchromosomic mice carrying parts of the human immune system rather than the mouse system. These transgenic and transchromosomic mice include mice referred to herein as the HuMAb Mouse™ and KM Mouse™, respectively, and are collectively referred to herein as "human Ig mice." The HuMAb Mouse™ (Medarex Inc.) contains human immunoglobulin gene miniloci that encode unrearranged human heavy μ and γ and κ light chain immunoglobulin sequences, together with targeted mutations that inactivate the endogenous μ and κ chain loci (see e.g., Lonberg, et al. (1994) Nature 368 (6474): 856-859). Accordingly, the mice exhibit reduced expression of mouse IgM or κ and in response to immunization, the introduced human heavy and light chain transgenes undergo class switching and somatic mutation to generate high affinity human IgG κ monoclonal (Lonberg, N. et al. (1994), supra; reviewed in Lonberg, N. (1994) Handbook of Experimental Pharmacology 113:49-101; Lonberg, N. and Huszar, D. (1995) Intern. Rev. Immunol. 13: 65-93, and Harding, F. and Lonberg, N. (1995) Ann. N.Y. Acad. Sci. 764:536-546). The preparation and use of the HuMab Mouse™, and the genomic modifications carried by such mice, is further described in Taylor, L. et al. (1992) Nucleic Acids Research 20:6287-6295; Chen, J. et al. (1993) International Immunology 5:647-656; Tuaillon et al. (1993) Proc. Natl. Acad. Sci. USA 90:3720-3724; Choi et al. (1993) Nature Genetics 4: 117-123; Chen, J. et al. (1993) EMBO J. 12: 821-830; Tuaillon et al. (1994) J. Immunol. 152:2912-2920; Taylor, L. et al. (1994) International Immunology 6:579-591; and Fishwild, D. et al. (1996) Nature Biotechnology 14: 845-851, the contents of all of which are hereby specifically incorporated by reference in their entirety. See further, U.S. Pat. Nos. 5,545,806; 5,569,825; 5,625,126; 5,633,425; 5,789,650; 5,877,397; 5,661,016; 5,814,318; 5,874,299; and 5,770,429; all to Lonberg and Kay; U.S. Pat. No. 5,545,807 to Surani et al.; PCT Publication Nos. WO 92/03918, WO 93/12227, WO 94/25585, WO 97/13852, WO 98/24884 and WO 99/45962, all to Lonberg and Kay; and PCT Publication No. WO 01/14424 to Korman et al.

In another embodiment, human antibodies according to at least some embodiments of the invention can be raised using a mouse that carries human immunoglobulin sequences on transgenes and transchomosomes, such as a mouse that carries a human heavy chain transgene and a human light chain transchromosome. Such mice, referred to herein as "KM Mice™", are described in detail in PCT Publication WO 02/43478 to Ishida et al.

Still further, alternative transgenic animal systems expressing human immunoglobulin genes are available in the art and can be used to raise anti-VSIG8 antibodies according to at least some embodiments of the invention. For example, an alternative transgenic system referred to as the Xenomouse (Abgenix, Inc.) can be used; such mice are described in, for example, U.S. Pat. Nos. 5,939,598; 6,075,181; 6,114,598; 6, 150,584 and 6,162,963 to Kucherlapati et al.

Moreover, alternative transchromosomic animal systems expressing human immunoglobulin genes are available in the art and can be used to raise anti-VSIG8 antibodies according to at least some embodiments of the invention. For example, mice carrying both a human heavy chain transchromosome and a human light chain transchromosome, referred to as "TC mice" can be used; such mice are described in Tomizuka et al. (2000) Proc. Natl. Acad Sci. USA 97:722-727. Furthermore, cows carrying human heavy and light chain transchromosomes have been described in the art (Kuroiwa et al. (2002) Nature Biotechnology 20:889-894) and can be used to raise anti-VSIG8 antibodies according to at least some embodiments of the invention.

Human monoclonal antibodies according to at least some embodiments of the invention can also be prepared using phage display methods for screening libraries of human immunoglobulin genes. Such phage display methods for isolating human antibodies are established in the art. See for example: U.S. Pat. Nos. 5,223,409; 5,403,484; and 5,571,698 to Ladner et al.; U.S. Pat. Nos. 5,427,908 and 5,580,717 to Dower et al.; U.S. Pat. Nos. 5,969,108 and 6,172,197 to McCafferty et al.; and U.S. Pat. Nos. 5,885,793; 6,521,404; 6,544,731; 6,555,313; 6,582,915 and 6,593,081 to Griffiths et al.

Human monoclonal antibodies according to at least some embodiments of the invention can also be prepared using SCID mice into which human immune cells have been reconstituted such that a human antibody response can be generated upon immunization. Such mice are described in, for example, U.S. Pat. Nos. 5,476,996 and 5,698,767 to Wilson et al.

Immunization of Human Ig Mice

In some embodiments human Ig mice are used to raise human anti-VSIG8 antibodies according to the invention, e.g., by immunizing such mice with a purified or enriched preparation of VSIG8 antigen and/or recombinant VSIG8, or VSIG8 fusion protein, as described by Lonberg, N. et al. (1994) Nature 368(6474): 856-859; Fishwild, D. et al. (1996) Nature Biotechnology 14: 845-851; and PCT Publication WO 98/24884 and WO 01/14424. Preferably, the mice will be 6-16 weeks of age upon the first infusion. For example, a purified or recombinant preparation (5-50 μg) of VSIG8 antigen can be used to Immunize the human Ig mice intraperitoneally.

In general transgenic mice respond when initially immunized intraperitoneally (IP) with antigen in complete Freund's adjuvant, followed by every other week IP immunizations (up to a total of 6) with antigen in incomplete Freund's adjuvant. However, adjuvants other than Freund's are also found to be effective. In addition, whole cells in the absence of adjuvant are found to be highly immunogenic. The immune response can be monitored over the course of the immunization protocol with plasma samples being obtained by retroorbital bleeds. The plasma can be screened by ELISA (as described below), and mice with sufficient titers of anti-VSIG8 human immunoglobulin can be used for fusions. Mice can be boosted intravenously with antigen 3 days before sacrifice and removal of the spleen. It is expected that 2-3 fusions for each immunization may need to be performed. Between 6 and 24 mice are typically immunized for each antigen. Usually both HCo7 and HCol2 strains are used. In addition, both HCo7 and HCol2 transgene can be bred together into a single mouse having two different human heavy chain transgenes (HCo7/HCo 12). Alternatively or additionally, the KM Mouse™ strain can be used.

Generation of Hybridomas Producing Human Monoclonal Antibodies

In certain embodiments, hybridomas producing a human monoclonal anti-VSIG8 antibody according to the invention may be generated using splenocytes and/or lymph node cells from immunized mice can be isolated and fused to an appropriate immortalized cell line, such as a mouse myeloma cell line. The resulting hybridomas can be screened for the production of antigen-specific antibodies. For example, single cell suspensions of splenic lymphocytes from immunized mice can be fused to one-sixth the number of P3X63-Ag8.653 nonsecreting mouse myeloma cells (ATCC, CRL 1580) with 50% PEG. Cells are plated at approximately $2\times10^5$ in flat bottom microtiter plate, followed by a two week incubation in selective medium containing 20% fetal Clone Serum, 18% "653" conditioned media, 5% origen (IGEN), 4 mM L-glutamine, 1 mM sodium pyruvate, 5 mM HEPES, 0.055 mM 2-mercaptoethanol, 50 units/ml penicillin, 50 mg/ml streptomycin, 50 mg/ml gentamycin and IX HAT (Sigma; the HAT is added 24 hours after the fusion). After approximately two weeks, cells can be cultured in medium in which the HAT is replaced with HT. Individual wells can then be screened by ELISA for human monoclonal IgM and IgG antibodies. Once extensive hybridoma growth occurs, medium can be observed usually after 10-14 days. The antibody secreting hybridomas can be replated, screened again, and if still positive for human IgG, the monoclonal antibodies can be subcloned at least twice by limiting dilution. The stable subclones can then be cultured in vitro to generate small amounts of antibody in tissue culture medium for characterization.

To purify human monoclonal antibodies, selected hybridomas can be grown in two-liter spinner-flasks for monoclonal antibody purification. Supernatants can be filtered and concentrated before affinity chromatography with protein A-Sepharose (Pharmacia, Piscataway, N.J.). Eluted IgG can be checked by gel electrophoresis and high performance liquid chromatography to ensure purity. The buffer solution can be exchanged into PBS, and the concentration can be determined by OD280 using 1.43 extinction coefficient. The monoclonal antibodies can be aliquoted and stored at −80° C.

Generation of Transfectomas Producing Monoclonal Antibodies

In certain embodiments, an anti-VSIG8 antibody according to the invention can be produced in a host cell transfectoma using, for example, a combination of recombinant DNA techniques and gene transfection methods as is well known in the art (e.g., Morrison, S. (1985) Science 229: 1202).

For example, to express the antibodies, or antibody fragments thereof, DNAs encoding partial or full-length light and heavy chains, can be obtained by standard molecular biology techniques (e.g., PCR amplification or cDNA cloning using a hybridoma that expresses the antibody of interest) and the DNAs can be inserted into expression vectors such that the genes are operatively linked to transcriptional and translational control sequences. In this context, the term "operatively linked" is intended to mean that an antibody gene is ligated into a vector such that transcriptional and translational control sequences within the vector serve their intended function of regulating the transcription and translation of the antibody gene. The expression vector and expression control sequences are chosen to be compatible with the expression host cell used. The antibody light chain gene and the antibody heavy chain gene can be inserted into separate vector or, more typically, both genes are inserted into the same expression vector. The antibody genes are inserted into the expression vector by standard methods (e.g., ligation of complementary restriction sites on the antibody gene fragment and vector, or blunt end ligation if no restriction sites are present). The light and heavy chain variable regions of the antibodies described herein can be used to create full-length antibody genes of any antibody isotype by inserting them into expression vectors already encoding heavy chain constant and light chain constant regions of the desired isotype such that the $V_H$ segment is operatively linked to the $C_H$ segments within the vector and the $V_L$ segment is operatively linked to the $C_L$ segment within the vector. Additionally or alternatively, the recombinant expression vector can encode a signal peptide that facilitates secretion of the antibody chain from a host cell. The antibody chain gene can be cloned into the vector such that the signal peptide is linked in-frame to the amino terminus of the antibody chain gene. The signal peptide can be an immunoglobulin signal peptide or a heterologous signal peptide (i.e., a signal peptide from a non-immunoglobulin protein).

Characterization of Antibody Binding to Antigen

In certain embodiments, the binding specificity of an anti-VSIG8 antibody according to the Invention is determined by known antibody binding assay techniques such as ELISA. In an exemplary ELISA, microtiter plates are coated with a purified antigen, herein VSIG8 at 0.25 μg/ml in PBS, and then blocked with 5% bovine serum albumin in PBS. Dilutions of antibody (e.g., dilutions of plasma from -immunized mice) are added to each well and incubated for 1-2 hours at 37° C. The plates are washed with PBS/Tween and then incubated with secondary reagent (e.g., for human antibodies, a goat-anti-human IgG Fc-specific polyclonal reagent) conjugated to alkaline phosphatase for 1 hour at 37° C. After washing, the plates are developed with pNPP substrate (1 mg/ml), and analyzed at OD of 405-650. Preferably, mice which develop the highest titers will be used for fusions.

An ELISA assay as described above can also be used to screen for hybridomas that show positive reactivity with VSIG8 immunogen. Hybridomas that bind with high avidity to VSIG8 are subcloned and further characterized. One clone from each hybridoma, which retains the reactivity of the parent cells (by ELISA), can be chosen for making a 5-10 vial cell bank stored at −140° C., and for antibody purification.

To purify anti-VSIG8 antibodies, selected hybridomas can be grown in two-liter spinner-flasks for monoclonal antibody purification. Supernatants can be filtered and concentrated before affinity chromatography with protein A-Sepharose (Pharmacia, Piscataway, N.J.). Eluted IgG can be checked by gel electrophoresis and high performance liquid chromatography to ensure purity. The buffer solution can be exchanged into PBS, and the concentration can be determined by OD280 using 1.43 extinction coefficient. The monoclonal antibodies can be aliquoted and stored at −80° C.

To determine if the selected anti-VSIG8 monoclonal antibodies bind to unique epitopes, each antibody can be biotinylated using commercially available reagents (Pierce, Rockford, 111). Competition studies using unlabeled monoclonal antibodies and biotinylated monoclonal antibodies can be performed using VSIG8 coated-ELISA plates as described above. Biotinylated mAb binding can be detected with a strep-avidin-alkaline phosphatase probe.

To determine the isotype of purified antibodies, isotype ELISAs can be performed using reagents specific for antibodies of a particular isotype. For example, to determine the isotype of a human monoclonal antibody, wells of microtiter plates can be coated with ^g/ml of anti-human immunoglobulin overnight at 4° C. After blocking with 1% BSA, the plates are reacted with 1 mug/ml or less of test monoclonal antibodies or purified isotype controls, at ambient temperature for one to two hours. The wells can then be reacted with either human IgGl or human IgM-specific alkaline phosphatase-conjugated probes. Plates are developed and analyzed as described above.

Anti-VSIG8 human IgGs can be further tested for reactivity with VSIG8 antigen, respectively, by Western blotting. Briefly, VSIG8 antigen can be prepared and subjected to sodium dodecyl sulfate polyacrylamide gel electrophoresis. After electrophoresis, the separated antigens are transferred to nitrocellulose membranes, blocked with 10% fetal calf serum, and probed with the monoclonal antibodies to be tested. Human IgG binding can be detected using anti-human IgG alkaline phosphatase and developed with BCIP/NBT substrate tablets (Sigma Chem. Co., St. Louis, Mo.).

Alternative Anti-VSIG8 Scaffolds

In certain embodiments, the present invention relates to an antigen-binding construct comprising a protein scaffold which is linked to one or more epitope-binding domains. Such engineered protein scaffolds are usually obtained by designing a random library with mutagenesis focused at a loop region or at an otherwise permissible surface area and by selection of variants against a given target via phage display or related techniques. According to at least some embodiments the invention relates to alternative scaffolds including, but not limited to, anticalins, DARPins, Armadillo repeat proteins, protein A, lipocalins, fibronectin domain, ankyrin consensus repeat domain, thioredoxin, chemically constrained peptides and the like. According to at least some embodiments the invention relates to alternative scaffolds that are used as therapeutic agents for treatment of cancer, autoimmune, infectious diseases, sepsis, or for inhibiting an undesirable immune activation that follows gene therapy, as well as for in vivo diagnostics.

According to at least some embodiments the invention further provides a pharmaceutical composition comprising an antigen-binding construct as described herein a pharmaceutically acceptable carrier.

The term ‘Protein Scaffold’ as used herein includes but is not limited to an immunoglobulin (Ig) scaffold, for example an IgG scaffold, which may be a four chain or two chain antibody, or which may comprise only the Fc region of an antibody, or which may comprise one or more constant regions from an antibody, which constant regions may be of human or primate origin, or which may be an artificial chimera of human and primate constant regions. Such protein scaffolds may comprise antigen-binding sites in addition to the one or more constant regions, for example where the protein scaffold comprises a full IgG. Such protein scaffolds will be capable of being linked to other protein domains, for example protein domains which have antigen-binding sites, for example epitope-binding domains or ScFv domains.

A “domain” is a folded protein structure which has tertiary structure independent of the rest of the protein. Generally, domains are responsible for discrete functional properties of proteins and in many cases may be added, removed or transferred to other proteins without loss of function of the remainder of the protein and/or of the domain. A “single antibody variable domain” is a folded polypeptide domain comprising sequences characteristic of antibody variable domains. It therefore includes complete antibody variable domains and modified variable domains, for example, in which one or more loops have been replaced by sequences which are not characteristic of antibody variable domains, or antibody variable domains which have been truncated or comprise N- or C-terminal extensions, as well as folded fragments of variable domains which retain at least the binding activity and specificity of the full-length domain.

The phrase "immunoglobulin single variable domain" refers to an antibody variable domain (VR, VRH, VL) that specifically binds an antigen or epitope independently of a different V region or domain. An immunoglobulin single variable domain can be present in a format (e.g., homo- or hetero-multimer) with other, different variable regions or variable domains where the other regions or domains are not required for antigen-binding by the single immunoglobulin variable domain (i.e., where the immunoglobulin single variable domain binds antigen independently of the additional variable domains). A "domain antibody" or "dAb" is the same as an "immunoglobulin single variable domain" which is capable of binding to an antigen as the term is used herein. An immunoglobulin single variable domain may be a human antibody variable domain, but also includes single antibody variable domains from other species such as rodent (for example, as disclosed in WO 00/29004), nurse shark and Camelid V-HH dAbs. Camelid V-$_{HH}$ are immunoglobulin single variable domain polypeptides that are derived from species including camel, llama, alpaca, dromedary, and guanaco, which produce heavy chain antibodies naturally devoid of light chains. Such V-HH domains may be humanized according to standard techniques available in the art, and such domains are still considered to be "domain antibodies" according to the invention. As used herein "VH includes camelid V-HH domains. NARV are another type of immunoglobulin single variable domain which was identified in cartilaginous fish including the nurse shark. These domains are also known as Novel Antigen Receptor variable region (commonly abbreviated to V (NAR) or NARV). See, e.g., Mol. Immunol. 44, 656-665 (2006) and US20050043519A.

The term "epitope-binding domain" refers to a domain that specifically binds an antigen or epitope independently of a different V region or domain, this may be a domain antibody (dAb), for example a human, camelid or shark immunoglobulin single variable domain or it may be a domain which is a derivative of a scaffold selected from the group consisting of CTLA-4 (Evibody®); lipocalin; Protein A derived molecules such as Z-domain of Protein A (Affibody®, SpA), A-domain (Avimer®/Maxibody®); Heat shock proteins such as GroEI and GroES; transferrin (transbody); ankyrin repeat protein (DARPin®); peptide aptamer, C-type lectin domain (Tetranectin); human γ -crystallin and human ubiquitin (affilins); PDZ domains; scorpion toxinkunitz type domains of human protease inhibitors; Armadillo repeat proteins, thioredoxin, and fibronectin (adnectin); which has been subjected to protein engineering in order to obtain binding to a ligand other than the natural ligand.

Loops corresponding to CDRs of antibodies can be substituted with heterologous sequence to confer different binding properties i.e. Evibodies. For further details see Journal of Immunological Methods 248 (1-2), 31-45 (2001) Lipocalins are a family of extracellular proteins which transport small hydrophobic molecules such as steroids, bilins, retinoids and lipids. They have a rigid secondary structure with a number of loops at the open end of the conical structure which can be engineered to bind to different target antigens. Anticalins are between 160-180 amino acids in size, and are derived from lipocalins. For further details see Biochim Biophys Acta 1482: 337-350 (2000), U.S. Pat. No. 7,250,297B 1 and US20070224633. An affibody is a scaffold derived from Protein A of *Staphylococcus aureus* which can be engineered to bind to antigen. The domain consists of a three-helical bundle of approximately 58 amino acids. Libraries have been generated by randomization of surface residues. For further details see Protein Eng. Des. Sel. 17, 455-462 (2004) and EP1641818A1 Avimers are multidomain proteins derived from the A-domain scaffold family. The native domains of approximately 35 amino acids adopt a defined disulphide bonded structure. Diversity is generated by shuffling of the natural variation exhibited by the family of A-domains. For further details see Nature Biotechnology 23(12), 1556-1561 (2005) and Expert Opinion on Investigational Drugs 16(6), 909-917 (June 2007) A transferrin is a monomeric serum transport glycoprotein. Transferrins can be engineered to bind different target antigens by insertion of peptide sequences in a permissive surface loop. Examples of engineered transferrin scaffolds include the Trans-body. For further details see J. Biol. Chem 274, 24066-24073 (1999).

Designed Ankyrin Repeat Proteins (DARPins) are derived from Ankyrin which is a family of proteins that mediate attachment of integral membrane proteins to the cytoskeleton. A single ankyrin repeat is a 33 residue motif consisting of two a helices; –P turn. They can be engineered to bind different target antigens by randomizing residues in the first a-helix and a β-turn of each repeat. Their binding interface can be Increased by increasing the number of modules (a method of affinity maturation). For further details see J. Mol. Biol. 332, 489-503 (2003), PNAS 100(4), 1700-1705 (2003) and J. Mol. Biol. 369, 1015-1028 (2007) and US20040132028A1.

Fibronectin is a scaffold which can be engineered to bind to antigen. Adnectins consists of a backbone of the natural amino acid sequence of the 10th domain of the 15 repeating units of human fibronectin type III (FN3). Three loops at one end of the P; -sandwich can be engineered to enable an Adnectin to specifically recognize a therapeutic target of interest. For further details see Protein Eng. Des. Sel. 18, 435-444 (2005), US200801 39791, WO2005056764 and U.S. Pat. No. 6,818,418B 1.

Peptide aptamers are combinatorial recognition molecules that consist of a constant scaffold protein, typically thioredoxin (TrxA) which contains a constrained variable peptide loop inserted at the active site. For further details see Expert Opin. Biol. Ther. 5:783-797 (2005).

Microbodies are derived from naturally occurring microproteins of 25-50 amino acids in length which contain 3-4 cysteine bridges—examples of microproteins include KalataBI and conotoxin and knottins. The microproteins have a loop which can be engineered to include up to 25 amino acids without affecting the overall fold of the microprotein. For further details of engineered knottin domains, see WO2008098796.

Other epitope binding domains include proteins which have been used as a scaffold to engineer different target antigen-binding properties include human β-crystallin and human ubiquitin (affilins), Kunitz type domains of human protease inhibitors, PDZ-domains of the Ras-binding protein AF-6, scorpion toxins (charybdo toxin), C-type lectin domain (tetranectins) are reviewed in Chapter 7—Non-Antibody Scaffolds from Handbook of Therapeutic Antibodies (2007, edited by Stefan Dubel) and Protein Science 15: 14-27 (2006). Epitope binding domains of the present invention could be derived from any of these alternative protein domains.

Conjugates or Immunoconjugates

The present invention encompasses conjugates of VSIG8 antigen for use in Immune therapy comprising the VSIG8 antigen and soluble portions thereof including the ectodomain or portions or variants thereof. For example the invention encompasses conjugates wherein the ECD of the VSIG8 antigen is attached to an immunoglobulin or fragment thereof. The invention contemplates the use thereof for promoting or inhibiting VSIG8 antigen activities such as immune stimulation and the use thereof in treating transplant, autoimmune, and cancer indications described herein.

In another aspect, the present invention features antibody-drug conjugates (ADCs), used for example for treatment of cancer, consisting of an antibody (or antibody fragment such as a single-chain variable fragment (scFv) linked to a payload drug (often cytotoxic). The antibody causes the ADC to bind to the target cancer cells. Often the ADC is then internalized by the cell and the drug is released into the cell. Because of the targeting, the side effects are lower and give a wider therapeutic window. Hydrophilic linkers (e.g., PEG4Mal) help prevent the drug being pumped out of resistant cancer cells through MDR (multiple drug resistance) transporters.

In another aspect, the present invention features immunoconjugates comprising an anti-VSIG8 antibody, or a fragment thereof, conjugated to a therapeutic agent, such as a cytotoxin, a drug (e.g., an immunosuppressant) or a radiotoxin. Such conjugates are referred to herein as "immunoconjugates". Immunoconjugates that include one or more cytotoxins are referred to as "immunotoxins." A cytotoxin or cytotoxic agent includes any agent that is detrimental to (e.g., kills) cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents also include, for example, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

Other preferred examples of therapeutic cytotoxins that can be conjugated to an antibody according to at least some embodiments of the invention include duocarmycins, calicheamicins, maytansines and auristatins, and derivatives thereof. An example of a calicheamicin antibody conjugate is commercially available (Mylotarg™ Wyeth).

Cytotoxins can be conjugated to antibodies according to at least some embodiments of the invention using linker technology available in the art. Examples of linker types that have been used to conjugate a cytotoxin to an antibody include, but are not limited to, hydrazones, thioethers, esters, disulfides and peptide-containing linkers. A linker can be chosen that is, for example, susceptible to cleavage by low pH within the lysosomal compartment or susceptible to cleavage by proteases, such as proteases preferentially expressed in tumor tissue such as cathepsins (e.g., cathepsins B, C, D). For further discussion of types of cytotoxins, linkers and methods for conjugating therapeutic agents to antibodies, see also Saito, G. et al. (2003) Adv. Drug Deliv. Rev. 55: 199-215; Trail, P. A. et al. (2003) Cancer Immunol. Immunother. 52:328-337; Payne, G. (2003) Cancer Cell 3:207-212; Allen, T. M. (2002) Nat. Rev. Cancer 2:750-763; Pastan, I. and Kreitman, R. J. (2002) Curr. Opin. Investig. Drugs 3: 1089-1091; Senter, P. D. and Springer, C. J. (2001) Adv. Drug Deliv. Rev. 53:247-264.

Antibodies of the present invention also can be conjugated to a radioactive isotope to generate cytotoxic radiopharmaceuticals, also referred to as radioimmunoconjugates. Examples of radioactive isotopes that can be conjugated to antibodies for use diagnostically or therapeutically include, but are not limited to, iodine 131, indium 111, yttrium 90 and lutetium 177. Methods for preparing radioimmunconjugates are established in the art. Radioimmunoconjugates are commercially available, including Zevalin® (BiogenIDEC) and Bexxar®. (Corixa Pharmaceuticals), and similar methods can be used to prepare radioimmunoconjugates using the antibodies according to at least some embodiments of the invention.

The antibody or VSIG8 fusion proteins disclosed herein or conjugates according to at least some embodiments of the invention can be used to modify a given biological response, and the drug moiety is not to be construed as limited to classical chemical therapeutic agents. For example, the drug moiety may be a protein or polypeptide possessing a desired biological activity. Such proteins may include, for example, an enzymatically active toxin, or active fragment thereof, such as abrin, ricin A, *pseudomonas* exotoxin, or diphtheria toxin; a protein such as tumor necrosis factor or interferon-γ; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors.

Techniques for conjugating such therapeutic moiety to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "or Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., "The Preparation And Cytotoxic Properties Of Antibody-Toxin Conjugates", Immunol. Rev., 62:119-58 (1982).

Bispecific Molecules

According to at least some embodiments the invention encompasses also a multispecific anti-VSIG8 antibody. Multispecific antibodies are monoclonal antibodies that have binding specificities for at least two different sites. In another aspect, the present invention features bispecific molecules comprising an anti-VSIG8 antibody, or a fragment thereof, according to at least some embodiments of the invention. An antibody according to at least some embodiments of the invention, or antigen-binding portions thereof, can be derivatized or linked to another functional molecule, e.g., another peptide or protein (e.g., another antibody or ligand for a receptor) to generate a bispecific molecule that binds to at least two different binding sites or target molecules. The antibody according to at least some embodiments of the invention may in fact be derivatized or linked to more than one other functional molecule to generate multispecific molecules that bind to more than two different binding sites and/or target molecules; such multispecific molecules are also intended to be encompassed by the term "bispecific molecule" as used herein. To create a bispecific molecule according to at least some embodiments of the invention, an antibody can be functionally linked (e.g., by chemical coupling, genetic fusion, noncovalent association or otherwise) to one or more other binding molecules, such as another antibody, antibody fragment, peptide or binding mimetic, such that a bispecific molecule results. In certain embodiments, one of the binding specificities of the bispecific antibodies is for VSIG8 and the other is for any other antigen. In certain embodiments, bispecific antibodies may bind to two different epitopes of VSIG8. Bispecific antibodies may also be used to localize cytotoxic agents to cells which express VSIG8. Bispecific antibodies can be prepared as full length antibodies or antibody fragments.

A bispecific antibody according to at least some embodiments of the invention is an antibody which can bind simultaneously to two targets which are of different structure. Bispecific antibodies (bsAb) and bispecific antibody fragments (bsFab) according to at least some embodiments of the Invention have at least one arm that specifically binds to a B-cell antigen or epitope and at least one other arm that specifically binds a targetable conjugate.

According to at least some embodiments the invention encompasses also a fusion antibody protein, which is a recombinantly produced antigen-binding molecule in which two or more different single-chain antibody or antibody fragment segments with the same or different specificities are linked. A variety of bispecific fusion antibody proteins can be produced using molecular engineering. In one form, the bispecific fusion antibody protein is monovalent, consisting of, for example, a sent with a single binding site for one antigen and a Fab fragment with a single binding site for a second antigen. In another form, the bispecific fusion antibody protein is divalent, consisting of, for example, an IgG with two binding sites for one antigen and two scFv with two binding sites for a second antigen.

The invention further encompasses also engineered antibodies with three or more functional antigen-binding sites, including "Octopus antibodies" (see, e.g. US 2006/0025576A1), and "Dual Acting FAb" or "DAF" antibodies comprising an antigen-binding site that binds to VSIG8 as well as another, different antigen (see e.g. US 2008/0069820).

Accordingly, the present invention includes bispecific molecules comprising at least one first binding specificity for VSIG8 and a second binding specificity for a second target epitope. According to at least some embodiments of the invention, the second target epitope is an Fc receptor, e.g., human FcγRI (CD64) or a human Fca receptor (CD89). Therefore, the invention includes bispecific molecules capable of binding both to FcγR, FcaR or FcεR expressing effector cells (e.g., monocytes, macrophages or polymorphonuclear cells (PMNs)), and to target cells expressing VSIG8, respectively. These bispecific molecules target VSIG8 expressing cells to effector cell and trigger Fc receptor-mediated effector cell activities, such as phagocytosis of an VSIG8 expressing cells, antibody dependent cell-mediated cytotoxicity (ADCC), cytokine release, or generation of superoxide anion.

According to at least some embodiments of the invention in which the bispecific molecule is multispecific, the molecule can further include a third binding specificity, in addition to an anti-Fc binding specificity. In one embodiment, the third binding specificity is an anti-enhancement factor (EF) portion, e.g., a molecule which binds to a surface protein involved in cytotoxic activity and thereby increases the immune response against the target cell.

The "anti-enhancement factor portion" can be an antibody, functional antibody fragment or a ligand that binds to a given molecule, e.g., an antigen or a receptor, and thereby results in an enhancement of the effect of the binding determinants for the Fc receptor or target cell antigen. The "anti-enhancement factor portion" can bind an Fc receptor or a target cell antigen. Alternatively, the anti-enhancement factor portion can bind to an entity that is different from the entity to which the first and second binding specificities bind. For example, the anti-enhancement factor portion can bind a cytotoxic T-cell (e.g., via CD2, CD3, CD8, CD28, CD4, CD40, ICAM-1 or other immune cell that results in an increased immune response against the target cell).

According to at least some embodiments of the invention, the bispecific molecules comprise as a binding specificity at least one antibody, or an antibody fragment thereof, including, e.g., an Fab, Fab', F(ab')2, Fv, or a single chain Fv. The antibody may also be a light chain or heavy chain dimer, or any minimal fragment thereof such as a Fv or a single chain construct as described in Ladner et al. U.S. Pat. No. 4,946,778, the contents of which are expressly incorporated by reference.

In one embodiment, the binding specificity for an Fey receptor is provided by a monoclonal antibody, the binding of which is not blocked by human immunoglobulin G (IgG). As used herein, the term "IgG receptor" refers to any of the eight γ-chain genes located on chromosome 1. These genes encode a total of twelve transmembrane or soluble receptor isoforms which are grouped into three Fey receptor classes: FcγRI (CD64), FcγRII(CD32), and FcuRIII (CD16). In one preferred embodiment, the Fc γ receptor is a human high affinity FcγRI. The human FcγRI is a 72 kDa molecule, which shows high affinity for monomeric IgG. The production and characterization of certain preferred anti-Fc γ monoclonal antibodies are described by Fanger et al. in PCT Publication WO 88/00052 and in U.S. Pat. No. 4,954,617, the teachings of which are fully incorporated by reference herein. These antibodies bind to an epitope of FcγRI, FcγRII or FcγRIII at a site which is distinct from the Fey binding site of the receptor and, thus, their binding Is not blocked substantially by physiological levels of IgG. Specific anti-FcγRI antibodies useful in this invention are mAb 22, mAb 32, mAb 44, mAb 62 and mAb 197. The hybridoma producing mAb 32 is available from the American Type Culture Collection, ATCC Accession No. HB9469. In other embodiments, the anti-Fey receptor antibody is a humanized form of monoclonal antibody 22 (H22). The production and characterization of the H22 antibody is described in Graziano, R. F. et al. (1995) J. Immunol. 155 (10): 4996-5002 and PCT Publication WO 94/10332. The H22 antibody producing cell line is deposited at the American Type Culture Collection under the designation HA022CLI and has the accession no. CRL 11177.

In still other preferred embodiments, the binding specificity for an Fc receptor is provided by an antibody that binds to a human IgA receptor, e.g., an Fc-a receptor (Fc αRI (CD89)), the binding of which is preferably not blocked by human immunoglobulin A (IgA). The term "IgA receptor" is intended to include the gene product of one a-gene (FcαRI) located on chromosome 19. This gene is known to encode several alternatively spliced transmembrane isoforms of 55 to 10 kDa. FcαRI (CD89) is constitutively expressed on monocytes/macrophages, eosinophilic and neutrophilic granulocytes, but not on non-effector cell populations. Fc αRI has medium affinity (Approximately $5\times10^{-7}$ $M^{-1}$) for both IgAI and IgA2, which is increased upon exposure to cytokines such as G-CSF or GM-CSF (Morton, H. C. et al. (1996) Critical Reviews in Immunology 16:423-440). Four FcaRI-specific monoclonal antibodies, identified as A3, A59, A62 and A77, which bind FcaRI outside the IgA ligand binding domain, have been described (Monteiro, R. C. et al. (1992) J. Immunol. 148: 1764).

FcαRI and FcyRI are preferred trigger receptors for use in the bispecific molecules according to at least some embodiments of the invention because they are (1) expressed primarily on immune effector cells, e.g., monocytes, PMNs, macrophages and dendritic cells; (2) expressed at high levels (e.g., 5,000-100,000 per cell); (3) mediators of cytotoxic activities (e.g., ADCC, phagocytosis); (4) mediate enhanced antigen presentation of antigens, including self-antigens, targeted to them.

While human monoclonal antibodies are preferred, other antibodies which can be employed in the bispecific molecules according to at least some embodiments of the invention are murine, chimeric and humanized monoclonal antibodies.

The bispecific molecules of the present invention can be prepared by conjugating the constituent binding specificities, e.g., the anti-FcR and anti-VSIG8 binding specificities, using methods known in the art. For example, the binding specificity of each bispecific molecule can be generated separately and then conjugated to one another. When the binding specificities are proteins or peptides, a variety of coupling or cross-linking agents can be used for covalent conjugation. Examples of cross-linking agents include protein A, carbodiimide, N-succinimidyl-S-acetyl-thioacetate (SATA), 5,5'-dithiobis(2-nitrobenzoic acid) (DTNB), o-phenylenedimaleimide (oPDM), N-succinimidyl-3-(2-pyridyldithio propionate (SPDP), and sulfosuccinimidyl 4-(N-maleimidomethyl)cyclohaxane-1-carboxylate (sulfo-SMCC) (see e.g., Karpovsky et al. (1984) *J. Exp. Med.* 160: 1686; Liu, M A et al. (1985) *Proc. Natl. Acad. Sci. USA* 82:8648). Other methods include those described in Paulus (1985) Behring Ins. Mitt. No. 78, 118-132; Brennan et al. (1985) *Science* 229:81-83), and Glennie et al. (1987) *J. Immunol.* 139: 2367-2375). Preferred conjugating agents are SATA and sulfo-SMCC, both available from Pierce Chemical Co. (Rockford, Ill.). When the binding moieties are antibodies, they can be conjugated via sulfhydryl bonding of the C-terminus hinge regions of the two heavy chains. In a particularly preferred embodiment, the hinge region is modified to contain an odd number of sulfhydryl residues, preferably one, prior to conjugation.

Alternatively, both binding specificities can be encoded in the same vector and expressed and assembled in the same host cell. This method is particularly useful where the bispecific molecule is a mAbXmAb, mAbXFab, FabXF $(ab')_2$ or ligand XFab fusion protein. A bispecific molecule according to at least some embodiments of the invention can be a single chain molecule comprising one single chain antibody and a binding determinant, or a single chain bispecific molecule comprising two binding determinants. Bispecific molecules may comprise at least two single chain molecules. Methods for preparing bispecific molecules are described for example in U.S. Pat. No. 5,260,203; U.S. Pat. No. 5,455,030; U.S. Pat. No. 4,881,175; U.S. Pat. No. 5,132,405; U.S. Pat. No. 5,091,513; U.S. Pat. No. 5,476,786; U.S. Pat. No. 5,013,653; U.S. Pat. No. 5,258,498; and U.S. Pat. No. 5,482,858.

Techniques for making multispecific antibodies include, but are not limited to, recombinant co-expression of two immunoglobulin heavy chain-light chain pairs having different specificities (see Milstein and Cuello, *Nature* 305: 537 (1983)), WO 93/08829, and Traunecker et al., *EMBO J.* 10: 3655 (1991)), and "knob-in-hole" engineering (see, e.g., U.S. Pat. No. 5,731,168). Multi-specific antibodies may also be made by engineering electrostatic steering effects for making antibody Fc-heterodimeric molecules (WO 2009/089004A1); controlled Fab-arm exchange (see Labrijn et al., PNAS 110(13):5145-50 (2013)); cross-linking two or more antibodies or fragments (see, e.g., U.S. Pat. No. 4,676,980, and Brennan et al., Science, 229: 81 (1985)); using leucine zippers to produce bi-specific antibodies (see, e.g., Kostelny et al., J. Immunol., 148(5): 1547-1553 (1992)); using "diabody" technology for making bispecific antibody fragments (see, e.g., Hollinger et al., Proc. Natl. Acad. Sci. USA 90:6444-6448 (1993)); and using single-chain Fv (sFv) dimers (see, e.g. Gruber et al., *J. Immunol.,* 152:5368 (1994)); and preparing trispecific antibodies as described, e.g., in Tutt et al. *J. Immunol.* 147: 60 (1991).

Binding of the bispecific molecules to their specific targets can be confirmed by, for example, enzyme-linked immunosorbent assay (ELISA), radioimmunoassay (RIA), FACS analysis, bioassay (e.g., growth inhibition), or Western Blot assay. Each of these assays generally detects the presence of protein-antibody complexes of particular interest by employing a labeled reagent (e.g., an antibody) specific for the complex of interest. For example, the FcR-antibody complexes can be detected using e.g., an enzyme-linked antibody or antibody fragment which recognizes and specifically binds to the antibody-FcR complexes. Alternatively, the complexes can be detected using any of a variety of other immunoassays. For example, the antibody can be radioactively labeled and used in a radioimmunoassay (RIA) (see, for example, Weintraub, B., Principles of Radioimmunoassays, Seventh Training Course on Radioligand Assay Techniques. The Endocrine Society, March, 1986, which is incorporated by reference herein). The radioactive isotope can be detected by such means as the use of a γ counter or a scintillation counter or by autoradiography.

Uses of Antibodies and Pharmaceutical Compositions Thereof

Cancer Immunotherapy

Unlike tumor-targeted therapies, which are aimed at inhibiting molecular pathways that are crucial for tumor growth and development, and/or depleting tumor cells, cancer immunotherapy is aimed to stimulate the patient's own immune system to eliminate cancer cells, providing long-lived tumor destruction. Various approaches can be used in cancer immunotherapy, among them are therapeutic cancer vaccines to induce tumor-specific T cell responses, and immunostimulatory antibodies (i.e. antagonists of inhibitory receptors=immune checkpoints) to remove immunosuppressive pathways.

Clinical responses with targeted therapy or conventional anti-cancer therapies tend to be transient as cancer cells develop resistance, and tumor recurrence takes place. However, the clinical use of cancer immunotherapy in the past few years has shown that this type of therapy can have durable clinical responses, showing dramatic impact on long term survival. However, although responses are long term, only a small number of patients respond (as opposed to conventional or targeted therapy, where a large number of patients respond, but responses are transient).

By the time a tumor is detected clinically, it has already evaded the immune-defense system by acquiring immunoresistant and immunosuppressive properties and creating an immunosuppressive tumor microenvironment through various mechanisms and a variety of immune cells. Thus, in cancer immunotherapy it is becoming increasingly clear that a combination of therapies is be required for clinical efficacy.

Combination approaches are needed and expected to increase the number of patients benefiting from immunotherapy and expand the number and types of cancers that are responsive, expanding the potential cancer indications for checkpoint agents well beyond the initial indications currently showing efficacy of immune checkpoint blockade as monotherapy. The combination of immunomodulatory approaches is meant to maximize the outcomes and overcome the resistance mechanisms of most tumors to a single approach. Thus, tumors traditionally thought of as non-immunogenic can likely become immunogenic and respond to immunotherapy though co-administration of pro-immunogenic therapies designed to increase the patient's anti-tumor immune responses. Potential priming agents are detailed herein below.

The underlying scientific rationale for the dramatic increased efficacy of combination therapy claims that immune checkpoint blockade as a monotherapy will induce tumor regressions only when there is pre-existing strong anti-tumor immune response to be 'unleashed' when the pathway is blocked. According to at least some embodiments of the present invention, VSIG8-specific antibodies, antibody fragments, conjugates and compositions comprising same, are used for treatment of all types of cancer in cancer immunotherapy in combination therapy.

The term "treatment" as used herein, refers to both therapeutic treatment and prophylactic or preventative measures, which in this Example relates to treatment of cancer; however, also as described below, uses of antibodies and pharmaceutical compositions are also provided for treatment of infectious disease, sepsis, and/or autoimmune conditions, and/or for inhibiting an undesirable immune activation that follows gene therapy. Those in need of treatment include those already with cancer as well as those in which the cancer is to be prevented. Hence, the mammal to be treated herein may have been diagnosed as having the cancer or may be predisposed or susceptible to the cancer. As used herein the term "treating" refers to preventing, delaying the onset of, curing, reversing, attenuating, alleviating, minimizing, suppressing, halting the deleterious effects or stabilizing of discernible symptoms of the above-described cancerous diseases, disorders or conditions. It also includes managing the cancer as described above. By "manage" it is meant reducing the severity of the disease, reducing the frequency of episodes of the disease, reducing the duration of such episodes, reducing the severity of such episodes, slowing/reducing cancer cell growth or proliferation, slowing progression of at least one symptom, amelioration of at least one measurable physical parameter and the like. For example, immunostimulatory anti-VSIG8 antibodies should promote T cell or NK or cytokine immunity against target cells, e.g., cancer, infected or pathogen cells and thereby treat cancer or infectious diseases by depleting the cells involved in the disease condition. Conversely, immunoinhibitory anti-VSIG8 antibodies should reduce T cell or NK activity and/or or the secretion of proinflammatory cytokines which are involved in the disease pathology of some immune disease such as autoimmune, inflammatory or allergic conditions and thereby treat or ameliorate the disease pathology and tissue destruction that may be associated with such conditions (e.g., joint destruction associated with rheumatoid arthritis conditions).

"Mammal" for purposes of treatment refers to any animal classified as a mammal, including humans, domestic and farm animals, and zoo, sports, or pet animals, such as dogs, horses, cats, cows, etc. Preferably, the mammal is human. Preferably the mammal is a human which is diagnosed with one of the disease, disorder or conditions described hereinabove, or alternatively one who is predisposed to at least one type of cancer.

The term "therapeutically effective amount" refers to an amount of agent according to the present invention that is effective to treat a disease or disorder in a mammal.

The therapeutic agents of the present invention can be provided to the subject alone, or as part of a pharmaceutical composition where they are mixed with a pharmaceutically acceptable carrier.

An anti-VSIG8 antibody, a fragment, a conjugate thereof or VSIG8 fusion protein as herein described and/or a pharmaceutical composition comprising same, according to at least some embodiments of the present invention also can be administered in combination therapy, i.e., combined with other potentiating agents and/or other therapies. According to at least some embodiments, the anti VSIG8 antibody or VSIG8 fusion proteins disclosed herein could be used in combination with any of the known in the art standard of care cancer treatment (as can be found, for example, in http://www.cancer.gov/cancertopics).

For example, the combination therapy can include an anti VSIG8 antibody, a fragment, a conjugate thereof and/or a pharmaceutical composition comprising same, combined with at least one other therapeutic or immune modulatory agent, other compounds or immunotherapies, or immuno stimulatory strategy as described herein.

According to at least some embodiments of the present invention, therapeutic agents that can be used in combination with anti-VSIG8 antibodies are potentiating agents that enhance anti-tumor responses.

Various strategies are available for combining an anti-VSIG8 immuno stimulatory antibody or VSIG8 fusion proteins disclosed herein with potentiating agents for cancer immunotherapy. According to at least some embodiments of the present invention, anti-VSIG8 antibody for cancer immunotherapy is used in combination with potentiating agents that are primarily geared to increase endogenous anti-tumor responses, such as Radiotherapy, Cryotherapy, Conventional/classical chemotherapy potentiating anti-tumor immune responses, Targeted therapy potentiating anti-tumor immune responses, Anti-angiogenic therapy, Therapeutic agents targeting immunosuppressive cells such as Tregs and MDSCs, Immuno stimulatory antibodies, Cytokine therapy, Therapeutic cancer vaccines, Adoptive cell transfer.

The scientific rationale behind the combined use with some chemotherapy or anti-cancer conventional drugs is that cancer cell death, a consequence of the cytotoxic action of most chemotherapeutic compounds, may result in increased levels of tumor antigen leading to enhanced antigen presentation and stimulation of anti-tumor immune responses (i.e. immunogenic cell death), resulting in potentiating effects with the anti VSIG8 antibody (Zitvogel et al, 2008, The journal of clinical investigation, vol. 118, pages 1991-2001; Galluzzi et al, 2012, Nature Reviews—Drug discovery, Volume 11, pages 215-233). Other combination therapies that may potentiate anti-tumor responses through tumor cell death are radiotherapy, Cryotherapy, surgery, and hormone deprivation. Each of these cancer therapies creates a source of tumor antigen in the host.

According to at least some embodiments of the present invention, anti-VSIG8 antibody or VSIG8 fusion proteins disclosed herein for cancer immunotherapy is used in combination with Bisphosphonates, especially amino-bisphosphonates (ABP), which have shown to have anti-cancer activity. Some of the activities associated with ABPs are on human γδT cells that straddle the interface of innate and adaptive immunity and have potent anti-tumour activity.

Targeted therapies can also stimulate tumor-specific immune response by inducing the immunogenic death of tumor cells or by engaging immune effector mechanisms (Galluzzi et al, 2012, Nature Reviews—Drug discovery, Volume 11, pages 215-233).

According to at least some embodiments of the invention, Targeted therapies used as agents for combination with anti VSIG8 antibodies for treatment of cancer are as described herein.

Other cancer immunotherapies that also increase endogenous anti-tumor responses could also potentiate the effect of the anti VSIG8 antibody or VSIG8 fusion proteins disclosed herein by enhancing immune effector mechanisms, such as Adoptive T cell therapy, Therapeutic cancer vaccines, reduced immune suppressive cells and their function, Cytokine therapy, or Immuno stimulatory antibodies.

According to at least some embodiments of the present invention, anti-VSIG8 antibody or VSIG8 fusion proteins disclosed herein for cancer immunotherapy is used in combination with Therapeutic agents targeting regulatory immunosuppressive cells such as regulatory T cells (Tregs) and myeloid derived suppressor cells (MDSCs). A number of commonly used chemotherapeutics exert non-specific targeting of Tregs and reduce the number or the immunosuppressive capacity of Tregs or MDSCs (Facciabene A. et al 2012 Cancer Res; 72(9) 2162-71; Byrne W L. et al 2011, Cancer Res. 71:691520; Gabrilovich D I. and Nagaraj S, Nature Reviews 2009 Volume 9, pages 162-174). In this regard, metronomic therapy with some chemotherapy drugs results in immuno stimulatory rather than immunosuppressive effects, via modulation of regulatory cells. Thus, according to at least some embodiments of the present invention, anti-VSIG8 antibody or VSIG8 fusion proteins disclosed herein for cancer immunotherapy is used in combination with drugs selected from but not limited to cyclophosphamide, gemcitabine, mitoxantrone, fludarabine, fludarabine, docetaxel, paclitaxel, thalidomide and thalidomide derivatives.

In addition, according to at least some embodiments of the present invention, anti-VSIG8 antibody or VSIG8 fusion proteins disclosed herein for cancer immunotherapy is used in combination with novel Treg-specific targeting agents including: 1) depleting or killing antibodies that directly target Tregs through recognition of Treg cell surface receptors such as anti-CD25 mAbs daclizumab, basiliximab or 2) ligand-directed toxins such as denileukin diftitox (Ontak)—a fusion protein of human IL-2 and diphtheria toxin, or LMB-2—a fusion between an scFv against CD25 and *Pseudomonas* exotoxin and 3) antibodies targeting Treg cell surface receptors such as CTLA4, PD-1, OX40 and GITR or 4) antibodies, small molecules or fusion proteins targeting other NK receptors such as previously identified.

According to at least some embodiments of the present invention, anti-VSIG8 antibody or VSIG8 fusion proteins disclosed herein for cancer immunotherapy is used in combination with any of the options described below for disrupting Treg induction and/or function, including TLR (toll like receptors) agonists; agents that interfere with the adenosinergic pathway, such as ectonucleotidase inhibitors, or inhibitors of the A2A adenosine receptor; TGF-β inhibitors, such as fresolimumab, lerdelimumab, metelimumab, trabedersen, LY2157299, LY210976; blockade of Tregs recruitment to tumor tissues including chemokine receptor inhibitors, such as the CCR4/CCL2/CCL22 pathway.

According to at least some embodiments of the present invention, anti-VSIG8 antibody or VSIG8 fusion proteins disclosed herein for cancer immunotherapy is used in combination with any of the options described below for inhibiting the immunosuppressive tumor microenvironment, including inhibitors of cytokines and enzymes which exert immunosuppressive activities, such as IDO (indoleamine-2,3-dioxygenase) inhibitors; inhibitors of anti-inflammatory cytokines which promote an immunosuppressive microenvironment, such as IL-10, IL-35, IL-4 and IL-13; Bevacizumab® which reduces Tregs and favors the differentiation of DCs.

According to at least some embodiments of the present invention, anti-VSIG8 antibody or VSIG8 fusion proteins disclosed herein for cancer immunotherapy is used in combination with any of the options described below for targeting MDSCs (myeloid-derived suppressive cells), including promoting their differentiation into mature myeloid cells that do not have suppressive functions by Vitamin D3, or Vitamin A metabolites, such as retinoic acid, all-trans retinoic acid (ATRA); inhibition of MDSCs suppressive activity by COX2 inhibitors, phosphodiesterase 5 inhibitors like sildenafil, ROS inhibitors such as nitroaspirin.

According to at least some embodiments of the present invention, anti-VSIG8 antibody or VSIG8 fusion proteins disclosed herein for cancer immunotherapy is used in combination with immuno stimulatory antibodies or other agents which potentiate anti-tumor immune responses (Pardoll J Exp Med. 2012; 209(2): 201-209). Immuno stimulatory antibodies promote anti-tumor immunity by directly modulating immune functions, i.e. blocking other inhibitory targets or enhancing immuno stimulatory proteins. According to at least some embodiments of the present invention, anti-VSIG8 antibody for cancer immunotherapy is used in combination with antagonistic antibodies targeting immune checkpoints including anti-CTLA4 mAbs, such as ipilimumab, tremelimumab; anti-PD-1 such as nivolumab BMS-936558/MDX-1106/ONO-4538, AMP224, CT-011, MK-3475, anti-PDL-1 antagonists such as BMS-936559/MDX-1105, MEDI4736. RG-7446/MPDL3280A; Anti-LAG-3 such as IMP-321), anti-TIM-3, anti-BTLA, anti-B7-H4, anti-B7-H3, Anti-VISTA; Agonistic antibodies targeting immunostimulatory proteins, including anti-CD40 mAbs such as CP-870,893, lucatumumab, dacetuzumab; anti-CD137 mAbs such as BMS-663513 urelumab, PF-05082566; anti-OX40 mAbs, such as anti-OX40; anti-GITR mAbs such as TRX518; anti-CD27 mAbs, such as CDX-1127; and anti-ICOS mAbs.

Cytokines are molecular messengers that allow the cells of the immune system to communicate with one another to generate a coordinated, robust, but self-limited response to a target antigen. Cytokine-based therapies embody a direct attempt to stimulate the patient's own immune system to reject cancer. The growing interest over the past two decades in harnessing the immune system to eradicate cancer has been accompanied by heightened efforts to characterize cytokines and exploit their vast signaling networks to develop cancer treatments. Cytokines directly stimulate immune effector cells and stromal cells at the tumor site and enhance tumor cell recognition by cytotoxic effector cells. Numerous animal tumor model studies have demonstrated that cytokines have broad anti-tumor activity and this has been translated into a number of cytokine-based approaches for cancer therapy (Lee and Margolin 2011, *Cancers* 3(4): 3856-93). A number of cytokines are in preclinical or clinical development as agents potentiating anti-tumor immune responses for cancer immunotherapy, including among others: IL-2, IL-7, IL-12, IL-15, IL-17, IL-18 and IL-21, IL-23, IL-27, GM-CSF, IFNα (interferon α), IFNβ, and IFNγ.

Several cytokines have been approved for therapy of cancer and many more are under development. However, therapeutic efficacy is often hampered by severe side effects and poor pharmacokinetic properties. Thus, in addition to systemic administration of cytokines, a variety of strategies can be employed for the delivery of therapeutic cytokines and their localization to the tumor site, in order to improve their pharmacokinetics, as well as their efficacy and/or toxicity, including antibody-cytokine fusion molecules (immunocytokines), chemical conjugation to polyethylene glycol (PEGylation), transgenic expression of cytokines in autologous whole tumor cells, incorporation of cytokine genes into DNA vaccines, recombinant viral vectors to deliver cytokine genes, etc. In the case of immunocytokines, fusion of cytokines to tumor-specific antibodies or antibody fragments allows for targeted delivery and therefore improved efficacy and pharmacokinetics, and reduced side effects.

According to at least some embodiments of the present invention, anti-VSIG8 antibody or VSIG8 fusion proteins disclosed herein for cancer immunotherapy is used in combination with Cytokine therapy, involving the use of cytokines as agents potentiating anti-tumor immune responses, including cytokines such as IL-2, IL-7, IL-12, IL-15, IL-17, IL-18 and IL-21, IL-23, IL-27, GM-CSF, IFNα (interferon α), IFNa-2b, IFNβ, IFNγ, and their different strategies for delivery, as described above.

Cancer vaccines are used to treat existing cancer (therapeutic) or prevent the development of cancer in certain high-risk individuals (prophylactic). Therapeutic cancer vaccines allow for improved priming of T cells and improved antigen presentation, and can be used as therapeutic agents for potentiating anti-tumor immune responses (Mellman I. et al., 2011, Nature, 480:22-29; Schlom J, 2012, J Natl Cancer Inst; 104:599-613).

Several types of therapeutic cancer vaccines are in preclinical and clinical development. These include for example:

1) Whole tumor cell vaccines, in which cancer cells removed during surgery are treated to enhance their immunogenicity, and injected into the patient to Induce immune responses against antigens in the tumor cells. The tumor cell vaccine can be autologous, i.e. a patient's own tumor, or allogeneic which typically contain two or three established and characterized human tumor cell lines of a given tumor type, such as the GVAX vaccine platforms.

2) Tumor antigen vaccines, in which a tumor antigen (or a combination of a few tumor antigens), usually proteins or peptides, are administered to boost the immune system (possibly with an adjuvant and/or with immune modulators or attractants of dendritic cells such as GM-CSF). The tumor antigens may be specific for a certain type of cancer, but they are not made for a specific patient.

3) Vector-based tumor antigen vaccines and DNA vaccines can be used as a way to provide a steady supply of antigens to stimulate an anti-tumor immune response.

Vectors encoding for tumor antigens are injected into the patient (possibly with proinflammatory or other attractants such as GM-CSF), taken up by cells in vivo to make the specific antigens, which would then provoke the desired immune response. Vectors may be used to deliver more than one tumor antigen at a time, to increase the immune response. In addition, recombinant virus, bacteria or yeast vectors should trigger their own immune responses, which may also enhance the overall immune response.

4) Oncolytic virus vaccines, such as OncoVex/T-VEC, which involves the intratumoral injection of replication-conditional herpes simplex virus which preferentially infects cancer cells. The virus, which is also engineered to express GM-CSF, is able to replicate inside a cancer cell causing its lysis, releasing new viruses and an array of tumor antigens, and secreting GM-CSF in the process. Thus, such oncolytic virus vaccines enhance DCs function in the tumor microenvironment to stimulate anti-tumor immune responses.

5) Dendritic cell vaccines (Palucka and Banchereau, 2102, Nat. Rev. Cancer, 12(4):265-277): Dendritic cells (DCs) phagocytose tumor cells and present tumor antigens to tumor specific T cells. In this approach, DCs are isolated from the cancer patient and primed for presenting tumor-specific T cells. To this end several methods can be used: DCs are loaded with tumor cells or lysates; DCs are loaded with fusion proteins or peptides of tumor antigens; coupling of tumor antigens to DC-targeting mAbs. The DCs are treated in the presence of a stimulating factor (such as GM-CSF), activated and matured ex vivo, and then re-infused back into the patient in order provoke an immune response to the cancer cells. Dendritic cells can also be primed in vivo by injection of patients with irradiated whole tumor cells engineered to secrete stimulating cytokines (such as GM-CSF). Similar approaches can be carried out with monocytes. Sipuleucel-T (Provenge), a therapeutic cancer vaccine which has been approved for treatment of advanced prostate cancer, is an example of a dendritic cell vaccine.

Thus, according to at least some embodiments of the present invention, anti-VSIG8 antibody or VSIG8 fusion proteins disclosed herein for cancer immunotherapy is used in combination with Therapeutic cancer vaccines. Non limiting examples of such therapeutic cancer vaccines include Whole tumor cell vaccines, Tumor antigen vaccines, Vector-based vaccines, Oncolytic virus vaccines, Dendritic-cell vaccines, as described above.

One approach to cancer immunotherapy is based on adoptive T cell therapy or adoptive cell transfer (ACT), which involves the ex vivo identification and expansion of autologous naturally occurring tumor specific T cells, which are then adoptively transferred back into the cancer patient (Restifo et al, 2013, Cancer Immunol. Immunother. 62(4): 727-36 (2013) Epub Dec. 4, 2012). Cells that are infused back into a patient after ex vivo expansion can traffic to the tumor and mediate its destruction. Prior to this adoptive transfer, hosts can be immunodepleted by irradiation and/or chemotherapy. The combination of lymphodepletion, adoptive cell transfer, and a T cell growth factor (such as IL-2), can lead to prolonged tumor eradication in tumor patients. A more novel approach involves the ex vivo genetic modification of normal peripheral blood T cells to confer specificity for tumor-associated antigens. For example, clones of TCRs of T cells with particularly good anti-tumor responses can be inserted into viral expression vectors and used to infect autologous T cells from the patient to be treated. Another option is the use of chimeric antigen receptors (CARs) which are essentially a chimeric immunoglobulin-TCR molecule, also known as a T-body. CARs have antibody-like specificities and recognize MHC-nonrestricted structures on the surface of target cells (the extracellular target-binding module), grafted onto the TCR intracellular domains capable of activating T cells (Restifo et al Cancer Immunol. Immunother. 62(4):727-36 (2013) Epub Dec. 4, 2012; and Shi et al, Nature 493: 111-115 2013.

According to at least some embodiments of the present invention, anti-VSIG8 antibody or VSIG8 fusion proteins disclosed herein for cancer immunotherapy is used in combination with Adoptive cell transfer to potentiate anti-tumor immune responses, including genetically modified T cells, as described above.

The VSIG8 specific antibodies, and/or alternative scaffolds and/or multispecific and bispecific molecules and immunoconjugates, compositions comprising same according to at least some embodiments of the present invention can be coadministered together with one or more other therapeutic agents, which acts in conjunction with or synergistically with the composition according to at least some embodiments of the present invention to treat or prevent the cancer. The VSIG8 related therapeutic agents and the one or more other therapeutic agents can be administered in either order or simultaneously. The other therapeutic agents are for example, a cytotoxic agent, a radiotoxic agent or an immunosuppressive agent. The composition can be linked to the agent (as an immunocomplex) or can be administered separately from the agent. In the latter case (separate administration), the composition can be administered before, after or concurrently with the agent or can be coadministered with other known therapies, e.g., an anti-cancer therapy, e.g., radiation. Such therapeutic agents include, among others, anti-neoplastic agents such as doxorubicin (Adriamycin), cisplatin bleomycin sulfate, carmustine, chlorambucil, and cyclophosphamide hydroxyurea which, by themselves, are only effective at levels which are toxic or subtoxic to a patient. Cisplatin is intravenously administered as a 100 mg/dose once every four weeks and Adriamycin is Intravenously administered as a 60-75 mg/ml dose once every 21 days. Co-administration of the human anti-VSIG8 antibodies, or antigen-binding fragments and/or alternative scaffolds thereof, according to at least some embodiments of the present invention with chemotherapeutic agents provides two anti-cancer agents which operate via different mechanisms which yield a cytotoxic effect to human tumor cells. Such co-administration can solve problems due to development of resistance to drugs or a change in the antigenicity of the tumor cells which would render them unreactive with the antibody. In other embodiments, the subject can be additionally treated with an agent that modulates, e.g., enhances or inhibits, the expression or activity of Fey or Fey receptors by, for example, treating the subject with a cytokine. Preferred cytokines for administration during treatment with the multispecific molecule include of granulocyte colony-stimulating factor (G-CSF), granulocyte-macrophage colony-stimulating factor (GM-CSF), interferon-γ (IFN-γ), and tumor necrosis factor (T Fa or T FP).

Target-specific effector cells, e.g., effector cells linked to compositions (e.g., human antibodies, multispecific and bispecific molecules) according to at least some embodiments of the present invention can also be used as therapeutic agents. Effector cells for targeting can be human leukocytes such as macrophages, neutrophils or monocytes. Other cells include eosinophils, natural killer cells and other IgG- or IgA-receptor bearing cells. If desired, effector cells can be obtained from the subject to be treated. The target-specific effector cells can be administered as a suspension of cells in a physiologically acceptable solution. The number of cells administered can be in the order of 10"8° to 10-9" but will vary depending on the therapeutic purpose. In general, the amount will be sufficient to obtain localization at the target cell, e.g., a tumor cell expressing VSIG8 proteins, and to effect cell killing e.g., by, e.g., phagocytosis. Routes of administration can also vary.

Therapy with target-specific effector cells can be performed in conjunction with other techniques for removal of targeted cells. For example, anti-tumor therapy using the compositions (e.g., human antibodies, multispecific and bispecific molecules) according to at least some embodiments of the present invention and/or effector cells armed with these compositions can be used in conjunction with chemotherapy.

Additionally, combination immunotherapy may be used to direct two distinct cytotoxic effector populations toward tumor cell rejection. For example, anti-VSIG8 antibodies linked to anti-Fc-γ RI or anti-CD3 may be used in conjunction with IgG- or IgA-receptor specific binding agents.

Bispecific and multispecific molecules according to at least some embodiments of the present invention can also be used to modulate FcyR or FcyR levels on effector cells, such as by capping and elimination of receptors on the cell surface. Mixtures of anti-Fc receptors can also be used for this purpose.

The therapeutic compositions (e.g., human antibodies, alternative scaffolds multispecific and bispecific molecules and immunoconjugates) according to at least some embodiments of the present invention which have complement binding sites, such as portions from IgGl, -2, or -3 or IgM which bind complement, can also be used in the presence of complement. In one embodiment, ex vivo treatment of a population of cells comprising target cells with a binding agent according to at least some embodiments of the present invention and appropriate effector cells can be supplemented by the addition of complement or serum containing complement. Phagocytosis of target cells coated with a binding agent according to at least some embodiments of the present invention can be improved by binding of complement proteins. In another embodiment target cells coated with the compositions (e.g., human antibodies, multispecific and bispecific molecules) according to at least some embodiments of the present invention can also be lysed by complement. In yet another embodiment, the compositions according to at least some embodiments of the present invention do not activate complement.

The therapeutic compositions (e.g., human antibodies, alternative scaffolds multispecific and bispecific molecules and immunoconjugates) according to at least some embodiments of the present invention can also be administered together with complement. Thus, according to at least some embodiments of the present invention there are compositions, comprising human antibodies, multispecific or bispecific molecules and serum or complement. These compositions are advantageous in that the complement is located in close proximity to the human antibodies, multispecific or bispecific molecules. Alternatively, the human antibodies, multispecific or bispecific molecules according to at least some embodiments of the present invention and the complement or serum can be administered separately.

A "therapeutically effective dosage" of an anti-VSIG8 antibody or VSIG8 fusion proteins disclosed herein according to at least some embodiments of the present invention preferably results in a decrease in severity of disease symptoms, an increase in frequency and duration of disease symptom-free periods, an increase in lifespan, disease remission, or a prevention or reduction of impairment or disability due to the disease affliction. For example, for the treatment of VSIG8 positive tumors, a "therapeutically effective dosage" preferably inhibits cell growth or tumor growth by at least about 20%, more preferably by at least about 40%, even more preferably by at least about 60%, and still more preferably by at least about 80% relative to untreated subjects. The ability of a compound to inhibit tumor growth can be evaluated in an animal model system predictive of efficacy in human tumors.

Alternatively, this property of a composition can be evaluated by examining the ability of the compound to inhibit, such inhibition in vitro by assays known to the skilled practitioner. A therapeutically effective amount of a therapeutic compound can decrease tumor size, or otherwise ameliorate symptoms in a subject.

One of ordinary skill in the art would be able to determine a therapeutically effective amount based on such factors as the subject's size, the severity of the subject's symptoms, and the particular composition or route of administration selected.

The anti-VSIG8 antibodies, according to at least some embodiments of the present invention, can be used as neutralizing antibodies. A Neutralizing antibody (Nabs), is an antibody that is capable of binding and neutralizing or inhibiting a specific antigen thereby inhibiting its biological effect, for example by blocking the receptors on the cell or the virus, inhibiting the binding of the virus to the host cell. NAbs will partially or completely abrogate the biological action of an agent by either blocking an important surface molecule needed for its activity or by interfering with the binding of the agent to its receptor on a target cell.

As used herein "therapeutic agent" is any one of the monoclonal and/or polyclonal antibodies, and/or antigen-binding fragments, and/or conjugates containing same, and/or alternative scaffolds, thereof comprising an antigen-binding site that binds specifically to any one of the VSIG8 polypeptides or an epitope thereof, adopted for treatment of cancer, as recited herein.

According to an additional aspect of the present invention the therapeutic agents can be used to prevent pathologic inhibition of T cell activity, such as that directed against cancer cells.

According to an additional aspect of the present invention the therapeutic agents can be used to inhibit T cell activation, as can be manifested for example by T cell proliferation and cytokine secretion.

Thus, according to an additional aspect of the present invention there is provided a method of treating cancer as recited herein, and/or for promoting immune stimulation mediated by the VSIG8 polypeptide in a subject by administering to a subject in need thereof an effective amount of any one of the therapeutic agents and/or a pharmaceutical composition comprising any of the therapeutic agents and further comprising a pharmaceutically acceptable diluent or carrier.

A therapeutic agent or pharmaceutical composition according to at least some embodiments of the present invention may also be administered in conjunction with other compounds or immunotherapies. For example, the combination therapy can include a compound of the present invention combined with at least one other therapeutic or immune modulatory agent, or immuno stimulatory strategy, including, but not limited to, tumor vaccines, adoptive T cell therapy, Treg depletion, antibodies (e.g. bevacizumab, Erbitux), peptides, peptibodies, small molecules, chemotherapeutic agents such as cytotoxic and cytostatic agents (e.g. paclitaxel, cisplatin, vinorelbine, docetaxel, gemcitabine, temozolomide, irinotecan, 5FU, carboplatin), immunological modifiers such as interferons and interleukins, immuno stimulatory antibodies, growth hormones or other cytokines, folic acid, vitamins, minerals, aromatase inhibitors, RNAi, Histone Deacetylase Inhibitors, proteasome inhibitors, and so forth.

According to at least some embodiments, immune cells, preferably T cells, can be contacted in vivo or ex vivo with the therapeutic agents to modulate immune responses. The T cells contacted with the therapeutic agents can be any cell which expresses the T cell receptor, including α/β and γ/δ T cell receptors. T-cells include all cells which express CD3, including T-cell subsets which also express CD4 and CDS. T-cells include both naive and memory cells and effector cells such as CTL. T-cells also include cells such as Th1, Tel, Th2, Th2, Th3, Thl7, Th22, Treg, and Trl cells. T-cells also include NKT-cells and similar unique classes of the T-cell lineage.

VSIG8 blockade may also be combined with standard cancer treatments. VSIG8 blockade may be effectively combined with chemotherapeutic regimes. In these instances, it may be possible to reduce the dose of chemotherapeutic reagent administered. An example of such a combination is an anti-VSIG8 antibody or VSIG8 fusion proteins disclosed herein in combination with Temsirolimus for the treatment of late stage renal cell cancer. Another example of such a combination is an anti-VSIG8 antibody or VSIG8 fusion proteins disclosed herein in combination with interleukin-2 (IL-2) for the treatment of late stage renal cell cancer as well as combination with Ipilimumab or BMS-936558. The scientific rationale behind the combined use of VSIG8 blockade and chemotherapy is that cell death, that is a consequence of the cytotoxic action of most chemotherapeutic compounds, should result in increased levels of tumor antigen in the antigen presentation pathway. Other combination therapies that may result in synergy with VSIG8 blockade through cell death are radiotherapy, cryotherapy, surgery, and hormone deprivation. Other additional combination therapies with additional immunomodulatory molecules will synergistically contribute to the stimulation of the immune system to eradicate the cancer. Each of these protocols creates a source of tumor antigen in the host. Angiogenesis inhibitors may also be combined with VSIG8 blockade. Inhibition of angiogenesis leads to tumor cell death which may feed tumor antigen into host antigen presentation pathways.

VSIG8 blocking antibodies can also be used in combination with bispecific antibodies that target Fca or Fey receptor-expressing effectors cells to tumor cells (see, e.g., U.S. Pat. Nos. 5,922,845 and 5,837,243). Bispecific antibodies can be used to target two separate antigens. For example anti-Fc receptor/anti-tumor antigen (e.g., Her-2/neu) bispecific antibodies have been used to target macrophages to sites of tumor. This targeting may more effectively activate tumor specific responses. The T cell arm of these responses would be augmented by the use of VSIG8 blockade. Alternatively, antigen may be delivered directly to DCs by the use of bispecific antibodies which bind to tumor antigen and a dendritic cell specific cell surface marker.

Tumors evade host immune surveillance by a large variety of mechanisms. Many of these mechanisms may be overcome by the inactivation of proteins which are expressed by the tumors and which are immunosuppressive. These include among others TGF-β (Kehrl, J. et al. (1986) J. Exp. Med. 163: 1037-1050), IL-10 (Howard, M. & O'Garra, A. (1992) Immunology Today 13: 198-200), and Fas ligand (Hahne, M. et al. (1996) Science 274: 1363-1365). Antibodies to each of these entities may be used in combination with anti-VSIG8 to counteract the effects of the immunosuppressive agent and favor tumor immune responses by the host.

Other antibodies which may be used to activate host immune responsiveness can be used in combination with anti-VSIG8. These include molecules on the surface of dendritic cells which activate DC function and antigen presentation. Anti-CD40 antibodies are able to substitute effectively for T cell helper activity (Ridge, J. et al. (1998) Nature 393: 474-478) and can be used in conjunction with VSIG8 antibodies (Ito, N. et al. (2000) Immunobiology 201 (5) 527-40). Activating antibodies to T cell costimulatory molecules such as OX-40 (Weinberg, A. et al. (2000) Immunol 164: 2160-2169), 4-1BB (Melero, I. et al. (1997) Nature Medicine 3: 682-685 (1997), and ICOS (Hutloff, A. et al. (1999) Nature 397: 262-266) as well as antibodies which block the activity of negative costimulatory molecules such as CTLA-4 (e.g., U.S. Pat. No. 5,811,097, implimumab) or BTLA (Watanabe, N. et al. (2003) Nat Immunol 4:670-9), B7-H4 (Sica, G L et al. (2003) Immunity 18:849-61) PD-1 (may also provide for increased levels of T cell activation.

Bone marrow transplantation is currently being used to treat a variety of tumors of hematopoietic origin. While graft versus host disease is a consequence of this treatment, therapeutic benefit may be obtained from graft vs. tumor responses. VSIG8 blockade can be used to increase the effectiveness of the donor engrafted tumor specific T cells. There are also several experimental treatment protocols that involve ex vivo activation and expansion of antigen specific T cells and adoptive transfer of these cells into recipients in order to antigen-specific T cells against tumor (Greenberg, R. & Riddell, S. (1999) Science 285: 546-51). These methods may also be used to activate T cell responses to infectious agents such as CMV. Ex vivo activation in the presence of anti-VSIG8 antibodies may be expected to increase the frequency and activity of the adoptively transferred T cells.

Optionally, antibodies to VSIG8 can be combined with an immunogenic agent, such as cancerous cells, purified tumor antigens (including recombinant proteins, peptides, and carbohydrate molecules), cells, and cells transfected with genes encoding immune stimulating cytokines (He et al (2004) J. Immunol. 173:4919-28). Non-limiting examples of tumor vaccines that can be used include peptides of MUC1 for treatment of colon cancer, peptides of MUC-1/CEA/TRICOM for the treatment of ovary cancer, or tumor cells transfected to express the cytokine GM-CSF (discussed further below).

In humans, some tumors have been shown to be immunogenic such as RCC. It is anticipated that by raising the threshold of T cell activation by VSIG8 blockade, we may expect to activate tumor responses in the host. VSIG8 blockade is likely to be most effective when combined with a vaccination protocol. Many experimental strategies for vaccination against tumors have been devised (see Rosenberg, S., 2000, Development of Cancer Vaccines, ASCO Educational Book Spring: 60-62; Logothetis, C, 2000, ASCO Educational Book Spring: 300-302; Khayat, D. 2000, ASCO Educational Book Spring: 414-428; Foon, K. 2000, ASCO Educational Book Spring: 730-738; see also Restifo, N. and Sznol, M., Cancer Vaccines, Ch. 61, pp. 3023-3043 in DeVita, V. et al. (eds.), 1997, Cancer: Principles and Practice of Oncology. Fifth Edition). In one of these strategies, a vaccine is prepared using autologous or allogeneic tumor cells. These cellular vaccines have been shown to be most effective when the tumor cells are transduced to express GM-CSF. GM-CSF has been shown to be a potent activator of antigen presentation for tumor vaccination Use of Anti-VSIG8 Antibodies or VSIG8 Fusion Proteins and Pharmaceutical Compositions Containing for Treatment of Autoimmune Disease According to at least some embodiments, VSIG8 antibodies, fragments, conjugates thereof or VSIG8 Fusion Proteins and/or a pharmaceutical composition comprising same, as described herein, which function as VSIG8 stimulating therapeutic agents, may optionally be used for treating an immune system related disease.

Optionally, the immune system related condition comprises an immune related condition, autoimmune diseases as recited herein, transplant rejection and graft versus host disease and/or for blocking or promoting immune stimulation mediated by VSIG8, immune related diseases as recited herein and/or for immunotherapy (promoting or inhibiting immune stimulation).

Optionally the immune condition is selected from autoimmune disease, transplant rejection, or graft versus host disease. Optionally the treatment is combined with another moiety useful for treating immune related condition.

Thus, treatment of multiple sclerosis using the agents according to at least some embodiments of the present invention may be combined with, for example, any known therapeutic agent or method for treating multiple sclerosis, optionally as described herein.

Thus, treatment of rheumatoid arthritis, using the agents according to at least some embodiments of the present invention may be combined with, for example, any known therapeutic agent or method for treating rheumatoid arthritis, optionally as described herein. Thus, treatment of IBD, using the agents according to at least some embodiments of the present invention may be combined with, for example, any known therapeutic agent or method for treating IBD, optionally as described herein.

Thus, treatment of psoriasis, using the agents according to at least some embodiments of the present invention may be combined with, for example, any known therapeutic agent or method for treating psoriasis, optionally as described herein.

Thus, treatment of type 1 diabetes, using the agents according to at least some embodiments of the present invention may be combined with, for example, any known therapeutic agent or method for treating type I diabetes, optionally as described herein.

Thus, treatment of uveitis, using the agents according to at least some embodiments of the present invention may be combined with, for example, any known therapeutic agent or method for treating uveitis, optionally as described herein.

Thus, treatment for Sjögren's syndrome, using the agents according to at least some embodiments of the present invention may be combined with, for example, any known therapeutic agent or method for treating for Sjögren's syndrome, optionally as described herein.

Thus, treatment for systemic lupus erythematosus, using the agents according to at least some embodiments of the present invention may be combined with, for example, any known therapeutic agent or method for treating for systemic lupus erythematosus, optionally as described herein.

In the above-described therapies preferably a subject with one of the aforementioned autoimmune or inflammatory conditions will be administered an immunoinhibitory anti-VSIG8 antibody or VSIG8 fusion proteins disclosed herein or antigen-binding fragment according to the invention, which antibody or VSIG8 fusion proteins disclosed herein mimics or agonizes at least one VSIG8 mediated effect on immunity, e.g., it suppresses cytotoxic T cells, or NK activity and/or the production of proinflammatory cytokines which are involved in the disease pathology, thereby preventing or ameliorating the disease symptoms and potentially resulting in prolonged disease remission, e.g., because of the induction of Tregs which elicit T cell tolerance or prolonged immunosuppression.

The therapeutic agents and/or a pharmaceutical composition comprising same, as recited herein, according to at least some embodiments of the invention, may be administered as the sole active ingredient or together with other drugs in immunomodulating regimens or other anti-inflammatory agents e.g. for the treatment or prevention of alio- or xenograft acute or chronic rejection or inflammatory or autoimmune disorders, or to induce tolerance.

Use of Antibodies or VSIG8 Fusion Proteins and Pharmaceutical Compositions for Treatment of Infectious Disease According to at least some embodiments, VSIG8 antibodies, fragments, conjugates thereof or VSIG8 Fusion Proteins and/or a pharmaceutical compositions as described herein, which function as VSIG8 blocking therapeutic agents, may optionally be used for treating infectious disease.

Chronic infections are often characterized by varying degrees of functional impairment of virus-specific T-cell responses, and this defect is a principal reason for the inability of the host to eliminate the persisting pathogen. Although functional effector T cells are initially generated during the early stages of infection, they gradually lose function during the course of the chronic infection as a result of persistent exposure to foreign antigen, giving rise to T cell exhaustion. Exhausted T cells express high levels of multiple co-inhibitory receptors such as CTLA-4, PD-1, and LAG3 (Crawford et al., Curr Opin Immunol. 2009; 21: 179-186; Kaufmann et al., J Immunol 2009; 182:5891-5897, Sharpe et al., Nat Immunol 2007; 8:239-245). PD-1 overexpression by exhausted T cells was observed clinically in patients suffering from chronic viral infections including HIV, HCV and HBV (Crawford et al., Curr Opin Immunol 2009; 21: 179-186; Kaufmann et al., J Immunol 2009; 182:5891-5897, Sharpe et al., Nat Immunol 2007; 8:239-245). There has been some investigation into this pathway in additional pathogens, including other viruses, bacteria, and parasites (Hofmeyer et al., J Biomed Biotechnol. Vol 2011, Art. ID 451694, Bhadra et al., Proc Natl. Acad Sci. 2011; 108(22):9196-201). For example, the PD-1 pathway was shown to be involved in controlling bacterial infection using a sepsis model induced by the standard cecal ligation and puncture method. The absence of PD-1 in knockout mice protected from sepsis-induced death in this model (Huang et al., PNAS 2009: 106; 6303-6308).

T cell exhaustion can be reversed by blocking co-inhibitory pathways such as PD-1 or CTLA-4 (Rivas et al., J Immunol. 2009; 183:4284-91; Golden-Mason et al., *J Virol.* 2009; 83:9122-30; Hofmeyer et al., J Biomed Biotechnol. Vol 2011, Art. ID 451694), thus allowing restoration of anti-viral immune function. The therapeutic potential of co-inhibition blockade for treating viral infection was extensively studied by blocking the PD-I/PD-LI pathway, which was shown to be efficacious in several animal models of infection including acute and chronic simian immunodeficiency virus (SrV) infection in rhesus macaques (Valu et al., Nature 2009; 458:206-210) and in mouse models of chronic viral infection, such as lymphocytic choriomeningitis virus (LCMV) (Barber et al., Nature. 2006; 439:682-7), and Theiler's murine encephalomyelitis virus (TMEV) model in SJL/J mice (Duncan and Miller *PLoS One.* 2011; 6:el8548). In these models PD-I/PD-LI blockade improved anti-viral responses and promoted clearance of the persisting viruses. In addition, PD-I/PD-LI blockade increased the humoral immunity manifested as elevated production of specific anti-virus antibodies in the plasma, which in combination with the improved cellular responses leads to decrease in plasma viral loads and increased survival.

As used herein the term "infectious disorder and/or disease" and/or "infection", used interchangeably, includes any disorder, disease and/or condition caused by presence and/or growth of pathogenic biological agent in an individual host organism. As used herein the term "infection" comprises the disorder, disease and/or condition as above, exhibiting clinically evident illness (i.e., characteristic medical signs and/or symptoms of disease) and/or which is asymtomatic for much or all of it course. As used herein the term "infection" also comprises disorder, disease and/or condition caused by persistence of foreign antigen that lead to exhaustion T cell phenotype characterized by impaired functionality which is manifested as reduced proliferation and cytokine production. As used herein the term "infectious disorder and/or disease" and/or "infection", further includes any of the below listed infectious disorders, diseases and/or conditions, caused by a bacterial infection, viral infection, fungal infection and/or parasite infection.

According to at least some embodiments of the present invention, there is provided use of a combination of the therapeutic agents and/or a pharmaceutical composition comprising same, as recited herein, and a known therapeutic agent effective for treating infection.

The therapeutic agents and/or a pharmaceutical composition comprising same, as recited herein, can be administered in combination with one or more additional therapeutic agents used for treatment of bacterial infections, optionally as described herein.

The therapeutic agents and/or a pharmaceutical composition comprising same, as recited herein, can be administered in combination with one or more additional therapeutic agents used for treatment of viral infections, optionally as described herein. The therapeutic agents and/or a pharmaceutical composition comprising same, as recited herein, can be administered in combination with one or more additional therapeutic agents used for treatment of fungal infections, optionally as described herein.

In the above-described therapies preferably a subject with one of the aforementioned infectious conditions will be administered an immunostimulatory anti-VSIG8 antibody or VSIG8 fusion proteins disclosed herein or antigen-binding fragment according to the invention, which antibody or VSIG8 fusion proteins disclosed herein antagonizes at least one VSIG8 mediated effect on immunity, e.g., its inhibitory effect on cytotoxic T cells or NK activity and/or its inhibitory effect on the production of proinflammatory cytokines, or inhibits the stimulatory effect of VSIG8 on Tregs thereby prompting the depletion or killing of the infected cells or the pathogen, and potentially resulting in disease remission based on enhanced killing of the pathogen or infected cells by the subject's immune cells.

Use of Anti-VSIG8 Antibodies or VSIG8 Fusion Proteins and Pharmaceutical Compositions Containing for Treatment of Sepsis According to at least some embodiments, VSIG8 antibodies, fragments, conjugates thereof and/or a pharmaceutical compositions as described herein, which function as VSIG8 blocking therapeutic agents, may optionally be used for treating sepsis.

Sepsis is a potentially life-threatening complication of an infection. Sepsis represents a complex clinical syndrome that develops when the initial host response against an infection becomes inappropriately amplified and dysregulated, becoming harmful to the host. The initial hyperinflammatory phase ('cytokine storm') in sepsis is followed by a state of immunosuppression (Hotchkiss et al 2013 Lancet Infect. Dis. 13:260-268). This latter phase of impaired immunity, also referred to as 'immunoparalysis', is manifested in failure to clear the primary infection, reactivation of viruses such as HSV and cytomegalovirus, and development of new, secondary infections, often with organisms that are not particularly virulent to the immunocompetent patient. The vast majority of septic patients today survive their Initial hyperinflammatory insult only to end up in the intensive care unit with sepsis-induced multi-organ dysfunction over the ensuing days to weeks. Sepsis-induced immunosuppression is increasingly recognized as the overriding immune dysfunction in these vulnerable patients. The impaired pathogen clearance after primary infection and/or susceptibility to secondary infections contribute to the high rates of morbidity and mortality associated with sepsis.

Upregulation of inhibitory proteins has lately emerged as one of the critical mechanisms underlying the immunosuppression in sepsis. The PD-I/PDL-1 pathway, for example, appears to be a determining factor of the outcome of sepsis, regulating the delicate balance between effectiveness and damage by the antimicrobial immune response. During sepsis in an experimental model, peritoneal macrophages and blood monocytes markedly increased PD-1 levels, which was associated with the development of cellular dysfunction (Huang et al 2009 PNAS 106:6303-6308). Similarly, in patients with septic shock the expression of PD-1 on peripheral T cells and of PDL-1 on monocytes was dramatically upregulated (Zhang et at 2011 Crit. Care 15:R70). Recent animal studies have shown that blockade of the PD-I/PDL-1 pathway by anti-PDI or anti-PDLI antibodies improved survival in sepsis (Brahmamdam et al 2010 *J. Leukoc. Biol.* 88:233-240; Zhang et al 2010 Critical Care 14:R220; Chang et al 2013 Critical Care 17:R85). Similarly, blockade of CTLA-4 with anti-CTLA4 antibodies improved survival in sepsis (Inoue et al 2011 Shock 36:38-44; Chang et al 2013 Critical Care 17:R85). Taken together, these findings suggest that blockade of inhibitory proteins, including negative costimulatory molecules, is a potential therapeutic approach to prevent the detrimental effects of sepsis (Goyert and Silver, *J Leuk. Biol.*, 88(2): 225-226, 2010).

According to at least some embodiments of the present invention, there is provided use of a combination of the therapeutic agents and/or a pharmaceutical composition comprising same, as recited herein, and a known therapeutic agent effective for treating sepsis.

The restoration of the delicate balance that normally exists between the active and suppressor arms of the immune system in sepsis patients may depend on the precise nature of the imbalance, i.e. the pathogenic organism responsible for the infection, its location, the amount of time passed since onset of infection, and other individual parameters. Thus, the correct choice of tools may well depend on the specific immune status or deficit of each individual patient, and may require combination of different drugs.

According to at least some embodiments of the present invention, there is provided use of a combination of the therapeutic agents and/or a pharmaceutical composition comprising same, as recited herein, can be combined with standard of care or novel treatments for sepsis, with therapies that block the cytokine storm in the initial hyperinflammatory phase of sepsis, and/or with therapies that have immunostimulatory effect in order to overcome the sepsis-induced immunosuppression phase.

Combination with standard of care treatments for sepsis, as recommended by the "International Guidelines for Management of Severe Sepsis and Septic Shock" (Dellinger et al 2013 Intensive Care Med 39: 165-228), some of which are described below.

Broad spectrum antibiotics having activity against all likely pathogens (bacterial and/or fungal—treatment starts when sepsis is diagnosed, but specific pathogen is not identified)—example Cefotaxime (Claforan®), Ticarcillin and clavulanate (Timentin®), Piperacillin and tazobactam (Zosyn®), Imipenem and cilastatin (Primaxin®), Meropenem (Merrem®), Clindamycin (Cleocin), Metronidazole (Flagyl®), Ceftriaxone (Rocephin®), Ciprofloxacin (Cipro®), Cefepime (Maxipime®), Levofloxacin (Levaquin®), Vancomycin or any combination of the listed drugs.

Vasopressors: example Norepinephrine, Dopamine, Epinephrine, vasopressin

Steroids: example: Hydrocortisone, Dexamethasone, or Fludrocortisone, intravenous or otherwise Inotropic therapy: example Dobutamine for sepsis patients with myocardial dysfunction Recombinant human activated protein C (rhAPC), such as drotrecogin alfa (activated) (DrotAA).

β-blockers additionally reduce local and systemic inflammation.

Metabolic interventions such as pyruvate, succinate or high dose insulin substitutions.

Combination with Novel Potential Therapies for Sepsis:

Selective inhibitors of sPLA2-IIA (such as LY315920NA/S-5920). Rationale: The Group IIA secretory phospholipase A2 (sPLA2-IIA), released during inflammation, is increased in severe sepsis, and plasma levels are inversely related to survival.

Phospholipid emulsion (such as GR270773). Rationale: Preclinical and ex vivo studies show that lipoproteins bind and neutralize endotoxin, and experimental animal studies demonstrate protection from septic death when lipoproteins are administered. Endotoxin neutralization correlates with the amount of phospholipid in the lipoprotein particles.

anti-TNF-α antibody: Rationale: Tumor necrosis factor-a (TNF-a) induces many of the pathophysiological signs and symptoms observed in sepsis anti-CD 14 antibody (such as IC14). Rationale: Upstream recognition molecules, like CD 14, play key roles in the pathogenesis. Bacterial cell wall components bind to CD 14 and co-receptors on myeloid cells, resulting in cellular activation and production of proinflammatory mediators. An anti-CD 14 monoclonal antibody (IC14) has been shown to decrease lipopolysaccharide-induced responses in animal and human models of endotoxemia.

Inhibitors of Toll-like receptors (TLRs) and their downstream signaling pathways. Rationale: Infecting microbes display highly conserved macromolecules (e.g., lipopolysaccharides, peptidoglycans) on their surface. When these macromolecules are recognized by pattern-recognition receptors (called Toll-like receptors [TLRs]) on the surface of immune cells, the host's immune response is initiated. This may contribute to the excess systemic inflammatory response that characterizes sepsis. Inhibition of several TLRs is being evaluated as a potential therapy for sepsis, in particular TLR4, the receptor for Gram-negative bacteria outer membrane lipopolysaccharide or endotoxin. Various drugs targeting TLR4 expression and pathway have a therapeutic potential in sepsis (Wittebole et al 2010 Mediators of Inflammation Vol 10 Article ID 568396). Among these are antibodies targeting TLR4, soluble TLR4, Statins (such as Rosuvastatin®, Simvastatin®), Ketamine, nicotinic analogues, eritoran (E5564), resatorvid (TAK242). In addition, antagonists of other TLRs such as chloroquine, inhibition of TLR-2 with a neutralizing antibody (anti-TLR-2).

Lansoprazole through its action on SOCS 1 (suppressor of cytokine secretion) Talactoferrin or Recombinant Human Lactoferrin. Rationale: Lactoferrin is a glycoprotein with anti-infective and anti-inflammatory properties found in secretions and immune cells. Talactoferrin alfa, a recombinant form of human lactoferrin, has similar properties and plays an important role in maintaining the gastrointestinal mucosal barrier integrity. Talactoferrin showed efficacy in animal models of sepsis, and in clinical trials in patients with severe sepsis (Guntupalli et al *Crit Care Med.* 2013; 41(3): 706-716).

Milk fat globule EGF factor VIII (MFG-E8)—a bridging molecule between apoptotic cells and phagocytes, which promotes phagocytosis of apoptotic cells.

Agonists of the 'cholinergic anti-inflammatory pathway', such as nicotine and analogues. Rationale: Stimulating the vagus nerve reduces the production of cytokines, or immune system mediators, and blocks inflammation. This nerve "circuitry", called the "inflammatory reflex", is carried out through the specific action of acetylcholine, released from the nerve endings, on the a7 subunit of the nicotinic acetylcholine receptor (a7nAChR) expressed on macrophages, a mechanism termed 'the cholinergic antiinflammatory pathway'. Activation of this pathway via vagus nerve stimulation or pharmacologic a7 agonists prevents tissue injury in multiple models of systemic inflammation, shock, and sepsis (Matsuda et al 2012 J Nippon Med Sch. 79:4-18; Huston 2012 Surg. Infect. 13: 187-193).

Therapeutic agents targeting the inflammasome pathways. Rationale: The inflammasome pathways greatly contribute to the inflammatory response in sepsis, and critical elements are responsible for driving the transition from localized inflammation to deleterious hyperinflammatory host response (Cinel and Opal 2009 Crit. Care Med. 37:291-304; Matsuda et al 2012 J Nippon Med Sch. 79:4-18).

Stem cell therapy. Rationale: Mesenchymal stem cells (MSCs) exhibit multiple beneficial properties through their capacity to home to injured tissue, activate resident stem cells, secrete paracrine signals to limit systemic and local inflammatory response, beneficially modulate immune cells, promote tissue healing by decreasing apoptosis in threatened tissues and stimulating neoangiogenesis, and exhibit direct antimicrobial activity. These effects are associated with reduced organ dysfunction and improved survival in sepsis animal models, which have provided evidence that MSCs may be useful therapeutic adjuncts (Wannemuehler et al 2012 J. Surg. Res. 173: 113-26).

Combination of anti-VSIG8 antibody or VSIG8 fusion proteins disclosed herein with other immunomodulatory agents, such as immunostimulatory antibodies, cytokine therapy, immunomodulatory drugs. Such agents bring about increased immune responsiveness, especially in situations in which immune defenses (whether innate and/or adaptive) have been degraded, such as in sepsis-induced hypoinflammatory and immunosuppressive condition. Reversal of sepsis-induced immunoparalysis by therapeutic agents that augments host immunity may reduce the incidence of secondary infections and improve outcome in patients who have documented immune suppression (Hotchkiss et al 2013 Lancet Infect. Dis. 13:260-268; Payen et al 2013 Crit Care. 17:118).

Immunostimulatory antibodies promote immune responses by directly modulating immune functions, i.e. blocking other inhibitory proteins or by enhancing costimulatory proteins. Experimental models of sepsis have shown that immuno stimulation by antibody blockade of inhibitory proteins, such as PD-1, PDL-1 or CTLA-4 improved survival in sepsis (Brahmamdam et al 2010 J. Leukoc. Biol. 88:233-240; Zhang et al 2010 Critical Care 14:R220; Chang et al 2013 Critical Care 17:R85; Inoue et al 2011 Shock 36:38-44), pointing to such immunostimulatory agents as potential therapies for preventing the detrimental effects of sepsis-induced immunosuppression (Goyert and Silver I Leuk. Biol. 88(2):225-226, 2010). Immunostimulatory antibodies include: 1) Antagonistic antibodies targeting inhibitory immune checkpoints include anti-CTLA4 mAbs (such as ipilimumab, tremelimumab), Anti-PD-1 (such as nivolumab BMS-936558/MDX-1106/ONO-4538, AMP224, CT-011, lambrozilumab MK-3475), Anti-PDL-1 antagonists (such as BMS-936559/MDX-1105, MEDI4736, RG-7446/MPDL3280A); Anti-LAG-3 such as IMP-321), Anti-TIM-3, Anti-BTLA, Anti-B7-H4, Anti-B7-H3, anti-VISTA. 2) Agonistic antibodies enhancing immunostimulatory proteins include Anti-CD40 mAbs (such as CP-870,893, lucatumumab, dacetuzumab), Anti-CD137 mAbs (such as BMS-663513 urelumab, PF-05082566), Anti-OX40 mAbs (such as Anti-OX40), Anti-GITR mAbs (such as TRX518), Anti-CD27 mAbs (such as CDX-1127), and Anti-ICOS mAbs.

Cytokines which directly stimulate immune effector cells and enhance immune responses can be used in combination with anti-GEN antibody for sepsis therapy: IL-2, IL-7, IL-12, IL-15, IL-17, IL-18 and IL-21, IL-23, IL-27, GM-CSF, IFNa (interferon a), ΓΙΤΝΓβ, IFNy. Rationale: Cytokine-based therapies embody a direct attempt to stimulate the patient's own immune system. Experimental models of sepsis have shown administration of cytokines, such as IL-7 and IL-15, promote T cell viability and result in improved survival in sepsis (Unsinger et al 2010 J. Immunol. 184:3768-3779; Inoue et al 2010 J. Immunol. 184: 1401-1409). Interferon-γ (TPNγ) reverses sepsis-induced immunoparalysis of monocytes in vitro. An in vivo study showed that IFNγ partially reverses immunoparalysis in vivo in humans. IFNγ and granulocyte-macrophage colony-stimulating factor (GM-CSF) restore immune competence of ex vivo stimulated leukocytes of patients with sepsis (Mouktaroudi et al Crit Care. 2010; 14: P17; Leentjens et al Am J Respir Crit Care Med Vol 186, pp 838-845, 2012).

Immunomodulatory drugs such as thymosin al. Rationale: Thymosin a 1 (Tal) is a naturally occurring thymic peptide which acts as an endogenous regulator of both the innate and adaptive immune systems. It is used worldwide for treating diseases associated with immune dysfunction including viral infections such as hepatitis B and C, certain cancers, and for vaccine enhancement. Notably, recent development in immunomodulatory research has indicated the beneficial effect of Tal treatment in septic patients (Wu et al. Critical Care 2013, 17:R8).

In the above-described sepsis therapies preferably a subject with sepsis or at risk of developing sepsis because of a virulent infection, e.g., one resistant to antibiotics or other drugs, will be administered an immunostimulatory anti- VSIG8 antibody or VSIG8 fusion proteins disclosed herein or antigen-binding fragment according to the invention, which antibody or VSIG8 fusion proteins disclosed herein antagonizes at least one VSIG8 mediated effect on immunity, e.g., its inhibitory effect on cytotoxic T cells or NK activity and/or its inhibitory effect on the production of proinflammatory cytokines, or inhibits the stimulatory effect of VSIG8 on Tregs thereby promoting the depletion or killing of the infected cells or the pathogen, and potentially resulting in disease remission based on enhanced killing of the pathogen or infected cells by the subject's endogenous immune cells. Because sepsis may rapidly result in organ failure, in this embodiment it may be beneficial to administer anti-VSIG8 antibody fragments such as Fabs rather than intact antibodies as they may reach the site of sepsis and infection quicker than intact antibodies. (In such treatment regimens antibody half-life may be of lesser concern due to the sometimes rapid morbidity of this disease).

Use of Anti-VSIG8 Antibodies or VSIG Fusion Proteins and Pharmaceutical Compositions Containing for Reducing the Undesirable Immune Activation that Follows Gene or Cell Therapy or Transplant As used herein the term "gene therapy" encompasses any type of gene therapy, vector-mediated gene therapy, gene transfer, virus-mediated gene transfer.

According to at least some embodiments of the present invention, VSIG8 antibodies, a fragment, a conjugate thereof and/or a pharmaceutical compositions as described herein, which target VSIG8 and have inhibitory activity on immune responses, could be used as therapeutic agents for reducing the undesirable immune activation that follows gene therapy used for treatment of various genetic diseases. Without wishing to be limited by a single hypothesis, such antibodies have VSIG8-like inhibitory activity on immune responses and/or enhance VSIG8 immune inhibitory activity, optionally by inhibition of pathogenic T cells and/or NK cells.

Gene therapy products for the treatment of genetic diseases are currently in clinical trials. Recent studies document therapeutic success for several genetic diseases using gene therapy vectors. Gene therapy strategies are characterized by 3 critical elements, the gene to be transferred, the target tissue into which the gene will be introduced, and the vector (gene delivery vehicle) used to facilitate entry of the gene to the target tissue. The vast majority of gene therapy clinical trials have exploited viral vectors as very efficient delivery vehicles, including retroviruses, lentiviruses, adenoviruses, adeno-associated viruses, pseudotype viruses and herpes simplex viruses. However, the interactions between the human immune system and all the components of gene therapy vectors seem to represent one of the major limitations to long-lasting therapeutic efficacy. Human studies have shown that the likelihood of a host immune response to the viral vector is high. Such immune responses to the virus or the transgene product itself, resulting in formation of neutralizing antibodies and/or destruction of transduced cells by cytotoxic cells, can greatly interfere with therapeutic efficacy (Seregin and Amalfitano 2010 Viruses 2:2013; Mingozzi and High 2013 Blood 122:23; Masat et al 2013 Discov Med. 15:379). Therefore, developing strategies to circumvent immune responses and facilitate long-term expression of transgenic therapeutic proteins is one of the main challenges for the success of gene therapy in the clinic.

Factors influencing the immune response against transgenic proteins encoded by viral vectors include route of administration, vector dose, immunogenicity of the transgenic protein, inflammatory status of the host and capsid serotype. These factors are thought to influence immunogenicity by triggering innate immunity, cytokine production, APC maturation, antigen presentation and, ultimately, priming of naive T lymphocytes to functional effectors (Mingozzi and High 2013 Blood 122:23). Therefore, the idea to dampen immune activation by interfering with these very mechanisms has logically emerged with the aim to induce a short-term immunosuppression, avoid the early Immune priming that follows vector administration and promote long-term tolerance.

As a strategy to inhibit the undesirable immune activation that follows gene therapy, particularly after multiple injections, immunomodulation treatment by targeting of two non-redundant checkpoints of the immune response at the time of vector delivery was tested in animal models. Studies of vector-mediated immune responses upon adenoviral vector instilled into the lung in mice or monkeys showed that transient treatment with an anti-CD40L antibody lead to suppression of adenovirus-induced immune responses; consequently, the animals could be re-administered with adenovirus vectors. Short treatment with this Ab resulted in long-term effects on immune functions and prolonged inhibition of the adenovirus-specific humoral response well beyond the time when the Ab effects were no longer significant, pointing to the therapeutic potential in blockade of this costimulatory pathway as an immunomodulatory regimen to enable administration of gene transfer vectors (Scaria et al. 1997 *Gene Ther.* 4: 611; Chirmule et al 2000 *J. Virol.* 74: 3345). Other studies showed that co-administration of CTLA4-Ig and an anti-CD40L Ab around the time of primary vector administration decreased immune responses to the vector, prolonged long term adenovirus-mediated gene expression and enabled secondary adenovirus-mediated gene transfer even after the immunosuppressive effects of these agents were no longer present, indicating that it may be possible to obtain persistence as well as secondary adenoviral-mediated gene transfer with transient immunosuppressive therapies (Kay et al 1997 Proc. Natl. Acad. Sci. U.S.A. 94:4686). In another study, similar administration of CTLA4-Ig and an anti-CD40L Ab abrogated the formation of neutralizing Abs against the vector, and enabled gene transfer expression, provided the treatment was administered during each gene transfer injection (Lorain et al 2008 Molecular Therapy 16:541). Furthermore, administration of CTLA4-Ig to mice, even as single administration, resulted in suppression of immune responses and prolonged transgene expression at early time points (Adriouch et al 2011 *Front. Microbiol.* 2: 199). However, CTLA4-Ig alone was not sufficient to permanently wipe out the immune responses against the transgene product. Combined treatment targeting two immune checkpoints with CTLA4-Ig and PD-LI or PDL-2 resulted in synergistic improvement of transgene tolerance at later time points, by probably targeting two non-redundant mechanisms of immunomodulation, resulting in long term transgene persistence and expression (Adriouch et al 2011 *Front. Microbiol.* 2: 199).

According to at least some embodiments of the present invention, nucleic acid sequences encoding soluble VSIG8 proteins and/or a fusion protein as described herein; alone or in combination with another immunomodulatory agent or in combination with any of the strategies and approaches tested to overcome the limitation of immune responses to gene therapy, could be used for reducing the undesirable immune activation that follows gene therapy.

Current approaches include exclusion of patients with antibodies to the delivery vector, administration of high vector doses, use of empty capsids to adsorb anti-vector antibodies allowing for subsequent vector transduction, repeated plasma exchange (plasmapheresis) cycles to adsorb immunoglobulins and reduce the anti-vector antibody titer.

Novel approaches attempting to overcome these limitations can be divided into two broad categories: selective modification of the Ad vector itself and pre-emptive immune modulation of the host (Seregin and Amalfitano 2010 Viruses 2:2013). The first category comprises several innovative strategies including: (1) Ad-capsid-display of specific inhibitors or ligands; (2) covalent modifications of the entire Ad vector capsid moiety; (3) the use of tissue specific promoters and local administration routes; (4) the use of genome modified Ads; and (5) the development of chimeric or alternative serotype Ads.

The second category of methods includes the use of immunosuppressive drugs or specific compounds to block important immune pathways, which are known to be induced by viral vectors. Immunosuppressive agents have been tested in preclinical studies and shown efficacy in prevention or eradication of immune responses to the transfer vector and transgene product. These include general immunosuppressive agents such as cyclosporine A; cyclophosphamide; FK506; glucocorticoids or steroids such as dexamethasone; TLR9 blockade such as the TLR9 antagonist oligonucleotide ODN-2088; TNF-a blockade with anti-TNF-a antibodies or TNFR-Ig antibody, Erk and other signaling inhibitors such as U0126. In the clinical setting, administration of glucocorticoids has been successfully used to blunt T cell responses directed against the viral capsid upon liver gene transfer of adenovirus-associated virus (AAV) vector expressing human factor IX transgene to severe hemophilia B patients (Nathwani et al 2011 N. Engl. J. Med. 365:2357).

In contrast to the previous approaches that utilize drugs that tend to "globally" and non-specifically immunosuppress the host, more selective immunosuppressive approaches have been developed. These include the use of agents which provide blockade of positive co-stimulatory interactions, such as between CD40 and CD 154, ICOS and ICOSL, CD28 and CD80 or CD86 (including CTLA4-Ig), NKG2D and NKG2D ligands, LFA-1 and ICAM, LFA-3 and CD2, 4-IBB and 4-1BBL, OX40 and OX40L, GITR and GITRL and agents that stimulate negative costimulatory receptors such as CTLA-4, PD-1, BTLA, LAG-3, TIM-1, TEVI-3, KIRs, and the receptors for B7-H4 and B7-H3. Some of these have been utilized in preclinical or clinical transplantation studies (Pilat et al 2011 *Sem. Immunol.* 23:293).

In the above-described gene or cell therapies or in treating transplant indications preferably a subject who has or is to receive cell or gene therapy or a transplanted tissue or organ will be administered an immunoinhibitory anti-VSIG8 antibody or VSIG8 fusion proteins disclosed herein or antigen-binding fragment according to the invention, which antibody or VSIG8 fusion proteins disclosed herein enhances, agonizes or mimics at least one VSIG8 mediated effect on immunity, e.g., its inhibitory effect on cytotoxic T cells or NK activity and/or its inhibitory effect on the production of proinflammatory cytokines, or its stimulatory effect on Tregs thereby preventing or reducing host immune responses against the cell or gene used in therapy or an undesired immune response against the transplanted cells, organ or tissue. Preferably the treatment will elicit prolonged immune tolerance against the transplanted or infused cells, tissue or organ. In some instances, e.g., in the case of transplanted cells, tissues or organs containing immune cells, the immunoinhibitory anti-VSIG8 antibody or VSIG8 fusion proteins disclosed herein or antigen-binding fragment may be contacted with the cells, tissue or organ prior to infusion or transplant, and/or potentially immune cells of the transplant recipient in order to tolerize the immune cells and potentially prevent an undesired immune response or GVHD immune reaction.

Pharmaceutical Compositions

In another aspect, the present invention provides a composition, e.g., a pharmaceutical composition, containing one or a combination of the therapeutic agent, according to at least some embodiments of the invention. Thus, the present invention features a pharmaceutical composition comprising a therapeutically effective amount of a therapeutic agent according to at least some embodiments of the present invention.

The pharmaceutical composition according to at least some embodiments of the present invention is further preferably used for the treatment of cancer, wherein the cancer is non-metastatic, invasive or metastatic, and/or for treatment of immune related disorder, infectious disorder and/or sepsis, as recited herein.

"Treatment" refers to both therapeutic treatment and prophylactic or preventative measures. Those in need of treatment include those already with the disorder as well as those in which the disorder is to be prevented. Hence, the mammal to be treated herein may have been diagnosed as having the disorder or may be predisposed or susceptible to the disorder. "Mammal" for purposes of treatment refers to any animal classified as a mammal, including humans, domestic and farm animals, and zoo, sports, or pet animals, such as dogs, horses, cats, cows, etc. Preferably, the mammal is human.

The term "therapeutically effective amount" refers to an amount of agent according to the present invention that is effective to treat a disease or disorder in a mammal.

The therapeutic agents of the present invention can be provided to the subject alone or as part of a pharmaceutical composition where they are mixed with a pharmaceutically acceptable carrier.

A composition is said to be a "pharmaceutically acceptable carrier" if its administration can be tolerated by a recipient patient. As used herein, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g., by injection or infusion).

Such compositions include sterile water, buffered saline (e.g., Tris-HCl, acetate, phosphate), pH and ionic strength and optionally additives such as detergents and solubilizing agents (e.g., Polysorbate 20, Polysorbate 80), antioxidants (e.g., ascorbic acid, sodium metabisulfite), preservatives (e.g., Thimersol, benzyl alcohol) and bulking substances (e.g., lactose, mannitol). Non-aqueous solvents or vehicles may also be used as detailed below.

Examples of suitable aqueous and nonaqueous carriers that may be employed in the pharmaceutical compositions according to at least some embodiments of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants. Depending on the route of administration, the active compound, i.e., monoclonal or polyclonal antibodies and antigen-binding fragments and conjugates containing same, and/or alternative scaffolds, that specifically bind any one of VSIG8 proteins, or bispecific molecule, may be coated in a material to protect the compound from the action of acids and other natural conditions that may inactivate the compound. The pharmaceutical compounds according to at least some embodiments of the invention may include one or more pharmaceutically acceptable salts. A "pharmaceutically acceptable salt" refers to a salt that retains the desired biological activity of the parent compound and does not impart any undesired toxicological effects (see e.g., Berge, S. M., et al. (1977) J. Pharm. Sci. 66: 1-19). Examples of such salts include acid addition salts and base addition salts. Acid addition salts include those derived from nontoxic inorganic acids, such as hydrochloric, nitric, phosphoric, sulfuric, hydrobromic, hydriodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

A pharmaceutical composition according to at least some embodiments of the Invention also may include a pharmaceutically acceptable anti-oxidant. Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, a-tocopherol, and the like; and (3) metal chelating agents, such as citric acid, ethylenediamine tetraacetic acid (EDTA), sorbitol, tartaric acid, phosphoric acid, and the like.

These compositions may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions according to at least some embodiments of the invention is contemplated. Supplementary active compounds can also be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin. Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

A composition of the present invention can be administered via one or more routes of administration using one or more of a variety of methods known in the art. As will be appreciated by the skilled artisan, the route and/or mode of administration will vary depending upon the desired results. Preferred routes of administration for therapeutic agents according to at least some embodiments of the invention include intravascular delivery (e.g. injection or infusion), intravenous, intramuscular, intradermal, intraperitoneal, subcutaneous, spinal, oral, enteral, rectal, pulmonary (e.g. inhalation), nasal, topical (including transdermal, buccal and sublingual), intravesical, intravitreal, intraperitoneal, vaginal, brain delivery (e.g. intra-cerebroventricular, intracerebral, and convection enhanced diffusion), CNS delivery (e.g. intrathecal, perispinal, and intra-spinal) or parenteral (including subcutaneous, intramuscular, intravenous and intradermal), transmucosal (e.g., sublingual administration), administration or administration via an implant, or other parenteral routes of administration, for example by injection or infusion, or other delivery routes and/or forms of administration known in the art. The phrase "parenteral administration" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion. In a specific embodiment, a protein, a therapeutic agent or a pharmaceutical composition according to at least some embodiments of the present invention can be administered intraperitoneally or intravenously.

Alternatively, an VSIG8 specific antibody or VSIG8 fusion proteins disclosed herein or can be administered via a non-parenteral route, such as a topical, epidermal or mucosal route of administration, for example, intranasally, orally, vaginally, rectally, sublingually or topically.

The active compounds can be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., Sustained and Controlled Release Drug Delivery Systems, J. R. Robinson, ed., Marcel Dekker, Inc., New York, 1978.

Therapeutic compositions can be administered with medical devices known in the art. For example, in a preferred embodiment, a therapeutic composition according to at least some embodiments of the invention can be administered with a needles hypodermic injection device, such as the devices disclosed in U.S. Pat. No. 5,399,163; 5,383,851; 5,312,335; 5,064,413; 4,941,880; 4,790,824; or 4,596,556. Examples of well-known implants and modules useful in the present invention include: U.S. Pat. No. 4,487,603, which discloses an implantable micro-infusion pump for dispensing medication at a controlled rate; U.S. Pat. No. 4,486,194, which discloses a therapeutic device for administering medicaments through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. These patents are incorporated herein by reference. Many other such implants, delivery systems, and modules are known to those skilled in the art.

In certain embodiments, the anti-VSIG8 antibodies can be formulated to ensure proper distribution in vivo. For example, the blood-brain barrier (BBB) excludes many highly hydrophilic compounds. To ensure that the therapeutic compounds according to at least some embodiments of the invention cross the BBB (if desired), they can be formulated, for example, in liposomes. For methods of manufacturing liposomes, see, e.g., U.S. Pat. Nos. 4,522,811; 5,374,548; and 5,399,331. The liposomes may comprise one or more moieties which are selectively transported into specific cells or organs, thus enhance targeted drug delivery (see, e.g., V. V. Ranade (1989) *J. Clin. Pharmacol.* 29:685). Exemplary targeting moieties include folate or biotin (see, e.g., U.S. Pat. No. 5,416,016 to Low et al.); mannosides (Umezawa et al., (1988) *Biochem. Biophys. Res. Commun.* 153: 1038); antibodies (P. G. Bloeman et al. (1995) *FEBS Lett.* 357: 140; M. Owais et al. (1995) Antimicrob. Agents Chemother. 39: 180); surfactant protein A receptor (Briscoe et al. (1995) Am. J Physiol. 1233: 134); pI20 (Schreier et al. (1994) J. Biol. Chem. 269:9090); see also K. Keinanen; M. L. Laukkanen (1994) FEBS Lett. 346: 123; J. J. Killion; and I. J. Fidler (1994) *Immunomethods* 4:273.

In yet another embodiment, immunoconjugates of the invention can be used to target compounds (e.g., therapeutic agents, labels, cytotoxins, radiotoxins immunosuppressants, etc.) to cells which have VSIG8 cell surface receptors by linking such compounds to the antibody or VSIG8 fusion proteins disclosed herein. Thus, the invention also provides methods for localizing ex vivo or in vivo cells expressing VSIG8 (e.g., with a detectable label, such as a radioisotope, a fluorescent compound, an enzyme, or an enzyme co-factor). Alternatively, the immunoconjugates can be used to kill cells which have VSIG8 cell surface receptors by targeting cytotoxins or radiotoxins to VSIG8 antigen.

As used herein, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g., by injection or infusion). Depending on the route of administration, the active compound, i.e., soluble polypeptide conjugate containing the ectodomain of the VSIG8 antigen, antibody, immunoconjugate, alternative scaffolds, and/or bispecific molecule, may be coated in a material to protect the compound from the action of acids and other natural conditions that may inactivate the compound. The pharmaceutical compounds according to at least some embodiments of the present invention may include one or more pharmaceutically acceptable salts. A "pharmaceutically acceptable salt" refers to a salt that retains the desired biological activity of the parent compound and does not impart any undesired toxicological effects (see e.g., Berge, S. M., et al. (1977) J. Pharm. Sci. 66: 1-19). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

A pharmaceutical composition according to at least some embodiments of the present invention also may include a pharmaceutically acceptable anti-oxidant. Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, a-tocopherol, and the like; and (3) metal chelating agents, such as citric acid, ethylenediamine tetraacetic acid (EDTA), sorbitol, tartaric acid, phosphoric acid, and the like. Examples of suitable aqueous and nonaqueous carriers that may be employed in the pharmaceutical compositions according to at least some embodiments of the present invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions according to at least some embodiments of the present invention is contemplated. Supplementary active compounds can also be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin. Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

The amount of active ingredient which can be combined with a carrier material to produce a single dosage form will vary depending upon the subject being treated, and the particular mode of administration. The amount of active ingredient which can be combined with a carrier material to produce a single dosage form will generally be that amount of the composition which produces a therapeutic effect. Generally, out of one hundred percent, this amount will range from about 0.01 percent to about ninety-nine percent of active ingredient, preferably from about 0.1 percent to about 70 percent, most preferably from about I percent to about 30 percent of active ingredient in combination with a pharmaceutically acceptable carrier.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms according to at least some embodiments of the present invention are dictated by and directly dependent on (a) the unique characteristics of the active compound and the particular therapeutic effect to be achieved, and (b) the limitations inherent in the art of compounding such an active compound for the treatment of sensitivity in individuals.

For administration of the antibody or VSIG8 fusion proteins disclosed herein, the dosage ranges from about 0.0001 to 100 mg/kg, and more usually 0.01 to 5 mg/kg, of the host body weight. For example dosages can be 0.3 mg/kg body weight, 1 mg/kg body weight, 3 mg/kg body weight, 5 mg/kg body weight or 10 mg/kg body weight or within the range of 1-10 mg/kg. An exemplary treatment regime entails administration once per week, once every two weeks, once every three weeks, once every four weeks, once a month, once every 3 months or once every three to 6 months. Preferred dosage regimens for an antibody or VSIG8 fusion proteins disclosed herein according to at least some embodiments of the present invention include 1 mg/kg body weight or 3 mg/kg body weight via intravenous administration, with the antibody or VSIG8 fusion proteins disclosed herein being given using one of the following dosing schedules: (i) every four weeks for six dosages, then every three months; (ii) every three weeks; (iii) 3 mg/kg body weight once followed by 1 mg/kg body weight every three weeks.

In some methods, two or more monoclonal antibodies with different binding specificities are administered simultaneously, in which case the dosage of each antibody or VSIG8 fusion proteins disclosed herein administered falls within the ranges indicated. Antibody or VSIG8 fusion proteins disclosed herein is usually administered on multiple occasions. Intervals between single dosages can be, for example, daily, weekly, monthly, every three months or yearly. Intervals can also be irregular as indicated by measuring blood levels of antibody to the target antigen in the patient. In some methods, dosage is adjusted to achieve a plasma antibody concentration of about 1-1000 mug/ml and in some methods about 25-300 microgram/ml.

Alternatively, therapeutic agent can be administered as a sustained release formulation, in which case less frequent administration is required. Dosage and frequency vary depending on the half-life of the therapeutic agent in the patient. In general, human antibodies show the longest half-life, followed by humanized antibodies, chimeric antibodies, and nonhuman antibodies. The half-life for fusion proteins may vary widely. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patient can be administered a prophylactic regime.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

Embodiments of the Invention are Further Described According to the Following Clauses Clause 1. A compound which agonizes or antagonizes the interaction of VISTA and V-R (VSIG8).

Clause 2. The compound of Clause 1 which is an antibody or antibody fragment that specifically binds VSIG8.

Clause 3. The compound of Clause 1, which is an agonistic anti-VSIG8 antibody or antibody fragment.

Clause 4. The compound of Clause 1, which is an antagonistic anti-VSIG8 antibody or antibody fragment.

Clause 5. The compound of Clause 2, 3 or 4, which is a humanized, human, primatized, or chimeric anti-VSIG8 antibody or antibody fragment.

Clause 6. The antibody of Clause 5, which comprises a human IgG1, IgG2, IgG3 or IgG4 constant region or fragment thereof, which optionally is mutagenized to eliminate FcR or complement binding.

Clause 7. The antibody of Clause 5, which comprises an IgG1 or IgG3 constant region or portion thereof, which optionally is mutagenized to enhance FcR or complement binding.

Clause 8. The compound of any of the foregoing Clauses which is a Fab, Fab', scFv or Fab2.

Clause 9. The compound of Clause 1 comprising at least one copy of a polypeptide comprising the extracellular region of VSIG8, a fragment thereof that elicits a suppressive effect on T cell immunity or a derivative of said VSIG8 polypeptide that possesses at least 80, 90, 95, 96, 97, 98 or 99% sequence identity to the extracellular region of VSIG8 or to SEQ ID NO:1, 2 or 3.

Clause 10. The compound of Clause 9, which comprises at least one polypeptide comprising the entire extracellular region of human, non-human primate or murine VSIG8.

Clause 11. The compound of Clause 9 or 10 which is a fusion protein.

Clause 12. The compound of Clause 11, which is an Ig fusion protein.

Clause 13. The compound of Clause 12, which comprises a human IgG1, IgG2, IgG3 or IgG4 constant region or fragment thereof, which optionally is mutagenized to eliminate FcR or complement binding.

Clause 14. The compound of Clause 12, which comprises an IgG1 or IgG3 constant region or portion thereof, which optionally is mutagenized to enhance FcR or complement binding.

Clause 15. A compound according to any one of Clauses 1-14, which is attached to a water soluble polymer to increase serum half-life.

Clause 16. The compound of Clause 15 which is Pegylated.

Clause 17. An Isolated complex comprising VISTA and VSIG8.

Clause 18. The complex of Clause 17, wherein said VISTA and/or VSIG8 is oligomeric or multimeric.

Clause 19. The complex of Clause 17 or 18 which is comprised on a recombinant cell that expresses VISTA or VSIG8.

Clause 20. An isolated cell membrane that comprises a complex according to Clause 17, 18 or 19.

Clause 21. An antibody or antibody fragment that specifically binds to the VISTA-VSIG8 complex of Clause 17, 18 or 19.

Clause 22. The antibody or antibody fragment of Clause 21 which is human, humanized, primatized or chimeric.

Clause 23. The antibody fragment of Clause 21 or 22 which is a Fab, Fab', scFv or Fab2.

Clause 24. The agonist or antagonist compound of Clause 1, which is a small molecule.

Clause 25. An antibody or an antigen-binding fragment according to any of the foregoing Clauses which comprises a human constant region, e.g., a human IgGl, IgG2, IgG3 or IgG4 constant region or variant thereof, which optionally contains one or more domains deleted.

Clause 26. An antibody or an antigen-binding fragment thereof according to any of the foregoing Clauses which comprises a human constant region which contains at least one mutation that increases or decreases an Fc effector function and/or glycosylation and/or a mutation which modulates or abrogates IgG4 Fab arm exchange.

Clause 27. An antibody or an antigen-binding fragment thereof according to Clause 26, wherein said effector functions include FcR binding, ADCC activity, CDC activity, degranulation, phagocytosis, and cytokine release.

Clause 28. An antibody or an antigen-binding fragment thereof to any of the foregoing Clauses, which is selected from the group consisting of a Fab, Fab', F(ab')2, F(ab'), F(ab), Fv or scFv fragment and a minimal recognition unit which optionally has an in vivo half-life of at least one week, 2 weeks, 3 weeks or a month.

Clause 29. An antibody or an antigen-binding fragment thereof according to any of the above Clauses, which is coupled to another moiety, e.g., a therapeutic moiety, detectable moiety, or a moiety that alters (increases or decreases) in vivo half-life.

Clause 30. An antibody or an antigen-binding fragment thereof according to any of the above Clauses, which is coupled to a therapeutic agent selected from a drug, a radionuclide, a fluorophore, an enzyme, a toxin, or a chemotherapeutic agent; and/or a detectable marker selected from a radioisotope, a metal chelator, an enzyme, a fluorescent compound, a bioluminescent compound or a chemiluminescent compound.

Clause 31. An antibody or an antigen-binding fragment thereof or VSIG8 fusion protein according to any of the above Clauses, which is not coupled to any other moiety.

Clause 32. An antibody or an antigen-binding fragment thereof or VSIG8 fusion protein according to any of the above Clauses, wherein the antibody or antigen-binding fragment is coupled to another antibody or antigen-binding fragment or fusion protein, e.g., an NK and/or T cell receptor, e.g., an NK cell receptor that agonizes or antagonizes NK cell activity or inhibits NK cell mediated cell depletion or is one that promotes or activates NK cell mediated cell depletion.

Clause 33. An antibody or an antigen-binding fragment thereof or VSIG8 fusion protein according to 32, wherein the inhibitory NK cell receptor is selected from the group consisting of KIR2DL1, KIR2DL2/3, KIR2DL4, KIR2DL5A, KIR2DL5B, KIR3DL1, KIR3DL2, KIR3DL3, LILRB 1, NKG2A, NKG2C, NKG2E and LILRB5. And the the NK activating receptor is selected from the group consisting of NKp30, NKp44, NKp46, NKp46, NKG2D, KIR2DS4 CD2, CD16, CD69, DNAX accessory molecule-1 (DNAM-1), 2B4, NK1.1; a killer immunoglobulin (Ig)-like activating receptors (KAR); ILTs/LIRs; NKRP-1, CD69; CD94/NKG2C and CD94/NKG2E heterodimers, NKG2D homodimer KIR2DS and KIR3DS.

Clause 34. An antibody or an antigen-binding fragment according to any one of the foregoing Clauses which binds human, primate or murine VSIG8 with a binding affinity ($K_D$) no more than 500 nM as determined by any of the binding affinity methods disclosed herein, e.g., a binding affinity ($K_D$) of about $10^{-5}$, $10^{-6}$, $10^{-7}$, $10^{-8}$, $10^{-9}$, $10^{-10}$, $10^{-11}$, $10^{-12}$ M or less as determined by any of the binding affinity methods disclosed herein.

Clause 35. An antibody or an antigen-binding fragment or VSIG8 fusion protein according to any one of the foregoing Clauses wherein such antibody or antigen-binding fragment either (1) enhances, agonizes or mimics, or (2) inhibits, antagonizes or blocks at least one effect elicited by the interaction of VSIG8 and VISTA on immunity or on one or more types of immune cells.

Clause 36. An antagonistic antibody or the antigen-binding fragment or VSIG8 fusion protein of any of the above Clauses, which mediates any combination of at least one of the following immunostimulatory effects on immunity: (i) increases immune response, (ii) increases T cell activation, (iii) increases cytotoxic T cell activity, (iv) increases NK cell activity, (v) alleviates T-cell suppression, (vi) increases pro-inflammatory cytokine secretion, (vii) increases IL-2 secretion; (viii) increases interferon-γ production, (ix) increases Th1 response, (x) decrease Th2 response, (xi) decreases or eliminates cell number and/or activity of at least one of regulatory T cells (Tregs), myeloid derived suppressor cells (MDSCs), iMCs, mesenchymal stromal cells, TIE2-expressing monocytes, (xii) reduces regulatory cell activity, and/or the activity of one or more of myeloid derived suppressor cells (MDSCs), iMCs, mesenchymal stromal cells, TIE2-expressing monocytes, (xiii) decreases or eliminates M2 macrophages, (xiv) reduces M2 macrophage pro-tumorigenic activity, (xv) decreases or eliminates N2 neutrophils, (xvi) reduces N2 neutrophils pro-tumorigenic activity, (xvii) reduces inhibition of T cell activation, (xviii) reduces inhibition of CTL activation, (xix) reduces inhibition of NK cell activation, (xx) reverses T cell exhaustion, (xxi) increases T cell response, (xxii) increases activity of cytotoxic cells, (xxiii) stimulates antigen-specific memory responses, (xxiv) elicits apoptosis or lysis of cancer cells, (xxv) stimulates cytotoxic or cytostatic effect on cancer cells, (xxvi) induces direct killing of cancer cells, (xxvii) increases Thl7 activity and/or (xxviii) induces complement dependent cytotoxicity and/or antibody dependent cell-mediated cytotoxicity, with the proviso that said antibody or antigen-binding fragment may elicit an opposite effect to one or more of (i)-(xxviii).

Clause 37. An agonistic antibody or the antigen-binding fragment or VSIG8 fusion protein of any of the foregoing Clauses, which mediates any combination of at least one of the following immunoinhibitory effects: (i) decreases immune response, (ii) decreases T cell activation, (iii) decreases cytotoxic T cell activity, (iv) decreases natural killer (NK) cell activity, (v) decreases T-cell activity, (vi) decreases pro-inflammatory cytokine secretion, (vii) decreases IL-2 secretion; (viii) decreases interferon-γ production, (ix) decreases Thl response, (x) decreases Th2 response, (xi) increases cell number and/or activity of regulatory T cells, (xii) increases regulatory cell activity and/or one or more of myeloid derived suppressor cells (MDSCs), iMCs, mesenchymal stromal cells, TIE2-expressing monocytes, (xiii) increases regulatory cell activity and/or the activity of one or more of myeloid derived suppressor cells (MDSCs), iMCs, mesenchymal stromal cells, TIE2-expressing monocytes, (xiii) increases M2 macrophages, (xiv) increases M2 macrophage activity, (xv) increases N2 neutrophils, (xvi) increases N2 neutrophils activity, (xvii) increases inhibition of T cell activation, (xviii) increases inhibition of CTL activation, (xix) increases inhibition of NK cell activation, (xx) increases T cell exhaustion, (xxi) decreases T cell response, (xxii) decreases activity of cytotoxic cells, (xxiii) reduces antigen-specific memory responses, (xxiv) inhibits apoptosis or lysis of cells, (xxv) decreases cytotoxic or cytostatic effect on cells, (xxvi) reduces direct killing of cells, (xxvii) decreases Thl7 activity, and/or (xxviii) reduces complement dependent cytotoxicity and/or antibody dependent cell-mediated cytotoxicity, with the proviso that said anti-VSIG8 antibody or the antigen-binding fragment may elicit an opposite effect to one or more of (i)-(xxviii).

Clause 38. An immunomodulatory antibody or an antigen-binding fragment thereof of any of the foregoing Clauses which increases the inhibitory effect of VSIG8 and/or VISTA on T cell immunity and/or which inhibits CTL activity and/or wherein inhibited CTL activity includes reduced secretion of one or more proinflammatory cytokines and/or reduced CTL mediated killing of target cells and/or inhibition of CD4+ T cell activation and/or CD4+ T cell proliferation and/or CD4+ T cell mediated cell depletion.

Clause 39. An immunomodulatory antibody or an immunomodulatory antigen-binding fragment thereof or VSIG8 fusion protein, of any of the foregoing Clauses which inhibit NK cell activity, and/or NK cell proliferation and/or NK cell mediated cell depletion.

Clause 40. An immunomodulatory antibody or an immunomodulatory antigen-binding fragment thereof or VSIG8 fusion protein of any of the foregoing Clauses which promotes antigen-specific tolerance or prolonged suppression of an antigen-specific immune responses e.g., against transplanted cells, tissue or organ by enhancing one or more of the effects of VSIG8 and/or VISTA on immunity.

Clause 41. An immunomodulatory antibody or an immunomodulatory antigen-binding fragment thereof or VSIG8 fusion protein of any of the foregoing Clauses which promotes which inhibits an immune response against an autoantigen, allergen, or inflammatory agent by promoting one or more of the effects of VSIG8 and/or VISTA on immunity.

Clause 42. An immunomodulatory antibody or an immunomodulatory antigen-binding fragment thereof or VSIG8 fusion protein of any of the foregoing Clauses, for use in inhibiting an immune response against an autoantigen, allergen, or inflammatory agent, and/or for treating an inflammatory disease or response and/or for treating an autoimmune disease and/or for reducing or prevent transplant rejection and/or graft vs host disease.

Clause 43. A pharmaceutical composition comprising at least one compound according to any of the above Clauses.

Clause 44. A vaccine composition comprising at least one compound according to any of the above Clauses and an antigen.

Clause 45. An immunosuppressive vaccine composition comprising at least one antibody or antigen-binding fragment thereof or VSIG8 fusion protein according to any of the above Clauses, wherein said antibody or antigen-binding fragment thereof in said composition suppresses antigen-specific T and/or B cell immunity or induces tolerance.

Clause 46. The vaccine composition of Clause 45 wherein the antigen to which immunity is suppressed is a human antigen, tumor antigen, infectious agent antigen, autoantigen, or an allergen, e.g., a human antigen, cell or antigen of a cell, tissue, or organ to be transplanted into a subject, autoantigen, inflammatory agent or an allergen.

Clause 47. The composition of any one of Clauses 43-46 which is suitable for administration by a route selected from intravascular delivery (e.g. injection or infusion), intravenous, intramuscular, intradermal, intraperitoneal, subcutaneous, spinal, oral, enteral, rectal, pulmonary (e.g. inhalation), nasal, topical (including transdermal, buccal and sublingual), intravesical, intravitreal, intraperitoneal, vaginal, brain delivery (e.g. intra-cerebroventricular, intracerebral, and convection enhanced diffusion), CNS delivery (e.g. intrathecal, perispinal, and intra-spinal) or parenteral (including subcutaneous, intramuscular, intravenous and intradermal), transmucosal (e.g., sublingual administration), administration or administration via an implant, or other parenteral routes of administration, wherein "parenteral administration" refers to modes of administration other than enteral and topical administration.

Clause 48. The composition of any one of Clauses 43-47, which comprises at least one other active agent, e.g., a therapeutic or diagnostic agent, e.g., another immunomodulatory compound, a chemo therapeutic, a drug, a cytokine, a radionuclide, and an enzyme.

Clause 49. The composition of any one of Clauses 43-47, which comprises an antigen that is expressed by a target cell (e.g., a tumor or infected cell).

Clause 50. The composition of any one of Clauses 43-49, which comprises or is used with another composition containing at least one immunomodulatory agent selected from PD-1 agonists and antagonists, PD-L1 and PD-L2 antibodies and antibody fragments, TLR agonists, CD40 agonists or antagonists, CTLA-4 fusion proteins, CD28 agonists or antagonists, 4-IBB agonists or antagonists, CD27 or CD70 agonists or antagonists, LAG3 agonists or antagonists, TIM3 agonists or antagonists, TIGIT agonists or antagonists, ICOS agonists or antagonists, ICOS ligand agonists or antagonists.

Clause 51. A method of treatment and/or diagnosis, or use of a composition containing a VSIG8 or VSIG8/VISTA agonist or antagonist according to any of the foregoing Clauses for diagnostic or therapeutic use, which method or use comprises the administration to a subject in need thereof at least one dosage or composition comprising a therapeutically or diagnostically effective amount of at least one VSIG8 or VSIG8/VISTA agonist or antagonist according to any of the foregoing Clauses or composition containing according to any of the above Clauses.

Clause 52. A diagnostic method or use of an antibody or antigen-binding fragment or VSIG8 fusion protein or composition containing in detecting whether an individual has a condition associated with an increase or decrease in VSIG8 and/or VISTA-mediated effects on immunity wherein the method or use includes contacting a tissue sample from the individual with a compound, e.g., an antibody, or antigen-binding fragment or composition according to any one of the foregoing Clauses and detecting specific binding thereto.

Clause 53. The method or use of Clause 51 or 52, wherein the disease is selected from the group consisting of cancer, autoimmune disease, or infectious disease.

Clause 54. The method or use of any of Clauses 51-53 which detects the upregulation of VSIG8 or expression and/or increased number of VSIG8 expressing cells or the downregulation of VSIG8 and/or VISTA expression and/or the decreased number of VSIG8 and/or VISTA expressing cells.

Clause 55. A diagnostic method or use of an anti-VSIG8 antibody or antigen-binding fragment or composition containing which includes detecting whether an individual has a condition associated with an increase or decrease in VSIG8-mediated effects on immunity comprising contacting a tissue sample from the individual with an antibody, or antigen-binding fragment or composition according to any one of the foregoing Clauses wherein the diagnostic method is performed in vivo, comprising administering to the subject with an immunomodulatory antibody, or antigen-binding fragment or composition according to any one of the foregoing Clauses and detecting specific binding thereto.

Clause 56. The method or use of Clause 55, wherein the disease is selected from the group consisting of cancer, autoimmune disease, inflammatory condition, allergic condition or an infectious disease.

Clause 57. A diagnostic method or use which includes an anti-VSIG8 antibody or antigen-binding fragment or composition containing, and which method or use includes diagnosing a disease in a subject, wherein the disease is selected from the group consisting of cancer, autoimmune disease, or an infectious disease wherein the diagnostic method is performed ex vivo or in vivo, comprising contacting a sample from the individual or administering the individual an antibody, or antigen-binding fragment or composition according to any one of the foregoing Clauses and detecting specific binding of the immune molecule or antibody of any of the above Clauses to a tissue of the subject.

Clause 58. The diagnostic method or use of any of the foregoing Clauses, wherein the diagnostic method or use is performed before administering to the individual a therapeutically effective amount of an antibody, antigen-binding fragment, or immunomodulatory polypeptide or pharmaceutical composition containing according to any one of the foregoing Clauses.

Clause 59. The diagnostic method or use of any one of the foregoing Clauses, wherein a therapeutically effective amount of an antibody, antigen-binding fragment, or immunomodulatory polypeptide or a pharmaceutical composition containing according to any one of the foregoing Clauses is only administered if the individual has a condition characterized by increased expression of VSIG8 and/or VISTA by diseased and/or APC cells and/or increased numbers of diseased and/or APC cells which express VSIG8 and/or VISTA, e.g., on is at least 1 on a scale of 0 to 3.

Clause 60. The method or use of any of the foregoing Clauses, wherein VSIG8 expression is detected on one or more of cancer cells, immune infiltrate or stromal cells.

Clause 61. A diagnostic method or use of an anti-VSIG8 antibody or antigen-binding fragment or VSIG8 fusion protein, which method or use includes diagnosing whether a tissue sample taken from a subject exhibits an immune condition associated with increased or decreased VSIG8 expression, comprising (i) contacting the sample with a compound or composition according to any one of the foregoing Clauses, or with a nucleic acid that detects VSIG8 expression and (ii) conducting a binding or amplification assay that detects VSIG8 expression, and (iii) based thereon diagnosing whether the sample is from an individual with a condition associated with an immune condition associated with increased or decreased VSIG8 expression.

Clause 62. The method or use of Clause 61, wherein the immune condition is selected from the group consisting of cancer, autoimmune disease, inflammatory condition, an allergic condition, an infectious disease or sepsis.

Clause 63. The method or use of any of the foregoing Clauses, wherein said anti-VSIG8 antibody or antigen-binding fragment or VSIG8 fusion protein is an immuno stimulatory antibody or compound which mediates any combination of at least one of the following immunostimulatory effects on immunity: (i) increases immune response, (ii) increases T cell activation, (iii) increases cytotoxic T cell activity, (iv) increases NK cell activity, (v) alleviates T-cell suppression, (vi) increases pro-inflammatory cytokine secretion, (vii) increases IL-2 secretion; (viii) increases interferon-γ production, (ix) increases Th1 response, (x) decrease Th2 response, (xi) decreases or eliminates cell number and/or activity of at least one of regulatory T cells (Tregs), myeloid derived suppressor cells (MDSCs), iMCs, mesenchymal stromal cells, TIE2-expressing monocytes, (xii) reduces regulatory cell activity, and/or the activity of one or more of myeloid derived suppressor cells (MDSCs), iMCs, mesenchymal stromal cells, TIE2-expressing monocytes, (xiii) decreases or eliminates M2 macrophages, (xiv) reduces M2 macrophage pro-tumorigenic activity, (xv) decreases or eliminates N2 neutrophils, (xvi) reduces N2 neutrophils pro-tumorigenic activity, (xvii) reduces inhibition of T cell activation, (xviii) reduces inhibition of CTL activation, (xix) reduces inhibition of NK cell activation, (xx) reverses T cell exhaustion, (xxi) increases T cell response, (xxii) increases activity of cytotoxic cells, (xxiii) stimulates antigen-specific memory responses, (xxiv) elicits apoptosis or lysis of cancer cells, (xxv) stimulates cytotoxic or cytostatic effect on cancer cells, (xxvi) Induces direct killing of cancer cells, (xxvii) increases Th17 activity and/or (xxviii) induces complement dependent cytotoxicity and/or antibody dependent cell-mediated cytotoxicity, with the proviso that said anti-VSIG8 antibody or antigen-binding fragment may elicit an opposite effect to one or more of (i)-(xxviii).

Clause 64. A method of treatment and/or diagnosis, or use of a composition containing an anti-VSIG8 antibody or antigen-binding fragment or VSIG8 fusion protein for diagnostic or therapeutic use, which comprises promoting T cell immunity or natural killer (NK) immunity and/or suppressing Tregs or MDSC's in a subject in need thereof, which comprises administering a therapeutically or diagnostically effective amount of at least one antibody, antigen-binding fragment or a composition containing according to any of the above Clauses, wherein such antibody or antigen-binding fragment inhibits, antagonizes or blocks at least one effect of a VSIG8 polypeptide having an amino acid sequence at least 90% identical to the polypeptide of SEQ ID NO: 1, 2, or 3 on immunity or immune cells.

Clause 65. The method or use of any of the foregoing Clauses, which uses a VSIG antagonist which suppresses the inhibitory effect of VSIG8 and/or VISTA on T cell immunity.

Clause 66. The method or use of any of the foregoing Clauses, which uses a VSIG antagonist which promotes CTL activity.

Clause 67. The method or use according to Clause 66, wherein CTL activity includes the secretion of one or more proinflammatory cytokines and/or CTL mediated killing of target cells.

Clause 68. The method or use of any of the foregoing Clauses, which uses a VSIG antagonist which promotes CD4+ T cell activation and/or CD4+ T cell proliferation and/or CD4+ T cell mediated cell depletion.

Clause 69. The method or use of any of the foregoing Clauses, which uses a VSIG antagonist which promotes CD8+ T cell activation and/or CD8+ T cell proliferation and/or CD8+ T cell mediated cell depletion.

Clause 70. The method or use of any of the foregoing Clauses, which uses a VSIG antagonist which enhances NK cell activity.

Clause 71. The method or use of Clause 70, wherein enhanced NK cell activity includes increased depletion of target cells and/or proinflammatory cytokine release.

Clause 72. The method or use of any of the foregoing Clauses, which uses a VSIG antagonist which suppresses and or decreases the differentiation, proliferation and/or activity of regulatory cells, such as Tregs and/or the differentiation, proliferation, infiltration and/or activity myeloid derived suppressor cells (MDSCs).

Clause 73. The method or use of any of the foregoing Clauses, which uses a VSIG antagonist which suppresses and/or decreases the infiltration of infiltration of regulatory cells, such as Tregs and MDSCs into a target site.

Clause 74. The method or use of Clause 73, wherein said target site is a transplanted cell, tissue or organ, or an autoimmune, allergic or inflammatory site or lesion.

Clause 75. The method or use of any of the foregoing Clauses, which uses a VSIG antagonist which promotes NK-mediated cell depletion.

Clause 76. The method or use of any of the foregoing Clauses, which uses a VSIG antagonist which promotes antitumor immunity by suppressing one or more of the effects of VSIG8 and/or VISTA on immunity.

Clause 77. The method or use of any of the foregoing Clauses, which uses a VSIG antagonist, which is used in the treatment of cancer, sepsis or an infectious condition or combination thereof.

Clause 78. A method of treatment and/or diagnosis and/or diagnosis, or use of a composition containing an anti-VSIG8 antibody or antigen-binding fragment or VSIG8 fusion protein for diagnostic or therapeutic use, which comprises promoting NK or T cell immunity in a subject in need thereof, and which comprises administering a therapeutically or diagnostically effective amount of at least one antibody, antigen-binding fragment or a composition containing according to any of the foregoing Clauses, wherein such antibody or antigen-binding fragment inhibits at least one effect of a polypeptide (VSIG8) having the amino acid sequence of SEQ ID NO: 1, 2, or 3, or a polypeptide having at least 90% sequence identity therewith or to a non-human VSIG8 ortholog on immunity or immune cells or to human VISTA.

Clause 79. The method or use of any of the foregoing Clauses, wherein the treated individual suffers from an infectious disease.

Clause 80. The method or use of Clause 79, wherein the infectious disease is caused by a virus, bacterium, parasite, nematode, yeast, mycoplasm, fungus or prion.

Clause 81. The method or use of Clauses 78 or 79, wherein the infectious disease is caused by a Retroviridae (e.g., human immunodeficiency viruses, such as HIV-1 or HIV-2, acquired immune deficiency (AIDS) also referred to as HTLV-III, LAV or HTLV-III/LAV, or HIV-III; and other isolates, such as HIV-LP; Picomaviridae (e.g., polio viruses, hepatitis A virus; enteroviruses, human coxsackie viruses, rhinoviruses, echoviruses); Calciviridae (e.g., strains that cause gastroenteritis); Togaviridae (e.g., equine encephalitis viruses, rubella viruses); Flaviridae (e.g., dengue viruses, encephalitis viruses, yellow fever viruses); Coronaviridae (e.g., coronaviruses); Rhabdoviridae (e.g., vesicular stomatitis viruses, rabies viruses); Filoviridae (e.g., ebola viruses); Paramyxoviridae (e.g., parainfluenza viruses, mumps virus, measles virus, respiratory syncytial virus); Orthomyxoviridae (e.g., influenza viruses); Bungaviridae (e.g., Hantaan viruses, bunga viruses, phleboviruses and Nairo viruses); Arena viridae (hemorrhagic fever virus); Reoviridae (e.g., reoviruses, orbiviruses and rotaviruses); Birnaviridae; Hepadnaviridae (Hepatitis B virus); Parvoviridae (parvoviruses); Papovaviridae (papilloma viruses, polyoma viruses); Adenoviridae (most adenoviruses); Herperviridae (herpes simplex virus (HSV) 1 and 2, varicella zoster virus, cytomegalovirus (CMV), herpes viruses); Poxviridae (variola virsues, vaccinia viruses, pox viruses); and Iridoviridae (e.g., African swine fever virus); an unclassified virus (e.g., the etiological agents of Spongiform encephalopathies, the agent of delta hepatitides, the agents of non-A, non-B hepatitis (class 1—internally transmitted; class 2—parenterally transmitted (i.e., Hepatitis C); Norwalk and related viruses, and astroviruses) as well as Severe acute respiratory syndrome virus and respiratory syncytial virus (RSV), West Nile encephalitis, coronavirus infection, rhinovirus infection, Influenza, dengue, hemorrhagic fever; an otological infection; severe acute respiratory syndrome (SARS), acute febrile pharyngitis, pharyngoconjunctival fever, epidemic keratoconjunctivitis, infantile gastroenteritis, infectious mononucleosis, Burkitt lymphoma, acute hepatitis, chronic hepatitis, hepatic cirrhosis, hepatocellular carcinoma, primary HSV-1 infection, (gingivostomatitis in children, tonsillitis & pharyngitis in adults, keratoconjunctivitis), latent HSV-1 infection (herpes labialis, cold sores), aseptic meningitis, Cytomegalovirus infection, Cytomegalic inclusion disease, Kaposi sarcoma, Castleman disease, primary effusion lymphoma, influenza, measles, encephalitis, postinfectious encephalomyelitis, Mumps, hyperplastic epithelial lesions (common, flat, plantar and anogenital warts, laryngeal papillomas, epidermodysplasia verruciformis), croup, pneumonia, bronchiolitis, Poliomyelitis, Rabies, bronchiolitis, pneumonia, German measles, congenital rubella, Hemorrhagic Fever, Chickenpox, Dengue, Ebola infection, Echovirus infection, EBV infection, Fifth Disease, Filovirus, Flavivirus, Hand, foot & mouth disease, Herpes Zoster Virus (Shingles), Human Papilloma Virus Associated Epidermal Lesions, Lassa Fever, Lymphocytic choriomeningitis, Parainfluenza Virus Infection, Paramyxovirus, Parvovirus B19 Infection, Picornavirus, Poxviruses infection, Rotavirus diarrhea, Rubella, Rubeola, Varicella, Variola infection.

Clause 82. The method or use of Clauses 79 or 80, wherein the infectious disease is a parasite infection caused by a parasite selected from a protozoa, such as Amebae, *Flagellates, Plasmodium falciparum, Toxoplasma gondii*, Ciliates, Coccidia, Micro sporidia, Sporozoa; helminthes, Nematodes (Roundworms), Cestodes (Tapeworms), Trematodes (Flukes), Arthropods, and aberrant proteins known as prions.

Clause 83. The method or use of Clauses 79 or 80, wherein the infectious disease is an infectious disorder and/or disease caused by bacteria selected from the group consisting of Sepsis, septic shock, sinusitis, skin infections, pneumonia, bronchitis, meningitis, Bacterial vaginosis, Urinary tract infection (UCI), Bacterial gastroenteritis, Impetigo and erysipelas, Erysipelas, Cellulitis, anthrax, whooping cough, lyme disease, Brucellosis, enteritis, acute enteritis, Tetanus, diphtheria, Pseudomembranous colitis, Gas gangrene, Acute food poisoning, Anaerobic cellulitis, Nosocomial infections, Diarrhea, Meningitis in infants, Traveller's diarrhea, Hemorrhagic colitis, Hemolytic-uremic syndrome, Tularemia, Peptic ulcer, Gastric and Duodenal ulcers, Legionnaire's Disease, Pontiac fever, Leptospirosis, Listeriosis, Leprosy (Hansen's disease), Tuberculosis, Gonorrhea, Ophthalmia neonatorum, Septic arthritis, Meningococcal disease including meningitis, Waterhouse-Friderichsen syndrome, *Pseudomonas* infection, Rocky mountain spotted fever, Typhoid fever type *salmonellosis, Salmonellosis* with gastroenteritis and enterocolitis, Bacillary dysentery/Shigellosis, Coagulase-positive staphylococcal infections: Localized skin infections including Diffuse skin infection (Impetigo), Deep localized infections, Acute infective endocarditis, Septicemia, Necrotizing pneumonia, Toxinoses such as Toxic shock syndrome and Staphylococcal food poisoning, Cystitis, Endometritis, Otitis media, Streptococcal pharyngitis, Scarlet fever, Rheumatic fever, Puerperal fever, Necrotizing fasciitis, Cholera, Plague (including Bubonic plague and Pneumonic plague), as well as any infection caused by a bacteria selected from but not limited to *Helicobacter pyloris, Boreliai burgdorferi, Legionella pneumophila, Mycobacteria* sps (e.g., *M. tuberculosis, M. avium, M. intracellulare, M. kansaii, M gordonae*), *Staphylococcus aureus, Neisseria gonorrhoeae, Neisseria meningitidis, Listeria monocytogenes, Streptococcus pyogenes* (Group A *Streptococcus*), *Streptococcus agalactiae* (Group B *Streptococcus*), *Streptococcus* (viridans group), *Streptococcus faecalis, Streptococcus bovis, Streptococcus* (anaerobic sps.), *Streptococcus pneumoniae*, pathogenic *Campylobacter* sp., *Enterococcus* sp., *Haemophilus influenzae, Bacillus anthracis, Corynebacterium diphtheriae, Corynebacterium* sp., *Erysipelothrix rhusiopathiae, Clostridium perfringens, Clostridium tetani, Enterobacter aerogenes, Klebsiella pneumoniae, Pasteurella multocida, Bacteroides* sp., *Fusobacterium nucleatum, Streptobacillus moniliformis, Treponema pallidum, Treponema pertenue, Leptospira*, and *Actinomyces israelii.*

Clause 84. The method or use of Clauses 79 or 80, wherein the infectious disease is an infectious disorder and/or disease caused by fungi selected from Allergic bronchopulmonary aspergillosis, Aspergilloma, Aspergillosis, Basidiobolomycosis, Blastomycosis, Candidiasis, Chronic pulmonary aspergillosis, Chytridiomycosis, Coccidioidomycosis, Conidiobolomycosis, Covered smut (barley), Cryptococcosis, Dermatophyte, Dermatophytid, Dermatophytosis, Endothrix, Entomopathogenic fungus, Epizootic lymphangitis, Epizootic ulcerative syndrome, Esophageal candidiasis, Exothrix, Fungemia, Histoplasmosis, Lobomycosis, Massospora cicadina, Mycosis, *Mycosphaerella fraganae*, Myringomycosis, Paracoccidioidomycosis, Pathogenic fungi, Penicilliosis, Thousand cankers disease, Tinea, Zeaspora, Zygomycosis; a parasite selected from the group consisting of but not limited to *Acanthamoeba*, Amoebiasis, Ascariasis, Ancylostomiasis, Anisakiasis, Babesiosis, Balantidiasis, Baylisascariasis, Blastocystosis, Candiru, Chagas disease, Clonorchiasis, *Cochliomyia*, Coccidia, Chinese Liver Fluke Cryptosporidiosis, Dientamoebiasis, Diphyllobothriasis, *Dioctophyme renalis* infection, Dracunculiasis, Echinococcosis, Elephantiasis, Enterobiasis, Fascioliasis, Fasciolopsiasis, Filariasis, Giardiasis, Gnathostomiasis, Hymenolepiasis, Halzoun Syndrome, Isosporiasis, Katayama fever, Leishmaniasis, lymphatic filariasis, Malaria, Metagonimiasis, Myiasis, Onchocerciasis, Pediculosis, Primary amoebic meningoencephalitis, Parasitic pneumonia, Paragonimiasis, Scabies, Schistosomiasis, Sleeping sickness, Strongyloidiasis, Sparganosis, Rhinosporidiosis, River blindness, Taeniasis (cause of Cysticercosis), Toxocarlasis, Toxoplasmosis, Trichinosis, Trichomoniasis, Trichuriasis, Trypanosomiasis, Tapeworm infection, *Cryptococcus neoformans, Histoplasma capsulatum, Coccidioides immitis, Blastomyces dermatitidis, Chlamydia trachomatis, Candida albicans.*

Clause 85. The method or use of any of Clauses 79-84, wherein the infectious disease is caused by any of hepatitis B, hepatitis C, infectious mononucleosis, EBV, cytomegalovirus, AIDS, HIV-1, HIV-2, tuberculosis, malaria and schistosomiasis.

Clause 86. An anti-VSIG8 antibody or antigen-binding fragment or composition, or method or use according to any of the foregoing Clauses which includes another therapeutic agent useful for treating bacterial infection, viral infection, fungal infection, parasitic infection or sepsis.

Clause 87. The method, composition, antibody or fragment or VSIG8 fusion protein, or use of any of the foregoing Clauses which promotes an immune response against an infectious agent by suppressing one or more of the effects of VSIG8 and/or VISTA on immunity.

Clause 88. The method, composition, antibody or fragment or VSIG8 fusion protein, or use of any of the foregoing Clauses further comprising one or more additional therapeutic agents used for treatment of bacterial infections.

Clause 89. The method, composition, antibody or fragment, or use of Clause 88, wherein said agent is selected from the group consisting of antibiotics including Aminoglycosides, Carbapenems, Cephalosporins, Macrolides, Lincosamides, Nitrofurans, penicillins, Polypeptides, Quinolones, Sulfonamides, Tetracyclines, drugs against mycobacteria including but not limited to Clofazimine, Cycloserine, Cycloserine, Rifabutin, Rifapentine, Streptomycin and other antibacterial drugs such as Chloramphenicol, Fosfomycin, Metronidazole, Mupirocin, and Tinidazole, or a combination thereof.

Clause 90. The method, composition, antibody or fragment or VSIG8 fusion protein, or use of any of the foregoing Clauses further comprising one or more additional therapeutic agents used for treatment of viral infections.

Clause 91. The method, composition, antibody or fragment or VSIG8 fusion protein, or use of Clause 90, wherein said agent is selected from the group consisting of antiviral drugs such as oseltamivir (brand name Tamiflu®) and zanamivir (brand name Relenza®) Arbidol®—adamantane derivatives (Amantadine®, Rimantadine®)—neuraminidase inhibitors (Oseltamivir®, Laninamivir®, Peramivir®, Zanamivir®) nucleotide analog reverse transcriptase inhibitor including Purine analogue guanine (Aciclovir®/Valacyclovir®, Ganciclovir®/Valganciclovir®, Penciclovir®/Famciclovir®) and adenine (Vidarabine®), Pyrimidine analogue, uridine (Idoxuridine®, Trifluridine®, Edoxudine®), thymine (Brivudine®), cytosine (Cytarabine®); Foscarnet; Nucleoside analogues/NARTIs: Entecavir, Lamivudine®, Telbivudine®, Clevudine®; Nucleotide analogues/NtRTIs: Adefovir®, Tenofovir; Nucleic acid inhibitors such as Cidofovir®; Interferoninterferon alfa-2b, Peginterferon a-2a; Ribavirin®/Taribavirin®; antiretroviral drugs including zidovudine, lamivudine, abacavir, lopinavir, ritonavir, tenofovir/emtricitabine, efavirenz each of them alone or a various combinations, gp41 (Enfuvirtide), Raltegravir®, protease inhibitors such as Fosamprenavir®, Lopinavir® and Atazanavir®, Methisazone®, Docosanol®, Fomivirsen®, and Tromantadine®.

Clause 92. The method, composition, antibody or fragment or VSIG8 fusion protein, or use of any of the foregoing Clauses further comprising one or more additional therapeutic agents used for treatment of fungal infections.

Clause 93. The method, composition, antibody or fragment or VSIG8 fusion protein, or use of Clause 92, selected from the group consisting of antifungal drugs of the Polyene antifungals, Imidazole, triazole, and thiazole antifungals, Allylamines, Echinocandins or other anti-fungal drugs.

Clause 94. The method or use of any of the foregoing Clauses, wherein the treated individual suffers from cancer.

Clause 95. The method or use of Clause 94, wherein the cancer is selected from the group consisting of breast cancer, cervical cancer, ovary cancer, endometrial cancer, melanoma, uveal melanoma, bladder cancer, lung cancer, pancreatic cancer, colorectal cancer, prostate cancer, leukemia, acute lymphocytic leukemia, chronic lymphocytic leukemia, B-cell lymphoma, Burkitt's lymphoma, multiple myeloma, Non-Hodgkin's lymphoma, myeloid leukemia, acute myelogenous leukemia (AML), chronic myelogenous leukemia, thyroid cancer, thyroid follicular cancer, myelodysplastic syndrome (MDS), fibrosarcomas and rhabdomyosarcomas, teratocarcinoma, neuroblastoma, glioma, glioblastoma, benign tumor of the skin, keratoacanthomas, renal cancer, anaplastic large-cell lymphoma, esophageal cancer, follicular dendritic cell carcinoma, seminal vesicle tumor, epidermal carcinoma, spleen cancer, bladder cancer, head and neck cancer, stomach cancer, liver cancer, bone cancer, brain cancer, cancer of the retina, biliary cancer, small bowel cancer, salivary gland cancer, cancer of uterus, cancer of testicles, cancer of connective tissue, myelodysplasia, Waldenstrom's macroglobinaemia, nasopharyngeal, neuroendocrine cancer, mesothelioma, angiosarcoma, Kaposi's sarcoma, carcinoid, fallopian tube cancer, peritoneal cancer, papillary serous miillerian cancer, malignant ascites, gastrointestinal stromal tumor (GIST), Li-Fraumeni syndrome and Von Hippel-Lindau syndrome (VHL), cancer of unknown origin either primary or metastatic, wherein the cancer is non-metastatic, invasive or metastatic.

Clause 96. The method or use of Clause 94, wherein the cancer is selected from B-cell lymphoma, Burkitt's lymphoma, thyroid cancer, thyroid follicular cancer, myelodysplastic syndrome (MDS), fibrosarcomas and rhabdomyosarcomas, melanoma, uveal melanoma, teratocarcinoma, neuroblastoma, glioma, glioblastoma cancer, keratoacanthomas, anaplastic large-cell lymphoma, esophageal squamous cells carcinoma, hepatocellular carcinoma cancer, follicular dendritic cell carcinoma, muscle-invasive cancer, seminal vesicle tumor, epidermal carcinoma, cancer of the retina, biliary cancer, small bowel cancer, salivary gland cancer, cancer of connective tissue, myelodysplasia, Waldenstrom's macroglobinaemia, nasopharyngeal, neuroendocrine cancer, myelodysplastic syndrome, mesothelioma, angiosarcoma, Kaposi's sarcoma, carcinoid, esophagogastric, fallopian tube cancer, peritoneal cancer, papillary serous mullerian cancer, malignant ascites, gastrointestinal stromal tumor (GIST), Li-Fraumeni syndrome and Von Hippel-Lindau syndrome (VHL); endometrial cancer, Breast carcinoma, preferably any of ductal-carcinoma, infiltrating ductal carcinoma, lobular carcinoma, mucinous adenocarcinoma, intra duct and invasive ductal carcinoma, and Scirrhous adenocarcinoma, Colorectal adenocarcinoma, preferably any of Poorly to Well Differentiated invasive and noninvasive Adenocarcinoma, Poorly to Well Differentiated Adenocarcinoma of the cecum, Well to Poorly Differentiated Adenocarcinoma of the colon, Tubular adenocarcinoma, preferably Grade 2 Tubular adenocarcinoma of the ascending colon, colon adenocarcinoma Duke's stage CI, invasive adenocarcinoma, Adenocarcinoma of the rectum, preferably Grade 3 Adenocarcinoma of the rectum, Moderately Differentiated Adenocarcinoma of the rectum, Moderately Differentiated Mucinous adenocarcinoma of the rectum; Lung cancer, preferably any of Well to Poorly differentiated Non-small cell carcinoma, Squamous Cell Carcinoma, preferably well to poorly Differentiated Squamous Cell Carcinoma, keratinizing squamous cell carcinoma, adenocarcinoma, preferably poorly to well differentiated adenocarcinoma, large cell adenocarcinoma, Small cell lung cancer, preferably Small cell lung carcinoma, more preferably undifferentiated Small cell lung carcinoma; Prostate adenocarcinoma, preferably any of Adenocarcinoma Gleason Grade 6 to 9, Infiltrating adenocarcinoma, High grade prostatic intraepithelial neoplasia, undifferentiated carcinoma; Stomach adenocarcinoma, preferably moderately differentiated gastric adenocarcinoma; Ovary carcinoma, preferably any of cystadenocarcinoma, serous papillary cystic carcinoma, Serous papillary cystic carcinoma, Invasive serous papillary carcinoma; Brain cancer, preferably any of Astrocytoma, with the proviso that it is not a grade 2 astrocytoma, preferably grade 4 Astrocytoma, Glioblastoma multiforme; Kidney carcinoma, preferably Clear cell renal cell carcinoma; Liver cancer, preferably any of Hepatocellular carcinoma, preferably Low Grade hepatocellular carcinoma, Fibrolamellar Hepatocellular Carcinoma; Lymphoma, preferably any of, Hodgkin's Lymphoma and High to low grade Non-Hodgkin's Lymphoma and with the proviso that if the cancer is brain cancer, it is not Astrocytoma grade 2, and if the cancer is Non-Hodgkin's Lymphoma, it is not a large cell Non-Hodgkin's Lymphoma, and wherein the cancer is non-metastatic, invasive or metastatic.

Clause 97. The method or use of any of the foregoing Clauses wherein the levels of VSIG8 and/or VISTA protein are elevated compared to normal cell samples.

Clause 98. The method or use of Clause any one the foregoing Clauses, wherein the treated individual suffers from a cancer wherein the cancer or other cells contained at the tumor sites do not express VSIG8 and/or VISTA protein or do not express VSIG8 and/or protein at levels higher than normal.

Clause 99. The method or use of any one of the foregoing Clauses, wherein the treated subject suffers from a cancer wherein the diseased cells, APC's, hematopoietic cells, NK cells, monocytes, dendritic cells, neutrophils, monocytes, or other immune cells at the disease site, e.g., myeloid suppressor cells express VSIG8 and/or VISTA protein.

Clause 100. An anti-VSIG8 antibody or antigen-binding fragment or VSIG8 fusion protein or composition, or method or use according to any of the foregoing Clauses which includes treatment with an anti-VSIG8 antibody or antigen-binding fragment or composition containing and the therapy comprises one or more of radiotherapy, cryotherapy, antibody therapy, chemotherapy, photodynamic therapy, surgery, hormonal deprivation or combination therapy with conventional drugs.

Clause 101. An anti-VSIG8 antibody or antigen-binding fragment or composition, or method or use according to any of the foregoing Clauses which includes treatment with an anti-VSIG8 antibody or antigen-binding fragment or VSIG8 fusion protein or composition containing and another therapeutic agent selected from the group consisting of cytotoxic drugs, tumor vaccines, antibodies, peptides, pepti-bodies, small molecules, chemotherapeutic agents, cytotoxic and cytostatic agents, immunological modifiers, interferons, interleukins, immuno stimulatory growth hormones, cytokines, vitamins, minerals, aromatase inhibitors, RNAi, Histone Deacetylase Inhibitors, and proteasome inhibitors.

Clause 102. An anti-VSIG8 antibody or antigen-binding fragment or VSIG8 fusion protein or composition, or method or use according to any of the foregoing Clauses which includes treatment with an anti-VSIG8 antibody or antigen-binding fragment or composition containing and another therapeutic or an imaging agent administered to a subject simultaneously or sequentially in combination with one or more potentiating agents to obtain a therapeutic effect, wherein said one or more potentiating agents is selected from the group consisting of radiotherapy, conventional/classical anti-cancer therapy potentiating anti-tumor immune responses, Targeted therapy potentiating anti-tumor immune responses, Therapeutic agents targeting immunosuppressive cells Tregs and/or MDSCs, Immuno stimulatory antibodies, Cytokine therapy, Adoptive cell transfer.

Clause 103. An anti-VSIG8 antibody or antigen-binding fragment or VSIG8 fusion protein or composition, or method or use according to any of the foregoing Clauses, wherein the conventional/classical anti-cancer agent is selected from platinum based compounds, antibiotics with anti-cancer activity, Anthracyclines, Anthracenediones, alkylating agents, antimetabolites, Antimitotic agents, Taxanes, Taxoids, microtubule inhibitors, *Vinca* alkaloids, Folate antagonists, Topoisomerase inhibitors, Antiestrogens, Antiandrogens, Aromatase inhibitors, GnRh analogs, inhibitors of 5a-reductase, biphosphonates.

Clause 104. An anti-VSIG8 antibody or antigen-binding fragment or composition, or method or use according to any of the foregoing Clauses or VSIG8 fusion protein further comprising Platinum based compounds such as oxaliplatin, cisplatin, carboplatin; Antibiotics with anti-cancer activity, such as dactinomycin, bleomycin, mitomycin-C, mithramycin and Anthracyclines, such as doxorubicin, daunorubicin, epirubicin, idarubicin; Anthracenediones, such as mitoxantrone; Alkylating agents, such as dacarbazine, melphalan, cyclophosphamide, temozolomide, chlorambucil, busulphan, nitrogen mustard, nitrosoureas; Antimetabolites, such as fluorouracil, raltitrexed, gemcitabine, cytosine arabinoside, hydroxyurea and Folate antagonists, such as methotrexate, trimethoprim, pyrimethamine, pemetrexed; Antimitotic agents such as polokinase inhibitors and Microtubule inhibitors, such as Taxanes and Taxoids, such as paclitaxel, docetaxel; *Vinca* alkaloids such as vincristine, vinblastine, vindesine, vinorelbine; Topoisomerase inhibitors, such as etoposide, teniposide, amsacrine, topotecan, irinotecan, camptothecin; Cytostatic agents including Antiestrogens such as tamoxifen, fulvestrant, toremifene, raloxifene, droloxifene, iodoxyfene, Antiandrogens such as bicalutamide, flutamide, nilutamide and cyproterone acetate, Progestogens such as megestrol acetate, Aromatase inhibitors such as anastrozole, letrozole, vorozole, exemestane; GnRH analogs, such as leuprorelin, goserelin, buserelin, degarelix; inhibitors of 5a-reductase such as finasteride.

Clause 105. An anti-VSIG8 antibody or antigen-binding fragment or VSIG8 fusion protein or composition, or method or use according to any of the foregoing Clauses, further comprising a Platinum based compound.

Clause 106. An anti-VSIG8 antibody or antigen-binding fragment or VSIG8 fusion protein or composition, or method or use according to any of the foregoing Clauses, further comprising a targeted therapy selected from the group consisting of but not limited to: histone deacetylase (HDAC) inhibitors, such as vorinostat, romidepsin, panobinostat, belinostat, mocetinostat, abexinostat, entinostat, resminostat, givinostat, quisinostat, sodium butyrate; Proteasome inhibitors, such as bortezomib, carfilzomib, disulfiram; mTOR pathway inhibitors, such as temsirolimus, rapamycin, everolimus; PI3K inhibitors, such as perifosine, CAL101, PX-866, IPI-145, BAY 80-6946; B-raf inhibitors such as vemurafenib, sorafenib; JAK2 Inhibitors, such as lestaurtinib, pacritinib; Tyrosine kinase inhibitors (TKIs), such as erlotinib, imatinib, sunitinib, lapatinib, gefitinib, sorafenib, nilotinib, toceranib, bosutinib, neratinib, vatalanib, regorafenib, cabozantinib; other Protein kinase inhibitors, such as crizotinib; Inhibitors of serine/threonine kinases for example Ras/Raf signalling inhibitors such as farnesyl transferase inhibitors; Inhibitors of serine proteases for example matriptase, hepsin, urokinase; Inhibitors of intracellular signaling such as tipifarnib, perifosine; Inhibitors of cell signalling through MEK and/or AKT kinases; aurora kinase inhibitors such as AZD1152, PH739358, VX-680, MLN8054, R763, MP235, MP529, VX-528, AX39459; Cyclin dependent kinase inhibitors such as CDK2 and/or CDK4 inhibitors; Inhibitors of survival signaling proteins including Bcl-2, Bcl-XL, such as ABT-737; HSP90 inhibitors; Therapeutic monoclonal antibodies, such as anti-EGFR mAbs cetuximab, panitumumab, nimotuzumab, anti-ERBB2 mAbs trastuzumab, pertuzumab, anti-CD20 mAbs such as rituximab, ofatumumab, veltuzumab and mAbs targeting other tumor antigens such as alemtuzumab, labetuzumab, adecatumumab, oregovomab, onartuzumab; TRAIL pathway agonists, such as dulanermin (soluble rhTRAIL), apomab, mapatumumab, lexatumumab, conatumumab, tigatuzumab; Antibody fragments, bi-specific antibodies and bi-specific T-cell engagers (BiTEs), such as catumaxomab, blinatumomab; Antibody drug conjugates (ADC) and other immunoconjugates, such as ibritumomab triuxetan, tositumomab, brentuximab vedotin, gemtuzumab ozogamicin, clivatuzumab tetraxetan, pemtumomab, trastuzumab emtansine; Anti-angiogenic therapy such as bevacizumab, etaracizumab, volociximab, ramucirumab, aflibercept, sorafenib, sunitinib, regorafenib, axitinib, nintedanib, motesanib, pazopanib, cediranib; Metalloproteinase inhibitors such as marimastat; Inhibitors of urokinase plasminogen activator receptor function; Inhibitors of cathepsin activity.

Clause 107. An anti-VSIG8 antibody or antigen-binding fragment or VSIG8 fusion protein or composition, or method or use according to Clause 106, the another therapeutic agent is another antibody selected from cetuximab, panitumumab, nimotuzumab, trastuzumab, pertuzumab, rituximab, ofatumumab, veltuzumab, alemtuzumab, labetuzumab, adecatumumab, oregovomab, onartuzumab; apomab, mapatumumab, lexatumumab, conatumumab, tigatuzumab, catumaxomab, blinatumomab, ibritumomab triuxetan, tositumomab, brentuximab vedotin, gemtuzumab ozogamicin, clivatuzumab tetraxetan, pemtumomab, trastuzumab emtansine, bevacizumab, etaracizumab, volociximab, ramucirumab, aflibercept.

Clause 108. An anti-VSIG8 antibody or antigen-binding fragment or VSIG8 fusion protein or composition, or method or use according to any of the foregoing Clauses, further comprising a Therapeutic cancer vaccine selected from exogenous cancer vaccines including proteins or peptides used to mount an immunogenic response to a tumor antigen, recombinant virus and bacteria vectors encoding tumor antigens, DNA-based vaccines encoding tumor antigens, proteins targeted to dendritic cell-based vaccines, whole tumor cell vaccines, gene modified tumor cells expressing GM-CSF, ICOS and/or Flt3-ligand, oncolytic virus vaccines.

Clause 109. An anti-VSIG8 antibody or antigen-binding fragment or VSIG8 fusion protein or composition, or method or use according to any of the foregoing Clauses, further comprising a Cytokine therapy selected from one or more of the following cytokines such as IL-2, IL-7, IL-12, IL-15, IL-17, IL-18 and IL-21, IL-23, IL-27, GM-CSF, IFNa (interferon α), IFNa-2b, IFN β, IFNγ, and their different strategies for delivery.

Clause 110. An anti-VSIG8 antibody or antigen-binding fragment or VSIG8 fusion protein or composition, or method or use according to any of the foregoing Clauses, further comprising adoptive cell transfer therapy which is carried out following ex vivo treatment selected from expansion of the patient autologous naturally occurring tumor specific T cells or genetic modification of T cells to confer specificity for tumor antigens.

Clause 111. The method or use of any of the foregoing Clauses, wherein said anti-VSIG8 antibody or antigen-binding fragment comprises an immunoinhibitory antibody or an antigen-binding fragment which mediates any combination of at least one of the following immunoinhibitory effects: (i) decreases immune response, (ii) decreases T cell activation, (iii) decreases cytotoxic T cell activity, (iv) decreases natural killer (NK) cell activity, (v) decreases T-cell activity, (vi) decreases pro-inflammatory cytokine secretion, (vii) decreases IL-2 secretion; (viii) decreases interferon-γ production, (ix) decreases Thl response, (x) decreases Th2 response, (xi) increases cell number and/or activity of regulatory T cells, (xii) increases regulatory cell activity and/or one or more of myeloid derived suppressor cells (MDSCs), iMCs, mesenchymal stromal cells, TIE2-expressing monocytes, (xiii) increases regulatory cell activity and/or the activity of one or more of myeloid derived suppressor cells (MDSCs), iMCs, mesenchymal stromal cells, TIE2-expressing monocytes, (xiii) increases M2 macrophages, (xiv) increases M2 macrophage activity, (xv) increases N2 neutrophils, (xvi) increases N2 neutrophils activity, (xvii) increases inhibition of T cell activation, (xviii) increases inhibition of CTL activation, (xix) increases inhibition of NK cell activation, (xx) increases T cell exhaustion, (xxi) decreases T cell response, (xxii) decreases activity of cytotoxic cells, (xxiii) reduces antigen-specific memory responses, (xxiv) inhibits apoptosis or lysis of cells, (xxv) decreases cytotoxic or cytostatic effect on cells, (xxvi) reduces direct killing of cells, (xxvii) decreases Thl7 activity, and/or (xxviii) reduces complement dependent cytotoxicity and/or antibody dependent cell-mediated cytotoxicity, with the proviso that said anti-VSIG8 antibody or antigen-binding fragment may elicit an opposite effect to one or more of (i)-(xxviii).

Clause 112. A method of treatment and/or diagnosis, or use of a composition containing an anti-VSIG8 antibody or antigen-binding fragment f or VSIG8 fusion protein or diagnostic or therapeutic use, which comprises suppressing T cell immunity or natural killer (NK) immunity and/or promoting Tregs or MDSC's in a subject in need thereof, which comprises administering a therapeutically or diagnostically effective amount of at least one antibody, antigen-binding fragment or a composition containing according to any one of the above Clauses, wherein such antibody or antigen-binding fragment agonizes, mimics or promotes at least one effect of a polypeptide (VSIG8) having the amino acid sequence of SEQ ID NO: 1, 2 or 3 or an ortholog on immunity or immune cells.

Clause 113. The method or use of Clauses 111 or 112, which is used in the treatment of allergy, autoimmunity, transplant, gene therapy, inflammation or combination thereof.

Clause 114. A method or use according to any one of the foregoing Clauses wherein the treated individual has or is to receive cell therapy, gene therapy or a transplanted tissue or organ, and the treatment reduces or inhibits the undesirable immune activation that is associated with such cell therapy, gene therapy or a transplanted tissue or organ.

Clause 115. The method or use of any one of the foregoing Clauses, wherein the antibody, or antigen-binding fragment thereof or VSIG8 fusion protein is an immunoinhibitory antibody or fragment which effects one or more of the following: (i) decreases immune response, (ii) decreases T cell activation, (iii) decreases cytotoxic T cell activity, (iv) decreases natural killer (NK) cell activity, (v) decreases T-cell activity, (vi) decreases pro-inflammatory cytokine secretion, (vii) decreases IL-2 secretion; (viii) decreases interferon-γ production, (ix) decreases Thl response, (x) decreases Th2 response, (xi) Increases cell number and/or activity of regulatory T cells, (xii) increases regulatory cell activity and/or one or more of myeloid derived suppressor cells (MDSCs), iMCs, mesenchymal stromal cells, TIE2-expressing monocytes, (xiii) increases regulatory cell activity and/or the activity of one or more of myeloid derived suppressor cells (MDSCs), iMCs, mesenchymal stromal cells, TIE2-expressing monocytes, (xiii) increases M2 macrophages, (xiv) increases M2 macrophage activity, (xv) increases N2 neutrophils, (xvi) increases N2 neutrophils activity, (xvii) increases inhibition of T cell activation, (xviii) increases inhibition of CTL activation, (xix) increases inhibition of NK cell activation, (xx) increases T cell exhaustion, (xxi) decreases T cell response, (xxii) decreases activity of cytotoxic cells, (xxiii) reduces antigen-specific memory responses, (xxiv) inhibits apoptosis or lysis of cells, (xxv) decreases cytotoxic or cytostatic effect on cells, (xxvi) reduces direct killing of cells, (xxvii) decreases Thl7 activity, and/or (xxviii) reduces complement dependent cytotoxicity and/or antibody dependent cell-mediated cytotoxicity, with the proviso that said anti-VSIG8 antibody or antigen-binding fragment may elicit an opposite effect to one or more of (i)-(xxviii).

Clause 116. The method or use of any one of the foregoing Clauses, which enhances, agonizes or mimics at least one effect of VSIG8 and/or VISTA on T or natural killer (NK) cell immunity.

Clause 117. The method or use of any one of the foregoing Clauses which increases the inhibitory effect of VSIG8 and/or VISTA on T cell immunity.

Clause 118. The method or use of any one of the foregoing Clauses which inhibits CTL activity.

Clause 119. The method or use of Clause 118, wherein inhibited CTL activity includes reduced secretion of one or more proinflammatory cytokines and/or reduced CTL mediated killing of target cells.

Clause 120. The method or use of any one of the foregoing Clauses which inhibits CD4+ T cell activation and/or CD4+ T cell proliferation and/or CD4+ T cell mediated cell depletion.

Clause 121. The method or use of any one of the foregoing Clauses which inhibits CD8+ T cell activation and/or CD8+ T cell proliferation and/or CD8+ T cell mediated cell depletion.

Clause 122. The method or use of any one of the foregoing Clauses which inhibits NK cell activity.

Clause 123. The method or use of Clause 122, wherein inhibited NK cell activity includes reduced depletion of target cells and/or proinflammatory cytokine release.

Clause 124. The method or use of any one of the foregoing Clauses which promotes and/or increases the differentiation, proliferation and/or activity of regulatory cells, such as T cells (Tregs) and/or the differentiation, proliferation, infiltration and/or activity of myeloid derived suppressor cells (MDSC's).

Clause 125. The method or use of any one the foregoing Clauses which promotes and/or increases the infiltration of regulatory cells, such as Tregs or MDSCs into a disease site.

Clause 126. The method or use of any one of the foregoing Clauses which inhibits an allergic, autoimmune or inflammatory immune response by promoting one or more of the effects of VSIG8 and/or VISTA on immunity.

Clause 127. The method or use of any one of the foregoing Clauses which promotes antigen-specific tolerance or prolonged suppression of an antigen-specific immune response by enhancing one or more of the effects of VSIG8 and/or VISTA on immunity.

Clause 128. The method or use of any one of the foregoing Clauses which elicits tolerance or prolonged suppression of antigen-specific immunity against transplanted cells, tissue or organ.

Clause 129. The method or use of any one of the foregoing Clauses which inhibits an immune response against an autoantigen, allergen, or inflammatory agent by promoting one or more of the effects of VSIG8 and/or VISTA on immunity.

Clause 130. The method or use of any one the foregoing Clauses wherein the treated individual has or is to receive cell therapy, gene therapy or a transplanted tissue or organ, and the treatment reduces or inhibits the undesirable immune activation that is associated with such cell therapy, gene therapy or a transplanted tissue or organ.

Clause 131. The method or use of any one of the foregoing Clauses which is used to treat an inflammatory or autoimmune disorder or a condition associated with inflammation selected from Acid Reflux/Heartburn, Acne, Acne Vulgaris, Allergies and Sensitivities, Alzheimer's Disease, Asthma, Atherosclerosis and Vascular Occlusive Disease, optionally Atherosclerosis, Ischemic Heart Disease, Myocardial Infarction, Stroke, Peripheral Vascular Disease, or Vascular Stent Restenosis, Autoimmune Diseases, Bronchitis, Cancer, Carditis, Cataracts, Celiac Disease, Chronic Pain, Chronic Prostatitis, Cirrhosis, Colitis, Connective Tissue Diseases, optionally Systemic Lupus Erythematosus, Systemic Sclerosis, Polymyositis, Dermatomyositis, or Sjogren's Syndrome and related conditions such as Sjogren's syndrome" herein includes one or more of Sjogren's syndrome, Primary Sjogren's syndrome and Secondary Sjogren's syndrome, as well as conditions or complications relating to Sjogren's syndrome including connective tissue disease, such as rheumatoid arthritis, systemic lupus erythematosus, or scleroderma, pneumonia, pulmonary fibrosis, interstitial nephritis, inflammation of the tissue around the kidney's filters, glomerulonephritis, renal tubular acidosis, carpal tunnel syndrome, peripheral neuropathy, cranial neuropathy, primary biliary cirrhosis (PBC), cirrhosis, Inflammation in the esophagus, stomach, pancreas, and liver (including hepatitis), Polymyositis, Raynaud's phenomenon, Vasculitis, Autoimmune thyroid problems, lymphoma, Corneal Disease, Crohn's Disease, Crystal Arthropathies, optionally Gout, Pseudogout, Calcium Pyrophosphate Deposition Disease, Dementia, Dermatitis, Diabetes, Dry Eyes, Eczema, Edema, Emphysema, Fibromyalgia, Gastroenteritis, Gingivitis, Glomerulonephritis, Heart Disease, Hepatitis, High Blood Pressure, Hypersensitivities, Inflammatory Bowel Diseases, Inflammatory Conditions including Consequences of Trauma or Ischaemia, Insulin Resistance, Interstitial Cystitis, Iridocyclitis, Iritis, Joint Pain, Arthritis, Lyme Disease, Metabolic Syndrome (Syndrome X), Multiple Sclerosis, Myositis, Nephritis, Obesity, Ocular Diseases including Uveitis, Osteopenia, Osteoporosis, Parkinson's Disease, Pelvic Inflammatory Disease, Periodontal Disease, Polyarteritis, Polychondritis, Polymyalgia Rheumatica, Psoriasis, Reperfusion Injury, Rheumatic Arthritis, Rheumatic Diseases, Rheumatoid Arthritis, Osteoarthritis, or Psoriatic Arthritis, Rheumatoid Arthritis, Sarcoidosis, Scleroderma, Sinusitis, "Sjogren's syndrome" and related conditions or complications associated therewith such as one or more of Sjogren's syndrome, Primary Sjogren's syndrome and Secondary Sjogren's syndrome, conditions relating to Sjogren's syndrome including connective tissue disease, such as rheumatoid arthritis, systemic lupus erythematosus, or scleroderma, and complications relating to Sjogren's syndrome such as pneumonia, pulmonary fibrosis, interstitial nephritis, inflammation of the tissue around the kidney's filters, glomerulonephritis, renal tubular acidosis, carpal tunnel syndrome, peripheral neuropathy, cranial neuropathy, primary biliary cirrhosis (PBC), cirrhosis, inflammation in the esophagus, stomach, pancreas, and liver (including hepatitis), Polymyositis, Raynaud's phenomenon, Vasculitis, Autoimmune thyroid problems, lymphoma, Sjogren's Syndrome, Spastic Colon, Spondyloarthropathies, optionally Ankylosing Spondylitis, Reactive Arthritis, or Reiter's Syndrome, Systemic Candidiasis, Tendonitis, Transplant Rejection, UTI's, Vaginitis, Vascular Diseases including Atherosclerotic Vascular Disease, Vasculitides, Polyarteritis *Nodosa*, Wegener's Granulomatosis, Churg-Strauss Syndrome, or vasculitis.

Clause 132. The method or use of any of the foregoing Clauses which is used to treat an autoimmune or allergic disease selected from acute anterior uveitis, Acute Disseminated Encephalomyelitis (ADEM), acute gouty arthritis, acute necrotizing hemorrhagic leukoencephalitis, acute or chronic sinusitis, acute purulent meningitis (or other central nervous system inflammatory disorders), acute serious inflammation, Addison's disease, adrenalitis, adult onset diabetes mellitus (Type II diabetes), adult-onset idiopathic hypoparathyroidism (AOIH), Agammaglobulinemia, agranulocytosis, vasculitides, including vasculitis, optionally, large vessel vasculitis, optionally, polymyalgia rheumatica and giant cell (Takayasu's) arthritis, allergic conditions, allergic contact dermatitis, allergic dermatitis, allergic granulomatous angiitis, allergic hypersensitivity disorders, allergic neuritis, allergic reaction, alopecia greata, alopecia totalis, Alport's syndrome, alveolitis, optionally allergic alveolitis or fibrosing alveolitis, Alzheimer's disease, amyloidosis, amylotrophic lateral sclerosis (ALS; Lou Gehrig's disease), an eosinophil-related disorder, optionally eosinophilia, anaphylaxis, ankylosing spondylitis, angiectasis, antibody-mediated nephritis, Anti-GBM/Anti-TBM nephritis, antigen-antibody complex-mediated diseases, antiglomerular basement membrane disease, anti-phospholipid antibody syndrome, antiphospholipid syndrome (APS), aphthae, aphthous stomatitis, aplastic anemia, arrhythmia, arteriosclerosis, arteriosclerotic disorders, arthritis, optionally rheumatoid arthritis such as acute arthritis, or chronic rheumatoid arthritis, arthritis chronica progrediente, arthritis deformans, ascariasis, aspergilloma, granulomas containing eosinophils, aspergillosis, aspermiogenese, asthma, optionally asthma bronchiale, bronchial asthma, or auto-immune asthma, ataxia telanglectasia, ataxic sclerosis, atherosclerosis, autism, autoimmune angioedema, autoimmune aplastic anemia, autoimmune atrophic gastritis, autoimmune diabetes, autoimmune disease of the testis and ovary including autoimmune orchitis and oophoritis, autoimmune disorders associated with collagen disease, autoimmune dysautonomia, autoimmune ear disease, optionally autoimmune inner ear disease (AGED), autoimmune endocrine diseases including thyroiditis such as autoimmune thyroiditis, autoimmune enteropathy syndrome, autoimmune gonadal failure, autoimmune hearing loss, autoimmune hemolysis, Autoimmune hepatitis, autoimmune hepatological disorder, autoimmune hyperlipidemia, autoimmune immunodeficiency, autoimmune inner ear disease (AIED), autoimmune myocarditis, autoimmune neutropenia, autoimmune pancreatitis, autoimmune polyendocrinopathies, autoimmune polyglandular syndrome type I, autoimmune retinopathy, autoimmune thrombocytopenic purpura (ATP), autoimmune thyroid disease, autoimmune urticaria, autoimmune-mediated gastrointestinal diseases, Axonal & neuronal neuropathies, Balo disease, Behcet's disease, benign familial and ischemia-reperfusion injury, benign lymphocytic angiitis, Berger's disease (IgA nephropathy), bird-fancier's lung, blindness, Boeck's disease, bronchiolitis obliterans (non-transplant) vs NSIP, bronchitis, bronchopneumonic aspergillosis, Bruton's syndrome, bullous pemphigoid, Caplan's syndrome, Cardiomyopathy, cardiovascular ischemia, Castleman's syndrome, Celiac disease, celiac sprue (gluten enteropathy), cerebellar degeneration, cerebral ischemia, and disease accompanying vascularization, Chagas disease, channelopathies, optionally epilepsy, channelopathies of the CNS, chorioretinitis, choroiditis, an autoimmune hematological disorder, chronic active hepatitis or autoimmune chronic active hepatitis, chronic contact dermatitis, chronic eosinophilic pneumonia, chronic fatigue syndrome, chronic hepatitis, chronic hypersensitivity pneumonitis, chronic inflammatory arthritis, Chronic inflammatory demyelinating polyneuropathy (CIDP), chronic intractable inflammation, chronic mucocutaneous candidiasis, chronic neuropathy, optionally IgM polyneuropathies or IgM-mediated neuropathy, chronic obstructive airway disease, chronic pulmonary inflammatory disease, Chronic recurrent multifocal osteomyelitis (CRMO), chronic thyroiditis (Hashimoto's thyroiditis) or subacute thyroiditis, Churg-Strauss syndrome, cicatricial pemphigoid/benign mucosal pemphigoid, CNS inflammatory disorders, CNS vasculitis, Coeliac disease, Cogan's syndrome, cold agglutinin disease, colitis polyposa, colitis such as ulcerative colitis, colitis ulcerosa, collagenous colitis, conditions involving infiltration of T cells and chronic inflammatory responses, congenital heart block, congenital rubella infection, Coombs positive anemia, coronary artery disease, Coxsackie myocarditis, CREST syndrome (calcinosis, Raynaud's phenomenon), Crohn's disease, cryoglobulinemia, Cushing's syndrome, cyclitis, optionally chronic cyclitis, heterochronic cyclitis, iridocyclitis, or Fuch's cyclitis, cystic fibrosis, cytokine-induced toxicity, deafness, degenerative arthritis, demyelinating diseases, optionally autoimmune demyelinating diseases, demyelinating neuropathies, dengue, dermatitis herpetiformis and atopic dermatitis, dermatitis including contact dermatitis, dermatomyositis, dermatoses with acute inflammatory components, Devic's disease (neuromyelitis optica), diabetic large-artery disorder, diabetic nephropathy, diabetic retinopathy, Diamond Blackfan anemia, diffuse interstitial pulmonary fibrosis, dilated cardiomyopathy, discoid lupus, diseases involving leukocyte diapedesis, Dressler's syndrome, Dupuytren's contracture, echovirus infection, eczema including allergic or atopic eczema, encephalitis such as Rasmussen's encephalitis and limbic and/or brainstem encephalitis, encephalomyelitis, optionally allergic encephalomyelitis or encephalomyelitis allergica and experimental allergic encephalomyelitis (EAE), endarterial hyperplasia, endocarditis, endocrine ophthalmopathy, endometriosis, endomyocardial fibrosis, endophthalmia phacoanaphylactica, endophthalmitis, enteritis allergica, eosinophilia-myalgia syndrome, eosinophilic fascitis, epidemic keratoconjunctivitis, epidermolysis bullosa acquisita (EBA), episclera, episcleritis, Epstein-Barr virus infection, erythema elevatum et diutinum, erythema multiforme, erythema nodosum leprosum, erythema nodosum, erythroblastosis fetalis, esophageal dysmotility, Essential mixed cryoglobulinemia, ethmoid, Evan's syndrome, Experimental Allergic Encephalomyelitis (EAE), Factor VIII deficiency, farmer's lung, febris rheumatica, Felty's syndrome, fibromyalgia, fibrosing alveolitis, filariasis, focal segmental glomerulosclerosis (FSGS), food poisoning, frontal, gastric atrophy, giant cell arthritis (temporal arthritis), giant cell hepatitis, giant cell polymyalgia, glomerulonephritides, glomerulonephritis (GN) with and without nephrotic syndrome such as chronic or acute glomerulonephritis (e.g., primary GN), Goodpasture's syndrome, gouty arthritis, granulocyte transfusion-associated syndromes, granulomatosis including lymphomatoid granulomatosis, granulomatosis with polyangiitis (GPA), granulomatous uveitis, Grave's disease, Guillain-Barre syndrome, gutatte psoriasis, hemoglobinuria paroxysmatica, Hamman-Rich's disease, Hashimoto's disease, Hashimoto's encephalitis, Hashimoto's thyroiditis, hemochromatosis, hemolytic anemia or immune hemolytic anemia including autoimmune hemolytic anemia (AIHA), hemolytic anemia, hemophilia A, Henoch-Schonlein purpura, Herpes gestationis, human immunodeficiency virus (HIV) Infection, hyperalgesia, hypogammaglobulinemia, hypogonadism, hypoparathyroidism, idiopathic diabetes insipidus, idiopathic facial paralysis, idiopathic hypothyroidism, idiopathic IgA nephropathy, idiopathic membranous GN or idiopathic membranous nephropathy, idiopathic nephritic syndrome, idiopathic pulmonary fibrosis, idiopathic sprue, Idiopathic thrombocytopenic purpura (ITP), IgA nephropathy, IgE-mediated diseases, optionally anaphylaxis and allergic or atopic rhinitis, IgG4-related sclerosing disease, ileitis regionalis, immune complex nephritis, immune responses associated with acute and delayed hypersensitivity mediated by cytokines and T-lymphocytes, immune-mediated GN, immunoregulatory lipoproteins, including adult or acute respiratory distress syndrome (ARDS), Inclusion body myositis, infectious arthritis, infertility due to antispermatozoan antibodies, inflammation of all or part of the uvea, inflammatory bowel disease (IBD) inflammatory hyperproliferative skin diseases, inflammatory myopathy, insulin-dependent diabetes (type I), insulitis, Interstitial cystitis, interstitial lung disease, interstitial lung fibrosis, iritis, ischemic re-perfusion disorder, joint inflammation, Juvenile arthritis, juvenile dermatomyositis, juvenile diabetes, juvenile onset (Type I) diabetes mellitus, including pediatric insulin-dependent diabetes mellitus (IDDM), juvenile-onset rheumatoid arthritis, Kawasaki syndrome, keratoconjunctivitis sicca, kypanosomiasis, Lambert-Eaton syndrome, leishmaniasis, leprosy, leucopenia, leukocyte adhesion deficiency, Leukocytoclastic vasculitis, leukopenia, lichen planus, lichen sclerosus, ligneous conjunctivitis, linear IgA dermatosis, Linear IgA disease (LAD), Loffler's syndrome, lupoid hepatitis, lupus (including nephritis, cerebritis, pediatric, non-renal, extra-renal, discoid, alopecia), Lupus (SLE), lupus erythematosus disseminatus, Lyme arthritis, Lyme disease, lymphoid interstitial pneumonitis, malaria, male and female autoimmune infertility, maxillary, medium vessel vasculitis (including Kawasaki's disease and polyarteritis *nodosa*), membrano- or membranous proliferative GN (MPGN), including Type I and Type II, and rapidly progressive GN, membranous GN (membranous nephropathy), Meniere's disease, meningitis, microscopic colitis, microscopic polyangiitis, migraine, minimal change nephropathy, Mixed connective tissue disease (MCTD), mononucleosis infectiosa, Mooren's ulcer, Mucha-Habermann disease, multifocal motor neuropathy, multiple endocrine failure, multiple organ injury syndrome such as those secondary to septicemia, trauma or hemorrhage, multiple organ injury syndrome, multiple sclerosis (MS) such as spino-optical MS, multiple sclerosis, mumps, muscular disorders, myasthenia gravis such as thymoma-associated myasthenia gravis, myasthenia gravis, myocarditis, myositis, narcolepsy, necrotizing enterocolitis, and transmural colitis, and autoimmune inflammatory bowel disease, necrotizing, cutaneous, or hypersensitivity vasculitis, neonatal lupus syndrome (NLE), nephrosis, nephrotic syndrome, neurological disease, neuromyelitis optica (Devic's), neuromyelitis optica, neuromyotonia, neutropenia, non-cancerous lymphocytosis, nongranulomatous uveitis, non-malignant thymoma, ocular and orbital inflammatory disorders, ocular cicatricial pemphigoid, oophoritis, ophthalmia symphatica, opsoclonus myoclonus syndrome (OMS), opsoclonus or opsoclonus myoclonus syndrome (OMS), and sensory neuropathy, optic neuritis, orchitis granulomatosa, osteoarthritis, palindromic rheumatism, pancreatitis, pancytopenia, PANDAS (Pediatric Autoimmune Neuropsychiatric Disorders Associated with *Streptococcus*), paraneoplastic cerebellar degeneration, paraneoplastic syndrome, paraneoplastic syndromes, including neurologic paraneoplastic syndromes, optionally Lambert-Eaton myasthenic syndrome or Eaton-Lambert syndrome, parasitic diseases such as *Leishmania*, paroxysmal nocturnal hemoglobinuria (PNH), Parry Romberg syndrome, pars planitis (peripheral uveitis), Parsonnage-Turner syndrome, parvovirus infection, pemphigoid such as pemphigoid bullous and skin pemphigoid, pemphigus (including pemphigus vulgaris), pemphigus erythematosus, pemphigus *foliaceus*, pemphigus mucus-membrane pemphigoid, pemphigus, peptic ulcer, periodic paralysis, peripheral neuropathy, perivenous encephalomyelitis, pernicious anemia (anemia perniciosa), pernicious anemia, phacoantigenic uveitis, pneumonocirrhosis, POEMS syndrome, polyarteritis *nodosa*, Type I, II, & III, polyarthritis chronica primaria, polychondritis (e.g., refractory or relapsed polychondritis), polyendocrine autoimmune disease, poly endocrine failure, polyglandular syndromes, optionally autoimmune polyglandular syndromes (or polyglandular endocrinopathy syndromes), polymyalgia rheumatica, polymyositis, polymyositis/dermatomyositis, polyneuropathies, polyradiculitis *acuta*, post-cardiotomy syndrome, posterior uveitis, or autoimmune uveitis, postmyocardial infarction syndrome, postpericardiotomy syndrome, post-streptococcal nephritis, post-vaccination syndromes, presenile dementia, primary biliary cirrhosis, primary hypothyroidism, primary idiopathic myxedema, primary lymphocytosis, which includes monoclonal B cell lymphocytosis, optionally benign monoclonal gammopathy and monoclonal gammopathy of undetermined significance, MGUS, primary myxedema, primary progressive MS (PPMS), and relapsing remitting MS (RRMS), primary sclerosing cholangitis, progesterone dermatitis, progressive systemic sclerosis, proliferative arthritis, psoriasis such as plaque psoriasis, psoriasis, psoriatic arthritis, pulmonary alveolar proteinosis, pulmonary infiltration eosinophilia, pure red cell anemia or aplasia (PRCA), pure red cell aplasia, purulent or nonpurulent sinusitis, pustular psoriasis and psoriasis of the nails, pyelitis, pyoderma gangrenosum, Quervain's thyroiditis, Raynaud's phenomenon, reactive arthritis, recurrent abortion, reduction in blood pressure response, reflex sympathetic dystrophy, refractory sprue, Reiter's disease or syndrome, relapsing polychondritis, reperfusion injury of myocardial or other tissues, reperfusion injury, respiratory distress syndrome, restless legs syndrome, retinal autoimmunity, retroperitoneal fibrosis, Reynaud's syndrome, rheumatic diseases, rheumatic fever, rheumatism, rheumatoid arthritis, rheumatoid spondylitis, rubella virus infection, Sampter's syndrome, sarcoidosis, schistosomiasis, Schmidt syndrome, SCID and Epstein-Barr virus-associated diseases, sclera, scleritis, sclerodactyl, scleroderma, optionally systemic scleroderma, sclerosing cholangitis, sclerosis disseminata, sclerosis such as systemic sclerosis, sensoneural hearing loss, seronegative spondyloarthritides, Sheehan's syndrome, Shulman's syndrome, silicosis, Sjogren's syndrome, sperm & testicular autoimmunity, sphenoid sinusitis, Stevens-Johnson syndrome, stiff-man (or stiff-person) syndrome, subacute bacterial endocarditis (SBE), subacute cutaneous lupus erythematosus, sudden hearing loss, Susac's syndrome, Sydenham's chorea, sympathetic ophthalmia, systemic lupus erythematosus (SLE) or systemic lupus erythematodes, cutaneous SLE, systemic necrotizing vasculitis, ANCA-associated vasculitis, optionally Churg-Strauss vasculitis or syndrome (CSS), tabes *dorsalis*, Takayasu's arteritis, telangiectasia, temporal arteritis/Giant cell arteritis, thromboangiitis ubiterans, thrombocytopenia, including thrombotic thrombocytopenic purpura (TTP) and autoimmune or immune-mediated thrombocytopenia such as idiopathic thrombocytopenic purpura (ITP) including chronic or acute ITP, thrombocytopenic purpura (TTP), thyrotoxicosis, tissue injury, Tolosa-Hunt syndrome, toxic epidermal necrolysis, toxic-shock syndrome, transfusion reaction, transient hypogammaglobulinemia of infancy, transverse myelitis, traverse myelitis, tropical pulmonary eosinophilia, tuberculosis, ulcerative colitis, undifferentiated connective tissue disease (UCTD), urticaria, optionally chronic allergic urticaria and chronic idiopathic urticaria, including chronic autoimmune urticaria, uveitis, anterior uveitis, uveoretinitis, valvulitis, vascular dysfunction, vasculitis, vertebral arthritis, vesiculobullous dermatosis, vitiligo, Wegener's granulomatosis (Granulomatosis with Polyangiitis (GPA)), Wiskott-Aldrich syndrome, or x-linked hyper IgM syndrome.

Clause 133. The method or use of any of the foregoing Clauses which is used to treat an autoimmune disease selected from the group consisting of multiple sclerosis, psoriasis; rheumatoid arthritis; psoriatic arthritis, systemic lupus erythematosus (SLE); discoid lupus erythematosus, inflammatory bowel disease, ulcerative colitis; Crohn's disease; benign lymphocytic angiitis, thrombocytopenic purpura, idiopathic thrombocytopenia, idiopathic autoimmune hemolytic anemia, pure red cell aplasia, Sjogren's syndrome, rheumatic disease, connective tissue disease, inflammatory rheumatism, degenerative rheumatism, extra-articular rheumatism, juvenile rheumatoid arthritis, arthritis uratica, muscular rheumatism, chronic polyarthritis, cryoglobulinemic vasculitis, ANCA-associated vasculitis, antiphospholipid syndrome, myasthenia gravis, autoimmune *haemolytica* anemia, Guillain-Barre syndrome, chronic immune polyneuropathy, autoimmune thyroiditis, insulin dependent diabetes mellitus, type I diabetes, Addison's disease, membranous glomerulonephropathy, Goodpasture's disease, autoimmune gastritis, autoimmune atrophic gastritis, pernicious anemia, pemphigus, pemphigus vulgaris, cirrhosis, primary biliary cirrhosis, dermatomyositis, polymyositis, fibromyositis, myogelosis, celiac disease, immunoglobulin A nephropathy, Henoch-Schonlein purpura, Evans syndrome, dermatitis, atopic dermatitis, psoriasis, psoriasis arthropathica, Graves' disease, Graves' ophthalmopathy, scleroderma, systemic scleroderma, progressive systemic scleroderma, asthma, allergy, primary biliary cirrhosis, Hashimoto's thyroiditis, primary myxedema, sympathetic ophthalmia, autoimmune uveitis, hepatitis, chronic action hepatitis, collagen diseases, ankylosing spondylitis, periarthritis humeroscapularis, panarteritis *nodosa*, chondrocalcinosis, Wegener's granulomatosis, microscopic polyangiitis, chronic urticaria, bullous skin disorders, pemphigoid, atopic eczema, childhood autoimmune hemolytic anemia, idiopathic autoimmune hemolytic anemia, Refractory or chronic Autoimmune Cytopenias, Prevention of development of Autoimmune Anti-Factor VIII Antibodies in Acquired Hemophilia A, Cold Agglutinin Disease, Neuromyelitis Optica, Stiff Person Syndrome, gingivitis, periodontitis, pancreatitis, idiopathic pericarditis, myocarditis, vasculitis, gastritis, gout, gouty arthritis, and inflammatory skin disorders, normocomplementemic urticarial vasculitis, pericarditis, myositis, anti-synthetase syndrome, scleritis, macrophage activation syndrome, Behcet's Syndrome, PAPA Syndrome, Blau's Syndrome, gout, adult and juvenile Still's disease, cryropyrinopathy, Muckle-Wells syndrome, familial cold-induced auto-inflammatory syndrome, neonatal onset multisystemic inflammatory disease, familial Mediterranean fever, chronic infantile neurologic, cutaneous and articular syndrome, a rheumatic disease, polymyalgia rheumatica, mixed connective tissue disease, inflammatory rheumatism, degenerative rheumatism, extraarticular rheumatism, juvenile arthritis, juvenile rheumatoid arthritis, systemic juvenile idiopathic arthritis, arthritis uratica, muscular rheumatism, chronic polyarthritis, reactive arthritis, Reiter's syndrome, rheumatic fever, relapsing polychondritis, Raynaud's phenomenon, vasculitis, cryoglobulinemic vasculitis, temporal arteritis, giant cell arteritis, Takayasu arteritis, Behcet's disease, chronic inflammatory demyelinating polyneuropathy, autoimmune thyroiditis, insulin dependent diabetes mellitus, type I diabetes, Addison's disease, membranous glomerulonephropathy, polyglandular autoimmune syndromes, Goodpasture's disease, autoimmune gastritis, autoimmune atrophic gastritis, pernicious anemia, pemphigus, pemphigus vulgaris, cirrhosis, primary biliary cirrhosis, idiopathic pulmonary fibrosis, myositis, dermatomyositis, juvenile dermatomyositis, polymyositis, fibromyositis, myogelosis, celiac disease, celiac sprue dermatitis, immunoglobulin A nephropathy, Henoch-Schonlein purpura, Evans syndrome, atopic dermatitis, psoriasis, psoriasis vulgaris, psoriasis arthropathica, Graves' disease, Graves' ophthalmopathy, scleroderma, systemic scleroderma, progressive systemic scleroderma, diffuse scleroderma, localized scleroderma, Crest syndrome, asthma, allergic asthma, allergy, primary biliary cirrhosis, fibromyalgia, chronic fatigue and immune dysfunction syndrome (CFIDS), autoimmune inner ear disease, Hyper IgD syndrome, Schnitzler's syndrome, autoimmune retinopathy, age-related macular degeneration, atherosclerosis, chronic prostatitis, alopecia, alopecia areata, alopecia universalis, alopecia totalis, autoimmune thrombocytopenic purpura, idiopathic thrombocytopenic purpura, pure red cell aplasia, and TNF receptor-associated periodic syndrome (TRAPS).

Clause 134. The method or use of any of the foregoing Clauses, wherein the diagnosis and/or treatment is combined with another moiety useful for treating immune related condition.

Clause 135. The method or use of Clause 134, wherein said other moiety useful for treating immune related condition is selected from immunosuppressants such as corticosteroids, cyclosporin, cyclophosphamide, prednisone, azathioprine, methotrexate, rapamycin, tacrolimus, lef unomide or an analog thereof; mizoribine; mycophenolic acid; mycophenolate mofetil; 15-deoxyspergualine or an analog thereof; biological agents such as TNF-a blockers or antagonists, or any other biological agent targeting any inflammatory cytokine, nonsteroidal antiinflammatory drugs/Cox-2 inhibitors, hydroxychloroquine, sulphasalazopryine, gold salts, etanercept, infliximab, mycophenolate mofetil, basiliximab, atacicept, rituximab, Cytoxan, interferon β-Ia, interferon β-Ib, glatiramer acetate, mitoxantrone hydrochloride, anakinra and/or other biologies and/or intravenous immunoglobulin (IVIG), interferons such as IFN-p-Ia (REBIF®. AVONEX® and CINNOVEX®) and IFN-p-Ib (BETASERON®); EXTAVIA®, BETAFERON®, ZIFERON®); glatiramer acetate (COPAXONE®), a polypeptide; natalizumab (TYSABRI®), mitoxantrone (NOVANTRONE®), a cytotoxic agent, a calcineurin inhibitor, e.g. cyclosporin A or FK506; an immunosuppressive macrolide, e.g. rapamycine or a derivative thereof; e.g. 40-O-(2-hydroxy)ethyl-rapamycin, a lymphocyte homing agent, e.g. FTY720 or an analog thereof, corticosteroids; cyclophosphamide; azathioprene; methotrexate; leflunomide or an analog thereof; mizoribine; mycophenolic acid; mycophenolate mofetil; 15-deoxyspergualine or an analog thereof; immunosuppressive monoclonal antibodies, e.g., monoclonal antibodies to leukocyte receptors, e.g., MHC, CD2, CD3, CD4, CDI Ia/CD18, CD7, CD25, CD27, B7, CD40, CD45, CD58, CD137, ICOS, CD150 (SLAM), OX40, 4-1BB or their ligands; or other immunomodulatory compounds, e.g. CTLA4-Ig (abatacept, ORENCIA®, belatacept), CD28-g, B7-H4-Ig, or other costimulatory agents, or adhesion molecule inhibitors, e.g. mAbs or low molecular weight inhibitors including LFA-1 antagonists, Selectin antagonists and VLA-4 antagonists, or another immunomodulatory agent.

Clause 136. An anti-VSIG8 antibody or antigen-binding fragment or VSIG8 fusion protein or composition, or method or use according to any of the foregoing Clauses which includes another moiety is useful for reducing the undesirable immune activation that follows gene therapy.

Clause 137. An anti-VSIG8 antibody or antigen-binding fragment or VSIG8 fusion protein or composition, or method or use according to any of the foregoing Clauses which includes treatment with an anti-VSIG8 antibody or antigen-binding fragment or composition containing combined with another therapeutic agent or therapy.

Clause 138. An anti-VSIG8 antibody or antigen-binding fragment or VSIG8 fusion protein or composition, or method or use according to any of the foregoing Clauses, further comprising a Therapeutic agent targeting immunosuppressive cells Tregs and/or MDSCs is selected from antimitotic drugs, cyclophosphamide, gemcitabine, mitoxantrone, fludarabine, thalidomide, thalidomide derivatives, COX-2 Inhibitors, depleting or killing antibodies that directly target Tregs through recognition of Treg cell surface receptors, anti-CD25 daclizumab, basiliximab, ligand-directed toxins, denileukin diftitox (Ontak)—a fusion protein of human IL-2 and diphtheria toxin, or LMB-2—a fusion between an scFv against CD25 and the *pseudomonas* exotoxin, antibodies targeting Treg cell surface receptors, TLR modulators, agents that interfere with the adenosinergic pathway, ectonucleotidase inhibitors, or inhibitors of the A2A adenosine receptor, TGF-β inhibitors, chemokine receptor inhibitors, retinoic acid, all-trans retinoic acid (ATRA), Vitamin D3, phosphodiesterase 5 inhibitors, sildenafil, ROS inhibitors and nitroaspirin.

Clause 139. An anti-VSIG8 antibody or antigen-binding fragment or VSIG8 fusion protein or composition, or method or use according to any of the foregoing Clauses, further comprising another antibody is selected from antagonistic antibodies targeting one or more of CTLA4, PD-1, PDL-1, LAG-3, TIM-3, BTLA, B7-H4, B7-H3, VISTA, and/or Agonistic antibodies targeting one or more of CD40, CD137, OX40, GITR, CD27, CD28 or ICOS.

Clause 140. The method or use of any of the foregoing Clauses, which includes assaying VSIG8 and/or VISTA protein by the individual's cells prior, concurrent and/or after treatment.

Clause 141. The method or use of Clause 140, wherein the method detects the expression of VSIG8 and/or VISTA protein by diseased and/or normal cells prior to treatment, optionally by the use of an antibody or nucleic acid that detects VSIG8 and/or VISTA expression.

Clause 142. The method or use of any one of the foregoing Clauses, which further includes the administration or use of another diagnostic or therapeutic agent, which may be administered prior, concurrent or after the administration of the anti-VSIG8 antibody, or antigen-binding fragment or composition containing according to any one of the foregoing Clauses.

Clause 143. The method or use of Clause 142, which includes the administration of another therapeutic agent.

Clause 144. The method or use of Clause 143, wherein the other therapeutic agent is selected from a drug, another immunomodulatory compound, a radionuclide, a fluorophore, an enzyme, a toxin, or a chemotherapeutic agent; and the detectable agent is selected from a radioisotope, a metal chelator, an enzyme, a fluorescent compound, a bioluminescent compound or a chemiluminescent compound.

Clause 145. The method or use of any one of the foregoing Clauses, which further includes the administration of an antibody or antigen-binding fragment thereof which specifically binds to a NK cell receptor.

Clause 146. The method or use of Clause 145, wherein the antibody or antigen-binding fragment thereof which specifically binds to an NK cell receptor agonizes the effect of said NK cell receptor.

Clause 147. The method or use of Clause 146, wherein the antibody or antigen-binding fragment thereof which specifically binds to an NK cell receptor antagonizes the effect of said NK cell receptor or one that inhibits NK cell activity.

Clause 148. The method or use of Clause 147, wherein the inhibitory NK cell receptor is selected from the group consisting of KIR2DL1, KIR2DL2/3, KIR2DL4, KIR2DL5A, KIR2DL5B, KIR3DL1, KIR3DL2, KIR3DL3, LILRB 1, NKG2A, NKG2C, NKG2E and LILRB5.

Clause 149. The method or use of Clause 145, wherein the NK cell receptor is one that promotes NK cell activity.

Clause 150. The method or use of Clause 149, wherein the NK cell activating receptor is selected from the group consisting of NKp30, NKp44, NKp46, NKp46, NKG2D, KIR2DS4 CD2, CD 16, CD69, DNAX accessory molecule-1 (DNAM-1), 2B4, NK1.1; a killer immunoglobulin (Ig)-like activating receptors (KAR); ILTs/LIRs; NKRP-1, CD69; CD94/NKG2C and CD94/NKG2E heterodimers, NKG2D homodimer KIR2DS and KIR3DS.

Clause 151. An assay method for selecting an anti-VSIG8 antibody or antigen-fragment or VSIG8 fusion protein according to any of the foregoing Clauses, or an anti-VSIG8 antibody or antigen-fragment suitable for use in a method or use according to any of the foregoing Clauses, wherein the method comprises (i) obtaining one or more antibodies or VSIG8 fusion protein that putatively bind to a VSIG8 polypeptide having a sequence selected from an amino acid sequence set forth in any of SEQ ID NOs: 1, 2, or 3, or binding to a polypeptide possessing at least 90% sequence identity therewith or to a non-human VSIG8 ortholog, or a fragment or variant thereof containing at least one VSIG8 epitope, which fragment or variant possesses at least 90% identity thereto, or to a non-human VSIG8 ortholog (ii) determining whether said antibody or antigen-binding fragment specifically binds to said VSIG8 polypeptide, (ii) determining whether said antibody or antigen-binding fragment modulates (agonizes or antagonizes) at least one effect of VSIG8 on immunity, and (iv) if (ii) and (ii) are satisfied selecting said antibody as one potentially useful in a method or use according to any of the foregoing Clauses.

Clause 152. The method of Clause 151 which further includes humanization, primatization or chimerization if the antibody or antigen-binding fragment is not a human or non-human primate antibody or a fragment thereof.

Clause 153. The method of Clauses 151 or 152 wherein the immunogen used to derive said antibody or antigen-binding fragment comprises a VSIG8 polypeptide having a sequence selected from an amino acid sequence set forth in any of SEQ ID NOs: 1, 2, and 3, or binding to a polypeptide possessing at least 90% sequence identity therewith or to a non-human VSIG8 ortholog or the same region of a nn-human VSIG8 ortholog, or a fragment or variant thereof containing at least one VSIG8 epitope.

Clause 154. The method of any of Clauses 151-153 wherein the immunogen used to derive said antibody or antigen-binding fragment comprises a VSIG8 polypeptide having a sequence selected from an amino acid sequence set forth in any of SEQ ID NOs: 1, 2, and 3 or binding to a polypeptide possessing at least 90% sequence identity therewith or to the same region of a non-human ortholog of hVSIG8.

Clause 155. The method of any of Clauses 151-154, wherein the immunogen used to derive said antibody or antigen-binding fragment thereof consists of a polypeptide having an amino acid sequence set forth in any of SEQ ID NOs: 1, 2 and 3, or binding to a polypeptide possessing at least 90% sequence identity therewith or to the same region of a non-human VSIG8 ortholog, or a conjugate thereof not containing another portion of any of the VSIG8 polypeptide.

Clause 156. The method of any of Clauses 151-155, wherein step (iii) detects whether the anti-VSIG8 antibody or antigen binding fragment antagonizes at least one effect of VSIG8 and/or VISTA on immunity.

Clause 157. The method of any of Clauses 151-156, wherein step (iii) detects whether the anti-VSIG8 antibody or antigen binding fragment agonizes at least one effect of VSIG8 and/or VISTA on immunity.

Clause 158. The method of any of Clauses 151-157, wherein the selected antibody or VSIG8 fusion protein is demonstrated to mediate at least one of the following effects: (i) increases immune response, (ii) increases T cell activation, (iii) increases cytotoxic T cell activity, (iv) increases NK cell activity, (v) alleviates T-cell suppression, (vi) increases pro-inflammatory cytokine secretion, (vii) increases IL-2 secretion; (viii) increases interferon-γ production, (ix) increases Thl response, (x) decrease Th2 response, (xi) decreases or eliminates cell number and/or activity of at least one of regulatory T cells (Tregs), myeloid derived suppressor cells (MDSCs), iMCs, mesenchymal stromal cells, TIE2-expressing monocytes, (xii) reduces regulatory cell activity, and/or the activity of one or more of myeloid derived suppressor cells (MDSCs), iMCs, mesenchymal stromal cells, TIE2-expressing monocytes, (xiii) decreases or eliminates M2 macrophages, (xiv) reduces M2 macrophage pro-tumorigenic activity, (xv) decreases or eliminates N2 neutrophils, (xvi) reduces N2 neutrophils pro-tumorigenic activity, (xvii) reduces inhibition of T cell activation, (xviii) reduces inhibition of CTL activation, (xix) reduces inhibition of NK cell activation, (xx) reverses T cell exhaustion, (xxi) increases T cell response, (xxii) increases activity of cytotoxic cells, (xxiii) stimulates antigen-specific memory responses, (xxiv) elicits apoptosis or lysis of cancer cells, (xxv) stimulates cytotoxic or cytostatic effect on cancer cells, (xxvi) induces direct killing of cancer cells, (xxvii) increases Thl 7 activity and/or (xxviii) induces complement dependent cytotoxicity and/or antibody dependent cell-mediated cytotoxicity, with the proviso that said anti-VSIG8 antibody or antigen-binding fragment may elicit an opposite effect to one or more of (i)-(xxviii).

Clause 159. The method of any of the foregoing Clauses, wherein the selected antibody or VSIG8 fusion protein is demonstrated to mediate at least one of the following effects: (i) decreases immune response, (ii) decreases T cell activation, (iii) decreases cytotoxic T cell activity, (iv) decreases natural killer (NK) cell activity, (v) decreases T-cell activity, (vi) decreases pro-inflammatory cytokine secretion, (vii) decreases IL-2 secretion; (viii) decreases interferon-γ production, (ix) decreases Thl response, (x) decreases Th2 response, (xi) increases cell number and/or activity of regulatory T cells, (xii) increases regulatory cell activity and/or one or more of myeloid derived suppressor cells (MDSCs), iMCs, mesenchymal stromal cells, TIE2-expressing monocytes, (xiii) increases regulatory cell activity and/or the activity of one or more of myeloid derived suppressor cells (MDSCs), iMCs, mesenchymal stromal cells, TIE2-expressing monocytes, (xiii) increases M2 macrophages, (xiv) increases M2 macrophage activity, (xv) increases N2 neutrophils, (xvi) increases N2 neutrophils activity, (xvii) increases inhibition of T cell activation, (xviii) increases inhibition of CTL activation, (xix) increases inhibition of NK cell activation, (xx) increases T cell exhaustion, (xxi) decreases T cell response, (xxii) decreases activity of cytotoxic cells, (xxiii) reduces antigen-specific memory responses, (xxiv) inhibits apoptosis or lysis of cells, (xxv) decreases cytotoxic or cytostatic effect on cells, (xxvi) reduces direct killing of cells, (xxvii) decreases Thl7 activity, and/or (xxviii) reduces complement dependent cytotoxicity and/or antibody dependent cell-mediated cytotoxicity, with the proviso that said anti-VSIG8 antibody or antigen-binding fragment may elicit an opposite effect to one or more of (i)-(xxviii).

Clause 160. The method of any of Clauses 149-159 wherein the selected antibody or VSIG8 fusion protein agonizes or antagonizes the effects of VSIG8 and/or VISTA on T cell activity, NK cell activity, and/or the production of one or more proinflammatory cytokines.

Clause 161. The method of any of Clauses 149-160 wherein the selected antibody or VSIG8 fusion protein is demonstrated to compete with binding to human or rodent VSIG8 to VISTA.

Clause 162. An immunomodulatory antibody or antigen-binding fragment or VSIG8 fusion protein according to any one of the foregoing Clauses or a pharmaceutical or diagnostic composition containing same.

Clause 163. Use of immunomodulatory antibody or antigen-binding fragment or VSIG8 fusion protein according to any one of the foregoing Clauses or a pharmaceutical or diagnostic composition containing same for treating or diagnosing a disease selected from cancer, infection, sepsis, autoimmunity, inflammation, allergic or other immune condition or to suppress an undesired immune reaction to a cell or gene therapy therapeutic or a transplanted cell, tissue or organ.

Clause 164. A transplant therapy which includes the transplant of cells, tissue or organ into a recipient, wherein the cells, tissue or organ or treated ex vivo using a composition containing an anti-VSIG8 antibody or antigen-binding fragment or VSIG8 fusion protein or composition according to any one of the foregoing Clauses prior to infusion or transplant of said cells, tissue or organ into the recipient.

Clause 165. The method of Clause 164, wherein the composition comprises immune cells of the donor and/or transplant recipient.

Clause 166. The method of Clauses 164 or 165 wherein the transplanted cells, tissue or organ comprises bone marrow, other lymphoid cells or tissue or stem cells.

Clause 167. A nucleic acid encoding the variable heavy and/or light region polypeptide of an anti-VSIG8 antibody or antibody fragment according to any one of the foregoing Clauses or a vector or virus containing.

Clause 168. An isolated or recombinant cell which comprises at least one nucleic acid or vector or virus according to Clause 167.

Clause 169. The cell of Clause 168 which is selected from a hybridoma and a recombinant bacterial, yeast or fungal, mammalian, insect, amphibian, reptilian, plant, and avian cell or egg.

Clause 170. A method of producing an anti-VSIG8 antibody or antibody fragment by culturing an isolated or recombinant cell according to Clause 169.

Clause 171. The method of Clause 170 wherein the cell is a bacterial, yeast, fungal, insect, plant, reptilian, mammalian cell or an avian egg.

Clause 172. An in vitro or in vivo method of using an antagonist compound according to any one of the foregoing Clauses to inhibit the interaction of VISTA and VSIG8.

Clause 173. An in vitro or in vivo method of using an antagonist compound according to any one of the foregoing Clauses to inhibit the suppressive effects of VISTA and/or VSIG8 on immune cells or immunity.

Clause 174. The method of Clause 172 or 173, which inhibits or blocks the suppressive effect of VISTA and/or VSIG8 on T cell activation, T cell proliferation or cytokine production or on myeloid dendritic cells.

Clause 175. The method of Clause 172 or 173, which inhibit or block the promoting effect of VISTA on T suppressor (Tsup) cells.

Clause 176. The method of any of Clause 172-175 which is used to treat a cancer or infectious disease.

Clause 177. The method of Clause 176, wherein the cancer is a solid tumor, e.g., a sarcoma, carcinoma or lymphoma or a blood cancer.

Clause 178. The method of Clause 176, wherein the infectious disease is a viral, bacterial, protozoan, yeast, fungal, or parasitic disease.

Clause 179. A method of using an agonist compound according to any one of the foregoing Clauses to enhance the interaction of VISTA and VSIG8.

Clause 180. The method of Clause 179, which enhances or promotes the suppressive effect of VISTA on T cell activation, proliferation or cytokine production.

Clause 181. The method of Clause 178 or 179, which is used to treat an autoimmune, allergic or inflammatory condition.

Clause 182. A compound according to any one of the foregoing Clauses, which is attached to a detectable label.

Clause 183. A diagnostic or therapeutic composition comprising a diagnostically or therapeutically effective amount of a compound according to any one of the foregoing Clauses.

Clause 184. The composition of Clause 183, which is suitable for use in human therapy.

Clause 185. The composition of Clause 184 which is an intravenous, subcutaneous or intramuscularly administrable composition.

Clause 186. A method according to any one of the foregoing Clauses, which further comprises the administration of an PD-1 or PD-L1 agonist or antagonist.

Clause 187. The method of Clause 186, wherein said PD-1 or PD-L1 agonist or antagonist is selected from an anti-PD-1 antibody or antibody fragment, an anti-PD-L1 antibody or antibody fragment, a PD-L1 polypeptide or fragment thereof which may be monovalent or multimeric, a PD-1 polypeptide or fragment thereof which may be monovalent or multimeric, or a complex or fusion protein comprising any of the foregoing.

Clause 188. A method of contacting immune cells with an agonist or antagonist compound according to any one of the foregoing Clauses.

Clause 189. The method of Clause 188, wherein said contacted cells are infused into a human subject.

Clause 190. The method of Clause 188 or 189, wherein the subject has cancer or an infectious disease.

Clause 191. The method of Clause 188 or 189, wherein the subject has an inflammatory, allergic or autoimmune condition.

Clause 192. A screening assay which comprises the use of VSIG8 alone or in association with VSIG8 to identify VSIG8/VISTA agonists or antagonists.

Clause 193. The assay of Clause 192 which is a binding assay that identifies compounds that bind VSIG8 and inhibit the VSIG8/VISTA interaction.

Clause 194. The assay of Clause 192 which is a binding assay that identifies compounds that bind VSIG8 and enhance the VSIG8/VISTA interaction.

Clause 195. The assay of Clause 192 which is a functional assay that screens for compounds that inhibit the effects the VISTA/VSIG8 interaction on T cell immunity or cytokine production.

Clause 196. The assay of Clause 192-195 which is a functional assay that screens for compounds that enhance the effects the VISTA/VSIG8 interaction on T cell immunity or cytokine production.

Clause 197. The assay of any one of Clauses 192-196 which uses human or rodent immune cells.

Clause 198. The assay of any one of Clauses 192-196 which uses a transgenic animal that expresses human VISTA and/or human VSIG8.

Clause 199. The assay of Clause 192-198 which is a high throughput screening assay.

Clause 200. The compound or method of any of the foregoing Clauses wherein said VSIG8 is a human, murine, or non-human primate VSIG8 protein.

Clause 201. An isolated polypeptide comprising a fragment of a VSIG8 ECD, wherein said fragment consists essentially of or consists of an amino acid sequence as set forth in any one of SEQ ID NOs: 1, 2 or 3 or a variant thereof that possesses at least 80, 85, 90, 95, 96, 97, 98, or 99% sequence identity therewith.

Clause 202. The isolated polypeptide of Clause 201, which comprises 2-10 of said VSIG8 ECD polypeptide fragments.

Clause 203. An isolated polypeptide according to Clauses 201 or 202, wherein said fragments are intervened by a heterologous linker, wherein said linker is not a fragment of a VSIG8 polypeptide.

Clause 204. The isolated peptide of Clause 203, wherein said linker is directly or indirectly conjugated to said fragments.

Clause 205. The isolated polypeptide of Clauses 202, 203 or 204, wherein said linker is an amino acid spacer.

Clause 206. The isolated peptide of Clause 205, wherein said amino acid spacer is of sufficient length of amino acid residues so that the different fragments can successfully bind to their individual targets.

Clause 207. The isolated polypeptide of Clauses 205 or 206, wherein said linker is a peptide comprising 5-50 amino acid residues, more preferably 5-25 amino acid residues.

Clause 208. The isolated peptide of Clause 207, wherein said linker is a peptide comprising 5-15 amino acid residues.

Clause 209. The isolated polypeptide of any of Clauses 205-208, wherein said linker comprises or consists essentially of glycine, serine, and/or alanine residues or predominantly (at least 50, 60, 70 or 80% of the residues) consists of glycine, serine, and/or alanine residues.

Clause 210. The isolated peptide of any of Clauses 205-209, wherein said linker comprises at least 4-40, 4-30, 4-20, or 4-12 glycine, serine, and/or alanine residues.

Clause 211. A fusion protein comprising the isolated polypeptide of any of the preceding Clauses, or SEQ ID NOs 1, 2 or 3, joined to a heterologous polypeptide and/or half-life extending moiety, with the proviso that said heterologous polypeptide or said half-life extending moiety is not a fragment of a VSIG8 polypeptide.

Clause 212. The fusion protein according to Clause 211, wherein said isolated polypeptide and said heterologous molecule are intervened by a heterologous linker, with the proviso that said linker does not comprise a polypeptide that is a fragment of a VSIG8 polypeptide.

Clause 213. The fusion protein of Clause 212, wherein said linker is directly or indirectly conjugated to said fragments.

Clause 214. The fusion protein of Clauses 212 or 213, wherein said linker is an amino acid spacer.

Clause 215. The fusion protein of Clause 214, wherein said amino acid spacer is of sufficient length of amino acid residues so that the different fragments can successfully bind to their individual targets.

Clause 216. The fusion protein of Clauses 214 or 215, wherein said linker is a peptide comprising 5-50 amino acid residues, more preferably 5-25 amino acid residues.

Clause 217. The fusion protein of Clause 216, wherein said linker is a peptide comprising 5-15 amino acid residues.

Clause 218. The fusion protein of any of Clauses 214-217, wherein said linker comprises or consists essentially of glycine, serine, and/or alanine residues or predominantly (at least 50, 60, 70 or 80% of the residues) consists of glycine, serine, and/or alanine residues.

Clause 219. The fusion protein of any of Clauses 214-218, wherein said linker comprises at least 4-40, 4-30, 4-20, or 4-12 glycine, serine, and/or alanine residues.

Clause 220. The fusion protein of any of the above Clauses, comprising or further comprising a half-life extending moiety.

Clause 221. The fusion protein according to any of Clauses 214-220, wherein the half-life extending moiety comprises polyethylene glycol (PEG), monomethoxy PEG (mPEG), an XTEN molecule, an rPEG molecule, an adnectin, a serum albumin, human serum albumin, immunoglobulin constant region or fragment thereof, or acyl group.

Clause 222. The fusion protein according to any one of Clauses 214-221, wherein the addition of said heterologous polypeptide, half-life extending moiety, or other heterologous molecule increases the in vivo half-life of said fusion protein by at least about 2-fold, at least about 3-fold, at least about 4-fold, at least about 5-fold, at least about 10-fold, or more, as compared to the identical molecule without such said heterologous polypeptide, half-life extending moiety, or other heterologous molecule.

Clause 223. The fusion protein according to any of the foregoing Clauses which comprises an immunoglobulin molecule or a fragment thereof.

Clause 224. The fusion protein according to Clause 214 wherein at least one of the heterologous polypeptides is a human or non-human immunoglobulin Fc polypeptide or fragment that comprises heavy and/or light chain Cm and Cm domains.

Clause 225. The fusion protein of Clauses 214 or 215, wherein at least one of the heterologous polypeptides is a human or non-human immunoglobulin Fc polypeptide or fragment that comprises heavy chain Cm and Cm domains.

Clause 226. The fusion protein according to any of Clauses 214-216 that comprises heavy and/or light chain CHI domains.

Clause 227. The fusion protein according to any of Clauses 214-216 that lacks heavy and/or light chain CHI domains.

Clause 228. The fusion protein according to any of Clauses 214-218 that lacks heavy chain CHI domains.

Clause 229. The fusion protein of any of the above Clauses, wherein said immunoglobulin molecule or a fragment thereof comprises a hinge region.

Clause 230. The fusion protein of Clause 229, wherein said hinge region is an intact hinge region.

Clause 231. The fusion protein of any of the above Clauses, wherein said immunoglobulin molecule or a fragment thereof does not feature a hinge region.

Clause 232. The fusion protein according to any of the foregoing Clauses which comprises a human immunoglobulin molecule or a fragment thereof.

Clause 233. The fusion protein of any of the foregoing Clauses, wherein said heterologous polypeptide comprises or consists of an Fc fragment of the immunoglobulin heavy chain constant region.

Clause 234. The fusion protein of any of the foregoing Clauses, wherein said heterologous polypeptide comprises or consists of an Fc fragment and hinge region of a human immunoglobulin heavy chain constant region.

Clause 235. The fusion protein of any of the foregoing Clauses comprising an immunoglobulin heavy chain constant region derived from an immunoglobulin isotype selected from the group consisting of an IgGl, IgG2, IgG3, IgG4, IgM, IgE, IgA and IgD.

Clause 236. The fusion protein of any of the foregoing Clauses comprising a human immunoglobulin heavy chain constant region selected from the group consisting of a human IgGl, IgG2, IgG3, and IgG4.

Clause 237. The fusion protein of any of the foregoing Clauses comprising a mouse IgGl, IgG2a or IgG2b immunoglobulin heavy chain constant region or fragment thereof.

Clause 238. The fusion protein of any of the foregoing Clauses, which comprises an immunoglobulin Fc region that contains at least one mutation that alters effector function and/or glycosylation.

Clause 239. The fusion protein of Clause 238 wherein said effector function is selected from FcR binding, complement binding, ADCC activity, CDC activity, degranulation, phagocytosis, and/or cytokine release.

Clause 240. The fusion protein according to any of the above Clauses, wherein the heterologous sequence comprises at least a portion of an immunoglobulin molecule that specifically binds to a target cell or comprises another moiety that specifically binds to a target cell.

Clause 241. The fusion protein according to Clause 41 wherein the target cell is a cancerous, immune, infectious agent cell, an infected cell, an immune cell, an inflammatory cell, a disease site or a cell which is to be transplanted into a human recipient.

Clause 242. The fusion protein of Clause 241, wherein said infectious agent cell is selected from the group consisting of a virus, bacterium, mycoplasm, fungus, yeast or parasite.

Clause 243. The fusion protein of Clauses 240 or 241, wherein said infected cell is infected with an infectious agent selected from the group consisting of a virus, bacterium, mycoplasm, fungus, yeast or parasite.

Clause 244. The fusion protein of any of the above Clauses, wherein at least one of the heterologous polypeptides is a receptor, hormone, cytokine, antigen, B-cell target, NK cell target, T cell target, TNF receptor superfamily member, Hedgehog family member, a receptor tyrosine kinase, a proteoglycan-related molecule, a TGF-β superfamily member, a Wnt-related molecule, a receptor ligand, a Dendritic cell target, a myeloid cell target, a monocyte/macrophage cell target or an angiogenesis target.

Clause 245. The fusion protein of Clause 244, wherein the antigen is a tumor antigen, autoantigen, allergen, or an infectious agent antigen.

Clause 246. The fusion protein of any of the above Clauses, wherein the at least one heterologous polypeptide includes an immunomodulatory polypeptide.

Clause 247. The fusion protein of any of Clauses 244-246, wherein the T cell target is selected from the group consisting of 2B4/SLAMF4, IL-2 Ra, 4-1BB/TNFRSF9, IL-2R, ALCAM, B7-1/CD80, IL-4R, B7-H3, BLAME/SLAMF8, BTLA, IL-6R, CCR3, IL-7 Ra, CCR4, CXCRI/IL-8 RA, CCR5, CCR6, IL-10 R a, CCR7, IL-10 Rβ, CCR8, IL-12 R i, CCR9, IL-12 Rβ2, CD2, IL-13Ral, IL-13, CD3, CD4, ILT2/CD85j, ILT3/CD85k, ILT4/CD85d, ILT5/CD85a, Integrin a 4/CD49d, CD5, Integrin aE/CD103, CD6, Integrin a M/CD1 Ib, CD8, Integrin a X/CD1 Ic, Integrin 2/CD18, KIR/CD158, CD27/TNFRSF7, KIR2DL1, CD28, KIR2DL3, CD30/TNFRSF8, KIR2DL4/CD158d, CD31/PECAM-1, KIR2DS4, CD40 Ligand/TNFSF5, LAG-3, CD43, LAIR1, CD45, LAIR2, CD83, Leukotriene B4 RI, CD84/SLAMF5, NCAM-L1, CD94, NKG2A, CD97, NKG2C, CD229/SLAMF3, NKG2D, CD2F-10/SLAMF9, NT-4, CD69, NTB-A/SLAMF6, Common γ Chain/IL-2 Ry, Osteopontin, CRACC/SLAMF7, PD-1, CRTAM, PSGL-1, CTLA-4, RANK/TNFRSF11 A, CX3CR1, CX3CL1, L-Selectin, CXCR3, SIRP βi, CXCR4, SLAM, CXCR6, TCCRAVSX-1, DNAM-1, Thymopoietin, EMMPRIN/CD 147, TIM-1, EphB6, TIM-2, Fas/TNFRSF6, TIM-3, Fas Ligand/TNFSF6, TIM-4, Fey RIII/CD16, TIM-6, GITR/TNFRSF18, TNF RI/TNFRSFIA, Granulysin, TNF R11/TNFRSF1B, HVEM/TNFRSF14, TRAIL RI/TNFRSFIOA, ICAM-1/CD54, TRAIL R2/TNFRSF10B, ICAM-2/CD102, TRAIL R3/TNFRSF10C, IFN-yRI, TRAIL R4/TNFRSF10D, IFN-yR2, TSLP, IL-1 RI and TSLP R.

Clause 248. The fusion protein of any of Clauses 244-246, wherein the monocyte/macrophage cell target is selected from the group consisting of B7-1/CD80, ILT4/CD85d, B7-H1, ILT5/CD85a, Common β Chain, Integrin a 4/CD49d, BLAME/SLAMF8, Integrin a X/CDI Ic, CCL6/C10, Integrin β2/CD18, CD155/PVR, Integrin β3/CD61, CD31/PECAM-1, Latexin, CD36/SR-B3, Leukotriene B4 RI, CD40/TNFRSF5, LIMPII/SR-B2, CD43, LMIR1/CD300A, CD45, LMIR2/CD300c, CD68, LMIR3/CD300LF, CD84/SLAMF5, LMIR5/CD300LB, CD97, LMIR6/CD300LE, CD163, LRP-1, CD2F-10/SLAMF9, MARCO, CRACC/SLAMF7, MD-1, ECF-L, MD-2, EMMPRIN/CD147, MGL2, Endoglin/CD105, Osteoactivin/GPNMB, Fc yRI/CD64, Osteopontin, Fc γ RIIB/CD32b, PD-L2, Fc yRIIC/CD32c, Siglec-3/CD33, Fey RIIA/CD32a, SIGNR1/CD209, Fey RIII/CD16, SLAM, GM-CSF R a, TCCR/WSX-1, ICAM-2/CD102, TLR3, IFN-y RI, TLR4, IFN-y R2, TREM-1, IL-1 RII, TREM-2, ILT2/CD85j, TREM-3, ILT3/CD85k, TREMLI/TLT-1, 2B4/SLAMF4, IL-10 R a, ALCAM, IL-10 R β, Aminopeptidase N/ANPEP, ILT2/CD85j, Common β Chain, ILT3/CD85k, Clq R1/CD93, ILT4/CD85d, CCR1, ILT5/CD85a, CCR2, Integrin a 4/CD49d, CCR5, Integrin a M/CDI Ib, CCR8, Integrin a X/CDI Ic, CD155/PVR, Integrin β2/CD18, CD14, Integrin β3/CD61, CD36/SR-B3, LAIR1, CD43, LAIR2, CD45, Leukotriene B4 RI, CD68, LIMPII/SR-B2, CD84/SLAMF5, LMIR1/CD300A, CD97, LMIR2/CD300c, CD 163, LMIR3/CD300LF, Coagulation Factor III/Tissue Factor, LMIR5/CD300LB, CX3CR1, CX3CL1, LMIR6/CD300LE, CXCR4, LRP-1, CXCR6, M-CSF R, DEP-1/CD148, MD-1, DNAM-1, MD-2, EMMPRIN/CD 147, MMR, Endoglin/CD105, NCAM-L1, Fc y R1/CD64, PSGL-1, Fc y RIII/CD16, RP105, G-CSF R, L-Selectin, GM-CSF R a, Siglec-3/CD33, HVEM/TNFRSF14, SLAM, ICAM-1/CD54, TCCR/WSX-1, ICAM-2/CD102, TREM-1, IL-6 R, TREM-2, CXCRI/IL-8 RA, TREM-3 and TREMLI/TLT-1.

Clause 249. The fusion protein of any of Clauses 244-246, wherein the Dendritic cell target is selected from the group consisting of CD36/SR-B3, LOX-1/SR-E1, CD68, MARCO, CD163, SR-AI/MSR, CD5L, SREC-I, CL-P1/COLEC12, SREC-II, LIMPII/SR-B2, RP105, TLR4, TLR1, TLR5, TLR2, TLR6, TLR3, TLR9, 4-1BB Ligand/TNFSF9, IL-12/IL-23 p40, 4-Amino-l,8-naphthalimide, ILT2/CD85j, CCL21/6Ckine, ILT3/CD85k, 8-oxo-dG, ILT4/CD85d, 8D6A, ILT5/CD85a, A2B5, Integrin a 4/CD49d, Aag, Integrin β2/CD18, AMICA, Langerin, B7-2/CD86, Leukotriene B4 RI, B7-H3, LMIR1/CD300A, BLAME/SLAMF8, LMIR2/CD300c, Clq R1/CD93, LMIR3/CD300LF, CCR6, LMIR5/CD300LB, CCR7, LMIR6/CD300LE, CD40/TNFRSF5, MAG/Siglec-4a, CD43, MCAM, CD45, MD-1, CD68, MD-2, CD83, MDL-1/CLEC5A, CD84/SLAMF5, MMR, CD97, NCAM-L1, CD2F-10/SL AMF9, Osteoactivin/GPNMB, Chem 23, PD-L2, CLEC-1, RP105, CLEC-2, Siglec-2/CD22, CR ACC/SLAMF7, Siglec-3/CD33, DC-SIGN, Siglec-5, DC-SIGNR/CD299, Siglec-6, DCAR, Siglec-7, DCIR/CLEC4A, Siglec-9, DEC-205, Siglec-10, Dectin-1/CLEC7A, Siglec-F, Dectin-2/CLEC6A, SIGNR1/CD209, DEP-1/CD 148, SIGNR4, DLEC, SLAM, EMMPRIN/CD 147, TCCRAVSX-1, Fc γ R1/CD64, TLR3, Fc γ RIIB/CD32b, TREM-1, Fc Y RIIC/CD32C, TREM-2, Fc γ RIIA/CD32a, TREM-3, Fc γ RIII/CD16, TREMLI/TLT-1, ICAM-2/CD102 and Vanilloid RI.

Clause 250. The fusion protein of any of Clauses 244-246, wherein the TNF receptor superfamily member is selected from the group consisting of 4-1BB/TNFRSF9, NGF R/TNFRSF16, BAFF R/TNFRSF13C, Osteoprotegerin/TNFRSFI IB, B CMA/TNFRSF 17, OX40/TNFRSF4, CD27/TNFRSF7, RANK/TNFRSF11 A, CD30/TNFRSF8, RELT/TNFRSF19L, CD40/TNFRSF5, TACI/TNFRSF13B, DcR3/TNFRSF6B, TNF RI/TNFRSF1A, DcTRAIL R1/TNFRSF23, TNF RII/TNFRSF1B, DcTRAIL R2/TNFRSF22, TRAIL R1/TNFRSF10A, DR3/TNFRSF25, TRAIL R2/TNFRSF10B, DR6/TNFRSF21, TRAIL R3/TNFRSF10C, EDAR, TRAIL R4/TNFRSF 10D, Fas/TNFRSF6, TROY/TNFRSF19, GITR/TNFRSF 18, TWEAK R/TNFRSF12, HVEM/TNFRSF14, XEDAR, Lymphotoxin β R/TNFRSF3, 4-1BB Ligand/TNFSF9, Lymphotoxin, APRIL/TNFSF 13, Lymphotoxin/TNFSF3, BAFF/TNFSF13C, OX40 Ligand/TNFSF4, CD27 Ligand/TNFSF7, TL1A/TNFSF15, CD30 Ligand/TNFSF8, TNF-a/TNFSFIA, CD40 Ligand/TNFSF5, TNF-/TNFSFIB, EDA-A2, TRAIL/TNFSF10, Fas Ligand/TNFSF6, TR ANCE/TNFSF 11, GITR Ligand/TNFSF18, TWEAK/TNFSF12 and LIGHT/TNFSF14.

Clause 251. The fusion protein of any of Clauses 244-246, wherein the Hedgehog family member is selected from the group consisting of Patched and Smoothened.

Clause 252. The fusion protein of any of Clauses 244-246, wherein the receptor tyrosine kinase is selected from the group consisting of Axl, FGF R4, Clq R1/CD93, FGF R5, DDR1, Flt-3, DDR2, HGF R, Dtk, IGF-I R, EGF R, IGF-II R, Eph, INSRR, EphAI, Insulin R/CD220, EphA2, M-CSF R, Eph A3, Mer, EphA4, MSP R/Ron, EphA5, MuSK, EphA6, PDGF R a, EphA7, PDGF R β, EphA8, Ret, EphB I, ROR1, EphB2, ROR2, EphB3, SCF R/c-kit, EphB4, Tie-1, EphB6, Tie-2, ErbB2, TrkA, ErbB3, TrkB, ErbB4, TrkC, FGF RI, VEGF RI/Flt-1, FGF R2, VEGF R2/Flk-1, FGF R3 and VEGF R3/Flt-4.

Clause 253. The fusion protein of any of Clauses 244-246, wherein the Transforming Growth Factor (TGF)-superfamily member is selected from the group consisting of Activin RIA/ALK-2, GFR a-1, Activin RIB/ALK-4, GFR a2, Activin RHA, GFR a-3, Activin RUB, GFR a-4, ALK-1, MIS RII, ALK-7, Ret, B MPR-I A/ALK-3, TGF-beta RI/ALK-5, BMPR-IB/ALK-6, TGF-β RII, BMPR-II, TGF-β RIIb, Endoglin/CD 105 and TGF-β RIII.

Clause 254. The fusion protein of any of Clauses 244-246, wherein the Wnt-related molecule selected from the group consisting of Frizzled-1, Frizzled-8, Frizzled-2, Frizzled-9, Frizzled-3, sFRP-1, Frizzled-4, sFRP-2, Frizzled-5, sFRP-3, Frizzled-6, sFRP-4, Frizzled-7, MFRP, LRP 5, LRP 6, Wnt-1, Wnt-8a, Wnt-3a, Wnt-IOb, Wnt-4, Wnt-11, Wnt-5a, Wnt-9a and Wnt-7a.

Clause 255. The fusion protein of any of Clauses 244-246, wherein the receptor ligand is selected from the group consisting of 4-1BB Ligand/TNFSF9, Lymphotoxin, APRIL/TNFSF13, Lymphotoxin/TNFSF3, BAFF/TNFSF13C, OX40 Ligand/TNFSF4, CD27 Ligand/TNFSF7, TL1A/TNFSF15, CD30 Ligand/TNFSF8, TNF-a/

TNFSFIA, CD40 Ligand/TNFSF5, TNF^/TNFSFIB, EDA-A2, TRAIL/TNFSF10, Fas Ligand/TNFSF6, TRANCE/TNFSF11, GITR Ligand/TNFSF18, TWEAK/TNFSF12, LIGHT/TNFSF 14, Amphiregulin, NRG1 isoform GGF2, Betacellulin, NRG1 Isoform SMDF, EGF, NRGI-a/HRGI-a, Epigen, NRGI-β I/HRGI-β 1, Epiregulin, TGF-a, HB-EGF, TMEFFI/Tomoregulin-1, Neuregulin-3, TMEFF2, IGF-I, IGF-II, Insulin, Activin A, Activin B, Activin AB, Activin C, BMP-2, BMP-7, BMP-3, BMP-8, BMP-3b/GDF-10, BMP-9, BMP-4, BMP-15, BMP-5, Decapentaplegic, BMP-6, GDF-1, GDF-8, GDF-3, GDF-9, GDF-5, GDF-11, GDF-6, GDF-15, GDF-7, Arternin, Neurturin, GDNF, Persephin, TGF-β, TGF-β 2, TGF-β 1, TGF-β 3, LAP (TGF-β 1), TGF-β 5, Latent TGF-β 1, Latent TGF-β bpl, TGF-β 1.2, Lefty, Nodal, MIS/AMH, FGF acidic, FGF-12, FGF basic, FGF-13, FGF-3, FGF-16, FGF-4, FGF-17, FGF-5, FGF-19, FGF-6, FGF-20, FGF-8, FGF-21, FGF-9, FGF-23, FGF-10, KGF/FGF-7, FGF-11, Neuropilin-1, P1GF, Neuropilin-2, P1GF-2, PDGF, PDGF-A, VEGF, PDGF-B, VEGF-B, PDGF-C, VEGF-C, PDGF-D, VEGF-D and PDGF-AB.

Clause 256. The fusion protein of any of Clauses 244-246, wherein the tumor antigen is selected from the group consisting of Squamous Cell Carcinoma Antigen 1 (SCCA-1), (PROTEIN T4-A), Squamous Cell Carcinoma Antigen 2 (SCCA-2), Ovarian carcinoma antigen CA125 (1A1-3B; KIAA0049), MUCIN 1 (TUMOR-ASSOCIATED MUCIN; Carcinoma-Associated Mucin; Polymorphic Epithelial Mucin; PEM; PEMT; EPISIALIN; Tumor-Associated Epithelial Membrane Antigen; EMA; H23AG; Peanut-Reactive Urinary Mucin; PUM; and Breast Carcinoma-Associated Antigen DF3), CTCL tumor antigen sel-1, CTCL tumor antigen sel4-3, CTCL tumor antigen se20-4, CTCL tumor antigen se20-9, CTCL tumor antigen se33-I, CTCL tumor antigen se37-2, CTCL tumor antigen se57-I, CTCL tumor antigen se89-I, Prostate-specific membrane antigen, 5T4 oncofetal trophoblast glycoprotein, Orf73 Kaposi's sarcoma-associated herpesvirus, MAGE-CI (cancer/testis antigen CT7), MAGE-B 1 ANTIGEN (MAGE-XP Antigen; DAM 10), MAGE-B2 Antigen (DAM6), MAGE-2 ANTIGEN, MAGE-4a antigen, MAGE-4b antigen, Colon cancer antigen NY-CO-45, Lung cancer antigen NY-LU-12 variant A, Cancer associated surface antigen, Adenocarcinoma antigen ART1, Paraneoplastic associated brain-testis-cancer antigen (onconeuronal antigen MA2; paraneoplastic neuronal antigen), Neuro-oncological ventral antigen 2 (NOVA2), Hepatocellular carcinoma antigen gene 520, Tumor-Associated Antigen CO-029, Tumor-associated antigen MAGE-X2, Synovial sarcoma, X breakpoint 2, Squamous cell carcinoma antigen recognized by T cell, Serologically defined colon cancer antigen 1, Serologically defined breast cancer antigen NY-BR-15, Serologically defined breast cancer antigen NY-BR-16, Chromogranin A, parathyroid secretory protein 1, DUPAN-2, CA 19-9, CA 72-4, CA 195 and L6.

Clause 257. The fusion protein of any of Clauses 244-246, wherein the B cell target is selected from the group consisting of CD10, CD19, CD20, CD21, CD22, CD23, CD24, CD37, CD38, CD39, CD40, CD72, CD73, CD74, CDw75, CDw76, CD77, CD78, CD79a/b, CD80, CD81, CD82, CD83, CD84, CD85, CD86, CD89, CD98, CD126, CD127, CDwl30, CD138 and CDwl50.

Clause 258. The fusion protein of any of Clauses 244-246, wherein the angiogenesis target is selected from the group consisting of Angiopoietin-1, Angiopoietin-like 2, Angiopoietin-2, Angiopoietin-like 3, Angiopoietin-3, Angiopoietin-like 7/CDT6, Angiopoietin-4, Tie-1, Angiopoietin-like 1, Tie-2, Angiogenin, iNOS, Coagulation Factor III/Tissue Factor, nNOS, CTGF/CCN2, NOV/CCN3, DANCE, OSM, EDG-1, Plfr, EG-VEGF/PK1, Proliferin, Endostatin, ROB04, Erythropoietin, Thrombospondin-1, Kininostatin, Thrombospondin-2, MFG-E8, Thrombospondin-4, Nitric Oxide, VG5Q, eNOS, EphAI, EphA5, EphA2, EphA6, EphA3, EphA7, EphA4, EphA8, EphBI, EphB4, EphB2, EphB6, EphB3, Ephrin-AI, Ephrin-A4, Ephrin-A2, Ephrin-A5, Ephrin-A3, Ephrin-B I, Ephrin-B3, Ephrin-B2, FGF acidic, FGF-12, FGF basic, FGF-13, FGF-3, FGF-16, FGF-4, FGF-17, FGF-5, FGF-19, FGF-6, FGF-20, FGF-8, FGF-21, FGF-9, FGF-23, FGF-10, KGF/FGF-7, FGF-11, FGF RI, FGF R4, FGF R2, FGF R5, FGF R3, Neuropilin-1, Neuropilin-2, Semaphorin 3 A, Semaphorin 6B, Semaphorin 3C, Semaphorin 6C, Semaphorin 3E, Semaphorin 6D, Semaphorin 6A, Semaphorin 7A, MMP, MMP-11, MMP-1, MMP-12, MMP-2, MMP-13, MMP-3, MMP-14, MMP-7, MMP-15, MMP-8, MMP-16/MT3-MMP, MMP-9, MMP-24/MT5-MMP, MMP-10, MMP-25/MT6-MMP, TIMP-1, TIMP-3, TIMP-2, TIMP-4, ACE, IL-13 R a 1, IL-13, Clq R1/CD93, Integrin a 4/CD49d, VE-Cadherin, Integrin β 2/CD18, CD31/PECAM-1, KLF4, CD36/SR-B3, LYVE-1, CD151, MCAM, CL-P1/COLEC12, Nectin-2/CD112, Coagulation Factor III/Tissue Factor, E-Selectin, D6, P-Selectin, DC-SIGNR/CD299, SLAM, EMMPRIN/CD 147, Tie-2, Endoglin/CD105, TNF RI/TNFRSF1A, EPCR, TNF RII/TNFRSF1B, Erythropoietin R, TRAIL RI/TNFRSFIOA, ESAM, TRAIL R2/TNFRSF10B, FABP5, VCAM-1, ICAM-1/CD54, VEGF R2/Flk-1, ICAM-2/CD102, VEGF R3/Flt-4, IL-1 RI and VG5Q.

Clause 259. An isolated polypeptide or the fusion protein according to any of the foregoing Clauses which agonizes at least one immune inhibitory effect of VSIG8 and/or VISTA.

Clause 260. An isolated polypeptide or fusion protein according to Clause 259 which mediates at least one of the following effects: (i) decreases immune response, (ii) decreases T cell activation, (iii) decreases cytotoxic T cell activity, (iv) decreases natural killer (NK) cell activity, (v) decreases T-cell activity, (vi) decreases pro-inflammatory cytokine secretion, (vii) decreases IL-2 secretion; (viii) decreases interferon-y production by T-cells, (ix) decreases Thl response, (x) decreases Th2 response, (xi) increases cell number and/or activity of regulatory T cells, (xii) increases regulatory cell activity and/or one or more of myeloid derived suppressor cells (MDSCs), iMCs, mesenchymal stromal cells, TIE2-expressing monocytes, (xiii) increases regulatory cell activity and/or the activity of one or more of myeloid derived suppressor cells (MDSCs), iMCs, mesenchymal stromal cells, TIE2-expressing monocytes, (xiii) increases M2 macrophages, (xiv) increases M2 macrophage activity, (xv) increases N2 neutrophils, (xvi) increases N2 neutrophils activity, (xvii) increases inhibition of T cell activation, (xviii) increases Inhibition of CTL activation, (xix) increases inhibition of NK cell activation, (xx) increases T cell exhaustion, (xxi) decreases T cell response, (xxii) decreases activity of cytotoxic cells, (xxiii) reduces antigen-specific memory responses, (xxiv) inhibits apoptosis or lysis of cells, (xxv) decreases cytotoxic or cytostatic effect on cells, (xxvi) reduces direct killing of cells, (xxvii) decreases Thl7 activity, and/or (xxviii) reduces complement dependent cytotoxicity and/or antibody dependent cell-mediated cytotoxicity, with the proviso that said isolated or recombinant VSIG8 polypeptide or fusion protein may elicit an opposite effect to one or more of (i)-(xxviii).

Clause 261. An isolated polypeptide or fusion protein according to any of the foregoing Clauses which antagonizes at least one immune inhibitory effect of VSIG8 and/or VISTA.

Clause 262. An isolated polypeptide or fusion protein according to Clause 261 which mediates at least one of the following effects (i) increases immune response, (ii) increases T cell activation, (iii) increases cytotoxic T cell activity, (iv) increases NK cell activity, (v) alleviates T-cell suppression, (vi) increases pro-inflammatory cytokine secretion, (vii) increases IL-2 secretion; (viii) increases interferon-y production by T-cells, (ix) increases Thl response, (x) decrease Th2 response, (xi) decreases or eliminates cell number and/or activity of at least one of regulatory T cells (Tregs), myeloid derived suppressor cells (MDSCs), iMCs, mesenchymal stromal cells, TIE2-expressing monocytes, (xii) reduces regulatory cell activity, and/or the activity of one or more of myeloid derived suppressor cells (MDSCs), iMCs, mesenchymal stromal cells, TIE2-expressing monocytes, (xiii) decreases or eliminates M2 macrophages, (xiv) reduces M2 macrophage pro-tumorigenic activity, (xv) decreases or eliminates N2 neutrophils, (xvi) reduces N2 neutrophils pro-tumorigenic activity, (xvii) reduces inhibition of T cell activation, (xviii) reduces inhibition of CTL activation, (xix) reduces inhibition of NK cell activation, (xx) reverses T cell exhaustion, (xxi) increases T cell response, (xxii) increases activity of cytotoxic cells, (xxiii) stimulates antigen-specific memory responses, (xxiv) elicits apoptosis or lysis of cancer cells, (xxv) stimulates cytotoxic or cytostatic effect on cancer cells, (xxiv) induces direct killing of cancer cells, (xxvi) increases Thl7 activity and/or (xxvii) induces complement dependent cytotoxicity and/or antibody dependent cell-mediated cytotoxicity, with the proviso that said isolated or recombinant VSIG8 polypeptide or fusion protein may elicit an opposite effect to one or more of (i)-(xxvii).

Clause 263. An isolated polypeptide or fusion protein according to any of the above Clauses which agonizes or antagonizes at least one effect of VSIG8 and/or VISTA on T cells, natural killer (NK) cells or the production of one or more proinflammatory cytokines.

Clause 264. An isolated polypeptide or fusion protein according to any of the above Clauses which inhibits or promotes one or more of CTL activity, CD4+ T cell activation and/or CD4+ T cell proliferation and/or cell depletion or the secretion of proinflammatory cytokines.

Clause 265. An isolated polypeptide or fusion protein according to any of the above Clauses which inhibits or promotes NK cell activity.

Clause 266. An Isolated polypeptide or fusion protein according to any of the above Clauses which inhibits or promotes the differentiation, proliferation and/or activity of Tregs, MDSCs, iMCs, mesenchymal stromal cells, TIE2-expressing monocytes, and/or the infiltration of Tregs (Tregs), MDSCs iMCs, mesenchymal stromal cells, TIE2-expressing monocytes.

Clause 267. The polypeptide or fusion protein of Clause 266, wherein said Tregs are inducible Tregs.

Clause 268. An isolated polypeptide or fusion protein according to any of the foregoing Clauses which specifically binds to a receptor expressed by NK cells.

Clause 269. An isolated polypeptide or fusion protein according to any of the foregoing Clauses which specifically binds to a receptor expressed by activated T cells or dendritic or myeloid suppressor or monocyte or neutrophil cells.

Clause 270. A polynucleotide encoding an isolated polypeptide or fusion protein according to any of the foregoing Clauses.

Clause 271. An expression vector or a virus, comprising at least one polynucleotide according to Clause 270.

Clause 272. A recombinant cell comprising an expression vector according to Clause 270 or a virus containing a polynucleotide according to Clause 271, wherein the cell constitutively or inducibly expresses the polypeptide encoded by the DNA segment.

Clause 273. A method of producing an isolated polypeptide or fusion protein according to any of Clauses 200-269, comprising culturing the recombinant cell according to Clause 272, under conditions whereby the cell expresses the polypeptide encoded by the DNA segment or nucleic acid and recovering said polypeptide.

Clause 274. A pharmaceutical composition comprising the isolated protein or fusion protein of any of Clauses 200-269 or comprising a VSIG8 ECD protein set forth in any of SEQ ID NOs:1, 2, 3, the polynucleotide of Clause 270, the expression vector or virus of Clause 271, or the recombinant cell of Clause 272.

Clause 275. A pharmaceutical composition according to Clause 274, the isolated polypeptide or fusion protein of any of Clauses 200-269, the polynucleotide of Clause 270, the expression vector or virus of Clause 271, the recombinant cell of Clause 272, for use in treatment in a subject suffering from cancer.

Clause 276. The pharmaceutical composition, cancer immunotherapy, the isolated polypeptide or fusion protein, the polynucleotide, the expression vector or virus, the recombinant cell or the use of Clause 275, for use in immunotherapy treatment of cancer.

Clause 277. The pharmaceutical composition, cancer immunotherapy, the isolated polypeptide or fusion protein, the polynucleotide, the expression vector or virus, the recombinant cell or the use of Clauses 275 or 276, wherein the cancer does not express sufficient levels of VSIG8 protein at diagnosis or prior to the treatment.

Clause 278. The pharmaceutical composition, cancer immunotherapy, the isolated polypeptide or fusion protein, the polynucleotide, the expression vector or virus, the recombinant cell or the use of Clauses 275 or 276, wherein the cancer does express sufficient levels of VSIG8 protein at diagnosis or prior to the treatment.

Clause 279. The pharmaceutical composition, cancer immunotherapy, the isolated polypeptide or fusion protein, the polynucleotide, the expression vector or virus, the recombinant cell or the use of any of Clauses 275-278, wherein said pharmaceutical composition, isolated polypeptide, fusion protein, polynucleotide, expression vector, virus or cell is administered to the subject in need thereof in combination with a therapeutic agent useful for treatment of cancer.

Clause 280. The pharmaceutical composition, cancer immunotherapy, the Isolated polypeptide or fusion protein, the polynucleotide, the expression vector or virus, the recombinant cell or the use of any of Clauses 275-279, for performing at least one of the following: (i) increasing immune response, (ii) increasing T cell activation, (iii) increasing cytotoxic T cell activity, (iv) increasing NK cell activity, (v) increasing Thl7 activity, (vi) alleviating T-cell suppression, (vii) increasing pro-inflammatory cytokine secretion, (viii) increasing IL-2 secretion; (ix) increasing interferon-y production by T-cells, (x) increasing Thl response, (xi) decreasing Th2 response, (xii) decreasing or eliminating at least one of regulatory T cells (Tregs), myeloid derived suppressor cells (MDSCs), iMCs, mesenchymal stromal cells, TIE2-expressing monocytes, (xiii) reducing regulatory cell activity and/or the activity of one or more of myeloid derived suppressor cells (MDSCs), iMCs, mesenchymal stromal cells, TIE2-expressing monocytes, (xiv) decreasing or eliminating M2 macrophages, (xv) reducing M2 macrophage pro-tumorigenic activity, (xvi) decreases or eliminates N2 neutrophils, (xvii) reduces N2 neutrophils pro-tumorigenic activity, (xviii) reducing inhibition of T cell activation, (xix) reducing inhibition of CTL activation, (xx) reducing inhibition of NK cell activation, (xxi) reversing T cell exhaustion, (xxii) increasing T cell response, (xxiii) increasing activity of cytotoxic cells, (xxiv) stimulating antigen-specific memory responses, (xxv) eliciting apoptosis or lysis of cancer cells, (xxvi) stimulating cytotoxic or cytostatic effect on cancer cells, (xxvii) inducing direct killing of cancer cells, and/or (xxviii) inducing complement dependent cytotoxicity and/or (xxix) inducing antibody dependent cell-mediated cytotoxicity.

Clause 281. The pharmaceutical composition, cancer immunotherapy, the isolated polypeptide or fusion protein, the polynucleotide, the expression vector or virus, the recombinant cell or the use of any of Clauses 275-280, further comprising administering an additional therapy comprising one or more of radiotherapy, cryotherapy, antibody therapy, chemotherapy, photodynamic therapy, surgery, hormonal deprivation, targeted therapy agent, a cancer vaccine or combination therapy with conventional drugs.

Clause 282. The pharmaceutical composition, cancer immunotherapy, the isolated polypeptide or fusion protein, the polynucleotide, the expression vector or virus, the recombinant cell or the use of any of Clauses 275-281, wherein the therapeutic agent or additional therapy is selected from the group consisting of cytotoxic drugs, tumor vaccines, antibodies, peptides, pepti-bodies, small molecules, chemotherapeutic agents, cytotoxic and cytostatic agents, immunological modifiers, interferons, interleukins, immunostimulatory growth hormones, cytokines, vitamins, minerals, aromatase inhibitors, RNAi, Histone Deacetylase Inhibitors, and proteasome inhibitors.

Clause 283. The pharmaceutical composition, cancer immunotherapy, the isolated polypeptide or fusion protein, the polynucleotide, the expression vector or virus, the recombinant cell or the use of any of Clauses 275-282, administered to a subject simultaneously or sequentially in combination with one or more therapeutic agents, additional therapy or potentiating agents to obtain a therapeutic effect, wherein said one or more potentiating agents is selected from the group consisting of radiotherapy, conventional/classical anti-cancer therapy potentiating anti-tumor immune responses, Targeted therapy potentiating anti-tumor immune responses, Therapeutic agents targeting immunosuppressive cells Tregs and/or MDSCs, Immunostimulatory antibodies, Cytokine therapy, and Adoptive cell transfer.

Clause 284. The pharmaceutical composition, cancer immunotherapy, the isolated polypeptide or fusion protein, the polynucleotide, the expression vector or virus, the recombinant cell or the use of any of Clauses 275-283, wherein the conventional/classical anti-cancer agent is selected from the group consisting of platinum based compounds, antibiotics with anti-cancer activity, Anthracyclines, Anthracenediones, alkylating agents, antimetabolites, Antimitotic agents, Taxanes, Taxoids, microtubule inhibitors, *Vinca* alkaloids, Folate antagonists, Topoisomerase inhibitors, Antiestrogens, Antiandrogens, Aromatase inhibitors, GnRh analogs, inhibitors of 5a-reductase, bisphosphonates and antibodies.

Clause 285. The pharmaceutical composition, cancer immunotherapy, the isolated polypeptide or fusion protein, the polynucleotide, the expression vector or virus, the recombinant cell or the use of any of Clauses 275-284, wherein the Targeted therapy agent is selected from the group consisting of histone deacetylase (HDAC) inhibitors, proteasome inhibitors, mTOR pathway inhibitors, JAK2 inhibitors, tyrosine kinase inhibitors (TKIs), PI3K inhibitors, Protein kinase inhibitors, Inhibitors of serine/threonine kinases, inhibitors of intracellular signaling, inhibitors of Ras/Raf signaling, MEK inhibitors, AKT inhibitors, inhibitors of survival signaling proteins, cyclin dependent kinase inhibitors, therapeutic monoclonal antibodies, TRAIL pathway agonists, anti-angiogenic agents, metalloproteinase inhibitors, cathepsin inhibitors, inhibitors of urokinase plasminogen activator receptor function, immunoconjugates, antibody drug conjugates, antibody fragments, bispecific antibodies, bispecific T cell engagers (BiTEs).

Clause 286. The pharmaceutical composition, cancer immunotherapy, the isolated polypeptide or fusion protein, the polynucleotide, the expression vector or virus, the recombinant cell or the use of any of Clauses 275-285, wherein the antibody is selected from cetuximab, panitumumab, nimotuzumab, trastuzumab, pertuzumab, rituximab, ofatumumab, veltuzumab, alemtuzumab, labetuzumab, adecatumumab, oregovomab, onartuzumab; apomab, mapatumumab, lexatumumab, conatumumab, tigatuzumab, catumaxomab, blinatumomab, ibritumomab triuxetan, tositumomab, brentuximab vedotin, gemtuzumab ozogamicin, clivatuzumab tetraxetan, pemtumomab, trastuzumab emtansine, bevacizumab, etaracizumab, volociximab, ramucirumab, aflibercept.

Clause 287. The pharmaceutical composition, cancer immunotherapy, the isolated polypeptide or fusion protein, the polynucleotide, the expression vector or virus, the recombinant cell or the use of any of Clauses 275-286, wherein the Therapeutic agent targeting immunosuppressive cells Tregs and/or MDSCs is selected from antimitotic drugs, cyclophosphamide, gemcitabine, mitoxantrone, fludarabine, thalidomide, thalidomide derivatives, COX-2 inhibitors, depleting or killing antibodies that directly target Tregs through recognition of Treg cell surface receptors, anti-CD25 daclizumab, basiliximab, ligand-directed toxins, denileukin diftitox (Ontak)—a fusion protein of human IL-2 and diphtheria toxin, or LMB-2—a fusion between an scFv against CD25 and the *pseudomonas* exotoxin, antibodies targeting Treg cell surface receptors, TLR modulators, agents that interfere with the adenosinergic pathway, ectonucleotidase inhibitors, or inhibitors of the A2A adenosine receptor, TGF-β inhibitors, chemokine receptor inhibitors, retinoic acid, all-trans retinoic acid (ATRA), Vitamin D3, phosphodiesterase 5 inhibitors, sildenafil, ROS inhibitors and nitroaspirin.

Clause 288. The pharmaceutical composition, cancer immunotherapy, the isolated polypeptide or fusion protein, the polynucleotide, the expression vector or virus, the recombinant cell or the use of any of Clauses 275-287, wherein the Immunostimulatory antibody is selected from antagonistic antibodies targeting one or more of CTLA4, PD-1, PDL-1, LAG-3, TIM-3, BTLA, B7-H4, B7-H3, VISTA, and/or Agonistic antibodies targeting one or more of CD40, CD 137, OX40, GITR, CD27, CD28 or ICOS.

Clause 289. The pharmaceutical composition, cancer immunotherapy, the isolated polypeptide or fusion protein, the polynucleotide, the expression vector or virus, the recombinant cell or the use of any of Clauses 275-288, wherein the therapeutic cancer vaccine is selected from exogenous cancer vaccines including proteins or peptides used to mount an immunogenic response to a tumor antigen, recombinant virus and bacteria vectors encoding tumor antigens, DNA-based vaccines encoding tumor antigens, proteins targeted to dendritic cell-based vaccines, whole tumor cell vaccines, gene modified tumor cells expressing GM-CSF, ICOS and/or Flt3-ligand, oncolytic virus vaccines.

Clause 290. The pharmaceutical composition, cancer immunotherapy, the isolated polypeptide or fusion protein, the polynucleotide, the expression vector or virus, the recombinant cell or the use of any of Clauses 275-289, wherein the cytokine therapy is selected from one or more of the cytokines IL-2, IL-7, IL-12, IL-15, IL-17, IL-18 and IL-21, IL23, IL-27, GM-CSF, IFNa (interferon alpha), IFNa-2b, IPNβ, IFNy, and their different strategies for delivery.

Clause 291. The pharmaceutical composition, cancer immunotherapy, the isolated polypeptide or fusion protein, the polynucleotide, the expression vector or virus, the recombinant cell or the use of any of Clauses 275-290, wherein the adoptive cell transfer therapy is carried out following ex vivo treatment selected from expansion of the patient autologous naturally occurring tumor specific T cells or genetic modification of T cells to confer specificity for tumor antigens.

Clause 292. An assay for diagnosing or aiding in the diagnosis of a disease in a subject, wherein the disease is selected from the group consisting of cancer, autoimmune disease, or an infectious disease, comprising the isolated polypeptide or fusion protein of any of the above Clauses and/or with VSIG8 ECD protein set forth in any of SEQ ID NOs: 1, 2, 3, and a detector for detecting specific binding of the isolated protein or fusion protein to a tissue sample taken from the subject.

Clause 293. A diagnostic method for diagnosing or aiding in the diagnosis of a disease in a subject, wherein the disease is selected from the group consisting of cancer, autoimmune disease, or infectious disease, comprising using the assay of Clause 292 for performing the method.

Clause 294. A diagnostic method for diagnosing or aiding in the diagnosis of a disease in a subject, wherein the disease is selected from the group consisting of cancer, autoimmune disease, or infectious disease, wherein the diagnostic method is performed ex vivo, and comprises contacting a tissue sample from the subject with the isolated polypeptide or fusion protein of any of the above Clauses and/or with VSIG8 ECD protein set forth in any of SEQ ID NOs: 1, 2, 3, and detecting specific binding to the tissue sample.

Clause 295. A diagnostic method for diagnosing or aiding in the diagnosis of a disease in a subject, wherein the disease is selected from the group consisting of cancer, autoimmune disease, or an infectious disease, wherein the diagnostic method is performed in vivo, comprising administering the isolated polypeptide or fusion protein of any of the above Clauses, and/or with VSIG8 ECD protein set forth in any of SEQ ID NOs: 1, 2, 3, to a subject and detecting specific binding to tissues.

Clause 296. The method of any of Clauses 293-295, or use of the assay of Clause 292 wherein the diagnostic method is performed before therapy or treatment comprising administering the isolated polypeptide or fusion protein of any of Clauses 200-269, the polynucleotide of Clause 270, the expression vector or virus of Clause 271, the recombinant cell of Clause 272, the pharmaceutical composition of Clause 274, the use of Clause 275, or the protein, the polynucleotide, the expression vector or virus, the recombinant cell, the pharmaceutical composition, or the use of any of Clauses 276-291, to the subject.

Clause 297. The method of any of Clauses 293-296, for screening for a disease, screening for VSIG8-mediated immunosuppression, detecting a presence or a severity of a disease, providing prognosis of a disease, monitoring disease progression or relapse, as well as assessment of treatment efficacy and/or relapse of a disease, disorder or condition, as well as selecting a therapy and/or a treatment for a disease, optimization of a given therapy for a disease, monitoring the treatment of a disease, and/or predicting the suitability of a therapy for specific patients or subpopulations or determining the appropriate dosing of a therapeutic product in patients or subpopulations.

Clause 298. The isolated polypeptide or fusion protein of any of Clauses 200-269, the polynucleotide of Clause 270, the expression vector or virus of Clause 271, the recombinant cell of Clause 272, the pharmaceutical composition of Clause 274, the use of Clause 275, or the protein, the polynucleotide, the expression vector or virus, the recombinant cell, the pharmaceutical composition, the use of any of Clauses 276-291, the assay of Clause 292 or the method of any of Clauses 94-98, wherein said cancer is selected from the group consisting of breast cancer, cervical cancer, ovary cancer, endometrial cancer, melanoma, uveal melanoma, bladder cancer, lung cancer, pancreatic cancer, colorectal cancer, prostate cancer, leukemia, acute lymphocytic leukemia, chronic lymphocytic leukemia, B-cell lymphoma, Burkitt's lymphoma, multiple myeloma, Non-Hodgkin's lymphoma, myeloid leukemia, acute myelogenous leukemia (AML), chronic myelogenous leukemia, thyroid cancer, thyroid follicular cancer, myelodysplastic syndrome (MDS), fibrosarcomas and rhabdomyosarcomas, teratocarcinoma, neuroblastoma, glioma, glioblastoma, benign tumor of the skin, keratoacanthomas, renal cancer, anaplastic large-cell lymphoma, esophageal cancer, follicular dendritic cell carcinoma, seminal vesicle tumor, epidermal carcinoma, spleen cancer, bladder cancer, head and neck cancer, stomach cancer, liver cancer, bone cancer, brain cancer, cancer of the retina, biliary cancer, small bowel cancer, salivary gland cancer, cancer of uterus, cancer of testicles, cancer of connective tissue, myelodysplasia, Waldenstrom's macroglobinaemia, nasopharyngeal, neuroendocrine cancer, mesothelioma, angiosarcoma, Kaposi's sarcoma, carcinoid, fallopian tube cancer, peritoneal cancer, papillary serous millierian cancer, malignant ascites, gastrointestinal stromal tumor (GIST), Li-Fraumeni syndrome and Von Hippel-Lindau syndrome (VHL), cancer of unknown origin either primary or metastatic, wherein the cancer is non-metastatic, invasive or metastatic.

Clause 299. The isolated protein, the fusion protein, the polynucleotide, the expression vector or virus, the recombinant cell, the pharmaceutical composition, the assay or the method of Clause 298, wherein said breast cancer is breast carcinoma, and is selected from the group consisting of ductal-carcinoma, infiltrating ductal carcinoma, lobular carcinoma, mucinous adenocarcinoma, intra duct and invasive ductal carcinoma, and Scirrhous adenocarcinoma.

Clause 300. The isolated protein, the fusion protein, the polynucleotide, the expression vector or virus, the recombinant cell, the pharmaceutical composition, the assay or the method of Clause 298, wherein said colon cancer is selected from the group consisting of Poorly to Well Differentiated invasive and noninvasive Adenocarcinoma, Poorly to Well Differentiated Adenocarcinoma of the cecum, Well to Poorly Differentiated Adenocarcinoma of the colon, Tubular adenocarcinoma, preferably Grade 2 Tubular adenocarcinoma of the ascending colon, colon adenocarcinoma Duke's stage CI, invasive adenocarcinoma, Adenocarcinoma of the rectum, preferably Grade 3 Adenocarcinoma of the rectum, Moderately Differentiated Adenocarcinoma of the rectum, Moderately Differentiated Mucinous adenocarcinoma of the rectum.

Clause 301. The isolated protein, the fusion protein, the polynucleotide, the expression vector or virus, the recombinant cell, the pharmaceutical composition, the assay or the method of Clause 298, wherein said lung cancer is selected from the group consisting of Well to Poorly differentiated Non-small cell carcinoma, Squamous Cell Carcinoma, preferably well to poorly Differentiated Squamous Cell Carcinoma, keratinizing squamous cell carcinoma, adenocarcinoma, preferably poorly to well differentiated adenocarcinoma, large cell adenocarcinoma, Small cell lung cancer, preferably Small cell lung carcinoma, more preferably undifferentiated Small cell lung carcinoma.

Clause 302. The isolated protein, the fusion protein, the polynucleotide, the expression vector or virus, the recombinant cell, the pharmaceutical composition, the assay or the method of Clause 298, wherein said prostate cancer is prostate adenocarcinoma and is selected from the group consisting of Adenocarcinoma Gleason Grade 6 to 9, Infiltrating adenocarcinoma, High grade prostatic intraepithelial neoplasia, undifferentiated carcinoma.

Clause 303. The isolated protein, the fusion protein, the polynucleotide, the expression vector or virus, the recombinant cell, the pharmaceutical composition, the assay or the method of Clause 298, wherein said stomach cancer is moderately differentiated gastric adenocarcinoma.

Clause 304. The isolated protein, the fusion protein, the polynucleotide, the expression vector or virus, the recombinant cell, the pharmaceutical composition, the assay or the method of Clause 298, wherein said ovarian cancer is selected from the group consisting of cystadenocarcinoma, serous papillary cystic carcinoma, Serous papillary cystic carcinoma, Invasive serous papillary carcinoma.

Clause 305. The isolated protein, the fusion protein, the polynucleotide, the expression vector or virus, the recombinant cell, the pharmaceutical composition, the assay or the method of Clause 298, wherein said brain cancer is selected from the group consisting of Astrocytoma, with the proviso that it is not a grade 2 astrocytoma, preferably grade 4 Astrocytoma, or Glioblastoma multiforme.

Clause 306. The isolated protein, the fusion protein, the polynucleotide, the expression vector or virus, the recombinant cell, the pharmaceutical composition, the assay or the method of Clause 298, wherein said brain cancer is astrocytoma.

Clause 307. The isolated protein, the fusion protein, the polynucleotide, the expression vector or virus, the recombinant cell, the pharmaceutical composition, the assay or the method of Clause 298, wherein said kidney cancer is clear cell renal cell carcinoma.

Clause 308. The isolated protein, the fusion protein, the polynucleotide, the expression vector or virus, the recombinant cell, the pharmaceutical composition, the assay or the method of Clause 298, wherein liver cancer is Hepatocellular carcinoma.

Clause 309. The isolated protein, the fusion protein, the polynucleotide, the expression vector or virus, the recombinant cell, the pharmaceutical composition, the assay or the method of Clause 308, wherein said Hepatocellular carcinoma is Low Grade hepatocellular carcinoma or Fibrolamellar Hepatocellular Carcinoma.

Clause 310. The isolated protein, the fusion protein, the polynucleotide, the expression vector or virus, the recombinant cell, the pharmaceutical composition, the assay or the method of Clause 298, wherein said lymphoma is selected from the group consisting of Hodgkin's Lymphoma and High to low grade Non-Hodgkin's Lymphoma.

Clause 311. The isolated protein, the fusion protein, the polynucleotide, the expression vector or virus, the recombinant cell, the pharmaceutical composition, the assay or the method of Clause 298, for treating a subject suffering from a disease selected from the group consisting of B-cell lymphoma, Burkitt's lymphoma, thyroid cancer, thyroid follicular cancer, myelodysplastic syndrome (MDS), fibrosarcomas and rhabdomyosarcomas, melanoma, uveal melanoma, teratocarcinoma, neuroblastoma, glioma, glioblastoma cancer, keratoacanthomas, anaplastic large-cell lymphoma, esophageal squamous cells carcinoma, hepatocellular carcinoma cancer, follicular dendritic cell carcinoma, muscle-invasive cancer, seminal vesicle tumor, epidermal carcinoma, cancer of the retina, biliary cancer, small bowel cancer, salivary gland cancer, cancer of connective tissue, myelodysplasia, Waldenstrom's macroglobinaemia, nasopharyngeal, neuroendocrine cancer, myelodysplastic syndrome, mesothelioma, angiosarcoma, Kaposi's sarcoma, carcinoid, esophagogastric, fallopian tube cancer, peritoneal cancer, papillary serous miillerian cancer, malignant ascites, gastrointestinal stromal tumor (GIST), Li-Fraumeni syndrome and Von Hippel-Lindau syndrome (VHL); endometrial cancer, Breast carcinoma, preferably any of ductal-carcinoma, infiltrating ductal carcinoma, lobular carcinoma, mucinous adenocarcinoma, intra duct and invasive ductal carcinoma, and Scirrhous adenocarcinoma, Colorectal adenocarcinoma, preferably any of Poorly to Well Differentiated invasive and noninvasive Adenocarcinoma, Poorly to Well Differentiated Adenocarcinoma of the cecum, Well to Poorly Differentiated Adenocarcinoma of the colon, Tubular adenocarcinoma, preferably Grade 2 Tubular adenocarcinoma of the ascending colon, colon adenocarcinoma Duke's stage CI, invasive adenocarcinoma, Adenocarcinoma of the rectum, preferably Grade 3 Adenocarcinoma of the rectum, Moderately Differentiated Adenocarcinoma of the rectum, Moderately Differentiated Mucinous adenocarcinoma of the rectum; Lung cancer, preferably any of Well to Poorly differentiated Non-small cell carcinoma, Squamous Cell Carcinoma, preferably well to poorly Differentiated Squamous Cell Carcinoma, keratinizing squamous cell carcinoma, adenocarcinoma, preferably poorly to well differentiated adenocarcinoma, large cell adenocarcinoma, Small cell lung cancer, preferably Small cell lung carcinoma, more preferably undifferentiated Small cell lung carcinoma; Prostate adenocarcinoma, preferably any of Adenocarcinoma Gleason Grade 6 to 9, Infiltrating adenocarcinoma, High grade prostatic intraepithelial neoplasia, undifferentiated carcinoma; Stomach adenocarcinoma, preferably moderately differentiated gastric adenocarcinoma; Ovary carcinoma, preferably any of cystadenocarcinoma, serous papillary cystic carcinoma, Serous papillary cystic carcinoma, Invasive serous papillary carcinoma; Brain cancer, preferably any of Astrocytoma, with the proviso that it is not a grade 2 astrocytoma, preferably grade 4 Astrocytoma, Glioblastoma multiforme; Kidney carcinoma, preferably Clear cell renal cell carcinoma; Liver cancer, preferably any of Hepatocellular carcinoma, preferably Low Grade hepatocellular carcinoma, Fibrolamellar Hepatocellular Carcinoma; Lymphoma, preferably any of, Hodgkin's Lymphoma and High to low grade Non-Hodgkin's Lymphoma.

Clause 312. A pharmaceutical composition according to Clause 274, the isolated polypeptide or fusion protein of any of Clauses 200-269, the polynucleotide of Clause 270, the expression vector or virus of Clause 271, or the recombinant cell of Clause 272, for use in the treatment of an immune condition in a subject suffering from same.

Clause 313. The pharmaceutical composition, the isolated polypeptide or fusion protein, the polynucleotide, the expression vector or virus, the recombinant cell or the use of Clause 312, wherein said pharmaceutical composition, isolated polypeptide, fusion protein, polynucleotide, expression vector, virus or cell is administered to the subject in need thereof in combination with a therapeutic agent useful for treatment of an immune condition.

Clause 314. The pharmaceutical composition, the isolated polypeptide or fusion protein, the polynucleotide, the expression vector or virus, the recombinant cell or the use of Clauses 312 or 313, for treating an immune condition, in a subject in need thereof.

Clause 315. The pharmaceutical composition, the isolated polypeptide or fusion protein, the polynucleotide, the expression vector or virus, the recombinant cell or the use of any of Clauses 312-314, wherein said protein, said polynucleotide, said expression vector or virus, said recombinant cell, or said pharmaceutical composition is used for treatment of treatment of immune related diseases and/or for reducing the undesirable immune activation that follows gene or cell therapy, or transplantation of cells, tissues, and/or organs into a subject, and is capable of at least one of: inhibiting immune response, reducing T cell activity, reducing NK cell activity, enhancing regulatory cell activity, enhancing T-cell suppression, enhancing immune regulatory cell activity, inducing establishment of immune tolerance, reducing pro-inflammatory cytokine secretion, re-establishing Thl-Th2 immune balance, reducing immune memory responses to self-antigens, decreasing or eliminating pro-inflammatory immune cells, decreasing or eliminating auto-reactive immune cells.

Clause 316. The pharmaceutical composition, the isolated polypeptide or fusion protein, the polynucleotide, the expression vector or virus, the recombinant cell or the use of any of Clauses 312-315, for performing at least one of the following: (i) decreasing immune response, (ii) decreasing T cell activation, (iii) decreasing cytotoxic T cell activity, (iv) decreasing natural killer (NK) cell activity, (v) decreasing T-cell activity, (vi) decreasing Thl7 activity, (vii) decreasing pro-inflammatory cytokine secretion, (viii) decreasing IL-2 secretion; (ix) decreasing interferon-y production by T-cells, (x) decreasing Thl response, (xi) decreasing Th2 response, (xii) increasing regulatory T cells and/or one or more of myeloid derived suppressor cells (MDSCs), iMCs, mesenchymal stromal cells, TIE2-expressing monocytes, (xiii) increasing regulatory cell activity and/or the activity of one or more of myeloid derived suppressor cells (MDSCs), iMCs, mesenchymal stromal cells, TIE2-expressing monocytes, (xiv) increasing M2 macrophages, (xv) increasing M2 macrophage activity, (xvi) increasing N2 neutrophils, (xvii) increasing N2 neutrophils activity, (xviii) increasing inhibition of T cell activation, (xix) increasing inhibition of CTL activation, (xx) increasing inhibition of NK cell activation, (xxi) increasing T cell exhaustion, (xxii) decreasing T cell response, (xxiii) decreasing activity of cytotoxic cells, (xxiv) reducing antigen-specific memory responses, (xxv) inhibiting apoptosis or lysis of cells, (xxvi) decreasing cytotoxic or cytostatic effect on cells, (xxvii) reducing direct killing of cells, and/or (xxviii) reducing complement dependent cytotoxicity and/or (xxix) reducing antibody dependent cell-mediated cytotoxicity.

Clause 317. The pharmaceutical composition, the isolated polypeptide or fusion protein, the polynucleotide, the expression vector or virus, the recombinant cell or the use of any of Clauses 312-316, wherein said immune condition is selected from the group consisting of autoimmune disease, transplant rejection, and graft versus host disease.

Clause 318. The pharmaceutical composition, the isolated polypeptide or fusion protein, the polynucleotide, the expression vector or virus, the recombinant cell or the use of any of Clauses 312-316, wherein said autoimmune disease is selected from the group consisting of multiple sclerosis, psoriasis; rheumatoid arthritis; psoriatic arthritis, systemic lupus erythematosus (SLE); discoid lupus erythematosus, inflammatory bowel disease, ulcerative colitis; Crohn's disease; benign lymphocytic angiitis, thrombocytopenic purpura, idiopathic thrombocytopenia, idiopathic autoimmune hemolytic anemia, pure red cell aplasia, Sjogren's syndrome, rheumatic disease, connective tissue disease, inflammatory rheumatism, degenerative rheumatism, extra-articular rheumatism, juvenile rheumatoid arthritis, arthritis uratica, muscular rheumatism, chronic polyarthritis, cryoglobulinemic vasculitis, ANCA-associated vasculitis, antiphospholipid syndrome, myasthenia gravis, autoimmune hemolytic anaemia, Guillain-Barre syndrome, chronic immune polyneuropathy, autoimmune thyroiditis, insulin dependent diabetes mellitus, type I diabetes, Addison's disease, membranous glomerulonephropathy, Goodpasture's disease, autoimmune gastritis, autoimmune atrophic gastritis, pernicious anaemia, pemphigus, pemphigus vulgaris, cirrhosis, primary biliary cirrhosis, dermatomyositis, polymyositis, fibromyositis, myogelosis, celiac disease, immunoglobulin A nephropathy, Henoch-Schonlein purpura, Evans syndrome, Dermatitis, atopic dermatitis, psoriasis, psoriasis arthropathica, Graves' disease, Graves' ophthalmopathy, scleroderma, systemic scleroderma, progressive systemic scleroderma, asthma, allergy, primary biliary cirrhosis, Hashimoto's thyroiditis, primary myxedema, sympathetic ophthalmia, autoimmune uveitis, hepatitis, chronic action hepatitis, collagen diseases, ankylosing spondylitis, periarthritis humeroscapularis, panarteritis *nodosa*, chondrocalcinosis, Wegener's granulomatosis, microscopic polyangiitis, chronic urticaria, bullous skin disorders, pemphigoid, atopic eczema, bullous pemphigoid, cicatricial pemphigoid, vitiligo, atopic eczema, eczema, chronic urticaria, autoimmune urticaria, normocomplementemic urticarial vasculitis, hypocomplementemic urticarial vasculitis, autoimmune lymphoproliferative syndrome, Devic's disease, sarcoidosis, pernicious anemia, childhood autoimmune hemolytic anemia, idiopathic autoimmune hemolytic anemia, Refractory or chronic Autoimmune Cytopenias, Prevention of development of Autoimmune Anti-Factor VIII Antibodies in Acquired Hemophilia A, Cold Agglutinin Disease, Neuromyelitis Optica, Stiff Person Syndrome, gingivitis, periodontitis, pancreatitis, myocarditis, vasculitis, gastritis, gout, gouty arthritis, and inflammatory skin disorders, normocomplementemic urticarial vasculitis, pericarditis, idiopathic pericarditis, myositis, anti-synthetase syndrome, scleritis, macrophage activation syndrome, Behcet's Syndrome, PAPA Syndrome, Blau's Syndrome, gout, adult and juvenile Still's disease, cryopyrinopathy, Muckle-Wells syndrome, familial cold-induced auto-inflammatory syndrome, neonatal onset multisystemic inflammatory disease, familial Mediterranean fever, chronic infantile neurologic, cutaneous and articular syndrome, a rheumatic disease, polymyalgia rheumatica, mixed connective tissue disease, inflammatory rheumatism, degenerative rheumatism, extra-articular rheumatism, juvenile arthritis, juvenile rheumatoid arthritis, systemic juvenile idiopathic arthritis, arthritis uratica, muscular rheumatism, chronic polyarthritis, reactive arthritis, Reiter's syndrome, rheumatic fever, relapsing polychondritis, Raynaud's phenomenon, vasculitis, cryoglobulinemic vasculitis, temporal arteritis, giant cell arteritis, Takayasu arteritis, Behcet's disease, chronic inflammatory demyelinating polyneuropathy, autoimmune thyroiditis, insulin dependent diabetes mellitus, type I diabetes, Addison's disease, membranous glomerulonephropathy, polyglandular autoimmune syndromes, Goodpasture's disease, autoimmune gastritis, autoimmune atrophic gastritis, pernicious anaemia, pemphigus, pemphigus vulgaris, cirrhosis, primary biliary cirrhosis, idiopathic pulmonary fibrosis, myositis, dermatomyositis, juvenile dermatomyositis, polymyositis, fibromyositis, myogelosis, celiac disease, celiac sprue dermatitis, immunoglobulin A nephropathy, Henoch-Schonlein purpura, Evans syndrome, atopic dermatitis, psoriasis, psoriasis vulgaris, psoriasis arthropathica, Graves' disease, Graves' ophthalmopathy, scleroderma, systemic scleroderma, progressive systemic scleroderma, diffuse scleroderma, localized scleroderma, Crest syndrome, asthma, allergic asthma, allergy, primary biliary cirrhosis, fibromyalgia, chronic fatigue and immune dysfunction syndrome (CFIDS), autoimmune inner ear disease, Hyper IgD syndrome, Schnitzler's syndrome, autoimmune retinopathy, age-related macular degeneration, atherosclerosis, chronic prostatitis, alopecia, alopecia areata, alopecia universalis, alopecia totalis, utoimmune thrombocytopenic purpura, idiopathic thrombocytopenic purpura, pure red cell aplasia, and TNF receptor-associated periodic syndrome (TRAPS).

Clause 319. The pharmaceutical composition, the isolated polypeptide or fusion protein, the polynucleotide, the expression vector or virus, the recombinant cell or the use of any of Clauses 312-317, for treating an autoimmune disease selected from relapsing-remitting multiple sclerosis, primary progressive multiple sclerosis, secondary progressive multiple sclerosis; progressive relapsing multiple sclerosis, chronic progressive multiple sclerosis, transitional/progressive multiple sclerosis, rapidly worsening multiple sclerosis, clinically-definite multiple sclerosis, malignant multiple sclerosis, also known as Marburg's Variant, acute multiple sclerosis, conditions relating to multiple sclerosis, psoriatic arthritis, gout and pseudo-gout, juvenile idiopathic arthritis, Still's disease, rheumatoid vasculitis, conditions relating to rheumatoid arthritis, discoid lupus, lupus arthritis, lupus pneumonitis, lupus nephritis, conditions relating to systemic lupus erythematosus include osteoarticular tuberculosis, antiphospholipid antibody syndrome, inflammation of various parts of the heart, such as pericarditis, myocarditis, and endocarditis, Lung and pleura inflammation, pleuritis, pleural effusion, chronic diffuse interstitial lung disease, pulmonary hypertension, pulmonary emboli, pulmonary hemorrhage, and shrinking lung syndrome, lupus headache, Guillain-Barre syndrome, aseptic meningitis, demyelinating syndrome, mononeuropathy, mononeuritis multiplex, myelopathy, cranial neuropathy, polyneuropathy, vasculitis, Collagenous colitis, Lymphocytic colitis, Ischaemic colitis, Diversion colitis, Behcet's disease, Indeterminate colitis, thrombocytopenic purpura, idiopathic autoimmune hemolytic anemia, pure red cell aplasia, cryoglobulinemic vasculitis, ANCA-associated vasculitis, antiphospholipid syndrome, autoimmune hemolytic anaemia, Guillain-Barre syndrome, chronic immune polyneuropathy, autoimmune thyroiditis, idiopathic diabetes, juvenile type I diabetes, maturity onset diabetes of the young, latent autoimmune diabetes in adults, gestational diabetes, conditions relating to type 1 diabetes, membranous glomerulonephropathy, autoimmune gastritis, pemphigus vulgaris, cirrhosis, fibromyositis, celiac disease, immunoglobulin A nephropathy, Henoch-Schonlein purpura, Evans syndrome, atopic dermatitis, psoriasis, Graves' ophthalmopathy, systemic scleroderma, asthma, allergy, anterior uveitis (or iridocyclitis), intermediate uveitis (pars planitis), posterior uveitis (or chorioretinitis), panuveitic form, hepatitis, Wegener's granulomatosis, microscopic polyangiitis, chronic urticaria, bullous skin disorders, pemphigoid, atopic eczema, Devic's disease, childhood autoimmune hemolytic anemia, Refractory or chronic Autoimmune Cytopenias, Prevention of development of Autoimmune Anti-Factor VIII Antibodies in Acquired Hemophilia A, Cold Agglutinin Disease, Neuromyelitis Optica, Stiff Person Syndrome, gingivitis, perodontitis, pancreatitis, myocarditis, vasculitis, gastritis, gout, gouty arthritis, and inflammatory skin disorders, selected from the group consisting of psoriasis, Nonpustular Psoriasis including Psoriasis vulgaris and Psoriatic erythroderma (erythrodermic psoriasis), Pustular psoriasis including Generalized pustular psoriasis (pustular psoriasis of von Zumbusch), Pustulosis palmaris et plantaris (persistent palmoplanar pustulosis, pustular psoriasis of the Barber type, pustular psoriasis of the extremities), Annular pustular psoriasis, Acrodermatitis continua, Impetigo herpetiformis, drug-induced psoriasis, Inverse psoriasis, Napkin psoriasis, Seborrheic-like psoriasis, Guttate psoriasis, Nail psoriasis, Psoriatic arthritis, atopic dermatitis, eczema, rosacea, urticaria, and acne, normocomplementemic urticarial vasculitis, pericarditis, anti-synthetase syndrome, scleritis, macrophage activation syndrome, Behcet's Syndrome, PAPA Syndrome, Blau's Syndrome, gout, adult and juvenile Still's disease, cryropyrinopathy, Muckle-Wells syndrome, familial cold-induced auto-inflammatory syndrome, neonatal onset multisystemic inflammatory disease, familial Mediterranean fever, chronic infantile neurologic, cutaneous and articular syndrome, systemic juvenile idiopathic arthritis, Hyper IgD syndrome, Schnitzler's syndrome, autoimmune retinopathy, age-related macular degeneration, atherosclerosis, chronic prostatitis and TNF receptor-associated periodic syndrome (TRAPS).

Clause 320. The pharmaceutical composition, the isolated polypeptide or fusion protein, the polynucleotide, the expression vector or virus, the recombinant cell or the use of any of Clauses 312-319, wherein the treatment is combined with another moiety useful for treating said condition.

Clause 321. The pharmaceutical composition, the isolated polypeptide or fusion protein, the polynucleotide, the expression vector or virus, the recombinant cell or the use of any of Clauses 312-320, wherein said other moiety useful for treating immune related condition is selected from immunosuppressants such as corticosteroids, cyclosporin, cyclophosphamide, prednisone, azathioprine, methotrexate, rapamycin, tacrolimus, leflunomide or an analog thereof; mizoribine; mycophenolic acid; mycophenolate mofetil; 15-deoxyspergualine or an analog thereof; biological agents such as TNF-alpha blockers or antagonists, or any other biological agent targeting any inflammatory cytokine, nonsteroidal antiinflammatory drugs/Cox-2 inhibitors, hydroxychloroquine, sulfasalazine, gold salts, etanercept, infliximab, mycophenolate mofetil, basiliximab, atacicept, rituximab, Cytoxan® (cyclophosphamide), interferon beta-Ia, interferon beta-Ib, glatiramer acetate, mitoxantrone hydrochloride, anakinra and/or other biologies and/or intravenous immunoglobulin (IVIG), interferons such as IFN-beta-Ia (REBIF®. AVONEX® and CINNOVEX®) and IFN-beta-Ib (BETASERON®); EXTAVIA®, BETASERON®, ZIFERON®); glatiramer acetate (COPAXONE®), a polypeptide; natalizumab (TYSABRI®), mitoxantrone (NOVANTRONE®), a cytotoxic agent, a calcineurin inhibitor; cyclosporin A; FK506; an immunosuppressive macrolide; rapamycin; a rapamycin derivative; 40-O-(2-hydroxy)ethyl-rapamycin, a lymphocyte homing agent, FTY720; an analog of FTY720; corticosteroids; cyclophosphamide; azathioprine; methotrexate; leflunomide or an analog thereof; mizoribine; mycophenolic acid; mycophenolate mofetil; 15-deoxyspergualine or an analog thereof; immunosuppressive monoclonal antibodies, monoclonal antibodies to leukocyte receptors, monoclonal antibodies to MHC, CD2, CD3, CD4, CDI Ia/CD18, CD7, CD25, CD27, B7, CD40, CD45, CD58, CD137, ICOS, CD150 (SLAM), OX40, 4-1BB or their ligands; or other immunomodulatory compounds, CTLA4-Ig (abatacept, ORENCIA®, belatacept), CD28-Ig, B7-H4-Ig, or other costimulatory agents, or adhesion molecule inhibitors, mAbs or low molecular weight inhibitors, LFA-1 antagonists, Selectin antagonists and VLA-4 antagonists, or another immunomodulatory agent.

Clause 322. A pharmaceutical composition according to Clause 274, the isolated polypeptide or fusion protein of any of Clauses 200-269, the polynucleotide of Clause 270, the expression vector or virus of Clause 271, or the recombinant cell of Clause 272, for use in treatment of Infectious disease in a subject suffering from same.

Clause 323. The pharmaceutical composition, the isolated polypeptide or fusion protein, the polynucleotide, the expression vector or virus, the recombinant cell or the use of Clause 322, wherein said protein, said polynucleotide, said expression vector or virus, said recombinant cell, said pharmaceutical composition or said use is used for treatment of infectious disease and is capable of at least one of the following: (i) increasing immune response, (ii) increasing T cell activation, (iii) increasing cytotoxic T cell activity, (iv) increasing NK cell activity, (v) increasing Thl7 activity, (vi) alleviating T-cell suppression, (vii) increasing pro-inflammatory cytokine secretion, (viii) increasing IL-2 secretion; (ix) increasing interferon-y production by T-cells, (x) increasing Thl response, (xi) decreasing Th2 response, (xii) decreasing or eliminating at least one of regulatory T cells (Tregs), myeloid derived suppressor cells (MDSCs), iMCs, mesenchymal stromal cells, TIE2-expressing monocytes, (xiii) reducing regulatory cell activity and/or the activity of one or more of myeloid derived suppressor cells (MDSCs), iMCs, mesenchymal stromal cells, TIE2-expressing monocytes, (xiv) decreasing or eliminating M2 macrophages, (xv) reducing M2 macrophage pro-tumorigenic activity, (xvi) decreasing N2 neutrophils, (xvii) decreasing N2 neutrophils activity, (xviii) reducing inhibition of T cell activation, (xix) reducing inhibition of CTL activation, (xx) reducing inhibition of NK cell activation, (xxi) reversing T cell exhaustion, (xxii) increasing T cell response, (xxiii) increasing activity of cytotoxic cells, (xxiv) stimulating antigen-specific memory responses, (xxv) eliciting apoptosis or lysis of cancer cells, (xxvi) stimulating cytotoxic or cytostatic effect on cancer cells, (xxvii) Inducing direct killing of cancer cells, and/or (xxviii) inducing complement dependent cytotoxicity and/or (xxix) inducing antibody dependent cell-mediated cytotoxicity.

Clause 324. The pharmaceutical composition, the isolated polypeptide or fusion protein, the polynucleotide, the expression vector or virus, the recombinant cell or the use of any of Clauses 321-323, wherein said infectious disease is chronic infectious disease and is selected from the disease caused by bacterial infection, viral infection, fungal infection and/or other parasite infection.

Clause 325. The pharmaceutical composition, the isolated polypeptide or fusion protein, the polynucleotide, the expression vector or virus, the recombinant cell or the use of any of Clauses 321-324, wherein said infectious disease results in sepsis.

Clause 326. The pharmaceutical composition, the isolated polypeptide or fusion protein, the polynucleotide, the expression vector or virus, the recombinant cell or the use of any of Clauses 321-324, wherein the infectious disease is selected from hepatitis B, hepatitis C, infectious mononucleosis, AIDS, tuberculosis, malaria and schistosomiasis.

Clause 327. The pharmaceutical composition, the isolated polypeptide or fusion protein, the polynucleotide, the expression vector or virus, the recombinant cell or the use of any of Clauses 321-326, wherein the treatment is combined with another moiety useful for treating infectious disease, or with another moiety useful for reducing the undesirable immune activation that follows gene therapy, in a subject in need thereof.

Clause 328. The pharmaceutical composition, the isolated polypeptide or fusion protein, the polynucleotide, the expression vector or virus, the recombinant cell or the use of any of Clauses 321-327, wherein said other moiety is a therapeutic agent useful for treating bacterial infection, viral infection, fungal infection, parasitic infection or sepsis.

Clause 329. A compound, composition, method or use according to any of the foregoing Clauses which further includes a VISTA agonist or antagonist compound which is separate or is conjugated to a VSIG8 agonist or antagonist compound.

Clause 330. A fusion protein, pharmaceutical composition, isolated polypeptide, polynucleotide, expression vector or virus, recombinant cell or method or use according to any of the foregoing Clauses which further includes a VISTA agonist or antagonist which is separate or conjugated to a VSIG8 agonist or antagonist compound which preferably comprises an anti-VSIG8 antibody, VSIG8 protein or VSIG8 fusion protein.

Clause 330. Method of using a VSIG8 fusion protein, pharmaceutical composition, isolated polypeptide, polynucleotide, expression vector or virus, recombinant cell or method or use according to any of the foregoing Clauses, in therapy, preferably for use in inhibiting T cell or NK immunity, e.g., in treating any of autoimmunity, allergy, inflammation, transplant or sepsis alone or in combination with any of the other therapeutics or actives disclosed herein, especially immune inhibitors.

EXAMPLES

Example 1: Initial Identification of Vsig8 as Putative Vista Receptor

VSIG8 Identified as V-R Based on its Binding to VISTA Multimer

A soluble oligomeric or multimeric version of VISTA, i.e., recombinant, fluorescent $VISTA_{19\text{-}dex}$ was used to screen a membrane protein library ≈3800 unique genes) created by Retrogenix (UK) to identify putative binding partners in a high throughput binding assay. This soluble ligand was designed in order to enhance the binding of V-R to VISTA by promoting VISTA oligomerization. Genes are expressed in an array of HEK293 cells and fluorochrome coupled ligand is used for detection of cells expressing a binding partner.

Using this screening method VSIG8 was identified as a binding partner for VISTA using $VISTA_{19}$-Dex. Based on this result VSIG8 was assessed in other binding and functional assays to corroborate whether this protein is a VISTA receptor.

Reversal of VISTA-Ig Mediated T Cell Suppression by Anti-VSIG8 Monoclonal Antibody Recombinant VISTA-Ig fusion protein suppresses anti-CD3 (OKT3) mediated in vitro T cell proliferation and cytokine production in a dose-dependent manner. Therefore, in the presence of an anti-VSIG8 antibody, e.g., one commercially available from Origene (a blocking/neutralizing antibody without agonistic or antagonistic activity) the suppressive effect of the VISTA-Fc should be inhibited.

In this assay 96 well plates will be coated with either anti-CD3 antibody (OKT3) alone or anti-CD3 plus VISTA-Ig at 37° C. for 1 hr. The anti-CD3 and VISTA-Ig will be used at a final concentration of 2.5 and 10 ug/ml respectively. Two hundred thousand purified human T cells from healthy donor peripheral blood will be added to each well.

A duplicate experiment will be carried out in the presence of anti-VSIG mAb. The plates will be incubated at 37° C. for 5 days. On the $5^{th}$ day 30 UL of supernatant are removed for cytokine (IFN-γ and IL-2) analysis and 25 UL of tritiated Thymidine is added to the cell culture. The cells will be cultured for another 8 hrs. before cell proliferation is measured by tritium incorporation. The results of this assay should reveal that the anti-VS/G8 antibody inhibits or reverses VISTA-Ig suppression of T cell activity.

Blocking of VISTA Function in VSIG8 Knockout Cell Line (Method 1)

VSIG8 gene specific shRNA lentiviral particles will be constructed to knock down the VSIG8 gene (Mission shRNA particles, TCR library from Sigma). Jurkat cells will be transduced with shRNA lentiviral particles at an optimized multiplicity of infection to achieve greater than 90% knock down of target gene without nonspecific gene deletion. The transduced cells will then be selected in the presence of puromycin drug. The specificity and the level of knockdown of the target gene will be confirmed by quantitative PCR. The cells will be stimulated with anti-CD3 in the presence or absence of VISTA-Ig. The level of CD69 is assessed by flow cytometry and IL-2 expression will be measured by ELISA in the culture supernatant after 72 hrs.

This assay should reveal that cells wherein the VSIG8 gene is knocked-out cells are unresponsive to VISTA-Ig mediated suppression.

Blocking of VISTA Function in VSIG8 Knockout Cell Line (Method 2)

VSIG8 gene specific shRNA lentiviral particles will be constructed to knock down the VSIG8 (Mission shRNA particles, TCR library from Sigma). T cells from healthy donor will be transduced with shRNA lentiviral particles at an optimized multiplicity of infection to achieve greater than 90% knock down of target gene without nonspecific gene deletion. The transduced cells will be selected in the presence of puromycin drug. The specificity and the level of knockdown of the target gene will be confirmed by quantitative PCR. The anti-CD3 mediated T cell proliferation assay will be performed as described above in the presence or absence of VISTA-Ig. The cytokine and cell proliferation will be assessed.

This assay should similarly reveal that cells wherein the VSIG8 gene is knocked-out cells are unresponsive to VISTA-Ig mediated suppression.

Detection of VSIG8 Expression by qPCR

To further confirm that VSIG8 is the receptor for VISTA assays were conducted which detect the expression of VSIG8 by T cells. Particularly, qPCR assays were conducted which compared the expression of VSIG8 in a population of enriched human T cells relative to a sample of total spleen cells.

cDNA samples were prepared from RNA isolated from the indicated cells. Relative expression of VSIG8 was calculated using Mock transfected COS7 cells as control. (A) Either mock or VSIG8 transfected COS7 cells were used as negative (−Ve) or positive (+Ve) controls respectively. VSIG8 expression was detected in VSIG8 transfected but not in mock-transfected COS7 cells. This validates the specificity of VSIG8 identification in the qPCR assay. Expression of VSIG8 was detected in total human spleen (B) and enriched $CD3^+$ T cells from human peripheral blood.

Figure 7:
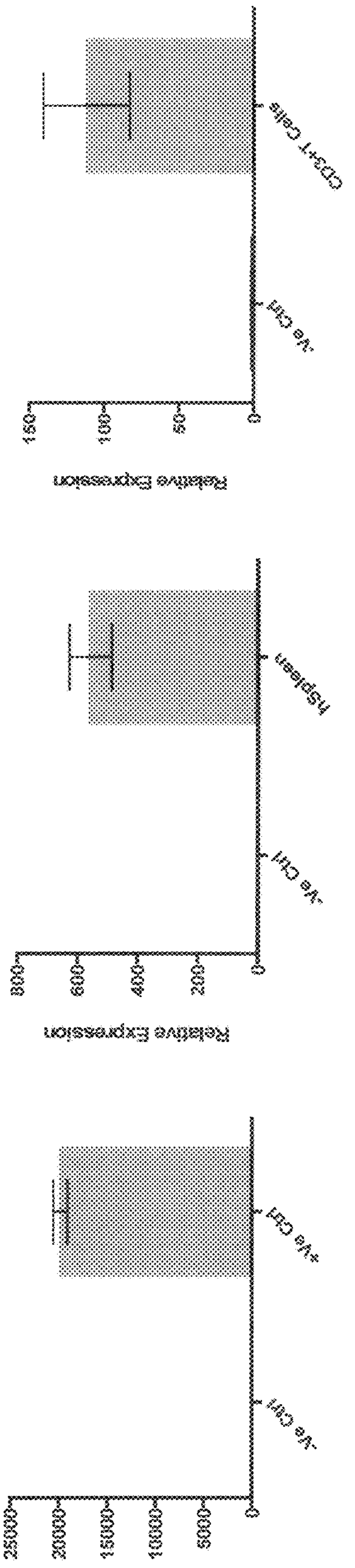
FIG. 7 contains the results of a qPCR assay which compared the expression of VSIG8 in an enriched T cell population relative to a sample containing total spleen cells.

The relative expression of VSIG8 was calculated using delta Ct expression formula. As anticipated, the enriched population of T cells expressed very high levels of VSIG8 mRNA as compared to the total spleen cell sample. These results are shown in FIG. 7.

Example 2: Experiments Corroborating that VSIG8 is VISTA Receptor

Materials and Methods

Experiments Confirming VSIG8 Specifically Binds to VISTA Polypeptides 293 cells were grown in DMEM (Hyclone) with 10% FBS (Hyclone). The day before transfection with VS/G8, the cells were trypsinized and split 1:4 into 10-cm dishes with total volume of 10 ml. On the day of transfection, when 293 cell density reach 60-80% confluence, the current media is removed and replaced with 5 ml of fresh media in 10-cm dish.

Transfections were performed by following instructions of Lipofectamine 3000 (Life Technologies). Five microgram of DNA is mixed with 30 UL Lipofectamine 3000 and incubated at room temperature for 10 minutes before adding onto 293 cells. The media is changed after 5-6 hours and 10 ml fresh media is added.

After 2 days, media is removed and 3 mls of PBS/0.5 mM EDTA/0.02% azide is added onto the 10-cm dish and incubated at RT for 10 minutes. Cells will be pipetted to make a single cell suspension. Cells will be centrifuged and resuspended in PBS with 5% FBS/0.5 mM EDTA and 0.02% sodium azide with either 20 μg/mlof VISTA-Fc (R&D Systems) or EpoR-Fc (R&D Systems). Cells will be incubated on ice for 30 minutes, washed with buffer and centrifuged as described above. The resultant incubated cells will be then resuspended in staining buffer with anti-human IgG Fc-APC at 1:200 (Biolegend) and incubated on ice for 30 minutes. Afterward the cells will be washed, centrifuged and run on a MACSQuant 8-parameter flow cytometer.

For blocking with anti-VSIG8 serum, 1:20 rat serum will be added, incubated on ice for 30 minutes, then washed and stained with VISTA-Ig as above-described.

To block with anti-VISTA antibodies, 4 μg/ml MABs or 2 μg/ml Fabs will be added to cells, followed by 20 ug/ml V-Ig or EPO-R-Ig. The mixture will be then incubated on ice for 30 minutes.

The DNA construct contains bi-cistronic GFP. GFP is usually expressed proportionally to target gene expression so $GFP^+$ cells will be gated for analysis.

Cell-Cell Conjugation Studies

A20 cells will be washed once in PBS then resuspended in PBS at $1\times10^6$/ml. UL Far-red or Violet dye (Life Technology, reconstituted in DMSO) will be added into 1 ml cells and the cells incubated at RT for 20 mins. Afterward 6 ml HBSS w 10% FBS will be added for 5 min. The cells will be resuspended in HBSS at $1\times10^6$/ml.

For binding, $1\times10^5$ Far Red-labeled cells (0.1 ml) will be combined with $1\times10^5$ violet-labeled cells (0.1 ml) in a 96-well plate. The cells will be mixed and incubated at 37° C. for 45 to 60 mins. Read cell fluorescence using flow cytometry (APC channel for Far-red signal, Violet 1 channel for Violet signal). Double-positive population indicates cell-cell binding.

VSIG8 Expression Analysis by Flow Cytometry

Blood samples were obtained from donors who were at least 18 years of age, generally healthy and selected randomly from the local population. The donor blood was then transferred from isolation tube to 50 ml conicals.

15 mls of Ficoll 1077 (SIGMA, 10771) per 25 mls of blood was underlaid while being careful not to mix with the blood. The cells were then centrifuged at 1250 g for 25 minutes at room temperature with no brake.

After centrifugation the white blood cells were isolated from the interphase of the Ficoll and the serum and the isolated cells then diluted into 40 ml of Hanks Balanced Salt Solution (HBSS). Afterward the cell mixture was centrifuged at 453 g (1500 rpm) for 10 minutes at 4° C.

The resultant centrifugate containing the cells was then resuspended in 50 mls of HBSS and counted by transferring 500 μl to a separate Eppendorf tube. $1\times10^5$ cells were added to each well which were centrifuged as described above.

The cells were then resuspended in 100 μL of PBS containing 10 ug/mL rabbit anti-VSIG8 (Abcam or Novus), 1:100 FcR inhibitor (eBioscience), 1.25 ug/mL Human IgG, 2 ug/mL anti-CD16 (R&D Systems), and lineage markers for CD14 BV421, CD20 PE, CD8 PerCP Cy5.5, CD4 PECy7, CD56 PECy7.

The cells were then incubated in the foregoing for 20 minutes at 4° C., and then washed with 100 μL of PBS and centrifuged as described above. The cells were then resuspended in 100 μL of PBS containing Goat anti-Rabbit IgG APC for 15 minutes at 4° C., and then washed with 100 μL of PBS and again centrifuged as described above.

The resultant samples were then run on a Miltenyi MACSQuant flow cytometer.

VSIG8 Expression Analysis by RNA-Seq qPCR assays were conducted which compared the expression of VSIG8 in a population of enriched human T cells relative to a sample of total spleen cells.

cDNA samples were prepared from RNA isolated from the indicated cells. Relative expression of VSIG8 was calculated using Mock transfected COS7 cells as control. (A) Either mock or VSIG8 transfected COS7 cells were used as negative (−Ve) or positive (+Ve) controls respectively.

VSIG8 expression was detected in VSIG8 transfected but not in mock-transfected COS7 cells. This validates the specificity of VSIG8 identification in the qPCR assay. Expression of VSIG8 was detected in total human spleen (B) and enriched CD3+ T cells from human peripheral blood.

The relative expression of VSIG8 was calculated using delta Ct expression formula. As anticipated, the enriched population of T cells expressed very high levels of VSIG8 mRNA as compared to the total spleen cell sample.

Functional Effects of VSIG8 Antisera in the A20/DO11 10 Assay

Cell Line Generation:

The full-length hVISTA cDNA was amplified and cloned into the NheI-EcoRI sites of the bicistronic vector pEF-MCS-IRES-ZsGreen from Blue Sky. Three constructs (hVISTA/GFP and GFP-only) were transfected in the A20 mouse B cell line using a Nucleofector kit V per manufacturer's instructions (Lonza, Cat# VACA 1003). Stable expressing cells were isolated by growth in G418 selection (1 mg/ml). Cells were sorted for high GFP expression and grown under G418 selection (1.0 mg/ml). GFP-high expressing cells were subsequently single cell sorted for each cell line and clonal populations were created by growth and passage under G418 selection. The resulting cell pools are designated A20-GFP (express only GFP) and A20-hVISTA (express full-length human VISTA and GFP).

Media Protocol:

Combined 500 ml of RPMI 1640 (Corning, 10-040-CV) with 50 ml of FBS (Corning CellGro, Lot #103283HI), 5 ml of Penicillin/Streptomycin (Lonza, 17-602E) 10,000 U/ml, 5 ml of L-glutamine (100×) (Gibco, 25030-081) and 5 ml of HEPES (1M) (Fisher, BP299-100), 50 μM β-mercaptoethanol (Fisher, Cat#03446-100). Media was made fresh for each experiment.

Isolation of DO11.10 T Cells:

DO11.10 CD4+ T cells were isolated directly from transgenic DO11.10 mice. Mice (6-10 weeks old) were euthanized and spleens were removed sterilely. Using two sterile glass slides, the spleen was processed into a single cell suspension in 5 ml of 10% FBS media and centrifuged the cells at 453 g for 5 minutes. Added 10 ml of 10% FBS media and filtered through a 40 μM cell strainer and centrifuged as above. CD4 T cells isolation was performed by negative selection using a CD4 T Cell isolation kit II (Miltenyi 130-095-248) following the manufacturer's directions.

A20-GFP and A20-hVISTA were cultured in G418 selection medium (1.0 mg/ml) until they reached ~2-3×$10^6$ cells/ml. Cells were washed with complete full medium and resuspended at a concentration of 1×$10^8$ cells/mi. Cells were irradiated with 10,000 rads. Centrifuged cells as described in step 5.3 and resuspended at a concentration of 2×106 cells/ml in 10% FBS media and added 50 μl to appropriate wells.

Added 4× concentration of Control or VSIG8 rat sera in 50 μl of complete medium to the A20 cells, and incubated at RT for 45 min. The final dilution of the sera was 1:200. Added 50 μl of primary DO11.10 T cells to the appropriate wells at a concentration of 2×$10^6$ cells/ml in 10% FBS media. Finally, OVA peptide (ISQ; ISQAVHAAHAEINEAGR, Peptides International, Cat # POV-3636-PI) was diluted to 4× concentration in 10% FBS medium and 50 μl was added to the A20 and DO11.10 cells to achieve desired final concentration. The ova peptide was included at a final concentration of 12.5 ng/ml, except where noted in the figure legends.

Cells were incubated for 3 days at 37° C. and 5% $CO_2$. On day 3, centrifuged the 96 well plate as described above and assayed for expression of CD25 as described below. Centrifuged the 96 well U-bottom plate for 5 minutes at 453 g and removed the supernatant (used in section 5 for IFNγ or IL-2 analysis). Washed cells with 200 μl staining buffer (5% FBS in 1×HBSS without Mg2+ & $Ca^{2+}$) and centrifuged again. Resuspended cells in 50 μl of staining buffer containing the following antibodies: CD25-APC 1:200 (Biolegend cat #102034) and mouse FcR binding inhibitor 1:200 (eBioscience cat #120-003-855). Incubated for 20 minutes on ice in the dark. Added 150 μl of staining buffer and centrifuged as above. Washed cells with 200 μl of staining buffer and centrifuged again, and resuspended cells in 100 μl of PBS with 1% BSA.

Samples were run on a Miltenyi MACSQuant 8-parameter flow cytometer and analyzed using FlowJo 9.7.5 for expression of CD25 on the $CD4^+$ T cell population. Geometric mean fluorescence intensity (MFI), a statistic that defines the central tendency of a set of numbers, was used as the defining statistic to compare treatments.

Results

Results of the experiments confirming that VSIG8 is the VISTA receptor effected as described in the Materials and Methods supra are provided below. These experiments provide further evidence corroborating that VSIG8 is the VISTA receptor.

Particularly, these experiments demonstrated that a VISTA-Ig chimeric protein was capable of binding VSIG8-overexpressing cells in a specific, antibody reversible manner; that VSIG8 mRNA and protein expression analyses revealed that VSIG8 is expressed by lymphocytes, with the highest expression in NK and $CD8^+$ T cells as would be expected for a putative VISTA receptor; and the functional assays demonstrated that antisera specific to VSIG8 reversed VISTA mediated suppression of T cell responses. Taken together, these results validate the inventors' hypothesis that VSIG8 is a functional binding partner, i.e., receptor for VISTA.

Binding Results

Human VSIG8 IRES GFP or PD1 IRES GFP were each transfected into 293 cells and then these cells were then stained with VISTA-Ig (R&D), EpoR-Ig (R&D), VISTA-Ig 19-mer, or hIX-5 (VISTA-IgG1 from INX). Binding was assessed on the GFP positive cells by flow cytometry.

Figure 8:
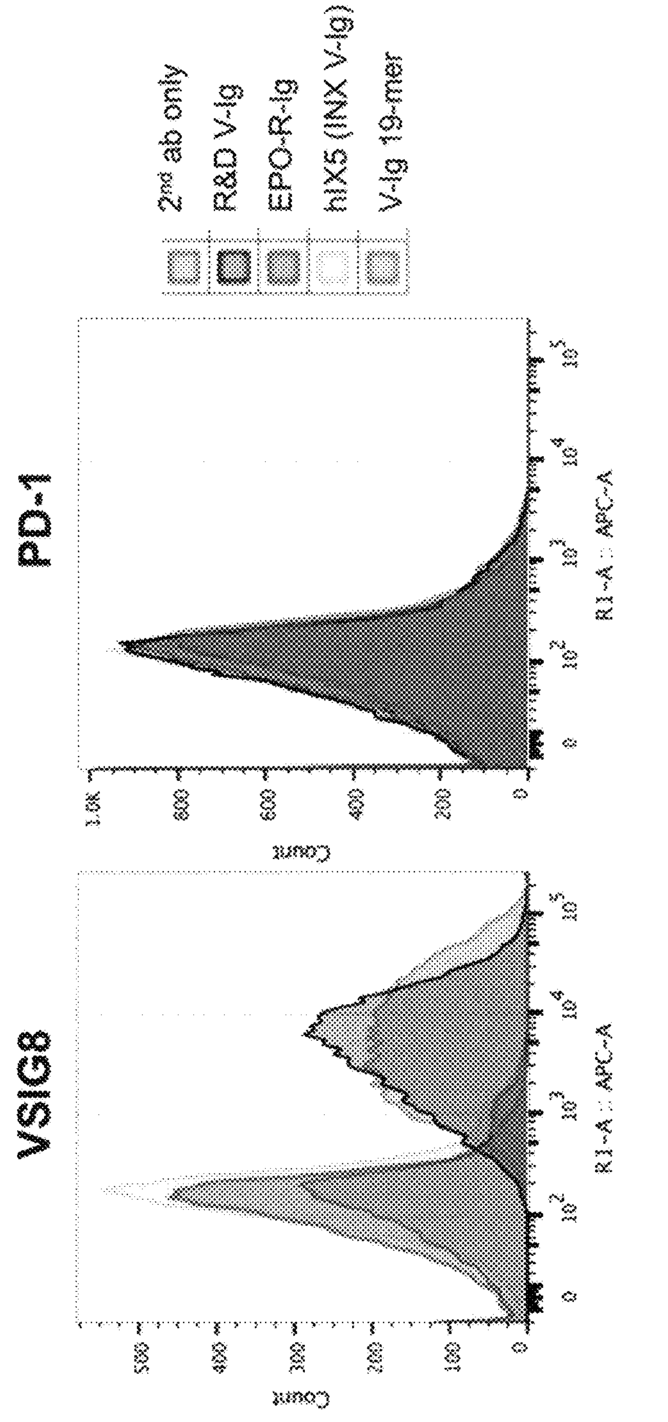
FIG. 8 contains experiments showing that VISTA fusion proteins specifically bind to VSIG8 over-expressing 293 cells.

As shown in FIG. 8 VISTA-Ig (R&D) as well as the VISTA-19mer both robustly stained the VSIG8 over-expressing cells while showing no sign of binding to the PD1 over-expressing cells (see FIG. 8). Also, hIX-5 and EpoR-Ig showed no sign of binding to either VSIG8 or PD1 overexpressing cells (see FIG. 8). These results corroborate that VISTA polypeptides specifically bind to VSIG-8 as expected for a predicted VISTA receptor. More specifically FIG. 8 shows that VISTA fusion proteins specifically bind to VSIG8 over-expressing 293 cells. In these binding experiments 293 cells were transfected with either VSIG8 or PD1 containing an IRES GFP bicistronic vector. GFP positive cells were gated and binding was assessed by flow cytometry for the following fusion proteins: VISTA Ig (R&D Systems) EpoR-Ig (R&D Systems), hIX-5 (INX VISTA-Ig) and VISTA 19mer (INX VISTA multimer). The fusion proteins were detected using an anti-IgG secondary antibody.

As shown in the experiments in FIG. 8, VISTA fusion proteins specifically bound to VSIG8 over-expressing 293 cells. In these experiments 293 cells were transfected with either VSIG8 or PD1 containing an IRES GFP bicistronic vector. GFP positive cells were gated and binding was assessed by flow cytometry for the following fusion proteins: VISTA Ig (R&D Systems) EpoR-Ig (R&D Systems), hIX-5 (INX VISTA-Ig) and VISTA 19mer (INX VISTA multimer). The fusion proteins were detected using an anti-IgG secondary.

To further test the specificity of the interaction between VISTA-Ig and VSIG8, experiments were conducted as depicted in FIG. 9 comparing the ability of antibodies against VSIG8 and VISTA to block the interaction between VISTA Ig and VSIG8. In these experiments 293 cells were transfected as described in FIG. 8 and stained with VISTA-Ig (R&D systems for A and B, VISTA 19mer for C). Sera from VSIG8 immunized rats or control rats was used to potentially block the interaction (A, C). Additionally, VISTA antibodies (mAb) and Fabs (Fab) were also tested for their ability to block the interaction compared to control antibodies (B, C).

Figures 9A, 9B, 9C:
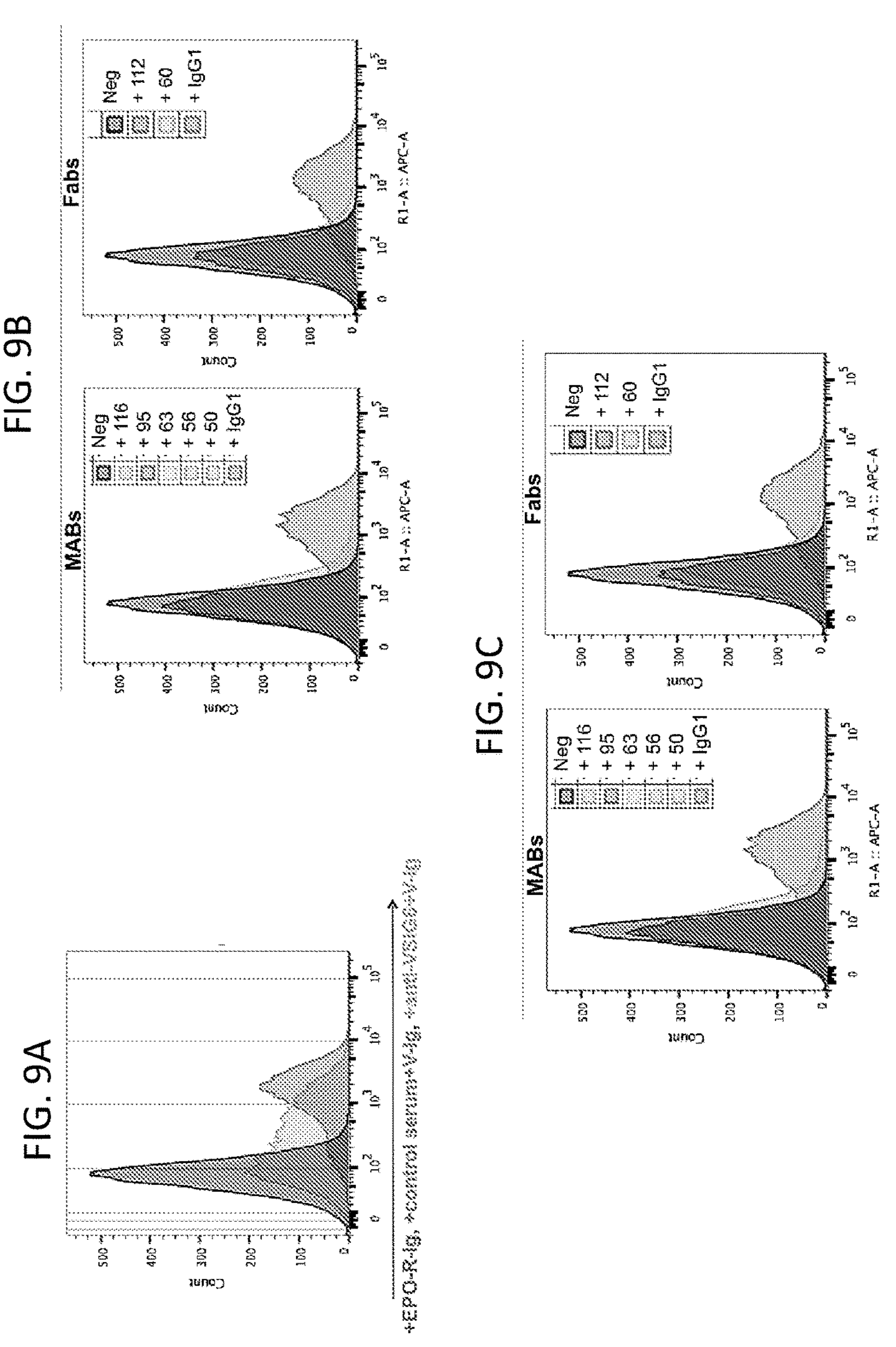
FIG. 9A-C contains experiments showing that antibodies against VSIG8 and VISTA block the interaction between VISTA Ig and VSIG8.

As can be seen from the experiments in FIG. 9, in the presence of anti-sera from VSIG8 immunized rats but not control rats, binding was greatly reduced indicating a specific interaction between VISTA-Ig and VSIG8 (FIG. 9A). Additionally, multiple anti-VISTA antibodies and Fabs were also able to specifically block the interaction between VISTA and VSIG8 (FIG. 9B). Moreover, when similar studies were done with the VISTA 19mer, reversal of VISTA binding was also observed (FIG. 9C).

Figure 10:
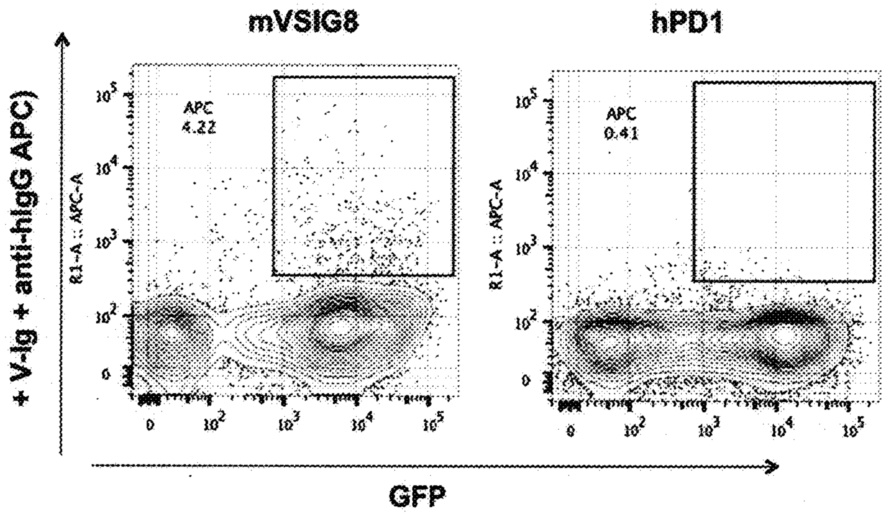
FIG. 10 contains experiments indicating that VISTA-Ig shows low-level ability to bind to mouse VSIG8 over-expressing cells.

Because mouse and human VSIG8 are 86% homologous, experiments were conducted to assess whether human VISTA-Ig would similarly preferentially bind to mouse VSIG8. These experiments are contained in FIG. 10. In these experiments 293 cells were transfected with mouse VSIG8 or PD1 and stained with human VISTA-Ig (R&D systems) as described above. The results in FIG. 10 indicate that VISTA-Ig exhibits a low-level ability to bind to mouse VSIG8 over-expressing cells. A small population of the GFP positive cells from the mVSIG8 group were bound by VISTA-Ig compared to the PD1 control group. Specifically, a small amount of binding was seen between VISTA-Ig and mVSIG8, while no binding was observed between VISTA-Ig and PD1 (FIG. 10).

Figure 11:
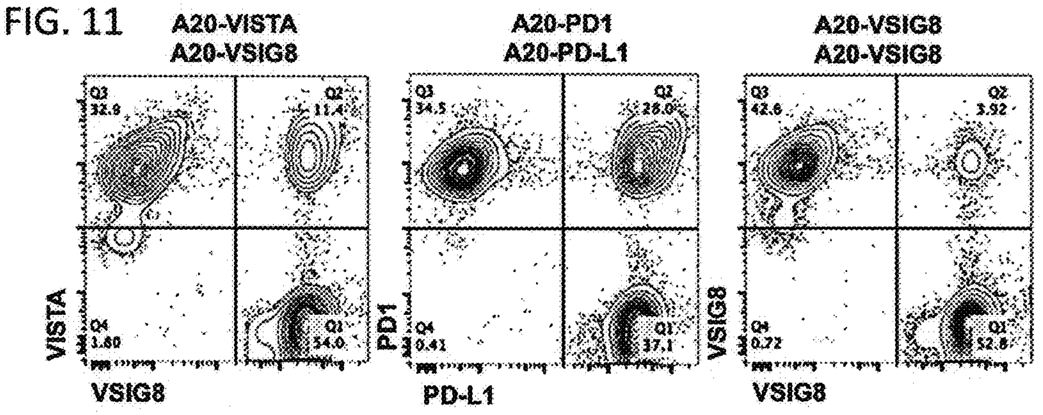
FIG. 11 contains experiments revealing that VISTA over-expressing cells specifically conjugate to VSIG8 overexpressing cells.

Additional experiments shown in FIG. 11 were conducted to assay the binding of VISTA and VSIG8. These experiments used a different system, i.e., a cell-cell conjugation assay to detect whether VISTA overexpressing cells bind to VSIG8 overexpressing cells. PDL1 and PD1 were used as a positive control and VSIG8-VSIG8 was used as a negative control. These experiments used A20 cells which were transfected with VISTA, VSIG8, PD-L1 or PD1 and then labeled with fluorescent dyes. These transfected cells were cultured together and checked for cellular conjugation or the binding of each cellular population by flow cytometry. The double positive cells indicate the level of conjugation. VSIG8/VSIG8 was used as a negative control and PD1/PD-L1 was used as a positive control. As expected using this system, VISTA and VSIG8 binding showed a higher level of binding than with the negative control samples. However the interaction was not as strong as seen with PD-L1 and PD1 based upon the percentage of conjugated cells.

Figure 12:
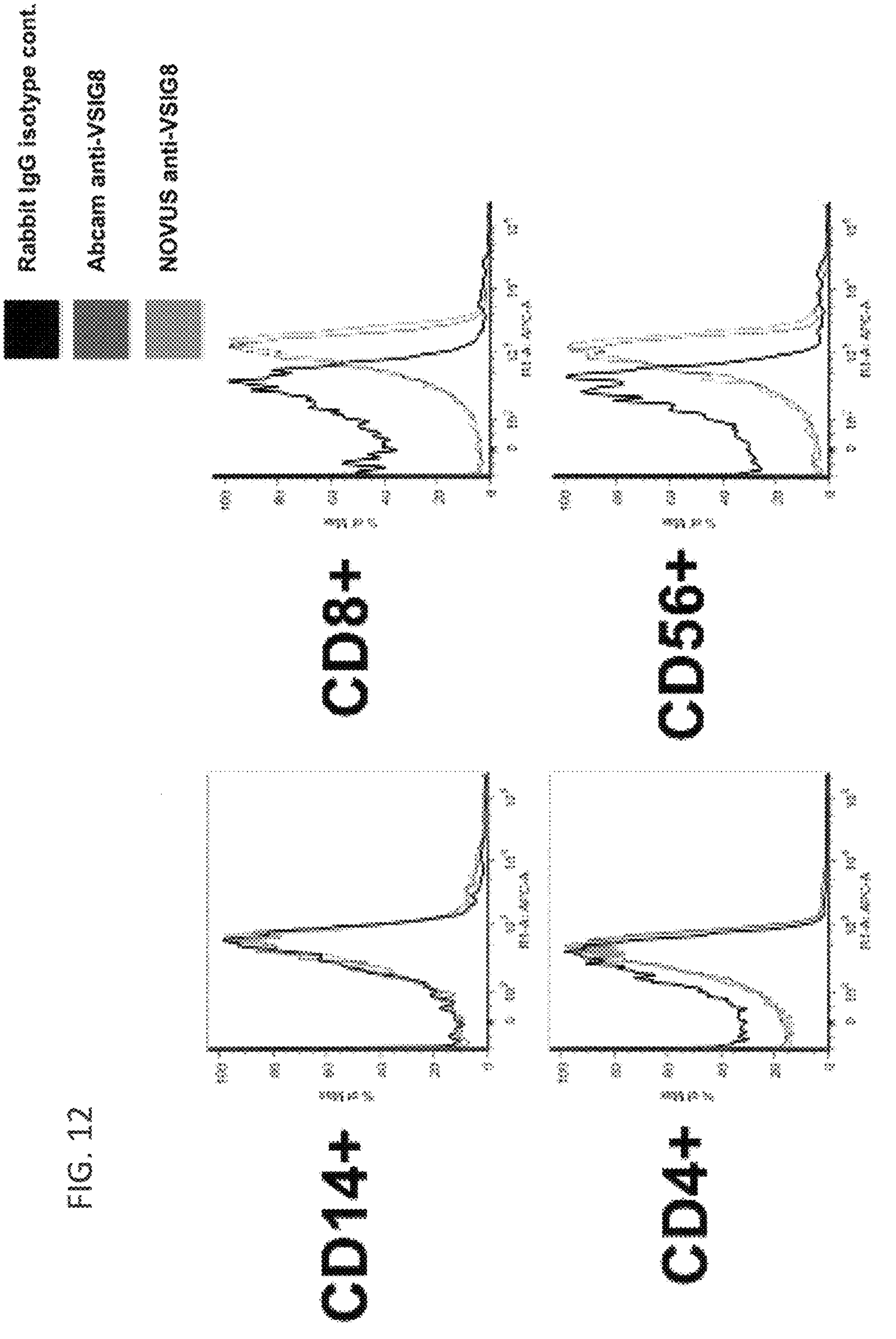
FIG. 12 contains experiments revealing that antibodies against VSIG8 bind to CD8 T cells and NK cells.
Figure 13:
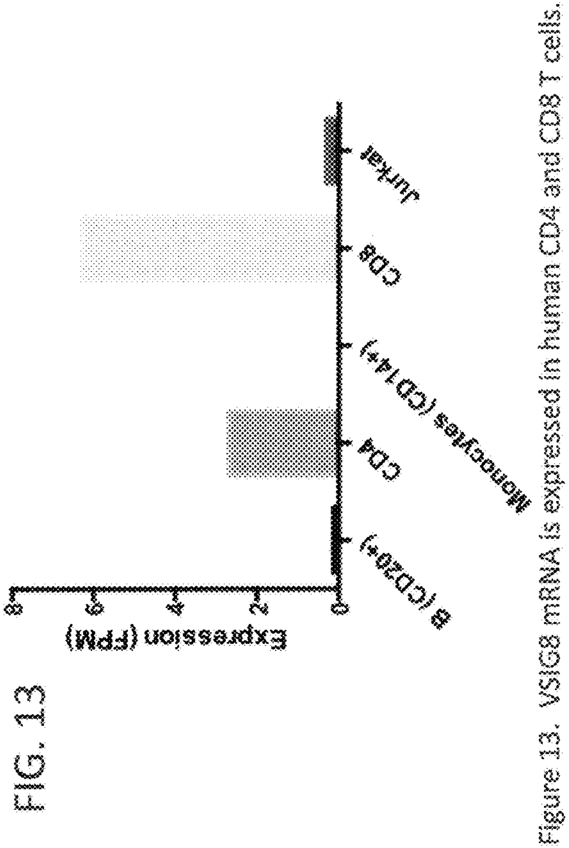
FIG. 13 contains experiments revealing that VSIG8 mRNA is expressed by human CD4 and CD8 T cells.

Additional experiments shown in FIGS. 12 and 13 were conducted to assay the expression of VS/G8 by specific cells by use of flow cytometry (to detect VS/G8 protein expression), and RNAseq (to detect VS/G8 mRNA expression). These experiments were conducted using two commercially available antibodies.

In the experiments in FIG. 12, it was shown that antibodies against VSIG8 bound to $CD8^+$ T cells and to NK cells. These experiments used human PMBCs isolated and stained with two commercially available anti-VSIG8 antibodies, i.e., sold by Abcam and NOVUS. Lineage stains for CD14, CD4, CD8 and CD56 were used to identify the different immune cell populations which bound to the anti-VSIG8 antibodies. The results of these experiments, particularly the staining pattern of human PBMCs indicated robust expression in the $CD8^+$ T cell population and $CD56^+$ NK cell population. $CD14^+$ monocytes and $CD4^+$ T cells did not stain positive by antibody analyses. Specifically, as shown in FIG. 12, the antibodies against VSIG8 specifically bound to the $CD8^+$ T cells and NK cells.

Additional experiments conducted by the inventors shown in FIG. 13 were conducted to detect VSIG8 mRNA expression using RNA-seq by other isolated PBMC populations. In the experiments human PBMCs were isolated by flow cytometry expression of mRNA determined by RNA-seq analysis of VSIG8. Using this technique, message was detected in $CD4^+$ T cells and $CD8^+$ T cells, but not in $CD20^+$ B cells or $CD14^+$ monocytes. Additionally, the Jurkat T cell line was checked for mRNA expression as well. The results in FIG. 13 revealed that VSIG8 mRNA is expressed in human $CD4^+$ and $CD8^+$ T cells.

Figure 14:
FIG. 14 contains experiments demonstrating that VISTA signals T cells via VSIG8 to suppress T cell activation. A20 cells expressing either GFP (Control) or VISTA+GFP were incubated with DO11.10 T cells in the presence of ISQ peptide. T cell activation was measured by CD25 expression at 72 hours.

Additional experiments were conducted by the inventors to assess the functional effects of the VSIG8/VISTA binding interaction on VISTA'S biological activities. As disclosed in this application VISTA has been shown to suppress T cell responses. These experiments which are contained in FIG. 14 and provide corroborative evidence that VISTA signals T cells via VSIG8 to suppress T cell activation. In these experiments A20 cells expressing either GFP (Control) or VISTA+GFP were incubated with DO11.10 T cells in the presence of ISQ peptide. T cell activation was measured by CD25 expression at 72 hours.

These experiments used A20 cells overexpressing human VISTA as these cells are capable of suppressing a murine T cell response in vitro. Specifically, in the experiments these A20 cells were pulsed with the ISQ peptide. DO11.10 $CD4^+$ T cells, which are specific for the ISQ peptide, were isolated from the spleens of mice and incubated with the pulsed A20 cells. After 72 hours, the activation status of the T cells was measured by the expression of CD25. In this system, the overexpression of VISTA on the A20 cells results in the suppression of the DO11.10 T cell response.

Anti-VISTA antibodies are capable of reversing the suppression (data not shown). Using this system, we tested whether the addition of VSIG8 anti-sera would analogously reverse or inhibit VISTA mediated suppression. As shown the control sera did not reverse the suppression of VISTA. By contrast, VSIG8 antisera addition resulted in an enhanced T cell response. This result further demonstrated that the binding of VISTA and VSIG8 has functional effects, i.e., this binding interaction elicits VISTA related biological activities, particularly its inhibitory effects on T cell responses and corroborates that VISTA antagonists may be used to inhibit the inhibitory effects of VISTA on immunity, e.g., VISTA'S inhibitory effect on T cell responses. The results in FIG. 14 substantiate that VSIG8 is a VISTA receptor and that VISTA signals to T cells via VSIG8 to induce a suppressive signal.

Other phenotypic data with a VSIG8 mouse provide secondary evidence of the functional relationship of VSIG8 and VISTA. Preliminary analyses reportedly exist of a VSIG8 knockout mouse. Several parameters reportedly were found to be statistically different between WT and VSIG8 KO mice including changes to the T cell and NK T cell compartment.

Example 3: A20 Functional Assay

The experiments disclosed in this example further assessed the function of VSIG8 in the same VSIG expressing A20 system (B cell). In general the assay comprises the following steps:

A20-VSIG8 cells were treated for 2 or 24 hours

1. Ig treatment: one group treated with EPOR-Ig, one treated with VISTA-Ig

2. Activation

PMA (10 ng/ml)/Ionomycin (0.5 ug/ml)

LPS (10 ug/ml)

aCD40 (10 ug/ml)/IL-4 (10 ng/ml)

No Treatment

3. Readouts:

i. Cell counts ii. Flow (CD86, CD25, CD69, PD1, MHC-II-1A)

iii. Cytokines (Luminex, 32-plex)

iv. RNA Seq

The detailed methods and materials used in this functional assay are set forth below.

Materials and Methods

An A20-hVSIG8 cell lines was created by transfecting DNA into A20 by electroporation. The cells were selected with neomycin and then sorted for $GFP^+$ cells (stable pool). Human VSIG8 Protein expression was confirmed by staining cells with rat anti-VSIG8 serum.

Half to one million A20 cells were seeded into 24-well plates with EPOR-Ig or VISTA-Ig. Four regimes of activation of the cells are used: 1—PMA (10 ng/ml)/Ionomycin (0.5 ug/ml), 2—LPS (10 ug/ml), 3—anti-CD40 (10 ug/ml)/IL-4 (10 ng/ml), 4—no treatment. The cells were harvested at two time points—2 hours and 24 hours of incubation separately. The analyses included cell counting, flow cytometer (CD86, PD1, MHC-II-1A), protein analysis of supernatant (Luminex), and gene expression analysis (RNA seq).

Results

Using the above-described methods A20-hVISG8 cells were activated using PMA/ionomycin treatment and with less intensity using LPS or anti-CD40/IL-4 for 24 hours. The results of this experiment are contained in FIG. 15. It can be seen that upon treatment of these cells with VISTA-Ig that PD1 is upregulated, with and without activation. Additionally, a control of A20-GFP was used to confirm that PD1 upregulation is specific, i.e., a result of VISTA/VSIG8 binding interaction.

REFERENCES CITED IN THIS APPLICATION

The following references are cited in this application. The contents of these references and all other references cited in this application are incorporated by reference in their entireties.

1 Dong, C., Juedes, A. E., Temann, U. A., Shresta, S., Allison, J. P., Ruddle, N. H. and Flavell, R. A., ICOS co-stimulatory receptor is essential for T-cell activation and function. *Nature* 2001. 409: 97-101.

2 Suh, W. K., Gajewska, B. U., Okada, H., Gronski, M. A., Bertram, E. M., Dawicki, W., Duncan, G. S., Bukczynski, J., Plyte, S., Ella, A., Wakeham, A., Itie, A., Chung, S., Da Costa, J., Arya, S., Horan, T., Campbell, P., Gaida, K., Ohashi, P. S., Watts, T. H., Yoshinaga, S. K., Bray, M. R., Jordana, M. and Mak, T. W., The B7 family member B7-H3 preferentially down-regulates T helper type 1-mediated immune responses. *Nat Immunol* 2003. 4: 899-906.

3 Borriello, F., Sethna, M. P., Boyd, S. D., Schweitzer, A. N., Tivol, E. A., Jacoby, D., Strom, T. B., Simpson, E. M., Freeman, G. J. and Sharpe, A. H., B7-1 and B7-2 have overlapping, critical roles in immunoglobulin class switching and germinal center formation. *Immunity* 1997. 6: 303-313.

4 Chambers, C. A., Sullivan, T. J. and Allison, J. P., Lymphoproliferation in CTLA-4-deficient mice is mediated by costimulation-dependent activation of CD4+ T cells. *Immunity* 1997. 7: 885-895.

5 Waterhouse, P., Penninger, J. M., Timms, E., Wakeham, A., Shahinian, A., Lee, K. P., Thompson, C. B., Griesser, H. and Mak, T. W., Lymphoproliferative disorders with early lethality in mice deficient in Ctla-4. *Science* 1995. 270: 985-988.

6 Tivol, E. A., Borriello, F., Schweitzer, A. N., Lynch, W. P., Bluestone, J. A. and Sharpe, A. H., Loss of CTLA-4 leads to massive lymphoproliferation and fatal multiorgan tissue destruction, revealing a critical negative regulatory role of CTLA-4. *Immunity* 1995. 3: 541-547.

7 Nishimura, H., Nose, M., Hiai, H., Minato, N. and Honjo, T., Development of lupus-like autoimmune diseases by disruption of the PD-1 gene encoding an ITIM motif-carrying immunoreceptor. *Immunity* 1999. 11: 141-151.

8 Keir, M. E., Lang, S. C., Guleria, I., Latchman, Y. E., Qipo, A., Albacker, L. A., Koulmanda, M., Freeman, G. J., Sayegh, M. H. and Sharpe, A. H., Tissue expression of PD-L1 mediates peripheral T cell tolerance. *J Exp Med* 2006. 203: 883-895.

9 Ortler, S., Leder, C., Mittelbronn, M., Zozulya, A. L., Knolle, P. A., Chen, L, Kroner, A. and Wiendl, H., B7-H1 restricts neuroantigen-specific T cell responses and confines inflammatory CNS damage: implications for the lesion pathogenesis of multiple sclerosis. *Eur J Immunol* 2008. 38: 1734-1744.

10 Zhu, G., Augustine, M. M., Azuma, T., Luo, L., Yao, S., Anand, S., Rietz, A. C., Huang, J., Xu, H., Flies, A. S., Flies, S. J., Tamada, K., Colonna, M., van Deursen, J. M. and Chen, L., B7-H4-deficient mice display augmented neutrophil-mediated innate immunity. *Blood* 2009. 113: 1759-1767.

11 Chen, Y., Wang, Q., Shi, B., Xu, P., Hu, Z., Bai, L. and Zhang, X., Development of a sandwich ELISA for evaluating soluble PD-L1 (CD274) in human sera of different ages as well as supernatants of PD-L1(+) cell lines. *Cytokine* 2011.

12 Greenwald, R. J., Freeman, G. J. and Sharpe, A. H., The B7 family revisited. *Annu Rev Immunol* 2005. 23: 515-548.

13 Zhu, Y., Yao, S., Iliopoulou, B. P., Han, X., Augustine, M. M., Xu, H., Phennicie, R. T., Flies, S. J., Broadwater, M., Ruff, W., Taube, J. M., Zheng, L., Luo, L., Zhu, G., Chen, J. and Chen, L., B7-H5 costimulates human T cells via CD28H. *Nat Commun* 2013. 4: 2043.

14 Brandt, C. S., Baratin, M., Yi, E. C., Kennedy, J., Gao, Z., Fox, B., Haldeman, B., Ostrander, C. D., Kaifu, T., Chabannon, C., Moretta, A., West, R., Xu, W., Vivier, E. and Levin, S. D., The B7 family member B7-H6 is a tumor cell ligand for the activating natural killer cell receptor NKp30 in humans. *J Exp Med* 2009. 206: 1495-1503.

15 Wang, L., Rubinstein, R., Lines, J. L., Wasluk, A., Ahonen, C., Guo, Y., Lu, L. F., Gondek, D., Wang, Y., Fava, R. A., Fiser, A., Almo, S. and Noelle, R. J., VISTA, a novel mouse Ig superfamily ligand that negatively regulates T cell responses. *J Exp Med* 2011. 208: 577-592.

16 Lines, J. L., Sempere, L F., Wang, L., Panttazi, E., Mak, J., O'Connell, S., Ceeraz, S., Suriawinata, A. A., Yan, S., Ernstoff, M. S. and Noelle, R. J., VISTA is an immune checkpoint regulator for human T cells. *in revision* (*Cancer Research*).

17 LeMercier, I., Lines, J. L., Sergent, P., Li, J., Noelle, R. J. and Wang, L., VISTA regulates the development of protective anti-tumor immunity. *in revision* (*Cancer Research*).

18 Wolchok, J. D., Kluger, H., Callahan, M. K., Postow, M. A., Rizvi, N. A., Lesokhin, A. M., Segal, N. H., Ariyan, C. E., Gordon, R. A., Reed, K., Burke, M. M., Caldwell, A., Kronenberg, S. A., Agunwamba, B. U., Zhang, X., Lowy, I., Inzunza, H. D., Feely, W., Horak, C. E., Hong, Q., Korman, A. J., Wigginton, J. M., Gupta, A. and Sznol, M., Nivolumab plus ipilimumab in advanced melanoma. *N Engl J Med* 2013. 369: 122-133.

19 Iliopoulos, D., Kavousanaki, M., Ioannou, M., Boumpas, D. and Verginis, P., The negative costimulatory molecule PD-1 modulates the balance between immunity and tolerance via miR-21. *Eur J Immunol* 2011. 41: 1754-1763.

20 Ansari, M. J., Salama, A. D., Chitnis, T., Smith, R. N., Yagita, H., Akiba, H., Yamazaki, T., Azuma, M., Iwai, H., Khoury, S. J., Auchincloss, H., Jr. and Sayegh, M. H., The programmed death-1 (PD-1) pathway regulates autoimmune diabetes in nonobese diabetic (NOD) mice. *J Exp Med* 2003. 198: 63-69.

21 Bertsias, G. K., Nakou, M., Choulaki, C., Raptopoulou, A., Papadimitraki, E., Goulielmos, G., Kritikos, H., Sidiropoulos, P., Tzardi, M., Kardassis, D., Mamalaki, C. and Boumpas, D. T., Genetic, immunologic, and immunohistochemical analysis of the programmed death 1/programmed death ligand 1 pathway in human systemic lupus erythematosus. *Arthritis Rheum* 2009. 60: 207-218.

22 Prokunina, L., Castillejo-Lopez, C., Oberg, F., Gunnarsson, I., Berg, L., Magnusson, V., Brookes, A. J., Tentler, D., Kristjansdottir, H., Grondal, G., Bolstad, A. I., Svenungsson, E., Lundberg, I., Sturfelt, G., Jonssen, A., Truedsson, L., Lima, G., Alcocer-Varela, J., Jonsson, R., Gyllensten, U. B., Harley, J. B., Alarcon-Segovia, D., Steinsson, K. and Alarcon-Riquelme, M. E., A regulatory polymorphism in PDCD1 is associated with susceptibility to systemic lupus erythematosus in humans. *Nat Genet* 2002. 32: 666-669.

23 Ozkaynak, E., Wang, L., Goodearl, A., McDonald, K., Qin, S., O'Keefe, T., Duong, T., Smith, T., Gutierrez-Ramos, J. C., Rottman, J. B., Coyle, A. J. and Hancock, W. W., Programmed death-1 targeting can promote allograft survival. *J Immunol* 2002. 169: 6546-6553.

24 Watson, M. P., George, A. J. and Larkin, D. F., Differential effects of costimulatory pathway modulation on corneal allograft survival. *Invest Ophthalmol Vis Sci* 2006. 47: 3417-3422.

25 Podojil, J. R., Liu, L. N., Marshall, S. A., Chiang, M. Y., Goings, G. E., Chen, L., Langermann, S. and Miller, S. D., B7-H4Ig inhibits mouse and human T-cell function and treats EAE via IL-10/Treg-dependent mechanisms. *J Autoimmun* 2013. 44: 71-81.

26 Sica, G. L., Choi, I. H., Zhu, G., Tamada, K., Wang, S. D., Tamura, H., Chapoval, A. I., Flies, D. B., Bajorath, J. and Chen, L., B7-H4, a molecule of the B7 family, negatively regulates T cell immunity. *Immunity* 2003. 18: 849-861.

27 Wang, X., Hao, J., Metzger, D. L., Mui, A., Ao, Z., Verchere, C. B., Chen, L., Ou, D. and Warnock, G. L., B7-H4 induces donor-specific tolerance in mouse islet allografts. *Cell Transplant* 2012. 21: 99-111.

28 Yamaura, K., Watanabe, T., Boenisch, O., Yeung, M., Yang, S., Magee, C. N., Padera, R., Datta, S., Schatton, T., Kamimura, Y., Azuma, M. and Najafian, N., In vivo function of immune inhibitory molecule B7-H4 in alloimmune responses. *Am J Transplant* 2010. 10: 2355-2362.

29 Yi, K. H. and Chen, L., Fine tuning the immune response through B7-H3 and B7-H4. *Immunol Rev* 2009. 229: 145-151.

30 Wang, X., Hao, J., Metzger, D. L., Ao, Z., Chen, L., Ou, D., Verchere, C. B., Mui, A. and Warnock, G. L., B7-H4 Treatment of T Cells Inhibits ERK, JNK, p38, and AKT Activation. *PLoS One* 2012. 7: e28232.

31 Terawaki, S., Tanaka, Y., Nagakura, T., Hayashi, T., Shibayama, S., Muroi, K., Okazaki, T., Mikami, B., Garboczi, D. N., Honjo, T. and Minato, N., Specific and high-affinity binding of tetramerized PD-L1 extracellular domain to PD-1-expressing cells: possible application to enhance T cell function. *Int Immunol* 2007. 19: 881-890.

32 Sedy, J. R., Gavrieli, M., Potter, K. G., Hurchla, M. A., Lindsley, R. C., Hildner, K., Scheu, S., Pfeffer, K., Ware, C. F., Murphy, T. L and Murphy, K. M., B and T lymphocyte attenuator regulates T cell activation through interaction with herpesvirus entry mediator. *Nat Immunol* 2005. 6: 90-98.

33 Parisi, S., Battista, M., Musto, A., Navarra, A., Tarantino, C. and Russo, T., A regulatory loop involving Dies1 and miR-125a controls BMP4 signaling in mouse embryonic stem cells. *FASEB J* 2012. 26: 3957-3968.

34 Youngnak, P., Kozono, Y., Kozono, H., Iwai, H., Otsuki, N., Jin, H., Omura, K., Yagita, H., Pardoll, D. M., Chen, L. and Azuma, M., Differential binding properties of B7-H1 and B7-DC to programmed death-1. *Biochem Biophys Res Commun* 2003. 307: 672-677.

35 Butte, M. J., Keir, M. E., Phamduy, T. B., Sharpe, A. H. and Freeman, G. J., Programmed death-1 ligand 1 interacts specifically with the b7-1 costimulatory molecule to inhibit T cell responses. *Immunity* 2007. 27: 111-122.

36 Sharpe, A. H. and Freeman, G. J., The B7-CD28 superfamily. *Nat Rev Immunol* 2002. 2: 116-126.

37 Bartel P. L. et al. (1993) Using the two-hybrid system to detect protein-protein interactions. In Cellular Interactions in Development: A Practical Approach, D. A. Hartley, Ed., Oxford University Press, Oxford; pp 153-179.

38 Béranger F. et al. (1997) Getting more from the two-hybrid system: N-terminal fusions to LexA are efficient and sensitive baits for two-hybrid studies. NAR 25: 2035-36.

39 Formstecher E. et al. (2005) Protein interaction mapping: a *Drosophila* case study. Genome Res. 15: 37684.

40 Fromont-Racine M., Rain J. C., and Legrain P. (1997) Toward a functional analysis of the yeast genome through exhaustive two-hybrid screens. Nat. Genet. 16: 277-82.

41 Rain J. C. et al. (2001) The protein-protein interaction map of *Helicobacter pylori*. Nature 409: 211-15.

42 Vojtek A. and Hollenberg S. M. (1995) Ras-Raf Interaction: two-hybrid analysis. Methods Enzymol. 255: 33142.

43 Wojcik J., Boneca I. G., and Legrain P. (2002) Prediction, assessment and validation of protein interaction maps in bacteria. J. Mol. Biol. 323: 763-70.

VSIG8 SEQUENCES

SEQ ID NO: 1: *Homo sapiens* VSIG8 POLYPEPTIDE SEQUENCE

```
  1  mrvggafhll lvclspalls avringdgqe vlylaegdnv rlgcpyvldp edygpngldi

 61  ewmqvnsdpa hhrenvflsy qdkrinhgsl phlqqrvrfa asdpsqydas inlmnlqvsd

121  tatyecrvkk ttmatrkviv tvqarpavpm cwteghmtyg ndvvlkcyas ggsqplsykw

181  akisghhypy ragsytsqhs yhselsyqes fhssinqgln ngdlvlkdis raddglyqct

241  vannvgysvc vvevkvsdsr rigviigivl gsllalgcla vgiwglvccc cggsgaggar
```

-continued

| VSIG8 SEQUENCES |
| --- |
| 301 gafgygnggg vgggacgdla seiredavap gckasgrgsr vthllgyptq nvsrslrrky |
| 361 apppcggped valapctaaa aceagpspvy vkvksaepad caegpvqckn gllv |
| SEQ ID NO: 2: *Mus muscutus* VSIG8 POLYPEPTIDE SEQUENCE |
| 1 mgvrgalhll lvclspalls avringdgqe vmylaegdnv rlgcpylldp edlgtnsldi |
| 61 ewmqvnseps hrenvfltyq dkrlghgnlp hlqqrvrfaa sdpsqydasi nlmnlqvsdt |
| 121 atyecrvkkt tmatrkvivt vqarpavpmc wteghmskgn dvvlkcfang gsqplsykwa |
| 181 kisghshpyr agayhsqhsf hselsyqesf hstinqglgn gdlllkgina dddglyqctv |
| 241 anhvgysvcv vevkvsdsqr vgmivgavlg sllmlaclal giwglicccc ggggaggarg |
| 301 afgygvgggv gggacgdlas eirvdaeapg ckasgrgsrv thllgyptqn vsrslrrkya |
| 361 pppcggpedv alvprtasas ceagpspvyi kvksaepadc adcaqveqrs ckdgllv |
| SEQ ID NO: 3: *Macaca fascicularis* VSIG8 POLYPEPTIDE SEQUENCE |
| 1 mgvggafhll lvclspalls avringdgqe vlylaegdnv rlgcpyvldp edygpngldi |
| 61 ewmqvnsdpa hhrenvflsy qdkrinhgnl phlqqrvrfa asdpsqydas inlmnlqvsd |
| 121 tatyecrvkk ttmatrkviv tvqarpavpm cwteghmthg ndvvlkcyan ggsqplsykw |
| 181 akisghhypy ragsytsqhs yhselsyqes fhssinqgln ngdlvlkdis raddglyqct |
| 241 vannvgysvc vvevkvsdsr rigviigail gsllalgcla vgiwglvccc cggsgaggar |
| 301 gafgygnggg vgggacgdla seiredavap gckasgrgsr vthllgyptq nvsrslrrky |
| 361 apppcggpen valapctaaa aceagpspvy vkvksaepad caegpvqckn gllv |
| SEQ ID NO: 4: *Homo sapiens* VSIG8 NUCLEIC ACID SEQUENCE |
| 1 agacggagga aacaccgagc ctagagacat gagagttgga ggagcattcc accttctact |
| 61 cgtgtgcctg agcccagcac tgctgtctgc tgtgcggatc aacggggatg gacaggaggt |
| 121 cctgtacctg gcagaaggtg ataatgtgag gctgggctgc ccctacgtcc tggaccctga |
| 181 ggactatggt cccaatgggc cggacatcga gtggatgcag gtcaactcag accccgccca |
| 241 ccaccgagag aacgtgttcc ttagtcacca ggacaagagg atcaaccatg gcagccttcc |
| 301 ccatctgcag cagagggtcc gctttgcagc ctcagaccca agccagtacg atgcctccat |
| 361 caacctcatg aacctgcagg tatctgatac agccacttat gagtgccggg tgaagaagac |
| 421 caccatggcc acccggaagg tcattgtcac tgtccaagca cgacctgcag tgcccatgtg |
| 481 ctggacagag ggccacatga catatggcaa cgatgtggtg ctgaagtgct atgccagtgg |
| 541 gggctcccag cccctctcct acaagtgggc caagatcagt gggcaccatt acccctatcg |
| 601 agctgggtct tacacctccc agcacagcta ccactcagag ctgtcctacc aggagtcctt |
| 661 ccacagctcc ataaaccaag gcctgaacaa tggggacctg gtgttgaagg atatctccag |
| 721 agcagatgat gggctgtatc agtgcacagt ggccaacaac gtgggctaca gtgcttgtgt |
| 781 ggtggaggtg aaggtctcag actcccggcg tataggcgtg atcatcggca tcgtcctggg |
| 841 ctctctgctc gcgctgggct gcctggccgt aggcatctgg gggctcgtct gctgctgctg |
| 901 cgggggctcc ggggctggcg gcgcccgcgg tgccttcggc tacggcaacg gcggcggggt |
| 961 cggcggaggg gcctgcggcg acttggctag tgagatcaga gaggacgccg tggcgcccgg |
| 1021 gtgcaaggcc agcgggcgcg gcagccgcgt cacccacctc ctggggtacc cgacgcagaa |
| 1081 cgtcagccgc tccctgcgcc gcaagtacgc gcctcccccc tgcggcggcc ccgaggacgt |
| 1141 ggccctggcg ccctgcaccg ccgccgccgc ctgcgaagcg ggcccctccc cggtctacgt |
| 1201 caaggtcaag agcgcggagc cggctgactg cgccgagggg ccggtgcagt gcaagaacgg |

-continued

| VSIG8 SEQUENCES |
|---|
| 1261 cctcttggtg tgagcgcgcg cgccgggccg ggctgcgccc cagccaggag gagggcgcgg |
| 1321 ggctctctgt ctgcagctgg ggacacgtcg gggctgggga cgacctcgct cgccccaggc |
| 1381 tgccaggcgg ctgggggtga aggcatttcc ctaaggaaat gcgtagggag gcagagc |
| SEQ ID NO: 5: *Mus musculus* VSIG8 NUCLEIC ACID SEQUENCE |
| 1 gactcattgc atcttcctgc caccccgggc agtgtctggg ccctccgctc cccctccctc |
| 61 cacctgcccc ttccacccac caccaccagc ccactggagc ccagctcagg cggaggaaag |
| 121 accaagccta gagacatggg agttcgagga gcactccatc ttctacttgt gtgcctgagc |
| 181 ccagcactgt tgtctgctgt aaggatcaac ggggatggcc aggaggtcat gtacctgqca |
| 241 gaaggtgaca atgtgaggct aggctgtccc tacctcctgg atcctgagga tttgggtacc |
| 301 aacagtctgg acattgagtg gatgcaagtc aactcagagc cctcacacag ggagaatgtt |
| 361 tttcttactt atcaagacaa gaggataggt catggcaacc tcccccatct gcagcagagg |
| 421 gtccgctttg cagcctcaga ccccagccag tacgatgcct ccatcaacct catgaacctg |
| 481 caggtatctg acacagcaac ctatgagtgc cgggtgaaga agaccaccat ggccaccagc |
| 541 aaggtcattg tcactgtcca agcacgtcct gcggtgccca tgtgttggac ggaaggccac |
| 601 atgtcaaagg gcaacgatgt ggtgctgaag tgctttgcca acggaggctc tcagcccctc |
| 661 tcctacaagt gggccaagat cagtgggcac agtcacccct accgagctgg ggcttaccac |
| 721 tcacagcaca gcttccactc tgagctttct taccaagagt cattccacag caccatcaac |
| 781 caaggcctgg gcaacggaga cctgctgttg aagggcatca acgcagacga cgatgggctg |
| 841 tatcagtgca cagtggccaa ccatgtgggc tacagcgtct gtgtggtaga ggtgaaagtc |
| 901 tcagactccc agcgagtagg catgatcgtt ggagcagtgc tgggctcttc gctcatgctg |
| 961 gcctgcctgg cactaggcat ctgggggctc atctgctgct gctgcggagg cggcggggcc |
| 1021 ggtggtgccc gaggtgcctt cggctacggg gtcggcggcg gggtcggcgg aggggcctgc |
| 1081 ggcgacttgg ctagtgagat cagagtggac gccgaggcgc ccgggtgtaa ggccagcggg |
| 1141 cgcggcagcc gcgtcaccca cctcctgggg tacccggcgc agaacgtcag ccgctccagg |
| 1201 cgccgcaagt acgcgcctcc gccctgcggc ggccccgagc acgtggccct agtgccccgc |
| 1261 accgcctccg cctcctgcga agcgggtccc tcccccgtct acatcaaggt caagagcgcg |
| 1321 gagccggccg actgcgccga ctgtgcccag gtcgagcagc gctcgtgcaa ggacggcctc |
| 1381 ttagtgtgag cgcacagcac cgggctgcgc cccggctggg aggtggttcg gggctctct |
| 1441 gcccgcagct ggggacaggt tcgggccagc agacctggct ctctcattgg ccacctagcg |
| 1501 gtggtaagga aatttccctc tgagaagcca agccgggcag accctcctcc cctgtagtgg |
| 1561 gaggagaggc gggggagaca gaaaacagtt cagagctctc cctcacccct ggtttccagg |
| 1621 gagaggaagg gagaggagag ctgtcggtat cccagaaccg cagaggtaca acccagatgt |
| 1681 ccccagccaa ggcgagggcc ccccagccct gggtaggtgg atgtcagggc tgaattgctc |
| 1741 tgtgtgtgag atctgagctc caaggcaaca gtgttagcac aataaagaaa cttaaagact |
| 1801 gg |
| SEQ ID NO: 6: *Homo sapiens* VISTA (Alternate names: B7-H5; B7H5; DD1alpha; GI24; PP2135; SISP1) AMINO ACID SEQUENCE |
| 1 mgvptaleag swrwgsllfa lflaaslgpv aafkvatpys lyvcpegqnv tltcrllgpv |
| 61 dkghdvtfyk twyrssrgev qtcserrpir nltfqdlhlh hgghqaants hdlaqrhgle |
| 121 sasdhhgnfs itmrnltlld sglycclvve irhhhsehrv hgamelqvqt gkdapsncvv |

-continued

VSIG8 SEQUENCES 181 ypsssqdsen itaaalatga civgilclpl illlvykqrq aasnrraqal vrmdsniqgi 241 enpgfeaspp aqgipeakvr hplsyvaqrq psesgrhlls epstplsppg pgdvffpsld 301 pvpdspnfev i SEQ ID NO: 7: *Mus musculus* VISTA AMINO ACID SEQUENCE
1 mgvpavpeas sprwgtllla iflaasrglv aafkvttpys lyvcpegqna tltcrilgpv 61 skghdvtiyk twylssrgev qmckehrpir nftlqhlqhh gshlkanash dqpqkhglel 121 asdhhgnfsi tlrnvtprds glycclviel knhhpeqrfy gsmelqvqag kgsgstcmas 181 neqdsdsita aalatgaciv gilclplill lvykqrqvas hrraqelvrm dsntqgienp 241 gfettppfqg mpeaktrppl syvaqrqpse sgryllsdps tplsppgpgd vffpsldpvp 301 dspnseai SEQ ID NO: 8: *Mus musculus* VISTA AMINO ACID SEQUENCE
1 mgvpavpeas sprwgtllla iflaasrglv aafkvttpys lyvcpegqna tltcrilgpv 61 skghdvtiyk twylssrgev qmckehrpir nftlqhlqhh gshlkanash dqpqkhglel 121 asdhhgnfsi tlrnvtprds glycclviel knhhpeqrfy gsmelqvqag kgsgstcmas 181 neqdsdsita aalatgaciv gilclplill lvykqrqvas hrraqelvrm dssntqgien 241 pgfettppfq gmpeaktrpp lsyvaqrqps esgryllsdp stplsppgpg dvffpsldpv 301 pdspnseai SEQ ID NO: 9: *Homo sapiens* VISTA (Alternate names: B7-H5; B7H5; DD1alpha; GI24; PP2135; SISP1) NUCLBIC ACID SEQUENCE
1 gggggcgggt gcctggagca cggcgctggg gccgcccgca gcgctcactc gctcgcactc 61 agtcgcggga ggcttccccg cgccggccgc gtcccgcccg ctccccggca ccagaagttc 121 ctctgcgcgt ccgacggcga catgggcgtc cccacggccc tggaggccgg cagctggcgc 181 tggggatccc tgctcttcgc tctcttcctg gctgcgtccc taggtccggc ggcagccttc 241 aaggtcgcca cgccgtattc cctgtatgtc tgtcccgagg ggcagaacgt caccctcacc 301 tgcaggctct tgggccctgc ggacaaaggg cacgatgtga ccttctacaa gacgtggcac 361 cgcagctcga ggggcgaggt gcagacctgc tcagagcgcc ggcccatccg caacctcacg 421 ttccaggacc ttcacctgca ccatggaggc caccaggctg ccaacaccag ccacgacctg 461 gctcagcgcc acgggctgga gtcggcctcc gaccaccatg gcaacttctc catcaccatg 541 cgcaacctga ccctgctgga tagcggcctc tactgctgcc tggtggtgga gatcaggcac 601 caccactcgg agcacagggt ccatggtgcc atggagctgc aggtgcagac aggcaaagat 661 gcaccatcca actgtgtggt gtacccatcc tcctcccagg atagtgaaaa catcacggct 721 gcagccctgg ctacgggtgc ctgcatcgta ggaatcctct gcctccccct catcctgctc 781 ctggtctaca agcaaaggca ggcagcctcc aaccgccgtg cccaggagct ggtgcggatg 841 gacagcaaca ttcaagggat tgaaaacccc ggctttgaag cctcaccacc tgcccagggg 901 atacccgagg ccaaagtcag gcacccccctg tcctatgtgg cccagcggca gccttctgag 961 tctgggcggc atctgctttc ggagcccagc acccccctgt ctcctccagg ccccggagac 1021 gtcttcttcc catccctgga ccctgtccct gactctccaa actttgaggt catctagccc 1081 agctggggga cagtgggctg ttgtggctgg gtctggggca ggtgcatttg agccagggct 1141 ggctctgtga gtggcctcct tggcctcggc cctggttccc tccctcctgc tctgggctca 1201 gatactgtga catcccagaa gcccagcccc tcaacccctc tggatgctac atggggatgc 1261 tggacggctc agcccctgtt ccaaggattt tggggtgctg agattctccc ctagagacct -continued

| VSIG8 SEQUENCES |
|---|

1321 gaaattcacc agctacagat gccaaatgac ttacatctta agaagtctca gaacgtccag
1381 cccttcagca gctctcgttc tgagacatga gccttgggat gtggcagcat cagtgggaca
1441 agatggacac tgggccaccc ccccaggcac cagacacagg gcacggtgga gagacttctc
1501 ccccgtggcc gccttggctc ccccgttttg cccgaggctg ctcttctgtc agacCtcctc
1561 tttgtaccac agtggctctg gggccaggcc tgcctgccca ctggccatcg ccaccttccc
1621 cagctgcctc ctaccagcag tttctctgaa gatctgtcaa caggttaagt caatctgggg
1681 cttccactgc ctgcattcca gtccccagag cttggtggtc ccgaaacggg aagtacatat
1741 tggggcatgg tggcctccgt gagcaaatgg tgtcttgggc aatctgaggc caggacagat
1801 gttgccccac ccactggaga tggtgctgag ggaggtgggt ggggccttct gggaaggtga
1861 gtggagaggg gcacctgccc cccgccctcc ccatccccta ctcccactgc tcagcgcggg
1921 ccattgcaag ggtgccacac aatgtcttgt ccaccctggg acacttctga gtatgaagcg
1981 ggatgctatt aaaaactaca tggggaaaca ggtgcaaacc ctggagatgg attgtaagag
2041 ccagtttaaa tctgcactct gctgctcctc ccccaccccc accttccact ccatacaatc
2101 tgggcctggt ggagtcttcg cttcagagcc attcggccag gtgcgggtga tgttcccatc
2161 tcctgcttgt gggcatgccc tggctttgtt tttatacaca taggcaaggt gaqtcctctg
2221 tggaattgtg attgaaggat tttaaagcag gggaggagag tagggggcac ctctgtacac
2281 tctgggggta aaacagggaa ggcagtgcct gagcatgggg acaggtgagg tggggctggg
2341 cagacccccct gtagcgttta gcaggatggg ggccccaggt actgtggaga gcatagtcca
2401 gcctgggcat ttgtctccta gcagcctaca ctggctctgc tgagctgggc ctgggtgctg
2461 aaagccagga tttggggcta ggcgggaaga tgttcgccca attgcttggg gggttggggg
2521 gatggaaaag gggagcacct ctaggcCgcc tggcaqcagt gagccctggg cctgtggcta
2581 cagccaggga accccacctg gacacatggc cctgcttcta agccccccag ttaggcccaa
2641 aggaatggtc cactgagggc ctcctgctct gcctgggctg ggccaggggc tttgaggaga
2701 gggtaaacat aggcccggag acggggctga cacctcgagt ggccagaata tgcccaaacc
2761 ccggcttctc ccctgtccct aggcagaggg gggtcccttc ttttgttccc tctggtcacc
2821 acaatgcttg atgccagctg ccataggaag agggtgctgg ctggccatgg tggcacacac
2881 ctgtcctccc agcactttgc agggctgagg tggaaggacc gcttaagccc aggtgttcaa
2941 ggctgctgtg agctgtgttc gagccactac actccagcct ggggacggag caaaactttg
3001 cctcaaaaca aattttaaaa agaaagaaag aaggaaagag ggtatgtttt tcacaattca
3061 tgggggcctg catggcagga gtggggacag gacacctgct gttcctggag tcgaaggaca
3121 agcccacagc ccagattccg gttctcccaa ctcaggaaga gcatgccctg ccctccgggg
3181 aggctggcct ggccccagcc ctcagctgct gaccttgagg cagagacaac ttctaagaat
3241 ttggctgcca gaccccaggc ctggctgctg ctgtgtggag agggaggcgg cccgcagcag
3301 aacagccacc gcacttcctc ctcagcttcc tctggtgcgg ccctgccctc tcttctctgg
3361 acccttctac aactgaacgc atctgggctt cgtggtttcc tgttttcagc gaaatttact
3421 ctgagctccc agttccatct tcatccatgg ccacaggccc tgcctacaac gcactaggga
3481 cgtccctccc tgctgctgct ggggaggggc aggctgccgg agccgccctc tgagttgccc
3541 gggatggtag tgcctctgat gccagccctg gtggctgtgg gctggggtgc atgggagagc -continued

| VSIG8 SEQUENCES |
| --- |
| 3601 tgggtgcgag aacatggcgc ctccaggggg cgggaggagc actaggggct ggggcaggag |
| 3661 gctcctggag cgctggattc gtggcacagt ctgaggccct gagagggaaa tccatgcttt |
| 3721 taagaaccaa tccattgtta ggagatcaat caggaattag ggccatcttt acctatctcc |
| 3781 tgacattcac agtttaatag agacttcctg cctttattcc ctcccaggga gaggctgaag |
| 3841 gaatggaatt gaaagcacca tttggagggt tttgctgaca cagcggggac tgctcagcac |
| 3901 tccctaaaaa cacaccatgg aggccaccgg tgactgctgg tgggcaggct ggccccgcct |
| 3961 gggggagtcc gtggcgatgg gcgctggggt ggaggtgcag gagccccagg acctgctttt |
| 4021 caaaagactt ctgcctgacc agagctccca ctacatgcag tggcccaggg cagaggggct |
| 4081 gatacatggc ctttttcagg gggtgctcct cgcgcggtgg acttgggagt gtgcagtggg |
| SEQ ID NO: 10: *Homo sapiens* VISTA (Alternate names: B7-H5; B7H5; DD1atpha; GI24; PP2135; SISP1) CODING NUCLEIC ACID SEQUENCE |
| 1 ctcgccgcgc tgagccgcct cgggacggag ccatgcggcg ctgggcctgg gccgcggtcg |
| 61 tggtcccct cgggccgcag ctcgtgctcc tcgggggcgt cggggcccgg cgggaggcac |
| 121 agaggacgca gcagcctggc cagcgcgcag atccccccaa cgccaccgcc agcgcgtcct |
| 181 cccgcgaggg gctgcccgag gcccccaagc catcccaggc ctcaggacct gagttctccg |
| 241 acgcccacat gacatggctg aactttgtcc ggcggccgga cgacggcgcc ttaaggaagc |
| 301 ggtgcggaag cagggacaag aagccgcggg atctcttcgg tcccccagga cctccaggtg |
| 361 cagaagtgac cgcggagact ctgcttcacg agtttcagga gctgctgaaa gaggccacgg |
| 421 agcgccggtc ctcagggctt ctggacccgc tgctgcccca gggggcgggc ctgcggctgg |
| 481 tgggcgaggc ctttcactgc cggctgcagg gtccccgccg ggtggacaag cggacgctgg |
| 541 tggagctgca tggtttccag gctcctgctg cccaaggtgc cttcctgcga ggctccggtc |
| 601 tgagcctggc ctcgggtcgg ttcacggccc ccgtgtccgg catcttccag ttctctgcca |
| 661 gtctgcacgt ggaccacagt gagctgcagg gcaaggcccg gctgcgggcc cgggacgtgg |
| 721 tgtgtgttct catctgtatt gagtccctgt gccagcgcca cacgtgcctg gaggccgtct |
| 781 caggcctgga gagcaacagc agggtcttca cgctacaggt gcaggggctg ctgcagctgc |
| 841 aggctggaca gtacgcttct gtgtttgtgg acaatggctc cggggccgtc ctcaccatcc |
| 901 aggcgggctc cagcttctcc gggctgctcc tgggcacgtg agggcgccca ggggggctgg |
| 961 cgaggagctg ccgccggatc ccggggaccc tcctactgat gcccgtggtc accacaataa |
| 1021 agagccctcc accctcaaaa aaaaaaaaaa aaaaa |
| SEQ ID NO: 11: *Mus musculus* VISTA CODING NUCLEIC ACID SEQUENCE |
| 1 ctcgccgcgc tgagccgcct cgggacggag ccatgcggcg ctgggcctgg gccgcggtcg |
| 61 tggtcccct cgggccgcag ctcgtgctcc tcgggggcgt cggggcccgg cgggaggcac |
| 121 agaggacgca gcagcctggc cagcgcgcag atccccccaa cgccaccgcc agcgcgtcct |
| 181 cccgcgaggg gctgcccgag gcccccaagc catcccaggc ctcaggacct gagttctccg |
| 241 acgcccacat gacatggctg aactttgtcc ggcggccgga cgacggcgcc ttaaggaagc |
| 301 ggtgcggaag cagggacaag aagccgcggg atctcttcgg tcccccagga cctccaggtg |
| 361 cagaagtgac cgcggagact ctgcttcacg agtttcagga gctgctgaaa gaggccacgg |
| 421 agcgccggtt ctcagggctt ctggacccgc tgctgcccca gggggcgggc ctgcggctgg |
| 481 tgggcgaggc ctttcactgc cggctgcagg gtccccgccg ggtggacaag cggacgctgg |
| 541 tggagctgca tggtttccag gctcctgctg cccaaggtgc cttcctgcga ggctccggtc |

-continued

VSIG8 SEQUENCES

```
 601  tgagcctggc ctcgggtcgg ttcacggccc ccgtgtccgg catcttccag ttctctgcca

 661  gtctgcacgt ggaccacagt gagctgcagg gcaaggcccg gctgcgggcc cgggacgtgg

 721  tgtgtgttct catctgtatt gagtccctgt gccagcgcca cacgtgcctg gaggccgtct

 781  caggcctgga gagcaacagc agggtcttca cgctacaggt gcaggggctg ctgcagctgc

 841  aggctggaca gtacgcttct gtgtttgtgg acaatggctc cggggccgtc ctcaccatcc

 901  aggcgggctc cagcttctcc gggctgctcc tgggcacgtg agggcgccca ggggggctgg

 961  cgaggagctg ccgccggatc ccggggaccc tcctactgat gcccgtggtc accacaataa

1021  agagccctcc accctcaaaa aaaaaaaaaa aaaaa
```

The invention claimed is:

1. A method of treating cancer which method comprises the administration to a subject in need thereof a therapeutically effective amount of at least one antibody or antigen binding antibody fragment that binds to a VSIG8 polypeptide which has a sequence selected from SEQ ID NO: 1, 2, and 3, and wherein said antibody or antigen binding antibody fragment potentiates $CD8^+$ T cell mediated anti-tumor immunity in said subject.

2. A method of treating an infectious disease, which method comprises the administration to a subject in need thereof of a therapeutically effective amount of at least one antibody or antigen binding antibody fragment that binds to a VSIG8 polypeptide having an amino acid sequence selected from SEQ ID NO: 1, 2, and 3, and wherein said antibody or antigen binding antibody fragment potentiates $CD8^+$ T cell mediated killing of infected cells in said subject.

3. The method of claim 1, wherein said antibody or antigen binding antibody fragment binds to the VSIG polypeptide of SEQ ID NO:1.

4. The method of claim 1, wherein said antibody or antigen binding antibody fragment binds to the VSIG polypeptide of SEQ ID NO:2.

5. The method of claim 1, wherein said antibody or antigen binding antibody fragment binds to the VSIG polypeptide of SEQ ID NO:3.

6. The method of claim 2, wherein said antibody or antigen binding antibody fragment binds to the VSIG polypeptide of SEQ ID NO:1.

7. The method of claim 2, wherein said antibody or antigen binding antibody fragment binds to the VSIG polypeptide of SEQ ID NO:2.

8. The method of claim 2, wherein said antibody or antigen binding antibody fragment binds to the VSIG polypeptide of SEQ ID NO:3.

9. The method of claim 1, wherein said antibody or antigen binding antibody fragment comprises a human IgG1, IgG2, IgG3 or IgG4.

10. The method of claim 2, wherein said antibody or antigen binding antibody fragment comprises a human IgG1, IgG2, IgG3 or IgG4.

11. The method of claim 1, wherein said antibody or antigen binding antibody fragment comprises an IgG1, IgG2, IgG3 or IgG4 which is mutated to impair FcR and/or complement binding.

12. The method of claim 2, wherein said antibody or antigen binding antibody fragment comprises an IgG1, IgG2, IgG3 or IgG4 which is mutated to impair FcR and/or complement binding.

13. The method of claim 1, which further comprises the administration of an anti-human VISTA antibody.

14. The method of claim 2, which further comprises the administration of an anti-human VISTA antibody.

* * * * *

SEQUENCE LISTING

<160> NUMBER OF SEQ ID NOS: 11

<210> SEQ ID NO 1
<211> LENGTH: 414
<212> TYPE: PRT
<213> ORGANISM: Homo sapiens

<400> SEQUENCE: 1

```
Met Arg Val Gly Gly Ala Phe His Leu Leu Leu Val Cys Leu Ser Pro
1               5                   10                  15

Ala Leu Leu Ser Ala Val Arg Ile Asn Gly Asp Gly Gln Glu Val Leu
            20                  25                  30

Tyr Leu Ala Glu Gly Asp Asn Val Arg Leu Gly Cys Pro Tyr Val Leu
        35                  40                  45

Asp Pro Glu Asp Tyr Gly Pro Asn Gly Leu Asp Ile Glu Trp Met Gln
    50                  55                  60

Val Asn Ser Asp Pro Ala His His Arg Glu Asn Val Phe Leu Ser Tyr
65                  70                  75                  80

Gln Asp Lys Arg Ile Asn His Gly Ser Leu Pro His Leu Gln Gln Arg
                85                  90                  95

Val Arg Phe Ala Ala Ser Asp Pro Ser Gln Tyr Asp Ala Ser Ile Asn
            100                 105                 110

Leu Met Asn Leu Gln Val Ser Asp Thr Ala Thr Tyr Glu Cys Arg Val
        115                 120                 125

Lys Lys Thr Thr Met Ala Thr Arg Lys Val Ile Val Thr Val Gln Ala
    130                 135                 140

Arg Pro Ala Val Pro Met Cys Trp Thr Glu Gly His Met Thr Tyr Gly
145                 150                 155                 160

Asn Asp Val Val Leu Lys Cys Tyr Ala Ser Gly Gly Ser Gln Pro Leu
                165                 170                 175

Ser Tyr Lys Trp Ala Lys Ile Ser Gly His His Tyr Pro Tyr Arg Ala
            180                 185                 190

Gly Ser Tyr Thr Ser Gln His Ser Tyr His Ser Glu Leu Ser Tyr Gln
        195                 200                 205

Glu Ser Phe His Ser Ser Ile Asn Gln Gly Leu Asn Asn Gly Asp Leu
    210                 215                 220

Val Leu Lys Asp Ile Ser Arg Ala Asp Asp Gly Leu Tyr Gln Cys Thr
225                 230                 235                 240
```

-continued

```
Val Ala Asn Asn Val Gly Tyr Ser Val Cys Val Val Glu Val Lys Val
                245                 250                 255

Ser Asp Ser Arg Arg Ile Gly Val Ile Ile Gly Ile Val Leu Gly Ser
            260                 265                 270

Leu Leu Ala Leu Gly Cys Leu Ala Val Gly Ile Trp Gly Leu Val Cys
        275                 280                 285

Cys Cys Cys Gly Gly Ser Gly Ala Gly Gly Ala Arg Gly Ala Phe Gly
    290                 295                 300

Tyr Gly Asn Gly Gly Gly Val Gly Gly Gly Ala Cys Gly Asp Leu Ala
305                 310                 315                 320

Ser Glu Ile Arg Glu Asp Ala Val Ala Pro Gly Cys Lys Ala Ser Gly
                325                 330                 335

Arg Gly Ser Arg Val Thr His Leu Leu Gly Tyr Pro Thr Gln Asn Val
            340                 345                 350

Ser Arg Ser Leu Arg Arg Lys Tyr Ala Pro Pro Pro Cys Gly Gly Pro
        355                 360                 365

Glu Asp Val Ala Leu Ala Pro Cys Thr Ala Ala Ala Ala Cys Glu Ala
    370                 375                 380

Gly Pro Ser Pro Val Tyr Val Lys Val Lys Ser Ala Glu Pro Ala Asp
385                 390                 395                 400

Cys Ala Glu Gly Pro Val Gln Cys Lys Asn Gly Leu Leu Val
                405                 410


<210> SEQ ID NO 2
<211> LENGTH: 417
<212> TYPE: PRT
<213> ORGANISM: Mus musculus

<400> SEQUENCE: 2

Met Gly Val Arg Gly Ala Leu His Leu Leu Leu Val Cys Leu Ser Pro
1               5                   10                  15

Ala Leu Leu Ser Ala Val Arg Ile Asn Gly Asp Gly Gln Glu Val Met
            20                  25                  30

Tyr Leu Ala Glu Gly Asp Asn Val Arg Leu Gly Cys Pro Tyr Leu Leu
        35                  40                  45

Asp Pro Glu Asp Leu Gly Thr Asn Ser Leu Asp Ile Glu Trp Met Gln
    50                  55                  60

Val Asn Ser Glu Pro Ser His Arg Glu Asn Val Phe Leu Thr Tyr Gln
65                  70                  75                  80

Asp Lys Arg Ile Gly His Gly Asn Leu Pro His Leu Gln Gln Arg Val
                85                  90                  95

Arg Phe Ala Ala Ser Asp Pro Ser Gln Tyr Asp Ala Ser Ile Asn Leu
            100                 105                 110

Met Asn Leu Gln Val Ser Asp Thr Ala Thr Tyr Glu Cys Arg Val Lys
        115                 120                 125

Lys Thr Thr Met Ala Thr Arg Lys Val Ile Val Thr Val Gln Ala Arg
    130                 135                 140

Pro Ala Val Pro Met Cys Trp Thr Glu Gly His Met Ser Lys Gly Asn
145                 150                 155                 160

Asp Val Val Leu Lys Cys Phe Ala Asn Gly Gly Ser Gln Pro Leu Ser
                165                 170                 175

Tyr Lys Trp Ala Lys Ile Ser Gly His Ser His Pro Tyr Arg Ala Gly
            180                 185                 190

Ala Tyr His Ser Gln His Ser Phe His Ser Glu Leu Ser Tyr Gln Glu
        195                 200                 205
```

```
Ser Phe His Ser Thr Ile Asn Gln Gly Leu Gly Asn Gly Asp Leu Leu
    210                 215                 220

Leu Lys Gly Ile Asn Ala Asp Asp Asp Gly Leu Tyr Gln Cys Thr Val
225                 230                 235                 240

Ala Asn His Val Gly Tyr Ser Val Cys Val Val Glu Val Lys Val Ser
                245                 250                 255

Asp Ser Gln Arg Val Gly Met Ile Val Gly Ala Val Leu Gly Ser Leu
            260                 265                 270

Leu Met Leu Ala Cys Leu Ala Leu Gly Ile Trp Gly Leu Ile Cys Cys
        275                 280                 285

Cys Cys Gly Gly Gly Gly Ala Gly Gly Ala Arg Gly Ala Phe Gly Tyr
    290                 295                 300

Gly Val Gly Gly Gly Val Gly Gly Gly Ala Cys Gly Asp Leu Ala Ser
305                 310                 315                 320

Glu Ile Arg Val Asp Ala Glu Ala Pro Gly Cys Lys Ala Ser Gly Arg
                325                 330                 335

Gly Ser Arg Val Thr His Leu Leu Gly Tyr Pro Thr Gln Asn Val Ser
            340                 345                 350

Arg Ser Leu Arg Arg Lys Tyr Ala Pro Pro Pro Cys Gly Gly Pro Glu
        355                 360                 365

Asp Val Ala Leu Val Pro Arg Thr Ala Ser Ala Ser Cys Glu Ala Gly
    370                 375                 380

Pro Ser Pro Val Tyr Ile Lys Val Lys Ser Ala Glu Pro Ala Asp Cys
385                 390                 395                 400

Ala Asp Cys Ala Gln Val Glu Gln Arg Ser Cys Lys Asp Gly Leu Leu
                405                 410                 415

Val


<210> SEQ ID NO 3
<211> LENGTH: 414
<212> TYPE: PRT
<213> ORGANISM: Macaca fascicularis

<400> SEQUENCE: 3

Met Gly Val Gly Gly Ala Phe His Leu Leu Leu Val Cys Leu Ser Pro
1               5                   10                  15

Ala Leu Leu Ser Ala Val Arg Ile Asn Gly Asp Gly Gln Glu Val Leu
            20                  25                  30

Tyr Leu Ala Glu Gly Asp Asn Val Arg Leu Gly Cys Pro Tyr Val Leu
        35                  40                  45

Asp Pro Glu Asp Tyr Gly Pro Asn Gly Leu Asp Ile Glu Trp Met Gln
    50                  55                  60

Val Asn Ser Asp Pro Ala His His Arg Glu Asn Val Phe Leu Ser Tyr
65                  70                  75                  80

Gln Asp Lys Arg Ile Asn His Gly Asn Leu Pro His Leu Gln Gln Arg
                85                  90                  95

Val Arg Phe Ala Ala Ser Asp Pro Ser Gln Tyr Asp Ala Ser Ile Asn
            100                 105                 110

Leu Met Asn Leu Gln Val Ser Asp Thr Ala Thr Tyr Glu Cys Arg Val
        115                 120                 125

Lys Lys Thr Thr Met Ala Thr Arg Lys Val Ile Val Thr Val Gln Ala
    130                 135                 140

Arg Pro Ala Val Pro Met Cys Trp Thr Glu Gly His Met Thr His Gly
145                 150                 155                 160
```

-continued

```
Asn Asp Val Val Leu Lys Cys Tyr Ala Asn Gly Gly Ser Gln Pro Leu
                165                 170                 175

Ser Tyr Lys Trp Ala Lys Ile Ser Gly His His Tyr Pro Tyr Arg Ala
            180                 185                 190

Gly Ser Tyr Thr Ser Gln His Ser Tyr His Ser Glu Leu Ser Tyr Gln
        195                 200                 205

Glu Ser Phe His Ser Ser Ile Asn Gln Gly Leu Asn Asn Gly Asp Leu
    210                 215                 220

Val Leu Lys Asp Ile Ser Arg Ala Asp Asp Gly Leu Tyr Gln Cys Thr
225                 230                 235                 240

Val Ala Asn Asn Val Gly Tyr Ser Val Cys Val Val Glu Val Lys Val
                245                 250                 255

Ser Asp Ser Arg Arg Ile Gly Val Ile Ile Gly Ala Ile Leu Gly Ser
            260                 265                 270

Leu Leu Ala Leu Gly Cys Leu Ala Val Gly Ile Trp Gly Leu Val Cys
        275                 280                 285

Cys Cys Cys Gly Gly Ser Gly Ala Gly Gly Ala Arg Gly Ala Phe Gly
    290                 295                 300

Tyr Gly Asn Gly Gly Gly Val Gly Gly Gly Ala Cys Gly Asp Leu Ala
305                 310                 315                 320

Ser Glu Ile Arg Glu Asp Ala Val Ala Pro Gly Cys Lys Ala Ser Gly
                325                 330                 335

Arg Gly Ser Arg Val Thr His Leu Leu Gly Tyr Pro Thr Gln Asn Val
            340                 345                 350

Ser Arg Ser Leu Arg Arg Lys Tyr Ala Pro Pro Pro Cys Gly Gly Pro
        355                 360                 365

Glu Asn Val Ala Leu Ala Pro Cys Thr Ala Ala Ala Ala Cys Glu Ala
    370                 375                 380

Gly Pro Ser Pro Val Tyr Val Lys Val Lys Ser Ala Glu Pro Ala Asp
385                 390                 395                 400

Cys Ala Glu Gly Pro Val Gln Cys Lys Asn Gly Leu Leu Val
                405                 410
```

<210> SEQ ID NO 4
<211> LENGTH: 1437
<212> TYPE: DNA
<213> ORGANISM: Homo sapiens

<400> SEQUENCE: 4

```
agacggagga aacaccgagc ctagagacat gagagttgga ggagcattcc accttctact     60

cgtgtgcctg agcccagcac tgctgtctgc tgtgcggatc aacggggatg gacaggaggt    120

cctgtacctg gcagaaggtg ataatgtgag gctgggctgc ccctacgtcc tggaccctga    180

ggactatggt cccaatgggc tggacatcga gtggatgcag gtcaactcag accccgccca    240

ccaccgagag aacgtgttcc ttagttacca ggacaagagg atcaaccatg gcagccttcc    300

ccatctgcag cagagggtcc gctttgcagc ctcagaccca agccagtacg atgcctccat    360

caacctcatg aacctgcagg tatctgatac agccacttat gagtgccggg tgaagaagac    420

caccatggcc acccggaagg tcattgtcac tgtccaagca cgacctgcag tgcccatgtg    480

ctggacagag ggccacatga catatggcaa cgatgtggtg ctgaagtgct atgccagtgg    540

gggctcccag cccctctcct acaagtgggc caagatcagt gggcaccatt acccctatcg    600

agctgggtct tacacctccc agcacagcta ccactcagag ctgtcctacc aggagtcctt    660
```

-continued

```
ccacagctcc ataaaccaag gcctgaacaa tggggacctg gtgttgaagg atatctccag    720

agcagatgat gggctgtatc agtgcacagt ggccaacaac gtgggctaca gtgtttgtgt    780

ggtggaggtg aaggtctcag actcccggcg tataggcgtg atcatcggca tcgtcctggg    840

ctctctgctc gcgctgggct gcctggccgt aggcatctgg gggctcgtct gctgctgctg    900

cgggggctcc ggggctggcg gcgcccgcgg tgccttcggc tacggcaacg gcggcggggt    960

cggcggaggg gcctgcggcg acttggctag tgagatcaga gaggacgccg tggcgcccgg   1020

gtgcaaggcc agcgggcgcg gcagccgcgt cacccacctc ctggggtacc cgacgcagaa   1080

cgtcagccgc tccctgcgcc gcaagtacgc gcctcccccc tgcggcggcc ccgaggacgt   1140

ggccctggcg ccctgcaccg ccgccgccgc ctgcgaagcg ggcccctccc cggtctacgt   1200

caaggtcaag agcgcggagc cggctgactg cgccgagggg ccggtgcagt gcaagaacgg   1260

cctcttggtg tgagcgcgcg cgccgggccg ggctgcgccc cagccaggag gagggcgcgg   1320

ggctctctgt ctgcagctgg ggacacgtcg gggctgggga cgacctcgct cgccccaggc   1380

tgccaggcgg ctgggggtga aggcatttcc ctaaggaaat gcgtagggag gcagagc      1437
```

<210> SEQ ID NO 5
<211> LENGTH: 1802
<212> TYPE: DNA
<213> ORGANISM: Mus musculus

<400> SEQUENCE: 5

```
gactcattgc atcttcctgc caccccgggc agtgtctggg ccctccgctc cccctccctc     60

cacctgcccc ttccacccac caccaccagc ccactggagc ccagctcagg cggaggaaag    120

accaagccta gagacatggg agttcgagga gcactccatc ttctacttgt gtgcctgagc    180

ccagcactgt tgtctgctgt aaggatcaac ggggatggcc aggaggtcat gtacctggca    240

gaaggtgaca atgtgaggct aggctgtccc tacctcctgg atcctgagga tttgggtacc    300

aacagtctgg acattgagtg gatgcaagtc aactcagagc cctcacacag ggagaatgtt    360

tttcttactt atcaagacaa gaggataggt catggcaacc tcccccatct gcagcagagg    420

gtccgctttg cagcctcaga ccccagccag tacgatgcct ccatcaacct catgaacctg    480

caggtatctg acacagcaac ctatgagtgc cgggtgaaga agaccaccat ggccaccagg    540

aaggtcattg tcactgtcca agcacgtcct gcggtgccca tgtgttggac ggaaggccac    600

atgtcaaagg gcaacgatgt ggtgctgaag tgctttgcca acggaggctc tcagcccctc    660

tcctacaagt gggccaagat cagtgggcac agtcacccct accgagctgg ggcttaccac    720

tcacagcaca gcttccactc tgagctttct taccaagagt cattccacag caccatcaac    780

caaggcctgg gcaacggaga cctgctgttg aagggcatca acgcagacga cgatgggctg    840

tatcagtgca cagtggccaa ccatgtgggc tacagcgtct gtgtggtaga ggtgaaagtc    900

tcagactccc agcgagtagg catgatcgtt ggagcagtgc tgggctcttt gctcatgctg    960

gcctgcctgg cactaggcat ctgggggctc atctgctgct gctgcggagg cggcggggcc   1020

ggtggtgccc gaggtgcctt cggctacggg gtcggcggcg gggtcggcgg aggggcctgc   1080

ggcgacttgg ctagtgagat cagagtggac gccgaggcgc ccgggtgtaa ggccagcggg   1140

cgcggcagcc gcgtcaccca cctcctgggg tacccggcgc agaacgtcag ccgctccagg   1200

cgccgcaagt acgcgcctcc gccctgcggc ggccccgagc acgtggccct agtgccccgc   1260

accgcctccg cctcctgcga agcgggtccc tcccccgtct acatcaaggt caagagcgcg   1320

gagccggccg actgcgccga ctgtgcccag gtcgagcagc gctcgtgcaa ggacggcctc   1380
```

-continued

```
ttagtgtgag cgcacagcac cgggctgcgc cccggctggg aggtggttcg ggggctctct   1440

gcccgcagct ggggacaggt tcgggccagc agacctggct ctctcattgg ccacctagcg   1500

gtggtaagga aatttccctc tgagaagcca agccgggcag accctcctcc cctgtagtgg   1560

gaggagaggc gggggagaca gaaaacagtt cagagctctc cctcacccct ggtttccagg   1620

gagaggaagg gagaggagag ctgtcggtat cccagaaccg cagaggtaca acccagatgt   1680

ccccagccaa ggcgagggcc ccccagccct gggtaggtgg atgtcagggc tgaattgctc   1740

tgtgtgtgag atctgagctc caaggcaaca gtgttagcac aataaagaaa cttaaagact   1800

gg                                                                  1802


<210> SEQ ID NO 6
<211> LENGTH: 311
<212> TYPE: PRT
<213> ORGANISM: Homo sapiens

<400> SEQUENCE: 6

Met Gly Val Pro Thr Ala Leu Glu Ala Gly Ser Trp Arg Trp Gly Ser
1               5                   10                  15

Leu Leu Phe Ala Leu Phe Leu Ala Ala Ser Leu Gly Pro Val Ala Ala
            20                  25                  30

Phe Lys Val Ala Thr Pro Tyr Ser Leu Tyr Val Cys Pro Glu Gly Gln
        35                  40                  45

Asn Val Thr Leu Thr Cys Arg Leu Leu Gly Pro Val Asp Lys Gly His
    50                  55                  60

Asp Val Thr Phe Tyr Lys Thr Trp Tyr Arg Ser Ser Arg Gly Glu Val
65                  70                  75                  80

Gln Thr Cys Ser Glu Arg Arg Pro Ile Arg Asn Leu Thr Phe Gln Asp
                85                  90                  95

Leu His Leu His His Gly Gly His Gln Ala Ala Asn Thr Ser His Asp
            100                 105                 110

Leu Ala Gln Arg His Gly Leu Glu Ser Ala Ser Asp His His Gly Asn
        115                 120                 125

Phe Ser Ile Thr Met Arg Asn Leu Thr Leu Leu Asp Ser Gly Leu Tyr
    130                 135                 140

Cys Cys Leu Val Val Glu Ile Arg His His His Ser Glu His Arg Val
145                 150                 155                 160

His Gly Ala Met Glu Leu Gln Val Gln Thr Gly Lys Asp Ala Pro Ser
                165                 170                 175

Asn Cys Val Val Tyr Pro Ser Ser Ser Gln Asp Ser Glu Asn Ile Thr
            180                 185                 190

Ala Ala Ala Leu Ala Thr Gly Ala Cys Ile Val Gly Ile Leu Cys Leu
        195                 200                 205

Pro Leu Ile Leu Leu Leu Val Tyr Lys Gln Arg Gln Ala Ala Ser Asn
    210                 215                 220

Arg Arg Ala Gln Glu Leu Val Arg Met Asp Ser Asn Ile Gln Gly Ile
225                 230                 235                 240

Glu Asn Pro Gly Phe Glu Ala Ser Pro Pro Ala Gln Gly Ile Pro Glu
                245                 250                 255

Ala Lys Val Arg His Pro Leu Ser Tyr Val Ala Gln Arg Gln Pro Ser
            260                 265                 270

Glu Ser Gly Arg His Leu Leu Ser Glu Pro Ser Thr Pro Leu Ser Pro
        275                 280                 285
```

```
Pro Gly Pro Gly Asp Val Phe Phe Pro Ser Leu Asp Pro Val Pro Asp
    290                 295                 300

Ser Pro Asn Phe Glu Val Ile
305                 310


<210> SEQ ID NO 7
<211> LENGTH: 308
<212> TYPE: PRT
<213> ORGANISM: Mus musculus

<400> SEQUENCE: 7

Met Gly Val Pro Ala Val Pro Glu Ala Ser Ser Pro Arg Trp Gly Thr
1               5                   10                  15

Leu Leu Leu Ala Ile Phe Leu Ala Ala Ser Arg Gly Leu Val Ala Ala
            20                  25                  30

Phe Lys Val Thr Thr Pro Tyr Ser Leu Tyr Val Cys Pro Glu Gly Gln
        35                  40                  45

Asn Ala Thr Leu Thr Cys Arg Ile Leu Gly Pro Val Ser Lys Gly His
    50                  55                  60

Asp Val Thr Ile Tyr Lys Thr Trp Tyr Leu Ser Ser Arg Gly Glu Val
65                  70                  75                  80

Gln Met Cys Lys Glu His Arg Pro Ile Arg Asn Phe Thr Leu Gln His
                85                  90                  95

Leu Gln His His Gly Ser His Leu Lys Ala Asn Ala Ser His Asp Gln
            100                 105                 110

Pro Gln Lys His Gly Leu Glu Leu Ala Ser Asp His His Gly Asn Phe
        115                 120                 125

Ser Ile Thr Leu Arg Asn Val Thr Pro Arg Asp Ser Gly Leu Tyr Cys
    130                 135                 140

Cys Leu Val Ile Glu Leu Lys Asn His His Pro Glu Gln Arg Phe Tyr
145                 150                 155                 160

Gly Ser Met Glu Leu Gln Val Gln Ala Gly Lys Gly Ser Gly Ser Thr
                165                 170                 175

Cys Met Ala Ser Asn Glu Gln Asp Ser Asp Ser Ile Thr Ala Ala Ala
            180                 185                 190

Leu Ala Thr Gly Ala Cys Ile Val Gly Ile Leu Cys Leu Pro Leu Ile
        195                 200                 205

Leu Leu Leu Val Tyr Lys Gln Arg Gln Val Ala Ser His Arg Arg Ala
    210                 215                 220

Gln Glu Leu Val Arg Met Asp Ser Asn Thr Gln Gly Ile Glu Asn Pro
225                 230                 235                 240

Gly Phe Glu Thr Thr Pro Pro Phe Gln Gly Met Pro Glu Ala Lys Thr
                245                 250                 255

Arg Pro Pro Leu Ser Tyr Val Ala Gln Arg Gln Pro Ser Glu Ser Gly
            260                 265                 270

Arg Tyr Leu Leu Ser Asp Pro Ser Thr Pro Leu Ser Pro Pro Gly Pro
        275                 280                 285

Gly Asp Val Phe Phe Pro Ser Leu Asp Pro Val Pro Asp Ser Pro Asn
    290                 295                 300

Ser Glu Ala Ile
305


<210> SEQ ID NO 8
<211> LENGTH: 309
<212> TYPE: PRT
<213> ORGANISM: Mus musculus
```

<400> SEQUENCE: 8

Met Gly Val Pro Ala Val Pro Glu Ala Ser Ser Pro Arg Trp Gly Thr
1 5 10 15

Leu Leu Leu Ala Ile Phe Leu Ala Ala Ser Arg Gly Leu Val Ala Ala
20 25 30

Phe Lys Val Thr Thr Pro Tyr Ser Leu Tyr Val Cys Pro Glu Gly Gln
35 40 45

Asn Ala Thr Leu Thr Cys Arg Ile Leu Gly Pro Val Ser Lys Gly His
50 55 60

Asp Val Thr Ile Tyr Lys Thr Trp Tyr Leu Ser Ser Arg Gly Glu Val
65 70 75 80

Gln Met Cys Lys Glu His Arg Pro Ile Arg Asn Phe Thr Leu Gln His
85 90 95

Leu Gln His His Gly Ser His Leu Lys Ala Asn Ala Ser His Asp Gln
100 105 110

Pro Gln Lys His Gly Leu Glu Leu Ala Ser Asp His His Gly Asn Phe
115 120 125

Ser Ile Thr Leu Arg Asn Val Thr Pro Arg Asp Ser Gly Leu Tyr Cys
130 135 140

Cys Leu Val Ile Glu Leu Lys Asn His His Pro Glu Gln Arg Phe Tyr
145 150 155 160

Gly Ser Met Glu Leu Gln Val Gln Ala Gly Lys Gly Ser Gly Ser Thr
165 170 175

Cys Met Ala Ser Asn Glu Gln Asp Ser Asp Ser Ile Thr Ala Ala Ala
180 185 190

Leu Ala Thr Gly Ala Cys Ile Val Gly Ile Leu Cys Leu Pro Leu Ile
195 200 205

Leu Leu Leu Val Tyr Lys Gln Arg Gln Val Ala Ser His Arg Arg Ala
210 215 220

Gln Glu Leu Val Arg Met Asp Ser Ser Asn Thr Gln Gly Ile Glu Asn
225 230 235 240

Pro Gly Phe Glu Thr Thr Pro Pro Phe Gln Gly Met Pro Glu Ala Lys
245 250 255

Thr Arg Pro Pro Leu Ser Tyr Val Ala Gln Arg Gln Pro Ser Glu Ser
260 265 270

Gly Arg Tyr Leu Leu Ser Asp Pro Ser Thr Pro Leu Ser Pro Pro Gly
275 280 285

Pro Gly Asp Val Phe Phe Pro Ser Leu Asp Pro Val Pro Asp Ser Pro
290 295 300

Asn Ser Glu Ala Ile
305

<210> SEQ ID NO 9
<211> LENGTH: 4774
<212> TYPE: DNA
<213> ORGANISM: Homo sapiens

<400> SEQUENCE: 9
gggggcgggt gcctggagca cggcgctggg gccgcccgca gcgctcactc gctcgcactc 60
agtcgcggga ggcttccccg cgccggccgc gtcccgcccg ctccccggca ccagaagttc 120
ctctgcgcgt ccgacggcga catgggcgtc cccacggccc tggaggccgg cagctggcgc 180
tggggatccc tgctcttcgc tctcttcctg gctgcgtccc taggtccggt ggcagccttc 240

-continued

```
aaggtcgcca cgccgtattc cctgtatgtc tgtcccgagg ggcagaacgt caccctcacc    300
tgcaggctct tgggccctgt ggacaaaggg cacgatgtga ccttctacaa gacgtggtac    360
cgcagctcga ggggcgaggt gcagacctgc tcagagcgcc ggcccatccg caacctcacg    420
ttccaggacc ttcacctgca ccatggaggc caccaggctg ccaacaccag ccacgacctg    480
gctcagcgcc acgggctgga gtcggcctcc gaccaccatg gcaacttctc catcaccatg    540
cgcaacctga ccctgctgga tagcggcctc tactgctgcc tggtggtgga gatcaggcac    600
caccactcgg agcacagggt ccatggtgcc atggagctgc aggtgcagac aggcaaagat    660
gcaccatcca actgtgtggt gtacccatcc tcctcccagg atagtgaaaa catcacggct    720
gcagccctgg ctacgggtgc ctgcatcgta ggaatcctct gcctcccct catcctgctc    780
ctggtctaca agcaaaggca ggcagcctcc aaccgccgtg cccaggagct ggtgcggatg    840
gacagcaaca ttcaagggat tgaaaacccc ggctttgaag cctcaccacc tgcccagggg    900
atacccgagg ccaaagtcag gcaccccctg tcctatgtgg cccagcggca gccttctgag    960
tctgggcggc atctgctttc ggagcccagc accccctgt ctcctccagg ccccggagac   1020
gtcttcttcc catccctgga ccctgtccct gactctccaa actttgaggt catctagccc   1080
agctggggga cagtgggctg ttgtggctgg gtctggggca ggtgcatttg agccagggct   1140
ggctctgtga gtggcctcct tggcctcggc cctggttccc tccctcctgc tctgggctca   1200
gatactgtga catcccagaa gcccagcccc tcaacccctc tggatgctac atggggatgc   1260
tggacggctc agcccctgtt ccaaggattt tggggtgctg agattctccc ctagagacct   1320
gaaattcacc agctacagat gccaaatgac ttacatctta agaagtctca gaacgtccag   1380
cccttcagca gctctcgttc tgagacatga gccttgggat gtggcagcat cagtgggaca   1440
agatggacac tgggccaccc tcccaggcac cagacacagg gcacggtgga gagacttctc   1500
ccccgtggcc gccttggctc ccccgttttg cccgaggctg ctcttctgtc agacttcctc   1560
tttgtaccac agtggctctg gggccaggcc tgcctgccca ctggccatcg ccaccttccc   1620
cagctgcctc ctaccagcag tttctctgaa gatctgtcaa caggttaagt caatctgggg   1680
cttccactgc ctgcattcca gtccccagag cttggtggtc ccgaaacggg aagtacatat   1740
tggggcatgg tggcctccgt gagcaaatgg tgtcttgggc aatctgaggc caggacagat   1800
gttgccccac ccactggaga tggtgctgag ggaggtgggt ggggccttct gggaaggtga   1860
gtggagaggg gcacctgccc cccgccctcc ccatccccta ctcccactgc tcagcgcggg   1920
ccattgcaag ggtgccacac aatgtcttgt ccaccctggg acacttctga gtatgaagcg   1980
ggatgctatt aaaaactaca tggggaaaca ggtgcaaacc ctggagatgg attgtaagag   2040
ccagtttaaa tctgcactct gctgctcctc ccccacccc accttccact ccatacaatc   2100
tgggcctggt ggagtcttcg cttcagagcc attcggccag gtgcgggtga tgttcccatc   2160
tcctgcttgt gggcatgccc tggctttgtt tttatacaca taggcaaggt gagtcctctg   2220
tggaattgtg attgaaggat tttaaagcag gggaggagag tagggggcat ctctgtacac   2280
tctgggggta aaacagggaa ggcagtgcct gagcatgggg acaggtgagg tggggctggg   2340
cagacccct gtagcgttta gcaggatggg ggccccaggt actgtggaga gcatagtcca   2400
gcctgggcat ttgtctccta gcagcctaca ctggctctgc tgagctgggc ctgggtgctg   2460
aaagccagga tttggggcta ggcgggaaga tgttcgccca attgcttggg gggttggggg   2520
gatggaaaag gggagcacct ctaggctgcc tggcagcagt gagccctggg cctgtggcta   2580
cagccaggga accccacctg gacacatggc cctgcttcta agccccccag ttaggcccaa   2640
```

-continued

```
aggaatggtc cactgagggc ctcctgctct gcctgggctg ggccaggggc tttgaggaga   2700

gggtaaacat aggcccggag atggggctga cacctcgagt ggccagaata tgcccaaacc   2760

ccggcttctc ccttgtccct aggcagaggg gggtcccttc ttttgttccc tctggtcacc   2820

acaatgcttg atgccagctg ccataggaag agggtgctgg ctggccatgg tggcacacac   2880

ctgtcctccc agcactttgc agggctgagg tggaaggacc gcttaagccc aggtgttcaa   2940

ggctgctgtg agctgtgttc gagccactac actccagcct ggggacggag caaaactttg   3000

cctcaaaaca aattttaaaa agaaagaaag aaggaaagag ggtatgtttt tcacaattca   3060

tgggggcctg catggcagga gtggggacag gacacctgct gttcctggag tcgaaggaca   3120

agcccacagc ccagattccg gttctcccaa ctcaggaaga gcatgccctg ccctctgggg   3180

aggctggcct ggccccagcc ctcagctgct gaccttgagg cagagacaac ttctaagaat   3240

ttggctgcca gaccccaggc ctggctgctg ctgtgtggag agggaggcgg cccgcagcag   3300

aacagccacc gcacttcctc ctcagcttcc tctggtgcgg ccctgccctc tcttctctgg   3360

accctttttac aactgaacgc atctgggctt cgtggtttcc tgttttcagc gaaatttact   3420

ctgagctccc agttccatct tcatccatgg ccacaggccc tgcctacaac gcactaggga   3480

cgtccctccc tgctgctgct ggggaggggc aggctgctgg agccgccctc tgagttgccc   3540

gggatggtag tgcctctgat gccagccctg gtggctgtgg gctggggtgc atgggagagc   3600

tgggtgcgag aacatggcgc ctccaggggg cgggaggagc actaggggct ggggcaggag   3660

gctcctggag cgctggattc gtggcacagt ctgaggccct gagagggaaa tccatgcttt   3720

taagaactaa ttcattgtta ggagatcaat caggaattag gggccatctt acctatctcc   3780

tgacattcac agtttaatag agacttcctg cctttattcc ctcccaggga gaggctgaag   3840

gaatggaatt gaaagcacca tttggagggt tttgctgaca cagcggggac tgctcagcac   3900

tccctaaaaa cacaccatgg aggccactgg tgactgctgg tgggcaggct ggccctgcct   3960

gggggagtcc gtggcgatgg gcgctggggt ggaggtgcag gagccccagg acctgctttt   4020

caaaagactt ctgcctgacc agagctccca ctacatgcag tggcccaggg cagaggggct   4080

gatacatggc ctttttcagg gggtgctcct cgcggggtgg acttgggagt gtgcagtggg   4140

acagggggct gcaggggtcc tgccaccacc gagcaccaac ttggcccctg gggtcctgcc   4200

tcatgaatga ggccttcccc agggctggcc tgactgtgct gggggctggg ttaacgtttt   4260

ctcagggaac cacaatgcac gaaagaggaa ctggggttgc taaccaggat gctgggaaca   4320

aaggcctctt gaagcccagc cacagcccag ctgagcatga ggcccagccc atagacggca   4380

caggccacct ggcccattcc ctgggcattc cctgctttgc attgctgctt ctcttcaccc   4440

catggaggct atgtcaccct aactatcctg gaatgtgttg agagggattc tgaatgatca   4500

atatagcttg gtgagacagt gccgagatag atagccatgt ctgccttggg cacgggagag   4560

ggaagtggca gcatgcatgc tgtttcttgg cctttctgt tagaatactt ggtgctttcc   4620

aacacacttt cacatgtgtt gtaacttgtt tgatccaccc ccttccctga aaatcctggg   4680

aggttttatt gctgccattt aacacagagg gcaatagagg ttctgaaagg tctgtgtctt   4740

gtcaaaacaa gtaaacggtg gaactacgac taaa                              4774
```

<210> SEQ ID NO 10
<211> LENGTH: 1055
<212> TYPE: DNA
<213> ORGANISM: Homo sapiens -continued

<400> SEQUENCE: 10

```
ctcgccgcgc tgagccgcct cgggacggag ccatgcggcg ctgggcctgg gccgcggtcg      60
tggtcccccct cgggccgcag ctcgtgctcc tcgggggcgt cggggcccgg cgggaggcac    120
agaggacgca gcagcctggc cagcgcgcag atccccccaa cgccaccgcc agcgcgtcct    180
cccgcgaggg gctgcccgag gcccccaagc catcccaggc ctcaggacct gagttctccg    240
acgcccacat gacatggctg aactttgtcc ggcggccgga cgacggcgcc ttaaggaagc    300
ggtgcggaag cagggacaag aagccgcggg atctcttcgg tcccccagga cctccaggtg    360
cagaagtgac cgcggagact ctgcttcacg agtttcagga gctgctgaaa gaggccacgg    420
agcgccggtt ctcagggctt ctggacccgc tgctgcccca gggggcgggc ctgcggctgg    480
tgggcgaggc ctttcactgc cggctgcagg gtccccgccg ggtggacaag cggacgctgg    540
tggagctgca tggtttccag gctcctgctg cccaaggtgc cttcctgcga ggctccggtc    600
tgagcctggc ctcgggtcgg ttcacggccc ccgtgtccgg catcttccag ttctctgcca    660
gtctgcacgt ggaccacagt gagctgcagg gcaaggcccg gctgcgggcc cgggacgtgg    720
tgtgtgttct catctgtatt gagtccctgt gccagcgcca cacgtgcctg gaggccgtct    780
caggcctgga gagcaacagc agggtcttca cgctacaggt gcaggggctg ctgcagctgc    840
aggctggaca gtacgcttct gtgtttgtgg acaatggctc cggggccgtc ctcaccatcc    900
aggcgggctc cagcttctcc gggctgctcc tgggcacgtg agggcgccca ggggggctgg    960
cgaggagctg ccgccggatc ccggggaccc tcctactgat gcccgtggtc accacaataa   1020
agagccctcc accctcaaaa aaaaaaaaaa aaaaa                              1055
```

<210> SEQ ID NO 11
<211> LENGTH: 1055
<212> TYPE: DNA
<213> ORGANISM: Mus musculus

<400> SEQUENCE: 11

```
ctcgccgcgc tgagccgcct cgggacggag ccatgcggcg ctgggcctgg gccgcggtcg      60
tggtcccccct cgggccgcag ctcgtgctcc tcgggggcgt cggggcccgg cgggaggcac    120
agaggacgca gcagcctggc cagcgcgcag atccccccaa cgccaccgcc agcgcgtcct    180
cccgcgaggg gctgcccgag gcccccaagc catcccaggc ctcaggacct gagttctccg    240
acgcccacat gacatggctg aactttgtcc ggcggccgga cgacggcgcc ttaaggaagc    300
ggtgcggaag cagggacaag aagccgcggg atctcttcgg tcccccagga cctccaggtg    360
cagaagtgac cgcggagact ctgcttcacg agtttcagga gctgctgaaa gaggccacgg    420
agcgccggtt ctcagggctt ctggacccgc tgctgcccca gggggcgggc ctgcggctgg    480
tgggcgaggc ctttcactgc cggctgcagg gtccccgccg ggtggacaag cggacgctgg    540
tggagctgca tggtttccag gctcctgctg cccaaggtgc cttcctgcga ggctccggtc    600
tgagcctggc ctcgggtcgg ttcacggccc ccgtgtccgg catcttccag ttctctgcca    660
gtctgcacgt ggaccacagt gagctgcagg gcaaggcccg gctgcgggcc cgggacgtgg    720
tgtgtgttct catctgtatt gagtccctgt gccagcgcca cacgtgcctg gaggccgtct    780
caggcctgga gagcaacagc agggtcttca cgctacaggt gcaggggctg ctgcagctgc    840
aggctggaca gtacgcttct gtgtttgtgg acaatggctc cggggccgtc ctcaccatcc    900
aggcgggctc cagcttctcc gggctgctcc tgggcacgtg agggcgccca ggggggctgg    960
```

-continued

```
cgaggagctg ccgccggatc ccggggaccc tcctactgat gcccgtggtc accacaataa   1020

agagccctcc accctcaaaa aaaaaaaaaa aaaaa                               1055
```